(12) United States Patent
Jensen

(10) Patent No.: US 10,865,242 B2
(45) Date of Patent: Dec. 15, 2020

(54) METHOD AND COMPOSITIONS FOR CELLULAR IMMUNOTHERAPY

(71) Applicant: Seattle Children's Hospital, Seattle, WA (US)

(72) Inventor: Michael C. Jensen, Bainbridge Island, WA (US)

(73) Assignee: Seattle Children's Hospital, Seattle, WA (US)

(\*) Notice: Subject to any disclaimer, the term of this patent is extended or adjusted under 35 U.S.C. 154(b) by 0 days.

(21) Appl. No.: 15/302,403

(22) PCT Filed: Apr. 8, 2015

(86) PCT No.: PCT/US2015/024882
§ 371 (c)(1),
(2) Date: Oct. 6, 2016

(87) PCT Pub. No.: WO2015/157391
PCT Pub. Date: Oct. 15, 2015

(65) Prior Publication Data
US 2018/0009891 A1    Jan. 11, 2018

Related U.S. Application Data

(60) Provisional application No. 61/977,751, filed on Apr. 10, 2014, provisional application No. 61/986,479, (Continued)

(51) Int. Cl.
| C07H 21/04 | (2006.01) |
|---|---|
| C12N 15/63 | (2006.01) |
| C12N 15/85 | (2006.01) |
| C07K 16/28 | (2006.01) |
| A61K 35/17 | (2015.01) |
| C12N 5/0783 | (2010.01) |
| C07K 14/725 | (2006.01) |
| C07K 14/705 | (2006.01) |
| A61K 35/28 | (2015.01) |
| A61K 38/17 | (2006.01) |
| C07K 14/71 | (2006.01) |
| C07K 14/715 | (2006.01) |

(Continued)

(52) U.S. Cl.
CPC .......... *C07K 16/2803* (2013.01); *A61K 35/17* (2013.01); *A61K 35/28* (2013.01); *A61K 38/179* (2013.01); *A61K 38/1774* (2013.01); *A61K 38/1793* (2013.01); *A61K 39/3955* (2013.01); *C07K 14/7051* (2013.01); *C07K 14/70517* (2013.01); *C07K 14/70521* (2013.01); *C07K 14/70578* (2013.01); *C07K 14/71* (2013.01); *C07K 14/7151* (2013.01); *C07K 16/2818* (2013.01); *C12N 5/0636* (2013.01); *C12N 9/12* (2013.01); *C12N 15/85* (2013.01); *C12Y 207/10001* (2013.01); *A61K 2035/124* (2013.01); *A61K 2039/505* (2013.01); *A61K 2039/5156* (2013.01); *A61K 2039/5158* (2013.01); *A61K 2039/572* (2013.01); *C07K 2317/14* (2013.01); *C07K 2317/524* (2013.01); *C07K 2317/526* (2013.01); *C07K 2317/53* (2013.01); *C07K 2317/622* (2013.01); *C07K 2317/73* (2013.01); *C07K 2319/02* (2013.01); *C07K 2319/03* (2013.01); *C07K 2319/33* (2013.01); *C12N 2510/00* (2013.01); *C12N 2800/90* (2013.01)

(58) Field of Classification Search
CPC ................ C07K 16/2803; C07K 16/32; C07K 16/2818; C12N 15/85; C12N 2510/00; A61K 2035/124

See application file for complete search history.

(56) References Cited

U.S. PATENT DOCUMENTS

| 5,783,186 A | 7/1998 | Arakawa et al. |
|---|---|---|
| 6,040,177 A | 3/2000 | Riddell et al. |

(Continued)

FOREIGN PATENT DOCUMENTS

| CN | 102227503 A | 10/2011 |
|---|---|---|
| DE | 10 2011 118 018 A1 | 4/2013 |

(Continued)

OTHER PUBLICATIONS

Kowolik et al. CD28 costimualtion provided through a CD19-specific chimeric antigen receptor enhances in vivo persistence and antitumor efficacy of adoptively transfered T cells. Cancer Res. 66:10995-11004, 2006.*

(Continued)

*Primary Examiner* — Quang Nguyen
(74) *Attorney, Agent, or Firm* — Knobbe, Martens, Olson & Bear LLP

(57) ABSTRACT

The present invention provides nucleic acids, vectors, host cells, methods and compositions to confer and/or augment immune responses mediated by cellular immunotherapy, such as by adoptively transferring CD8+ central memory T cells or combinations of central memory T cells with CD4+ T cells that are genetically modified to express a chimeric receptor. In some alternatives the genetically modified host cell comprises a nucleic acid comprising a polynucleotide coding for a ligand binding domain, a polynucleotide comprising a customized spacer region, a polynucleotide comprising a transmembrane domain, and a polynucleotide comprising an intracellular signaling domain. In some alternatives, the ligand binding domains binds to CD171.

17 Claims, 100 Drawing Sheets
Specification includes a Sequence Listing.

Related U.S. Application Data filed on Apr. 30, 2014, provisional application No. 62/058,973, filed on Oct. 2, 2014, provisional application No. 62/088,363, filed on Dec. 5, 2014, provisional application No. 62/089,730, filed on Dec. 9, 2014, provisional application No. 62/090,845, filed on Dec. 11, 2014.

(51) Int. Cl.

| C07K 16/32 | (2006.01) |
|---|---|
| A61K 39/395 | (2006.01) |
| C12N 9/12 | (2006.01) |
| A01K 67/00 | (2006.01) |
| A61K 39/00 | (2006.01) |
| A61K 35/12 | (2015.01) |

(56) References Cited

U.S. PATENT DOCUMENTS

| 7,070,995 | B2* | 7/2006 | Jensen | C07H 21/04 435/325 |
|---|---|---|---|---|
| 7,709,253 | B2 | 5/2010 | Gambhir et al. | |
| 7,910,101 | B2* | 3/2011 | Cunningham | A61K 38/34 424/134.1 |
| 8,822,647 | B2 | 9/2014 | Jensen | |
| 10,266,592 | B2 | 4/2019 | Jensen | |
| 2002/0111474 | A1 | 8/2002 | Capon et al. | |
| 2003/0148982 | A1 | 8/2003 | Brenner et al. | |
| 2005/0060762 | A1 | 3/2005 | Bleck | |
| 2005/0129671 | A1* | 6/2005 | Cooper | A61K 39/0011 424/93.21 |
| 2006/0160090 | A1 | 7/2006 | Anzures et al. | |
| 2007/0087346 | A1 | 4/2007 | Ciliberto et al. | |
| 2007/0166318 | A1 | 7/2007 | Macina et al. | |
| 2009/0098142 | A1 | 4/2009 | Kasaian et al. | |
| 2009/0098604 | A1 | 4/2009 | Gallo et al. | |
| 2010/0226901 | A1 | 9/2010 | Smolke | |
| 2011/0028020 | A1 | 11/2011 | Gruber | |
| 2011/0287020 | A1 | 11/2011 | Gruber et al. | |
| 2012/0297493 | A1 | 11/2012 | Cooper et al. | |
| 2012/0301447 | A1 | 11/2012 | Jensen | |
| 2013/0011394 | A1 | 1/2013 | Knoetgen | |
| 2013/0143559 | A1 | 6/2013 | Nishida et al. | |
| 2013/0280220 | A1 | 10/2013 | Ahmed et al. | |
| 2013/0287748 | A1 | 10/2013 | June et al. | |
| 2014/0056868 | A1 | 2/2014 | Zechiedrich et al. | |
| 2014/0112956 | A1 | 4/2014 | Karlsson-Parra et al. | |
| 2014/0271635 | A1 | 9/2014 | Brogdon et al. | |
| 2014/0314795 | A1* | 10/2014 | Riddell et al. | |
| 2015/0038694 | A1 | 2/2015 | Nicotra | |
| 2015/0120622 | A1 | 4/2015 | Kobatake | |
| 2015/0299656 | A1 | 10/2015 | Gattinoni et al. | |
| 2015/0329640 | A1* | 11/2015 | Finer | |
| 2016/0017048 | A1 | 1/2016 | Dotti et al. | |
| 2017/0015746 | A1 | 1/2017 | Jensen | |
| 2017/0029774 | A1 | 2/2017 | Jensen et al. | |
| 2017/0152297 | A1 | 6/2017 | Jensen | |
| 2017/0209543 | A9 | 7/2017 | Jensen | |
| 2017/0224733 | A1 | 8/2017 | Badie et al. | |
| 2017/0267742 | A1 | 9/2017 | Jensen et al. | |
| 2018/0028567 | A1* | 2/2018 | Li | A61K 39/0011 |
| 2019/0248891 | A1 | 8/2019 | Jensen et al. | |

FOREIGN PATENT DOCUMENTS

| RU | 2003 129 528 A | 4/2005 |
|---|---|---|
| WO | WO 92/08796 | 5/1992 |
| WO | WO 94/00143 | 1/1994 |
| WO | WO 98/18923 | 5/1998 |
| WO | WO 00/23573 A2 | 4/2000 |
| WO | WO 01/098506 | 12/2001 |
| WO | WO 02/097099 A1 | 12/2002 |
| WO | WO 03/025228 | 3/2003 |
| WO | WO 03/087338 A2 | 10/2003 |
| WO | WO 04/029284 | 4/2004 |
| WO | WO 05/017102 | 2/2005 |
| WO | WO 2005/040212 A2 | 5/2005 |
| WO | WO 07/137267 | 11/2007 |
| WO | WO 2008/012237 | 1/2008 |
| WO | WO 2009/013359 A2 | 1/2009 |
| WO | WO 2010/036986 A2 | 4/2010 |
| WO | WO 2010/141543 A1 | 12/2010 |
| WO | WO 2011/056894 A2 | 5/2011 |
| WO | WO 2012/031744 A1 | 3/2012 |
| WO | WO 2012/079000 A1 | 6/2012 |
| WO | WO 2012/099973 A2 | 7/2012 |
| WO | WO 2012/129514 | 9/2012 |
| WO | WO 12/140130 | 10/2012 |
| WO | WO 12/167192 | 12/2012 |
| WO | WO 2013/074916 | 5/2013 |
| WO | WO 2013/123061 A1 | 8/2013 |
| WO | WO 2013/154760 | 10/2013 |
| WO | WO 2013/177533 | 11/2013 |
| WO | WO 2013/178635 A1 | 12/2013 |
| WO | WO 2014/031687 A1 | 2/2014 |
| WO | WO 2014/039044 A1 | 3/2014 |
| WO | WO 14/055657 | 4/2014 |
| WO | WO 14/139672 | 9/2014 |
| WO | WO 15/075468 | 5/2015 |
| WO | WO 2015/066551 A2 | 5/2015 |
| WO | WO 2015/105522 | 7/2015 |
| WO | WO 15/142675 | 9/2015 |
| WO | WO2015142675 | 9/2015 |
| WO | WO 15/157399 | 10/2015 |
| WO | WO 2015/157399 A1 | 10/2015 |
| WO | WO 2015/157432 A1 | 10/2015 |

OTHER PUBLICATIONS

Kunkele, A., et al., "Functional Tuning of CARs Reveals Signaling Threshold above which CD8+ CTL Antitumor Potency is Attenuated Due to Cell Fas-FasL-Dependent AICD," Cancer Immunol Res., vol. 3, No. 4, pp. 368-379, Jan. 9, 2015.

Maher, J., "Immunotherpay of Malignant Disease Using Chimeric Antigen Receptor Engrafted T Cells," ISRN Oncology, vol. 2012, pp. 1-23, Nov. 14, 2012.

Park, Jr., et al., "Adoptive Transfer of Chimeric Antigen Receptor Re-Directed Cytolytic T Lmphocyte Clones in Patients with Neuroblastoma," Mol. Ther., vol. 15, No. 4; pp. 825-833, Apr. 2007.

International Search Report and Written Opinion dated Jul. 10, 2015, received in PCT/US2015/24882 filed Apr. 8, 2015.

Further Examination Report dated Oct. 26, 2017, received in New Zealand Application No. 725078 filed Oct. 12, 2016.

Extended European Search Report dated Oct. 11, 2017, received in the European Application 14777020.7 filed Oct. 20, 2016.

Gianpietro Dotti et al.: "Design and development of therapies using chimeric antigen receptor-expressing T cells", Immunological Reviews, vol. 257, No. 1, Dec. 13, 2013 (Dec. 13, 2013), pp. 107-126.

M. Hudecek et al: "Receptor Affinity and Extracellular Domain Modifications Affect Tumor Recognition by ROR1-Specific Chimeric Antigen Receptor T Cells", Clinical Cancer Research, vol. 19, No. 12, Apr. 25, 2013 (Apr. 25, 2013), pp. 3153-3164.

Michael C Jensen et al: "Design and implementation of adoptive therapy with chimeric antigen receptor-modified T cells ", Immunological Reviews., vol. 257, No. 1, Special Issue, Dec. 13, 2013 (Dec. 13, 2013).

M. Hudecek et al: "The Nonsignaling Extracellular Spacer Domain of Chimeric Antigen Receptors Is Decisive for In Vivo Antitumor Activity", Cancer Immunology Research, vol. 3, No. 2, Sep. 11, 2014 (Sep. 11, 2014), pp. 125-135.

First Examination Report dated Feb. 28, 2017 received in New Zealand Application No. 725078 filed Oct. 12, 2016.

Ahmed et al., "Regression of experimental medulloblastoma following transfer of HER2-specific T cells," Cancer Res. (Jun. 15, 2007) 67(12):5957-64.

Ahmed, Nabil, "Her2 Chimeric Antigen Receptor Expressing T Cells in Advanced Sarcoma," ClinicalTrials.gov Identifier: NCT00902044 (May 14, 2009) pp. 1-11.-

(56) References Cited

OTHER PUBLICATIONS

Ahmed, Nabil, "CMV-specific Cytotoxic T Lymphocytes Expressing CAR Targeting HER2 in Patients With GBM (HERT-GBM)," ClinicalTrials.gov Identifier: NCT01109095 (Apr. 22, 2010) pp. 1-8.

Altschul et al., "Local Alignment Statistics, [27] Multiple Alignment and Phylogenetic Trees," Methods in Enzymology (1996) 266:460-480.

Bejcek et al. "Development and Characterization of Three Recombinant Single Chain Antibody Fragments (scFvs) Directed against the CD19 Antigen," Cancer Res (1995) 55:2346-2351.

Brentjens et al: "CD19-targeted T cells rapidly induce molecular remissions in adults with chemotherapy-refractory acute lymphoblastic leukemia", Science Translational Medicine (Mar. 20, 2013) 5(177).

Budde et al., "Combining a CD20 Chimeric Antigen Receptor and an Inducible Caspase 9 Suicide Switch to Improve the Efficacy and Safety of T Cell Adoptive Immunotherapy for Lymphoma", PLOS ONE (2013) 8(12): e82742. https://doi.org/10.1371/journal.pone.0082742.

Cartellieri et al., "A Novel Ex Vivo Isolation and Expansion Procedure for Chimeric Antigen Receptor Engrafted Human T Cells," PLOS ONE (Apr. 3, 2014) vol. 9, No. 4, e93745, pp. 1-12.

Cha et al., "IL-7 + IL-15 are superior to IL-2 for the ex vivo expansion of 4T1 mammary carcinoma-specific T cells with greater efficacy against tumors in vivo," Breast Cancer Research and Treatment, Springer, NY, US (Oct. 14, 2009) vol. 122, No. 2, pp. 359-369.

Chen et al., "Minicircle DNA vectors devoid of bacterial DNA result in persistent and high-level transgene expression in vivo", Mol Ther. (2003) 8(3), 495-500.

Chen et al., "Ex vivo expansion of dendritic-cell-activated antigen-specific CD4+ T cells with anti-CD3/CD28, interleukin 7, and interleukin-15: Potential for adoptive T-cell immunotherapy," Clinical Immunology (2006) vol. 119, pp. 21-31.

Chen et al., "Fusion Protein Linkers: Property, Design and Functionality," Adv Drug Deliv Rev (Oct. 15, 2013) vol. 65, pp. 1357-1369.

Cho et al., "Structure of the extracellular region of HER2 alone and in complex with the Herceptin Fab", Nature (Feb. 13, 2003) 421(6924):756-760.

Converse et al: "Counterselection and Co-Delivery of Transposon and Transposase Functions for Sleeping Beauty-Mediated Transposition in Cultured Mammalian Cells", Bioscience Reports, Kluwer Academic Publishers-Plenum Publishers, NE (Dec. 1, 2004) vol. 24, No. 6, pp. 577-594.

Crewe et al., "Metabolism of Tamoxifen by recombinant human cytochrome P-450 enzymes: Formation of the 4-hydroxy, 4'-hydroxy and N-desmethyl metabolites and isomerization of trans-4-hydroxytamoxifen," Drug Metab Dispos (2002) 30(8): 869-874.

Database Geneseq [Online] May 5, 2005 (May 5, 2005), "Human splice variant protein expressed in ovary cells DEX0487 002.orf. 4.", XP002771301, retrieved from EBI accession No. GSP:ADY30515. Database accession No. ADY30515 ; & WO 2005/017102 A2 (Diadexus Inc [US]; Macina Roberto A [US]; Turner Leah R [US]; Sun Yong) Feb. 24, 2005 (Feb. 24, 2005).

Database UniProt [Online] Oct. 3, (Oct. 3, 2012), "SubName: Full=Receptor tyrosine-protein kinase erbB-2 {ECO: 00003131Ensembl:ENSP00000464252}; Flags: Fragment;", XP002771300, retrieved from EBI accession No. UNIPROT:J3QRJ7 Database accession No. J3QRJ7.

Gallinari et al., "A Functionally Orthogonal Estrogen Receptor-Based Transcription Switch Specifically Induced by a Nonsteroid Synthetic Ligand," Chemistry and Biology (Aug. 1, 2005) vol. 12, No. 8, pp. 883-893.

Gargett et al., "Different cytokine and stimulation conditions influence the expansion and immune phenotype of third-generation chimeric antigen receptor T cells specific for tumor antigen GD2," Cytotherapy (2015) 17.4: 487-495.

Garrett et al., "Novel engineered trastuzumab conformational epitopes demonstrate in vitro and in vivo antitumor properties against HER-2/neu," The Journal of Immunology (Jun. 1, 2007) 178:7120-7131.

Gianpietro et al., "Design and development of therapies using chimeric antigen receptor-expressing T cells," Immunological Reviews (Dec. 13, 2013) vol. 257, No. 1, pp. 107-126.

Giry-Laterriere et al., "Polyswitch lentivetors: 'all-in-one' lentiviral vectors for drug-inducible gene expression, live selection, and recombination cloning," Human Gene Therapy (Oct. 2011) 22:1255-1267.

Gottschalk, Stephen, "Her2 and TGFBeta CTLs in Treatment of Her2 Positive Malignancy (HERCREEM)", ClinicalTrials.gov Identifier: NCT00889954 (Apr. 29, 2009) pp. 1-9.

Grada et al., "TanCAR: A Novel Bispecific Chimeric Antigen Receptor for Cancer Immunotherapy", Mol Ther Nucleic Acids, (Jul. 9, 2013) 2:e105. doi: 10.1038/mtna.2013.32.

Han Weidong, "Treatment of Chemotherapy Refractory Human Epidermalgrowth Factor Receptor-2(HER-2) Positive Advanced Solid Tumors (CART-HER-2)", (Sep. 5, 2013) ClinicalTrials.gov Identifier: NCT01935843, pp. 1-7.

Holtkamp et al., "Modification of antigen-encoding RNA increases stability, tgranslational efficacy, and T-cell stimulatory capacity of dendritic cells," Blood (Oct. 28, 2014), 2006/108:509-4017.

Hong et al., "Diverse solid tumors expressing a restricted eptitope of L1-CAM can be targeted by chimeric antigen receptor redirected T lymphocytes," J Immunotherapy (2014) vol. 37, No. 2, pp. 93-104.

Huls et al., "First Clinical Trials Employing Sleeping Beauty Gene Transfer System and Artificial Antigen Presenting Cells to Generate and Infuse T Cells Expressing CD19-Specific Chimeric Antigen Receptor," Blood (2013) 122:166-166.

Johnston et al., "Regulated expression of erythropoietin from an AAV vector safely improves the anemia of beta-thalassemia in a mouse model," Mol Ther. (Apr. 1, 2003) 7(4):493-497.

Jonnalagadda et al., "Efficient selection of genetically modified human T cells using methotrexate-resistant human dihydrofolate reductase", Gene Therapy (2013) 20:853-860.

Kacherovsky et al., "Combination of Sleeping Beauty transposition and chemically induced dimerization selection for robust production of engineered cells," Nucleic Acids Research (2012) 49(11):e85.

Kacherovsky et al., "Multiplexed 1-16 gene transfer to a human T-cell line by combining Sleeping Beauty transposon system with methotrexate selection", Biotechnology and Bioengineering (Jul. 23, 2015) vol. 112, No. 7, pp. 1429-1436.

Kay et al., "A robust system for production of minicircle DNA vectors," Nature Biotechnology (2010) 28: 1287-1296.

Klebanoff et al., "IL-15 enhances the in vivo antitumor activity of tumor-reactive CD8+ T Cells," PNAS (Feb. 17, 2004) vol. 101, No. 7, pp. 1969-1974.

Leung et al., "Luminescent detection of DNA-binding proteins," Nuc Acids Res (2012) 40(3): 941-955.

Lemaigre et al., "Transcriptional control of genes that regulate glycolysis and gluconeogenesis in adult liver," Biochem. J. (1994) 303:1-14.

Littlewood et al., "A modified oestrogen receptor ligand-binding domain as an improved switch for the regulation of heterologous proteins," Nucleic Acids Res (May 25, 1995) 23(10):686-1690.

Litvinova et al., "The influence of immunoregulatory cytokines IL-2, IL-7, and IL-15 upon activation, proliferation, and apoptosis of immune memory T-cells in vitro," Cell and Tissue Biology (Dec. 11, 2013) vol. 7, No. 6, pp. 539-544.

Loeken, Mary R., "Effects of mutation of the CREB binding site of the somatostatin promoter on cyclic AMP responsiveness in CV-1 cells", Gene Expression (1993) 3(3):253-264.

Lupton et al., "Dominant positive and negative selection using a hygromycin phosphotransferase-thymidine kinase fusion gene," Mol Cell Biol. (Jun. 1991) 11(6):3374-3378.

McGehee et al., "Differentiation-specific element: a cis-acting developmental switch required for the sustained transcriptional expression of the angiotensinogen gene during hormonal-induced differentiation of 3T3-L1 fibroblasts to adipocytes," Mol. Endocrinol. (Apr. 1993) 7(4):551-560.

(56) References Cited

OTHER PUBLICATIONS

Morgan et al., "Case report of a serious adverse event following the administration of T cells transduced with a chimeric antigen receptor recognizing ERBB2," Mol Ther. (Apr. 2010) 18(4):843-51. doi: 10.1038/mt.2010.24. Epub Feb. 23, 2010.
O'Reilly et al., "Identification of an activating transcription factor (ATF) binding site in the human transforming growth factor-beta 2 promoter," J. Biol. Chem. (Oct. 5, 1992) 267:19938-19943.
Papapetrou et al., "Harnessing endogenous miR-181a to segregate transgenic antigen receptor expression in developing versus post-thymic T cells in murine hematopoietic chimeras," The Journal of Clinical Investigation Jan. 5, 2009; 119(1): pp. 157-168.
Pezzutto et al., "CD19 monoclonal antibody HD37 inhibits anti-immunoglobulin-induced B cell activation and proliferation," J Immunol. (May 1, 1987) 138(9):2793-2799.
Pollock et al., "Delivery of a stringent dimerizer-regulated gene expression system in a single retroviral vector," PNAS USA (Nov. 21, 2000) 97(24):13221-1326.
Promega, "pSP64 Poly(A) Vector Sequence and Map," Technical Bulletin No. 052, Revised May 2000, pp. 1-8.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (1992) 3(3):319-338.
Riddell et al., "Adoptive Therapy With Chimeric Antigen Receptor-Modified T Cells of Defined Subset Composition," The Cancer Journal (Mar./Apr. 2014) vol. 20, No. 2, pp. 141-144.
Roscilli et al., "Long-term and tight control of gene expression in mouse skeletal muscle by a new hybrid human transcription factor," Molecular Therapy (Nov. 2002) 1;6(5):653-63.
Sadelain et al., "The basic principles of chimeric antigen receptor (CAR) design," Cancer discovery (2013) 3 (4): 388-98. DOI: 10.1158/2159-8290.CD-12-0548.
Schmittgen et al. "Analyzing real-time PCR data by the comparative C(T) method", Nature Protocols (2008) 3(6):1101-8.
Sharma et al., "Efficient Sleeping Beauty DNA Transposition from DNA Minicircles," Mol Ther Nuc Acids (2013) 2:e74, 1-10.
Terakura et al., "Generation of CD19-chimeric antigen receptor modified CD8+ T cells derived from virus-specific central memory T cells," Gene Therapy (Oct. 26, 2011) 119(1), pp. 72-82.
Treisman, Richard, "The SRE: a growth factor responsive transcriptional regulator," Seminars in Cancer Biology (Feb. 1, 1990) 1(1):47-58.
Wang et. al., "A transgene-encoded cell surface polypeptide for selection, in vivo tracking, and ablation of engineered cells," Blood (Aug. 4, 2011) vol. 118, No. 5, pp. 1255-1263.
Wang et al., "Phenotypic and Functional Attributes of Lentivirus Modified CD19-specific Human CD8+ Central Memory Tcells Manufactured at Clinical Scale," J Immunotherapy (2012) vol. 35, pp. 689-701.
Weill et al., "Translational control by changes in poly(A) tail length: recycling mRNAs," Nature Structural & Molecular Biology (Jun. 2012) vol. 19, No. 6, pp. 577-585.
Xu et al., "Closely related T-memory stem cells correlate with in vivo expansion of CAR.CD19-T cells and are preserved by IL-7 and IL-15," Blood (Jun. 12, 2014) vol. 123, No. 24, pp. 3750-3759.
Yant et al. "Mutational Analysis of the N-Terminal DNA-Binding Domain of Sleeping Beauty Transposase: Critical Residues for DNA Binding and Hyperactivity in Mammalian Cells," Mol. Cell. Biol. (2004) 24(20):9239-9247.
Ye et al., "Characterization of a silencer regulatory element in the human interferon-gamma promoter," J. Biol. Chem., (Oct. 14, 1994) 269:25728-25734.
Aalberse et al., "IgG4 breaking the rules," Immunology (2002) 105:9-19.
Aertgeerts et al., "Structural analysis of the mechanism of inhibition and allosteric activation of the kinase domain of HER2 protein," Journal of Biological Chemistry (2011) vol. 286, No. 21, p. 18756-18765, Весь текст, c.18759-18765.
Berglund et al., "The epitope space of the human proteome," Protein Science (2008) 17:606-613.
Circosta et al., "T Cell Receptor (TCR) Gene Transfer with Lentiviral Vectors Allows Efficient Redirection of Tumor Specificity ikn Naïve and Memory T Cells Without Prior Stimulation of Endogenous TCR," Human Gene Therapy (Nov. 18, 2009) vol. 20, No. 12, pp. 1576-1588.
Ercikan-Abali et al., "Active Site-Directed Double Mutants of Dihydrofolate Reductase," Cancer Res., (1996) vol. 56, No. 18, pp. 4142-4145.
Frankel et al., "Characterization of diphtheria fusion proteins targeted to the human interleukin-3 receptor," Protein engineering (2000) vol. 13, No. 8, p. 575-581.
Gagnon et al., "IL-6, in Synergy with IL-7 or IL-15, Stimulates TCR-Independent Proliferation and Functional Differentiation of CD8+ T Lymphocytes," The Journal of Immunology (2008) 180:7958-7968.
Ghatar et al., "Epitope Mapping of Human HER2 Specific Mouse Monoclonal Antibodies Using Recombinant Extracellular Subdomains," Asian Pacific Journal of Cancer Prevention (2017) 18(11):3103-3110.
Godiska et al., "Linear plasmid vector for cloning of repectitive or unstable sequences in *Excherichia coli*," (Dec. 29, 2009) Nuc Acids Res, vol. 38, No. 6, e88, pp. 1-9.
Hudecek et al., "The Non-Signaling Extracellular Spacer Domain of CD19-Specific Chimeric Antigen Receptors Is Decisive for in Vivo Anti-Tumor Activity," Blood (2012) vol. 120, No. 21, Abstract 951, 3 pages.
Jensen et al., "Design and implementation of adoptive therapy with chimeric antigen receptor-modified T cells," Immunological Reviews (2014) vol. 257, No. 1, pp. 127-144, with a 1 page Corrigendum.
Johansen et al., "Evaluation of Tet-on system to avoid transgene down-regulation in ex vivo gene transfer to the CNS," Gene Therapy (2002) 9:1291-1301.
Likar et al., "Using a mutated variant human deoxycytidine-kinase as a reporter gene for assessing adoptive T-cell therapy," Questions hematology, oncology and immunopathology in pediatrics (2012) vol. 11, No. 2, pp. 23-31. (Russian Language).
Liu et al., "IL-21 synergizes with IL-7 to augment expansion and anti-tumor function of cytotoxic T cells," International Immunology (2007) vol. 19, No. 10, pp. 1213-1221.
Mátes et al., "Molecular evolution of a novelhyperactive Sleeping Beauty transposase enables robust stable gene transfer in vertebrates," Nature Genetics (Jun. 2009) vol. 41, No. 6, pp. 753-761.
McKinlay et al., "Blood monocytes, myeloid dendritic cells and the cytokines interleukin (IL)-7 and IL-15 maintain human CD4+ T memory cellls with mixed helper/regulatory function," Immunology (2006) vol. 120, pp. 392-403.
Muftuoglu et al., "CD161 Expression Identifies a Distinct Subset of Drug-Effluxing Viral-Specific Memory CD4+ T Cells That Preferentially Survive Cytotoxic Chemotherapy," Blood (2012) 122(21):2024.
Pakula et al., "Genetic analysis of protein stability and function," Annual review of genetics (1989) vol. 23, No. 1, p. 289-310, c.305-306.
Roscilli et al., "Long-term and tight control of gene expression in mouse skeletal muscle by a new hybrid human transcription factor," Molecular Therapy (Nov. 1, 2002) 6(5):653-63.
Sengupta et al., "Interleukin-13 Receptor Alpha 2-Targeted Glioblastoma Immunotherapy," BioMed Research International, (Aug. 27, 2014) vol. 2014, Article ID: 952128, pp. 1-8.
Surh et al., "Homeostatsis of memory T cells," Immunological Reviews (2006) vol. 211, pp. 154-163.
Vigna et al., "Robust and Efficient Regulation of Transgene Expression in Vivo by Improved Tetracycline-Dependent Lentiviral Vectors," Mol. Therapy (2002) 5(3):252-261.
Vogt et al., "Doxycycline-regulated gene expression in the opportunistic fungal pathogen Aspergillus fumigatus," BMC Microbiol. (2005) 5(1):11 pages.

(56) References Cited

OTHER PUBLICATIONS

Zambon et al., "Increased Expression of the Pro-Apoptotic Protein BIM: A Mechanism for cAMP/PKA-Induced Apoptosis of Immature T Cells," J. Biol. Chem. (2011) 286(38):33260-33267.

Zeng et al., "Synergy of IL-21 and IL-15 in regulating CD8+ T cell expansion and function," JEM (Jan. 3, 2005) vol. 201, No. 1, pp. 139-148.

Zheng, Changyu et al., "All Human EF1"Promoters Are Not Equal: Markedly Affect Gene Expression in Constructs from Different Sources," International Journal of Medical Sciences (2014) 11(5):404-408.

Chen et al., Jan. 2007, Generation of a transgenic mouse model with chondrocyte-specific and tamoxifen-inducible espression of cre recombinase, Genesis, 45:44-50.

Dotti, Gianpietro, et al. "Design and development of therapies using chimeric antigen receptor-expressing T cells." Immunological reviews 257.1 (2014): 107-126.

Jensen et al., "Designing chimeric antigen receptors to effectively and safely target tumors," Curr Opin Immunol. (Apr. 2015) 33:9-15.

Pelloquin et al., Dec. 1986, Human B lymphocytes immortalization by Epstein-Barr virus in the presence of cyclosprin A, In Vitro Cell Dev Biol, 22(12):689-694.

Robinsons et al., Jan. 1991, Metabolites, pharamcodynamics, and pharamcokinetics of tamoxifen in rats and mice compared to the breast cancer patient, Drug Metab Dispos, 19(1):36-43.

Wilke et al., Apr. 27, 2012, Dual targeting of ErbB2 and MUC1 in breast cancer using chimeric antigen receptors engineered to provide complementary signaling, Journal of Clinical Immunology, 32(5):1059-1070.

\* cited by examiner

Panel 3
Medium

Panel 4
Long

Panel 1

Panel 2

Panel 3

```
   1  GTTAGACCAG ATCTGAGCCT GGGAGCTCTC TGGCTAACTA GGGAACCCAC TGCTTAAGCC TCAATAAAGC TTGCCTTGAG TGCTTCAAGT AGTGTGTGCC
      CAATCTGGTC TAGACTCGGA CCCTCGAGAG ACCGATTGAT CCCTTGGGTG ACGAATTCGG AGTTATTTCG AACGGAACTC ACGAAGTTCA TCACACACGG
 101  CGTCTGTTGT GTGACTCTGG TAACTAGAGA TCCCTCAGAC CCTTTTAGTC AGTGTGGAAA ATCTCTAGCA GTGGCGCCCG AACAGGGACT TGAAAGCGAA
      GCAGACAACA CACTGAGACC ATTGATCTCT AGGGAGTCTG GGAAAATCAG TCACACCTTT TAGAGATCGT CACCGCGGGC TTGTCCCTGA ACTTTCGCTT
                                                                                 psi
 201  AGGGAAACCA GAGGAGCTCT CTCGACGCAG GACTCGGCTT GCTGAAGCGC GCACGGCAAG AGGCGAGGGG CGGGCGACTGG TGAGTACGCC AAAAATTTTG
      TCCCTTTGGT CTCCTCGAGA GAGCTGCGTC CTGAGCCGAA CGACTTCGCG CGTGCCGTTC TCCGCTCCCC GCCGCTGACC ACTCATGCGG TTTTTAAAAC
                              psi
 301  ACTAGCGGAG GCTAGAAGGA GAGAGATGGG TGCGAGAGCG TCAGTATTAA GCGGGGGAGA ATTAGATCGA TGGGAAAAAA TTCGGTTAAG GCCAGGGGGA
      TGATCGCCTC CGATCTTCCT CTCTCTACCC ACGCTCTCGC AGTCATAATT CGCCCCCTCT TAATCTAGCT ACCCTTTTTT AAGCCAATTC CGGTCCCCCT
 401  AAGAAAAAAT ATAAATTAAA ACATATAGTA TGGGCAAGCA GGGAGCTAGA ACGATTCGCA GTTAATCCTG GCCTGTTAGA AACATCAGAA GGCTGTAGAC
      TTCTTTTTTA TATTTAATTT TGTATATCAT ACCCGTTCGT CCCTCGATCT TGCTAAGCGT CAATTAGGAC CGGACAATCT TTGTAGTCTT CCGACATCTG
 501  AAATACTGGG ACAGCTACAA CCATCCCTTC AGACAGGATC AGAAGAACTT AGATCATTAT ATAATACAGT AGCAACCCTC TATTGTGTGC ATCAAAGGAT
      TTTATGACCC TGTCGATGTT GGTAGGGAAG TCTGTCCTAG TCTTCTTGAA TCTAGTAATA TATTATGTCA TCGTTGGGAG ATAACACACG TAGTTTCCTA
 601  AGAGATAAAA GACACCAAGG AAGCTTTAGA CAAGATAGAG GAAGAGCAAA ACAAAAAGTAA GAAAAAAGCA CAGCAAGCAG CAGCTGACAC AGGACACAGC
      TCTCTATTTT CTGTGGTTCC TTCGAAATCT GTTCTATCTC CTTCTCGTTT TGTTTTTCATT CTTTTTTCGT GTCGTTCGTC GTCGACTGTG TCCTGTGTCG
 701  AATCAGTCA GCCAAAATTA CCCTATAGTG CAGAACATCC AGGGGCAAAT GGTACATCAG GCCATATCAC CTAGAACTTT AAATGCATGG GTAAAAGTAG
      TTAGTCAGT CGGTTTTAAT GGGATATCAC GTCTTGTAGG TCCCCGTTTA CCATGTAGTC GGATCTTGTG GATCTTGAAA CATTTTCATC ACACAGTGGG
 801  TAGAAGAGAA GGCTTTCAGC CCAGAAGTGA TACCCATGTT TTCAGCATTA TCAGAAGGAG CCACCCCACA AGATTTAAAC ACCATGCTAA ACACAGTGGG
      ATCTTCTCTT CCGAAAGTCG GGTCTTCACT ATGGGTACAA AAGTCGTAAT AGTCTTCCTC GGTGGGGTGT TCTAAATTTG TGGTACGATT TGTGTCACCC
                                                                                                            RRE
 901  GGGACATCAA GCAGCCATGC AAATGTTAAA AGAGACCATC AATGAGGAAG CTGCAGGCAA AGAGAAGAGT GGTGCAGAGA GAAAAAAGAG CAGTGGGAAT
      CCCTGTAGTT CGTCGGTACG TTTACAATTT TCTCTGGTAG TTACTCCTTC GACGTCCGTT TCTCTTCTCA CCACGTCTCT CTTTTTTCTC GTCACCCTTA
                               RRE
1001  AGGAGCTTTG TTCCTTGGGT TCTTGGGAGC AGCAGGAAGC ACTATGGGCG CAGCGTCAAT GACGCTGACG GTACAGGCCA GACAATTATT GTCTGGTATA
      TCCTCGAAAC AAGGAACCCA AGAACCCTCG TCGTCCTTCG TGATACCCGC GTCGCAGTTA CTGCGACTGC CATGTCCGGT CTGTTAATAA CAGACCATAT
                               RRE
1101  GTGCAGCAGC AGAACAATTT GCTGAGGGCT ATTGAGGCGC AACAGCATCT GTTGCAACTC ACAGTCTGGG GCATCAAGCA GCTCCAGGCA AGAATCCTGG
      CACGTCGTCG TCTTGTTAAA CGACTCCCGA TAACTCCGCG TTGTCGTAGA CAACGTTGAG TGTCAGACCC CGTAGTTCGT CGAGGTCCGT TCTTAGGACC
                                                                                                    flap
1201  CTGTTGGAAAG ATACCTAAAG GATCAACAGC TCCTGGGGAT TTGGGGTTGC TCTGGAAAAC TCATTTGCAC CACTGCTGTG CCTTGGATCT ACAAATGGCA
      GACACCTTTC TATGGATTTC CTAGTTGTCG AGGACCCCTA AACCCCAACG AGACCTTTTG AGTAAACGTG GTGACGACAC GGAACCTAGA TGTTTACCGT
```

FIG. 5

```
                                                                                            flaP
1301  GTATTCATCC ACAATTTTAA AAGAAAAGGG GGGATPGGGG GGTACAGTGC AGGGGAAAGA ATAGTAGACA TAATAGCAAC AGACATACAA ACTAAAGAAT
      CATAAGTAGG TGTTAAAATT TTCTTTTCCC CCCTAACCCC CCATGTCACG TCCCCTTTCT TATCATCTGT ATTATCGTTG TCTGTATGTT TGATTCTTA
                                                          flaP
1401  TACAAAAACA AATTACAAAA ATTCAAAATT TTCGGGTTTA TTACAGGGAC AGCAGAGATC CAGTTTGGGG ATCAATTGCA TGAAGAATCT GCTTAGGGTT
      ATGTTTTTGT TTAATGTTTT TAAGTTTTAA AAGCCCAAAT AATGTCCCTG TCGTCTCTAG GTCAAACCCC GTCAAACCGT ACTTCTTAGA CGAATCCCAA
                                                                          EF1p
1501  AGGCGTTTTG CGCTGCTTCG CGAGGATCTG CGATCGCTCC GGTGCCCGTC AGTGGGCAGA GCGCACATCG CCCACAGTCC CCGAGAAGTT GGGGGAGGG
      TCCGCAAAAC GCGACGAAGC GCTCCTAGAC GCTAGCGAGG CCACGGGCAG TCACCCGTCT CGCGTGTAGC GGGTGTCAGG GGCTCTTCAA CCCCCTCTCC
                                                                 EF1p
1601  GTCGGCAATT GAACCGGTGC CTAGAGAAGG TGGCCGGGGG TAAACTGGGA AAGTGATGTC GTGTACTGGC TCCCGCCTTT TCCCGAGGGT GGGGAGAAC
      CAGCCGTTAA CTTGGCCACG GATCTCTTCC ACCGGCCCCC ATTTGACCCT TTCACTACAG CACATGACCG AGGCGGAAAA AGGGCTCCCA CCCCCTCTTG
                                                                     EF1p
1701  CGTATATAAG TGCAGTAGTC GCCGTGAACG TTCTTTTTCG CAACGGGTTT GCCGCCAGAA CACAGCTGAA GCTTCGAGGG GCTCGCATCT CTCCTTCACG
      GCATATATTC ACGTCATCAG CGGCACTTGC AAGAAAAAGC GTTGCCCAAA CGGCGGTCTT GTGTCGACTT CGAAGCTCCC CGAGCGTAGA GAGGAAGTGC
                                               EF1p
1801  CGCCCGCCGC CCTACCTGAG AGTCCGGTTG AGTCGGCGTT GCCGCCCTCC TGCCGCCTCC CGCTCGTGGT GCCTCCTGAA CTGCTTCCGC CGTCTAGTTA
      GCGGGCGGCG GGATGGACTC TCAGGCCAAC TCAGCCGCAA ACGGCGGAGG ACGGCGGAGG GCGAGCACCA CGGAGGACTT GACGAAGGCG GCAGATCCAT
                                                               EF1p
1901  AGTTTAAAGC TCAGGTCGAG ACCGGGCCTT TGTCCGGCGC AGTCCGGCGC TCCCCTTGGAG CCTACCTAGA CTCAGCCGGC TCTCCACGCT TTGCCTTGCC CTGCTTGCTC
      TCAAATTTCG AGTCCAGCTC TGGCCCGGAA ACAGGCCGCG TCGGCCGCG AGGGAACCTC GGATGGATCT GAGTCGGCCG AGAGGTGCGA AACGGACTGG GACGAACGAG
                                                                                                                      Ce7scFv
2001  AACTCTACGT CTTTGTTTCG TGCCCGTTA CAGATCCAAG CTGTGACCGG CGCCTACGG TAGCGCCGCC ACCATGCTGC TGCTGGTGAC
      TTGAGATGCA GAAACAAAGC ACGGCCCAAT GTCTAGGTTC GACACTGGCC GCGGATGCC ATCGCGGCGG TGGTACGACG ACGACCACTG
2101  CAGCCTGCTG CTGTGCGAGC TGCCCCACCC CGCCTTTCTG CTGATCCCCC AGTGTCAGCT GCAGCAGCCT GGCGCCGAGC TGGTGAAGCC AGGCGCCAGC
      GTCGGACGAC GACACGCTCG ACGGGGTGGG GCGGAAAGAC GACTAGGGGG TCACAGTCGA CGTCGTCGGA CCGCGGCTCG ACCACTTCGG TCCGCGGTCG
                                                        Ce7scFv
2201  GTGAAGCTGT CCTGCAAGGC CAGCGGCTAC ACCTTCACCG GCTACTGGAT GCACTGGGTG AAGCAGAGAC CCGGCCACGG CCTGGAATGG ATCGGCGAGA
      CACTTCGACA GGACGTTCCG GTCGCCGATG TGGAAGTGGC CGATGACCTA CGTGACCCAC TTCGTCTCTG GGCCGGTGCC GGACCTTACC TAGCCGCTCT
                                                           Ce7scFv
2301  TCAACCCCAG CAACGGCCGG ACCAACTACA ACGAGCAAG CCGGCGGTT CAAGAGCAAG GCCACCCTGA CCGTGGACAA GAGCAGCACC ACCGCCTTCA TGCAGCTGTC
      AGTTGGGGTC GTTGCCGGCC TGGTTGATGT TGCTCGTTC GTTCGCCAA GTTCTCGTTC CGGTGGGACT GGCACCCTGT CTCGCGTCGTGG TGGCGGAAGT ACGTCGACAG
                                                          Ce7scFv
2401  CGGCCTGACC AGCGAGGACA GCGCCGTGTA CTTCTGCGCC AGGGACTACT ACGGCACCAG CTACAACTTC GACTACTGGG GCCAGGGCAC CACACTGACC
```

FIG. 5 (Continued)

```
     GCCGGACTGG TGCCTCCTGT CGCGGCACAT GAAGACCGCG TCCCTGATGA TGCCGTGGTC GATGTTGAAG CTGATGACCC CGGTCCCGTG GTGTGACTGG
                                                               Ce7scFv
2501 GTGAGCAGCG GCGGAGGGGG CTCTGGCGGC GGAGGATCTG GGGGAGGGGG CAGCGACATC CAGATGACCC AGAGCAGCAG CAGCTTCAGC GTGAGCCTGG
     CACTCGTCGC CGCCTCCCCC GAGACCGCCG CCTCCTAGAC CCCCTCCCCC GTCGCTGTAG TCTACTGGG TCTCGTCGTC GTCGAAGTCG CACTCGGACC
                                                               Ce7scFv
2601 GCGACCGGGT GACCATCACC TGTAAGGCCA ACGAGGACAT CAACAACCGG CTGGCCTGGT ATCAGCAGAA CCCCGGCAAC AGCCCCAGGC TGCTGATCAG
     CGCTGGCCCA CTGGTAGTGG ACATTCCGGT TGCTCCTGTA GTTGTTGGCC GACCGGACCA TAGTCGTCTG GGGGCCGTTG TCGGGGTCCG ACGACTAGTC
                                                               Ce7scFv
2701 CGGCGCCACC AACCTGGTGA CCGGCGTGCC CAGCCGGTTT AGCGGCAGCG GCTCCGGCAA GGACTACACC CTGACCATCA CAAGCCTGCA GGCCGAGGAC
     GCCGCGGTGG TTGGACCACT GGCCGCACGG GTCGGCCAAA TCGCCGTCGC CGAGGCCGTT CCGAGGCCGT GACTGGTAGT GTTCGGACGT CCGGCTCCTG
                                                               Ce7scFv                                           IgG4 Hinge
2801 TTCGCCACCT ACTACTGCCA GCAGTACTGG TCCACCCCCT TCACCTTCGG AGCGGCACCC GAGCTGAAA TCAAAGAGAG CAAGTACGGA CCGCCCTGCC
     AAGCGGTGGA TGATGACGGT CGTCATGACC AGTGGGGGGA GTGGAAGCC TCGCCGTGGG CTCGACCTTT AGTTTCTCTC GTTCATGCCT GGCGGGACGG
           IgG4 Hinge                                                               IgG4 CH2
2901 CCCCTTGCCC TGCCCCCGAG TTCCTGGGCG GACCCAGCGT GTTCCTGTTC CCCCCCAAGC CCAAGGACAC CCTGATGATC AGCCGGACCC CCGAGGTGAC
     GGGGAACGGG ACGGGGGCTC AAGGACCCGC CTGGGTCGCA CAAGGACAAG GGGGGGTTCG GGTTCCTGTG GGACTACTAG TCGGCCTGGG GGCTCCACTG
                                                               IgG4 CH2
3001 CTGCGTGGTG GTGGACGTGA GCCAGGAAGA TCCCGAGGTC CAGTTCAATT GGTACGTGGA CGGCGTGGAA GTGCACAACG CCAAGACCAA GCCCAGAGAG
     GACGCACCAC CACCTGCACT CGGTCCTTCT AGGGCTCCAG GTCAAGTTAA CCATGCACCT GCCGCACCTT CACGTGTTGC GGTTCTGGTT CGGGTCTCTC
                                                               IgG4 CH2
3101 GAACAGTTCA ACAGCACCTA CCGGGTGGTG TCTGTGCTGA CCGTGCTGCA CCAGGACTGG CTGAACGGCA AAGAATACAA GTGCAAGGTG TCCAACAAGG
     CTTGTCAAGT TGTCGTGGAT GGCCCACCAC AGACACGACT GGCACGACGT GGTCCTGACC GACTTGCCGT TTCTTATGTT CACGTTCCAC AGGTTGTTCC
                                                               IgG4 CH3
3201 GCCTGCCCAG CAGCATCGAA AAGACCATCA GCAAGGCCAA GGGCCAGCCT CGCGAGCCCC AGGTGTACAC CCTGCCTCCC TCCCAGGAAG AGATGACCAA
     CGGACGGGTC GTCGTAGCTT TTCTGGTAGT CGTTCCGGTT CCCGGTCGGA GCGCTCGGGG TCCACATGTG GGACGGAGGG AGGGTCCTTC TCTACTGGTT
                                                               IgG4 CH3
3301 GAACCAGGTG TCCCTGACCT GCCTGGTGAA GGGCTTCTAC CCCAGCGACA TCGCCGTGGA GTGGGAGAGC CTGAGAACAA CTACAAGACC GATGTTCTGG
     CTTGGTCCAC AGGGACTGGA CGGACCACTT CCCGAAGATG GGGTCGCTGT AGCGGCACCT CACCCTCTCG GACTCTTGTT GATGTTCTGG
                                                               IgG4 CH3
3401 ACCCCTCCCG TGCTGGACAG CGACGGCAGC TTCTTCCTGT ACAGCCGGCT GACCGTGGAC AAGAGCCGGT GGCAGGAAGG CAACGTCTTT AGCTGCAGCG
     TGGGGAGGGC ACGACCTGTC GCTGCCGTCG AAGAAGGACA TGTCGGCCGA CTGGCACCTG TTCTCGGCCA CCGTCCTTCC GTTGCAGAAA TCGACGTCGC
```

FIG. 5 (Continued)

```
                                                              CD28tm
              IgG4 CH3                        ~~~~~~~~~~~~~~~~~~~~~~~~~~~~~~~~~~~~~~~~~~~~~~~~~~~~~~~~~~~~~~~~~
3501 TGATGCACGA ~GGCCCTGCAC ~AACCACTACA ~CCCAGAAGAG ~CCTGAGCCTG ~TCCCTGGGCA ~AGATGTTCTG ~GTGCTGGTG ~GTGCTGGGCG ~GGTGCTGGC
     ACTACGTGCT  CCGGGACGTG  TTGGTGATGT  GGGTCTTCTC  GGACTCGGAC  AGGGACCCGT  TCTACAAGAC  CCACGACCAC  CACCACCCGC  CCCACGACCG
                                    CD28tm                                           4-1BB
3601 ~CTGCTACAGC ~CTGCTGGTGA ~CAGTTGGCCTT ~CATCATCTTT ~TGGGTGAAAC ~GGGGCAGAAA ~GAAACTCCTG ~TATATATTCA ~AACAACCATT ~TATGAGACCA
      GACGATGTCG  GACGACCACT  GTCACCGGAA  GTAGTAGAAA  ACCCACTTTG  CCCCGTCTTT  CTTTGAGGAC  ATATATAAGT  TTGTTGGTAA  ATACTCTGGT
                                         4-1BB                                                                     Zeta
3701 ~GTACAAACTA ~CTTCAAGAGA ~AGATGGCTGT ~AGCTGCCGAT ~TTCCAGAAGA ~AGAAGAAGGA ~GGATGTGAAC ~TGCGGGTGAA ~GTTCAGCAGA ~AGCGCCGACG
      CATGTTTGAT  GAAGTTCTCT  TCTACCGACA  TCGACGGCTA  AAGGTCTTCT  TCTTCTTCCT  CCTACACTTG  ACGCCCACTT  CAAGTCGTCT  TCGCGGCTGC
                                                                                 Zeta
3801 ~CCCCTGCCTA ~CCAGCAGGGC ~CAGAATCAGC ~TGTACAACGA ~GCTGAACCTG ~GGCAGAAGGG ~AAGAGTACGA ~CGTCCTGGAT ~AAGCGGAGAG ~GCCGGGACCC
      GGGGACGGAT  GGTCGTCCCG  GTCTTAGTCG  ACATGTTGCT  CGACTTGGAC  CCGTCTTCCC  TTCTCATGCT  GCAGGACCTA  TTCGCCTCTC  CGGCCCTGGG
                                                                  Zeta
3901 ~TGAGATGGGC ~GGCAAGCCTC ~GGAGGCGGG ~CAAGGGGCGGG ~GACGGCCTGT ~ATCAGGGCCT ~GTCCACCGCC ~ACCAAGGATA ~CCTACGACGC ~CCTGCACATG ~CAGGCCCTGC
      ACTCTACCCG  CCGTTCGGAG  CCTCCGCCCC  GTTCCCCGCCC  CTGCCGGACA  TAGTCCCGGA  CAGGTGGCGG  TGGTTCCTAT  GGATGCTGCT  GGACGTGTAC
                    Zeta                                                                                                           
4001 ~AAGGGCGAGC ~GGAGGCGGG ~CAAGGGCCGG ~GACGGCCTGT ~ATCAGGGCCT ~GTCCACCGCC ~ACCAAGGATA ~CCTACGACGC ~CCTGCACATG ~CAGGCCCTGC
      TTCCCGCTCG  CCTCCGCCCC  GTTCCCGGCC  CTGCCGGACA  TAGTCCCGGA  CAGGTGGCGG  TGGTTCCTAT  GGATGCTGCT  GGACGTGTAC  GTCCGGGACG
       Zeta       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                      T2A                                                                        EGFRt
4101 ~CCCCAAGGCT ~CGAGGCGGC ~GGAGAGGGCA ~GGAGAAGTCT ~TCTAACATGC ~GGTGACGTGG ~AGGAGAATCC ~CGGCCCTAGG ~ATGCTTCTCC ~TGGTGACAAG
      GGGGTTCCGA  GCTCCGCCG  CCTCTCCCGT  CCTCTTCAGA  AGATTGTACG  CCACTGCACC  TCCTCTTAGG  GCCGGGATCC  TACGAAGAGG  ACCACTGTTC
                                                         EGFRt
4201 ~CCTTTCGCTC ~TGTGAGTTAC ~CACACCCAGC ~ATTCCTCCTG ~CACACCGGCA ~AAGTGTGTAA ~CGGAATAGGT ~GCCTTATCCA ~TTAAAGACTC ~ACTCTCCATA
      GGAAGACGAG  ACACTCAATG  GTGTGGGTCG  TAAGGAGGAC  GTGTGGCCGT  TTCACACATT  GCCTTATCCA  TAACCACTTA  AATTTCTGAG  TGAGAGGTAT
                                          EGFRt
4301 ~AATGCTACGA ~ATATTAAACA ~CTTCAAAAAC ~TGCACCTCCA ~TCAGTGGCGA ~TCTCCACATC ~CTGCCGGTGG ~CATTTAGGGG ~TGACTCCTTC ~ACACATACTC
      TTACGATGCT  TATAATTTGT  GAAGTTTTTG  ACGTGGAGGT  AGTCACCGCT  AGAGGTGTAG  GACGGCCACC  GTAAATCCCC  ACTGAGGAAG  TGTGTATGAG
                                          EGFRt
4401 ~CTTCCTCTGGA ~TCCACAGGAA ~CTGGATATTC ~TGAAATATTC ~AAAGGAAATC ~ACAGGGTTTT ~TGCTGATTCA ~GGCTTGGCCT ~GAAAACAGGA ~CGGACCTCCA
```

FIG. 5 (Continued)

```
      GAGGAGACCT AGGTGTCCTT GACCTATAAG ACTTTTGGCA TTTCCTTTAG TGTCCCAAAA ACGACTAAGT CCGAACCCGA CTTTTGTCCT GCCTGGAGT
4501  TGCCTTTGAG AACCTAGAAA TCATACGCGG CAGGACCAAG GTTTTCTCT AGTTTCTCT TGCAGTCGTC AGCCTGAACA TAACATCCTT GGGATTACGC
      ACGGAAACTC TTGGATCTTT AGTATGCGCC GTCCTGGTTC GTTGTACCAG TCAAAAGAGA ACGTCAGCAG TCGGACTTGT ATTGTAGGAA CCCTAATGCG
                                       EGFRt
4601  TCCCTCAAGG AGATAAGTGA TGGAGATGTG ATAATTTCAG GAAACAAAAA TTTGTGCTAT GCAAATACAA TAAACTGGAA AAAACTGTTT GGGACCTCCG
      AGGGAGTTCC TCTATTCACT ACCTCTACAC TATTAAAGTC CTTTGTTTTT AAACACGATA CGTTTATGTT ATTTGACCTT TTTTGACAAA CCCTGGAGGC
                                                             EGFRt
4701  GTCAGAAAAC CAAAATTATA AGCAACAGAG GTGAAAACAG CTGCAAGGCC ACAGGCCAGG TGTCCGGTCC AGACGGTACG TCTGCCATGC CTTGTGCTCC CCCGAGGGCT GCTGGGGCCC
      CAGTCTTTTG GTTTTAATAT TCGTTGTCTC CACTTTTGTC GACGTTCCGG TGTCCGGTCC TGCCATGGCC ACAGGCCAGG AGACGGTACG GAACAGGAGG GGGCTCCCGA CGACCCCGG
                                       EGFRt
4801  GGAGCCCAGG GACTGCGTCT CTTGCCGGAA TGTCAGCCGA GGCAGGGAAT GCGTGGACAA GTGCAACCTT CTGGAGGGTG AGCCAAGGGA GTTGTGGAG
      CCTCGGGTCC CTGACGCAGA GAACGGCCTT ACAGTCGGCT CCGTCCCTTA CGCACCTGTT CACGTTGGAA GACCTCCCAC TCGGTTCCCT CAACACCTC
                                       EGFRt
4901  AACTCTGAGT GCATACAGTG CCACCCAGAG TGCCTGCCTC AGGCCATGAA CATCACCTGC ACAGGACGGG GACCAGACAA CTGTATCCAG TGTGCCCACT
      TTGAGACTCA CGTATGTCAC GGTGGGTCTC ACGGACGGAG TCCGGTACTT GTAGTGGACG TGTCCTGCCC CTGGTCTGTT GACATAGGTC ACACGGGTGA
                                       EGFRt
5001  ACATTGACGG CCCCACTGC GTCAAGACCT GCCCGGCAGG AGTCATGGGA GAAAACAACA CCCTGGTCTG GAAGTACGCA GACGCCGGCC ATGTGTGCCA
      TGTAACTGCC GGGGTGACG CAGTTCTGGA CGGGCCGTCC TCAGTACCCT CTTTTGTTGT GGGACCAGAC CTTCATGCGT CTGCGGCCGG TACACACGGT
                                       EGFRt
5101  CCTGTGCCAT CCAAACTGCA CCTACGGATG CACTGGGCCA GGTCCTGAAG GCTGTCCAAC GAATGGGCCT AAGATCCCGT CCATCGCCAC TGGGATGGTG
      GGACACGGTA GGTTTGACGT GGATGCCTAC GTGACCCGGT CCAGGACTTC CGACAGGTTG CTTACCCGGA TTCTAGGGCA GGTAGCGGTG ACCTACCAC
                                       EGFRt                                                                WPRE
5201  GGGCCCTCC TCTTGCTGCT GGTGGTGGCC CTGGGGATCG GCCTCTTCAT GTGAGCGGCC CACTCGCCCG GAGAAGTA CACTCGCCCG GCCCGACGTC GAGATCTGG
      CCCCGGGAGG AGAACGACGA CCACCACCGG GACCCCTAGC CGGAGAAGTA CACTCGCCGG GCCTTCTTAT GTGAGCGGCC CGAGATCTGG CCCGGAGAATA
                                                                       WPRE
5301  CGATAATCAA CCCTCTGGAT ACAAAATTTG TGAAAGATTG ACTGGTATTC TTAACTATGT TGACCATAAG AATTGATACA ACGAGAAAAA TGCCATGCCT CTATGCGACG AAATTACGGA
      GCTATTAGTT GGAGACCTAA TGTTTTAAAC ACTTTCTAAC TGACCATAAG AATTGATACA ACTGGTATTT ACGCTATGTG TGCTCCTTTT GATACGCTGC TTTAATGCCT
                                                                       WPRE
5401  TTGTATCATG CTATTGCTTC CCGTATGGCT TTCATTTTCT CCTCCCTGTA TAAATCCTGG TTGCTGTCTC TTTATGAGGA GTTGTGGCCC GTTGTCAGGC
      AACATAGTAC GATAACGAAG GGCATACCGA AAGTAAAAGA GGAGGGACAT ATTTAGGACC AACGACAGAG AAATACTCCT CAACACGGG CAACAGTCCG
                                                                       WPRE
5501  AACGTGGCGT GGTGTGCACT GTGTTTGCTG ACGCAACCCC CACTGGTTGG GGCATTGCCA CCACCTGTCA GCTCCTTTCC GGGACTTTCG CTTTCCCCCT
      TTGCACCGCA CCACACGTGA CACAAACGAC TGCGTTGGGG GTGACCGGTT CCGTAACCGT GGTGGACAGT CGAGGAAAGG CCCTGAAAGC GAAAGGGGGA
```

```
8301  TCCTGTTACC AGTGGCTGCT GCCAGTGGCG ATAAGTCGTG TCTTACCGGG TTGGACTCAA GACGATAGTT ACCGGATAAG GCGCAGCGGT CGGGCTGAAC
      AGGACAATGG TCACCGACGA CGGTCACCGC TATTCAGCAC AGAATGGCCC AACCTGAGTT CTGCTATCAA TGGCCTATTC CCGCGTCGCCA GCCCGACTTG
                                 CoE1 ori
                      CoE1 ori 8401  GGGGGGTTCG TGCACACAGC CCAGCTTGGA GCGAACGACC TACACCGAAC TGAGATACCT ACAGCGTGAG CTATGAGAAA GCGCCACGCT TCCCGAAGGG
      CCCCCAAGC ACGTGTGTCG GGTCGAACCT CGCTTGCTGG ATGTGGCTTG ACTCTATGGA TGTCGCACTC GATACTCTTT CGCGGTGCGA AGGGCTTCCC
                                 CoE1 ori 8501  AGAAAGGCCG ACAGTATCC GGTAAGCGGC AGGGTCGGAA CAGGAGAGCG CACGAGGGAG CTTCCAGGGG GAAACGCCTG GTATCTTTAT AGTCCTGTCG
      TCTTTCCGGC TGTCCATAGG CCATTGCCCG TCCCAGCCTT GTCCTCTCGC GTGCTCCCTC GAAGGTCCCC CTTTGCGGAC CATAGAAATA TCAGGACAGC
                                 CoE1 ori 8601  GGTTTCGCCA CCTCTGACTT GAGCGTCGAT TTTTGTGATG CTCGTCAGGG GGGCGGAGCC TATGGAAAAA CGCCAGCAAC GCGGCCTTTT TACGGTTCCT
      CCAAAGCGGT GGAGACTGAA CTCGCAGCTA AAAACACTAC GAGCAGTCCC CCCGCCTCGG ATACCTTTTT GCGGTCGTTG CGCCGGAAAA ATGCCAAGGA
                                 CoE1 ori 8701  GGCCTTTTGC TGGCCTTTTG CTCACATGTT CTTTCCTGCG TTATCCCCTG GAAAGGACGC AATAGGCATAA TAACCGTATT ACCGCCTTTG AGTGAGCTGA TACCGCTCGC
      CCGGAAAACG ACCGGAAAAC GAGTGTACAA GAAAGGACGC AATAGGGGAC AATAAGCATAA ATTGGCATAA TGGCGGAAAC TCACTCGACT ATGGCGAGCG 8801  CGCAGCCGAA CGACCGAGCG CAGCGAGTCA GTGAGCGAGG AAGCGGAAGA GCGCCCAATA CGCAAACCGC CTCTCCCCGC GCGTTGGCCG ATTCATTAAT
      GCGTCGGCTT GCTGGCTCGC GTCGCTCAGT CACTCGCTCC TTCGCCTTCT CGCGGGTTAT GCGTTTGGCG GAGAGGGGCG CGCAACCGGC TAAGTAATTA 8901  GCAGCTGGCA CGACAGGTTT CCCGACTGGA AAGCGGGCAG TGAGCGCAAC GCAATTAATG TGAGTTAGCT CACTCATTAG GCACCCCAGG CTTTACACTT
      CGTCGACCGT GCTGTCCAAA GGGCTGACCT TTCGCCCGTC ACTCGCGTTG CGTTAATTAC ACTCAATCGA GTGAGTAATC CGTGGGGTCC GAAATGTGAA 9001  TATGCTTCCG GCTCGTATGT TGTGTGGAAT TGTGAGCGGA TAACAATTTC ACACAGGAAA CAGCTATGAC CATGATTACG CCAAGCTCGA AATTAACCCT
      ATACGAAGGC CGAGCATACA ACACACCTTA ACACTCGCCT ATTGTTAAAG TGTGTCCTTT GTCGATACTG GTACTAATGC GGTTCGAGCT TTAATTGGGA 9101  CACTAAAGGG AACAAAAGCT GGAGCTCCAC CGCGGTGGCG GCCGCTGGCG CCCTCGAGGT GCCATGGCGG TCGACCAGCA ACCATAGTCC CGCCCCCTAAC CCGGCCCATC
      GTGATTTCCC TTGTTTTTCGA CCTCGAGGTG GCGCCACCGC CGGACGCCCA GCTCTAGGCC AGCTGGTCGT TGGTATCAGG GCGGGGATTG AGGCGGGTAG
                                 SV40

9201  CCGCCCCTAA CTCCGCCCAG TTCCGCCCAT TCTCCGCCCC ATGGCTGACT AATTTTTTTT ATTTATGCAG AGGCCGAGGC CGCCTCGGCC TCTGAGCTAT
      GGCGGGGATT GAGGCGGGTC AAGGCGGGTA AGAGGCGGGG TACCGACTGA TTAAAAAAAA TAAATACGTC TCCGGCTCCG GCGGAGCCGG AGACTCGATA
                      SV40                                                                                  CMV

9301  TCCAGAAGTA GTGAGGAGGC TTTTTGGAG GCCTAGGCTT TTGCAAAAAG CTTCGACGGT ATCGATTGGC TCATGTCCAA CATTACCGCC ATGTTGACAT
      AGGTCTTCAT CACTCCTCCG AAAAACCTC CGGATCCGAA AACGTTTTTC GAAGCTGCCA TAGCTAACCG AGTACAGGTT GTAATGGCGG TACAACTGTA
                                                                                                       CMV

9401  TGATTATTGA CTAGTTATTA ATAGTAATCA ATTACGGGGT CATTAGTTCA TAGCCCATAT ATGGAGTTCC GCGTTACATA ACTTACGGTA AATGGCCCGC
      ACTAATAACT GATCAATAAT TATCATTAGT TAATGCCCCA GTAATCAAGT ATCGGGTATA TACCTCAAGG CGCAATGTAT TGAATGCCAT TTACCGGGCG
      CMV

9501  CTGGCTGACC CCCCAACGAC CCCCGCCCAT TGACGTCAAT AATGACGTAT GTTCCCATAG TAACGCCAAT AGGGACTTTC CATTGACGTC AATGGGTGGA
```

FIG. 5 (Continued)

```
      GACCGACTGG CGGGTTGCTG GGGGCGGGTA ACTGCAGTTA TTACTGCATA CAAGGGTATC ATTGCGGTTA TCCCTGAAAG GTAACTGCAG TTACCCACCT
                                                              CMV
 9601 GTATTTACGG TAAACTGCCC ACTTGGCAGT ACATCAAGTG TATCATATGC CAAGTACGCC CCCTATTGAC GTCAATGACG GTAAATGGCC CGCCTGGCAT
                                                              CMV
      CATAAATGCC ATTTGACGGG TGAACCGTCA TGTAGTTCAC ATAGTATACG GTTCATGCGC CAGTTACTGC CATTTACCGG GCGGACCGTA
 9701 TATGCCCAGT ACATGACCTT ATGGGACTTT CCTACTTGGC AGTACATCTA CGTATTAGTC ATCGCTATTA CCATGGTGAT GCGGTTTTGG CAGTACATCA
                                                              CMV
      ATACGGGTCA TGTACTGGAA TACCCTGAAA GGATGAACCG TCATGTAGAT GCATAATCAG TAGCGATAAT GGTACCACTA CGCCAAAACC GTCATGTAGT
 9801 ATGGGCGTGG ATAGCGGTTT GACTCACGGG TCTCCACCCC ATTTGGCCAC ATGGGAGTTT GTTTTGGCAC CAAAATCAAC GGGACTTTCC CCTGAAAGG
      TACCCGCACC TATCGCCAAA CTGAGTGCCC CTAAAGGTTC AGAGGTGGGG TAACTGCAGT TACCCTCAAA CAAAACCGTG GTTTTAGTTG CCCTGAAAGG
                                                              CMV
 9901 AAAATGTCGT AACAACTCCG CCCCATTGAC GCAAATGGGC GGTAGGCGTG TACGGAATTC GGAGTGGCGA GCCCTCAGAT CCTGCATATA AGCAGCTGCT
      TTTTACAGCA TTGTTGAGGC GGGGTAACTG CGTTTACCCG CCATCCGCAC CCTCACCGCT CGGGAGTCTA GGACGTATAT TCGTCGACGA
10001 TTTTGCCTGT ACTGGGTCTC TCTG
      AAAACGGACA TGACCCAGAG AGAC
```

FIG. 5 (Continued)

```
   1  GTTAGACCAG ATCTGAGCCT GGGAGCTCTC TGGCTAACTA GGGAACCCAC TGCTTAAGCC TTGCCTTGAG TGCTTCAAGT AGTGTGTGCC
      CAATCTGGTC TAGACTCGGA CCCTCGAGAG ACCGATTGAT CCCTTGGGTG ACGAATTCGG AACGGAACTC ACGAAGTTCA TCACACACGG
 101  CGTCTGTTGT GTGACTCTGG TAACTAGAGA TCCCTCAGAC CCTTTTAGTC AGTGTGGAAA ATCTCTAGCA GTGGCGCCCG AACAGGGACT
      GCAGACAACA CACTGAGACC ATTGATCTCT AGGGAGTCTG GGAAAATCAG TCACACCTTT TAGAGATCGT CACCGCGGGC TTGTCCCTGA ACTTTCGTT
 201  AGGGAAACCA GAGGAGCTCT CTCGACGCAG GACTCGGCTT GCTGAAGCGC GCACGGCAAG AGGCGAGGGG CGGCGACTGG TGAGTACGCC AAAAATTTTG
      TCCCTTTGGT CTCCTCGAGA GAGCTGCGTC CTGAGCCGAA CGACTTCGCG CGTGCCGTTC TCCGCTCCCC GCCGCTGACC ACTCATGCGG TTTTTAAAAC
 301  ACTAGCGGAG GCTAGAAGGA GAGAGATGGG TGCGAGAGCG TCAGTATTAA GCGGGGGAGA ATTAGATCGA TGGGAAAAAA TTCGGTTAAG GCCAGGGGGA
      TGATCGCCTC CGATCTTCCT CTCTCTACCC ACGCTCTCGC AGTCATAATT CGCCCCCTCT TAATCTAGCT ACCCTTTTTT AAGCCAATTC CGGTCCCCCT
 401  AAGAAAAAAT ATAAATTAAA ACATATAGTA TGGGCAAGCA GGGAGCTAGA ACGATTCGCA GTTAATCCTG GCCTGTTAGA AACATCAGAA GGCTGTAGAC
      TTCTTTTTTA TATTTAATTT TGTATATCAT ACCCGTTCGT CCCTCGATCT TGCTAAGCGT CAATTAGGAC CGGACAATCT TTGTAGTCTT CCGACATCTG
 501  AAATACTGGG ACAGCTACAA CCATCCCTTC AGACAGGATC AGAAGAACTT AGATCATTAT ATAATACAGT AGCAACCCTC TATTGTGTGC ATCAAAGGAT
      TTTATGACCC TGTCGATGTT GGTAGGGAAG TCTGTCCTAG TCTTCTTGAA TCTAGTAATA TATTATGTCA TCGTTGGGAG ATAACACACG TAGTTTCCTA
 601  AGAGATAAAA GACACCAAGG AAGCTTTAGA CAAGATAGAG GAAGAGCAAA ACAAAAGTAA GAAAAAAGCA CAGCAAGCAG CAGCTGACAC AGGACACAGC
      TCTCTATTTT CTGTGGTTCC TTCGAAATCT GTTCTATCTC CTTCTCGTTT TGTTTTCATT CTTTTTCGT GTCGTTCGTC GTCGACTGTG TCCTGTGTCG
 701  AATCAGGTCA GCCAAAATTA CCCTATAGTG CAGAACATCC AGGGGCAAAT GGTACATCAG GCCATATCAC CTAGAACTTT AAATGCATGG GTAAAAGTAG
      TTAGTCCAGT CGGTTTTAAT GGGATATCAC GTCTTGTAGG TCCCCGTTTA CCATGTAGTC CGGTATAGTG GATCTTGAAA TTTACGTACC CATTTTCATC
 801  TAGAAGAGAA GGCTTTCAGC CCAGAAGTGA TACCCATGTT TTCAGCATTA TCAGAAGGAG CCACCCCACA AGATTTAAAC ACCATGCTAA ACACAGTGGG
      ATCTTCTCTT CCGAAAGTCG GGTCTTCACT ATGGGTACAA AAGTCGTAAT AGTCTTCCTC GGTGGGGTGT TCTAAATTTG TGGTACGATT TGTGTCACCC
 901  GGGACATCAA GCAGCCATGC AAATGTTAAA AGAGACCATC AATGAGGAAG CTGCAGGCAA AGAGAAGAGT GGTGCAGAGA GAAAAAGAG CAGTGGGAAT
      CCCTGTAGTT CGTCGGTACG TTTACAATTT TCTCTGGTAG TTACTCCTTC GACGTCCGTT TCTCTTCTCA CCACGTCTCT CTTTTTTCTC GTCACCCTTA
1001  AGGAGCTTTG TTCCTTGGGT TCTTGGGAGC AGCAGGAAGC ACTATGGGCG CAGCGTCAAT GACGCTGACG GTACAGGCCA GACAATTATT GTCTGGTATA
      TCCTCGAAAC AAGGAACCCA AGAACCCTCG TCGTCCTTCG TGATACCCGC GTCGCAGTTA CTGCGACTGC CATGTCCGGT CTGTTAATAA CAGACCATAT
1101  GTGCAACAGC AGAACAATTT GCTGAGGGCT ATTGAGGCGC AACAGCATCT GTTGCAACTC ACAGTCTGGG GCATCAAGCA GCTCCAGGCA AGAATCCTGG
      CACGTTGTCG TCTTGTTAAA CGACTCCCGA TAACTCCGCG TTGTCGTAGA CAACGTTGAG TGTCAGACCC CGTAGTTCGT CGAGGTCCGT TCTTAGGACC
1201  CTGTGGAAAG ATACCTAAAG GATCAACAGC TCCTGGGGAT TTGGGGTTGC TCTGGAAAAC TCATTTGCAC CACTGCTGTG CCTTGGAATC ACAAATGGCA
      GACACCTTTC TATGGATTTC CTAGTTGTCG AGGACCCCTA AACCCCAACG AGACCTTTTG AGTAAACGTG GTGACGACAC GGAACCTTAG TGTTTACCGT
```

FIG. 7

```
1301  GTATTCATCC  ACAATTTTAA  AAGAAAAGGG  GGGATTGGGG  GGTACAGTGC  AGGGAAAGA   ATAGTAGACA  TAATAGCAAC  AGACATACAA  ACTAAAGAAT
      CATAAGTAGG  TGTTAAAATT  TTCTTTTCCC  CCCTAACCCC  CCATGTCACG  TCCCTTTCT   TATCATCTGT  ATTATCGTTG  TCTGTATGTT  TGATTTCTTA
                                          flap 1401  TACAAAAACA  AATTACAAAA  ATTCAAAATT  TTCGGGTTTA  TTACAGGGAC  AGCAGAGATC  CAGTTTGGGG  ATCAATTGCA  TGAAGAATCT  GCTTAGGGTT
      ATGTTTTTGT  TTAATGTTTT  TAAGTTTTAA  AAGCCCAAAT  AATGTCCCTG  TCGTCTCTAG  GTCAAACCCC  TAGTTAACGT  ACTTCTTAGA  CGAATCCCAA
                                                                             EF1p 1501  AGGCGTTTTG  CGCTGCTTCG  CGAGGATCTG  CCATCGCTCC  GGTCCCCGTC  AGTGGGCAGA  GCGCACATCG  CCCACAGTCC  CCGAGAAGTT  GGGGGGAGGG
      TCCGCAAAAC  GCGACGAAGC  GCTCCTAGAC  GGTAGCGAGG  CCAGGGGCAG  TCACCCGTCT  CGCGTGTAGC  GGGTGTCAGG  GGCTCTTCAA  CCCCCCTCCC
                                                                             EF1p 1601  GTCGGCAATT  GAACCGGTGC  CTAGAGAAGG  TGGGCGCGGG  TAAACTGGGA  AAGTGATGTC  TTCACTCACAG  CACAGCTGGC  TCCCGAGGGT  GGGGAGAAC
      CAGCCGTTAA  CTTGGCCACG  GATCTCTTCC  ACCCGCGCCC  ATTTGACCCT  TTCACTACAG  AAGTGAGTGTC  GTGTCGACCG  AGGGCTCCCA  CCCCCTCTTG
                                                                             EF1p 1701  CGTATATAAG  TGCAGTAGTC  GCCGTGAACG  TTCTTTTTCG  CAACGGGTTT  GCCGCCAGAA  CACAGCTGAA  GCTTCGAGGG  GCTCGCATCT  CTCCTTCACG
      GCATATATTC  ACGTCATCAG  CGGCACTTGC  AAGAAAAAGC  GTTGCCCAAA  CGGCGGTCTT  GTGTCGACTT  CGAAGCTCCC  CGAGCGTAGA  GAGGAAGTGC
                                                                             EF1p 1801  CGGCCCGCGC  CCTACCTGAG  GCCGCCATCC  ACGCCGGTTG  AGTCGCGTTC  TGCCGCCTCC  TGCCTGTGGT  GCCTCCTGAA  CTGCGTCCGC  CGTCTAGTTA
      GCCGGGCGCG  GGATGGACTC  CGGGCGGTAGG  TGCGGCCAAC  TCAGCGCAAG  ACGGCGGAGG  ACGGACACCA  CGGAGGACTT  GACGCAGGCG  GCAGATCCAT
                                                                             EF1p 1901  AGTTTAAAGC  TCAAGTTCGAG  ACCGGGCCTT  TGTCCGCGCC  TCCCTTGGAG  CCTACCTAGA  CTCAGCCGGC  TTCTCCACGCT  TTGCCTTGCTC  CTGCTTGCTC
      TCAAATTTCG  AGTCCAGCTC  TGGCCCGGAA  ACAGGCCGCG  AGGGAACCTC  GGATGGATCT  GAGTCGGCCG  AGAGGTGCGA  AACGGACTGG  GACGAACGAG
                                                                                                     CE7R scFv 2001  AACTCTACGT  CTTTGTTTCG  TTTTCTGTTC  TGGCGCCTTA  CAGATCCAAG  CTGTGACCGG  CGCCTACGGC  TAGCGCCGCC  ACCATGCTGC  TGCTGGTGAC
      TTGAGATGCA  GAAACAAAGC  AAAAGACAAG  ACCGCGGAAT  GTCTAGGTTC  GACACTGGCC  GCGGATGCCG  ATCGCGGCGG  TGGTACGACG  ACGACCACTG
                                                                                                     CE7R scFv 2101  CAGCCTGCTG  CTGTGCGAGC  TGCCCCACCC  CGCCTTTCTG  CTGATCCCCC  AGGTGCAGCT  GCAGCAGCCT  GGCGCCGAGC  TGGTGAAGCC  AGGCGCCAGC
      GTCGGACGAC  GACACGCTCG  ACGGGGTGGG  GCGGAAAGAC  GACTAGGGGG  TCCACGTCGA  CGTCGTCGGA  CCGCGGCTCG  ACCACTTCGG  TCCGCGGTCG
                                                                                                     CE7R scFv 2201  GTGAAGCTGT  CCTGCAAGGC  CAGCGGCTAC  ACCTTCACCG  GCTACTGGAT  GCACTGGGTG  AAGCAGAGAC  CCGGCCACGG  CCTGGAATGG  ATCGGCAGA
      CACTTCGACA  GGACGTTCCG  GTCGCCGATG  TGGAAGTGGC  CGATGACCTA  CGTGACCCAC  TTCGTCTCTG  GGCCGGTGCC  GGACCTTACC  TAGCCGCTCT
                                                                                                     CE7R scFv 2301  TCAACCCCAG  CAACGGCCGG  ACCAACTACA  ACGAGCGGTT  CAAGAGCAAG  GCCACCCTGA  CCGTGGACAA  GAGCAGCAGC  ACCGCCTTCA  TGCAGCTGTC
      AGTTGGGGTC  GTTGCCGGCC  TGGTTGATGT  TGCTCGCCAA  GTTCTCGTTC  CGGTGGGACT  GGCACCTGTT  CTCGTCGTCG  TGGCGGAAGT  ACGTCGACAG
                                                                                                     CE7R scFv 2401  CGGCCTGACC  AGCGAGGACA  GCGCCGTGTA  CTTCTGCGCC  AGGGACTACT  ACGGCACCAG  CTACAACTTC  GACTACTGGG  GCCAGGGCAC  CACACTGACC
      GCCGGACTGG  TCGCTCCTGT  CGCGGCACAT  GAAGACGCGG  TCCCTGATGA  TGCCGTGGTC  GATGTTGAAG  CTGATGACCC  CGGTCCCGTG  GTGTGACTGG
                                                                                                     CE7R scFv
```

FIG. 7 (Continued)

```
2501 GTGAGCAGCG GCGGAGGGGG CTCTGGCGGC GGGGAGGGGG CAGCGACATC CAGATGACCC AGAGCAGCAG CAGCTTCAGC GTGAGCCTGG
     CACTCGTCGC CGCCTCCCCC GAGACCGCCG CCCCTCCCCC GTCGCTGTAG GTCGCTGGGG TCTCGTCGTC GTCGAAGTCG CACTCGGACC
                                                            CE7R scFv

2601 GCGACCGGGT GACCATCACC TGTAAGGCCA ACGAGGACAT CAACAACCGG CTGGCCTGGT ATCAGCAGAC CCCCGGCAAC AGCCCCAGGC TGCTGATCAG
     CGCTGGCCCA CTGGTAGTGG ACATTCCGGT TGCTCCTGTA GTTGTTGGCC GACCGGACCA TAGTCGTCTG GGGGCCGTTG TCGGGGTCCG ACGACTAGTC
                                                            CE7R scFv

2701 CGGCGCCACC AACCTGGTGA CCGGCGTGCC CAGCCGGTTT AGCGGCAGCG GCTCCGGCAA GGACTACACC CTGACCATCA GCAGCCTGCA GGCCGAGGAC
     GCCGCGGTGG TTGGACCACT GGCCGCACGG GTCGGCCAAA TCGCCGTCGC CGAGGCCGTT CCTGATGTGG GACTGGTAGT GTCGGACGT CCGGCTCCTG
                                                            CE7R scFv

2801 TTCGCCACCT ACTACTGCCA GCAGTACTGG TCCACCCCCT TCACCTTCGG CAGCGGCACC GAGCTGGAAA TCAAAGAATC TAAGTACGGA CCGCCCTGCC
     AAGCGGTGGA TGATGACGGT CGTCATGACC AGGTGGGGGA AGTGGAAGCC GTCGCCGTGG CTCGACCTTT AGTTTCTTAG ATTCATGCCT GGCGGGACGG
     IgG4 Hinge                                             IgG4 CH3

2901 CCCCTTGCCC TGGCCAGCCT AGAGAACCCC AGGTGTACAC CCTGCCCCCC AGCCAGGAAG AGATGACCAA GAACCAGGTG TCCCTGACCT GCCTGGTCAA
     GGGGAACGGG ACCGGTCGGA TCTCTTGGGG TCCACATGTG GGACGGAGGG TCGGTCCTTC TCTACTGGTT CTTGGTCCAC AGGGACTGGA CGGACCAGTT
                                                            IgG4 CH3

3001 AGGCTTCTAC CCCAGCGATA TCGCCGTGGA ATGGGAGAGC AACGGCCAGC CCGAGAACAA CTACAAGACC ACCCCCCCTG TGCTGGACAG CGACGGCAGC
     TCCGAAGATG GGGTCGCTAT AGCGGCACCT TACCCTCCTG TTGCCGGTCG GGCTCTTGTT GATGTTCTGG TGGGGGGGAC ACGACCTGTC GCTGCCGTCG
                                                            IgG4 CH3

3101 TTCTTCCTGT ACTCCCGGCT GACCGTGGAC AAGAGCCGGT GGCAGGAAGG CAACGTCTTC AGCTGCAGCG TGATGCACGA GGCCCTGCAC AACCACTACA
     AAGAAGGACA TGAGGGCCGA CTGGCACCTG TTCTCGGCCA CCGTCCTTCC GTTGCAGAAG TCGACGTCGC ACTACGTGCT CCGGGACGTG TTGGTGATGT
                                                            CD28tm

3201 CCCAGAAGTC CCTGAGCCTG AGCCTGGGCA AGATGTTCTG GGTGCTGGTG GTGGTCGGTG GCTGCTGGCC CTGCTACAGC CTGCTGGTCA CCCTGGCCTT
     GGGTCTTCAG GGACTCGGAC TCGGACCCGT TCTACAAGAC CCACGACCAC CACCAGCCTC CGACGACCGG GACGATGTCG GACGACCAGT GGGACCGGAA
                CD28tm                                      4-1BB

3301 CATCATCTTT TGGGTGAAAC GGGGCAGAAA GAAACTCCTG TATATATTCA AACAACCATT TATGAGACCA GTACAAACTA CTCAAGAGGA AGATGGCTGT
     GTAGTAGAAA ACCCACTTTG CCCCGTCTTT CTTTGAGGAC ATATATAAGT TTGTTGGTAA ATACTCTGGT CATGTTTGAT GAGTTCTCCT TCTACCGACA
     4-1BB                                                  Zeta
```

FIG. 7 (Continued)

```
3401  AGCTGCCGAT TTCCAGAAGA AGAAGAAGGA GGATGTGAAC TGCCGGGTGAA GTTCAGCAGA AGCGCCAACG CCCCTGCCTA AGCGCCAACG CAGAATCAGC
      TCGACGGCTA AAGGTCTTCT TCTTCTTCCT CCTACACTTG ACGCCCACTT CAAGTCGTCT TCGCGGCTGC GGGGACGGAT GGTCGTCCCG GTCTTAGTCG
                                                     Zeta
3501  TGTACAACGA GCTGAACCTG GGCAGAAGGG AAGAGTACGA CGTCCTGGAT AAGCGGACCC GCCGGGACCC TGAGATGGGC GGCAAGCCTC GGCGGAAGAA
      ACATGTTGCT CGACTTGGAC CCGTCTTCCC TTCTCATGCT GCAGGACCTA TTCGCCTCTC CGGCCCTGGG ACTCTACCCG ACTCTACCCG CCGGCTTCTT
                                                     Zeta
3601  CCCCCAGGAA GGCCTGTATA ACGAACTGCA GAAAGACAAG ATGGCCGAGG CCTACAGCGA GATCGGCATG AAGGGCGAGC GGAGGCGGGG CAAGGGCCAC
      GGGGGTCCTT CCGGACATAT TGCTTGACGT CTTTCTGTTC TACCGGCTCC GGATGTCGCT CTAGCCGTAC TTCCCGCTCG CCTCCGCCCC GTTCCCGGTG
                                       Zeta                                                       T2A
3701  GACGGCCTGT ATCAGGGCCT GTCCACGCGC ACCAAGGATA CCCTGTACAG CAGGCTGAGC CCTGCACATG CCCCAAGGCT CGAGGGCGGC GGAGAGGGCA
      CTGCCGGACA TAGTCCCGGA CAGGTGCGCG TGGTTCCTAT GGGACATGTC GTCCGACTCG GGACGTGTAC GGGGTTCCGA GCTCCCGCCG CCTCTCCCGT
                                                                                                 EGFRt
3801  GAGGAAGTCT TCTAACATGC GGTGACGTGG AGGAGAATCC CGGCCCTAGG ATGCTTCTCC TGGTGACAAG CCTTCTGCTC TGTGAGTTAC CACACCCAGC
      CTCCTTCAGA AGATTGTACG CCACTGCACC TCCTCTTAGG GCCGGGATCC TACGAAGACC ACCACTGTTC GGAAGACGAG ACACTCAATG GTGTGGGTCG
                                                        EGFRt
3901  ATTCCTCCTG ATCCCACGCA AAGTGTGTAA CGGAATAGGT ATTGGTGAAT TTAAAGACTC ACTCTCCATA AATGCTACGA ATATTAAACA CTTCAAAAAC
      TAAGGAGGAC TAGGGTGCGT TTCACACATT GCCTTATCCA TAACCACTTA AATTTCTGAG TGAGAGGTAT TTACGATGCT TATAATTTGT GAAGTTTTTG
                                                        EGFRt
4001  TGCACCTCCA TCAGTGGCGA TCTCCACATC CTGCCGGTGG CATTTAGGGG TGACTCCTTC ACACACTACT CTCCCTTTGA TCCACAGGAA CTGGATATTC
      ACGTGGAGGT AGTCACCGCT AGAGGTGTAG GACGGCCACC GTAAATCCCC ACTGAGGAAG TGTGTATGAT GAGGGAAACT AGGTGTCCTT GACCTATAAG
                                                        EGFRt
4101  TGAAAACCGT AAAGGAAATC ACAGGGTTTT TGCTGATTCA GGCTTGGCCT GAAAACAGGA CGGACCTCCA TGCCTTTGAG AACCTAGAAA TCATACGCGG
      ACTTTTGGCA TTTCCTTTAG TGTCCCAAAA ACGACTAAGT CCGAACCGGA CTTTTGTCCT GCCTGGAGGT ACGGAAACTC TTGGATCTTT AGTATGCGCC
                                                        EGFRt
4201  CAGGACCAAG CAACATGGTC AGTTTTCTCT TGCAGTCGTC AGCCTGAACA TAACATCCTT GGGATTACGC TCCCTCAAGG AGATAAGTGA TGGAGATGTG
      GTCCTGGTTC GTTGTACCAG TCAAAAGAGA ACGTCAGCAG TCGGACTTGT ATTGTAGGAA CCCTAATGCG AGGGAGTTCC TCTATTCACT ACCTCTACAC
                                                        EGFRt
4301  ATAATTTCAG GAAACAAAAA TTTGTGCTAT GCAAATACAA TAAACTGGAA AAAACTGTTT GGGACCTCCG GTCAGAAAAC CAAAATTATA AGCAACAGAG
      TATTAAAGTC CTTTGTTTTT AAACACGATA CGTTTATGTT ATTTGACAAT TTTTGACAAA CCCTGGAGGC CAGTCTTTTG GTTTTAATAT TCGTTGTCTC
                                                        EGFRt
4401  GTGAAAACAG CTGCAAGGCC ACAGGCCAGG TCTGTGCTCC CTTGTGCTGC CCCGAGGGCT GCTGGGGCCC GGAGCCCAGG GACTGCGTCT CTTGCCGGAA
      CACTTTTGTC GACGTTCCGG TGTCCGGTCC AGACACGAGG GAACACGACG GGGCTCCCGA CGACCCCGGG CCTCGGGTCC CTGACGCAGA GAACGGCCTT
                                                        EGFRt
```

FIG. 7 (Continued)

```
4501  TGTCAGCCGA GGCAGGGAAT GGCTGGACAA GTGCAACCTT CTGGGAGGTG AGCCAAGGGA GTTTGTGGAG AACTCTGAGT GCATACAGTG CCACCCAGAG
      ACAGTCGGCT CCGTCCCTTA CGGACCTGTT CACGTTGGAA GACCCTCCAC TCGGTTCCCT CAAACACCTC TTGAGACTCA CGTATGTCAC GGTGGGTCTC
                                                             EGFRt
4601  TGCCTGCCTC AGGCCATGAA CATCACCTGC ACAGGACGGG GACCAGAGAA CTGGTCTGC GACATAGGTC TGTGCCCACT ACATTGACGG CCCCCACTGC GTCAAGACCT
      ACGGACGGAG TCCGGTACTT GTAGTGGACG TGTCCTGCCC CTGGTCTCTT GACCAGACG CTGTATCCAG ACACGGGTGA TGTAACTGCC GGGGGTGACG CAGTTCTGGA
                                                        EGFRt
4701  GCCCGGCAGG AGTCATGGGA GAAAACAACA CCCTGGTCTG GAAGTACGCA GACGCCCGCC AGTGTGCCA CCTCTGCCAT CCAAACTGCA CCTACGGATG
      CGGGCCGTCC TCAGTACCCT CTTTTGTTGT GGGACCAGAC CTTCATGCGT CTGCGGGCGG TCACACGGT TACACACGGT GGTTTGACGT GGATGCCTAC
                                                        EGFRt
4801  CACTGGGCCA GGTCTTGAAG CTGTCCAAC AAGATCCCGT CCATCGCCAC TGGGATGGTG GGGCCCCTCC TCTTGCTGCT GGTGGTGGCC
      GTGACCCGGT CCAGAACTTC CGACAGGTTG CTTACCGGGA GGTAGCGGTG ACCCTACCAC CCCGGGAGG AGAACGACGA CCACCACCGG
                                                                                                    WPRE
4901  CTGGGGATCG GCCTCTTCAT GTGAGCGGCC CGGGCTAGACC GAATTCGATA TCAAGCTTAT AGTTCGAATA CCCTCTGATT ACAAAATTTG
      GACCCCTAGC CGGAGAAGTA CACTCGCCGG GCCGATCTGG GCCCGATCTG CTTAAGCTAT AGTTCGAATA CCCTCTGATT ACAAAATTTG
                                                             WPRE
5001  TGAAAGATTG ACTGGTATTC TTAACTATGT TGCTCCTTTT ACGCTATGTG GATATGCTGC TTTAATGCCT TTGTATCATG CCGTATGGCT
      ACTTTCTAAC TGACCATAAG AATTGATACA ACGAGGAAAA TGCGATACAC CTATATGACG AAATTACGGA GATAACGAAG GGCATACCGA
                                                             WPRE
5101  TTCATTTTCT CCTCCTTGTA TAAATCCTGG TTGCTGTCTC TTTATGAGGA GTTGTGGCCC GTTGTCAGGC AACGTGGCGT GGTGTGCACT GTGTTTGCTG
      AAGTAAAAGA GGAGGAACAT ATTTAGGACC AACGACAGAG AAATACTCCT CAACACCGGG CAACAGTCCG TTGCACCGCA CCACACGTGA CACAAACGAC
                                                             WPRE
5201  ACGCAACCCC CACTGGTTGG GGCATTGCCA CCACCTGTCA GCTCCTTTCC GGGACTTTCG CTTTCCCCCT CCCTATTGCC ACGGCGGAAC TCATCGCCGC
      TGCGTTGGGG GTGACCAACC CCGTAACGGT GGTGGACAGT CGAGGAAAGG CCCTGAAAGC GAAAGGGGGA GGGATAACGG TGCCGCCTTG AGTAGCGGCG
                                                             WPRE
5301  CTGCCTTGCC CGCTGCTGGA CAGGGGCTCG GCTGTTGGGC ACTGACAATT CCGTGGTGTT GTCGGGGAAA TCATCGTCCT TTCCTTGGCT GCTCGCCTGT
      GACGGAACGG GCGACGACCT GTCCCCGAGC CGACAACCCG TGACTGTTAA GGCACCACAA CAGCCCCTTT AGTAGCAGGA AAGGAACCGA CGAGCGGACA
                                                             WPRE
5401  GTTGCCACCT GGATTCTGCG CGGGACGTCC TCCCTTGGC CCTCAATCCA GCGGACCTTC CTTCCCGCGG CCTGCTGCCG GCTCTGCGGC
      CAACGGTGGA CCTAAGACGC GCCCTGCAGG AAGACGATGC GGGAGTTAGGT CGCCTGGAAG GAAGGGCGCC GGACGACGGC CGAGACGCCG
                                                                                                   del U3
5501  CTCTTCCGCG TCTTTCGGCT TGGATTCTGCG CGGGACGTCC TCCCTTGGC CCTCAATCCA GCGGACCTTC CTTCCCGCGG CCTGCTGCCG GCTCTGCGGC
      GAGAAGGCGC AGAAGCCGAA GCGGGAGTCT GCTCAGGAGG GCGGGAGTCT CTCCTTCCC GAGGGAAACC CGGGAGGCTA GGGAAGGCGC CGAAGACGCC
                     del U3
```

| | | | | | | | |
|---|---|---|---|---|---|---|---|
| 7201 | CACTATTGTG | ACGCCGGTTG | AATGAAGACT | GTTGCTAGCC | TCCTGGCTTC | CTCGATTGGC | GAAAAAACGT | GTTGTACCCC | CTAGTACATT | GAGCGGAACT |
| 7201 | TCGTTGGGAA | CCGGAGCTGA | ATGAAGCCAT | ACCAAACGAC | GAGCGTGACA | CCACGATGCC | TGTAGCAATG | GCAACAACGT | ATTAACTGGC |
| | AGCAACCCTT | GGCCCTCGACT | TACTTCGGTA | TGGTTTGCTG | CTCCGCACTGT | GGTGCTACGG | ACATCGTTAC | CGTTGTTGCA | ACGGCGTTTGA | TAATTGACCG |
| 7301 | GAACTACTTA | CTCTAGCTTC | CCGGCAACAA | THAATAACAA | GGATGGAGGC | GGATAAAGTT | GCAGGACCAC | TTCGTGCGTC | GGCCCCTTCCG | GCTGGCTGGT |
| | CTTGATGAAT | GAGATCGAAG | GGCCGTTGTT | AATTATCTGA | CCTATTTCAA | CGTCCTGGTG | AAGACGCGAG | CGGGGAAGGC | CGACCGACCA |
| 7401 | TTTATTGCTGA | TAAATCTGGA | GCCGGTGAGC | CGTGGTCTCG | CGGTATCATT | GCAGCACTGG | GGCCAGATGG | TAAGCCCTCC | CGTATCGTAG | TTATCTACAC |
| | AATAACGACT | ATTTAGACCT | CGGCCACTCG | CACCAGAGC | GCCATAGTAA | CGTCGTGACC | CCGGTCTACC | ATTCGGGAGG | GCATAGCATC | AATAGATGTG |
| | | | Ampr | | | | | | | |
| 7501 | GACGGGGAGT | CAGGCAACTA | TGGATGAACG | AAATAGACAG | ATCCGCTGAGA | TAGGTGCCTC | ACTGATTAAG | CATTGGTAAC | TGTCAGACCA | AGTTTACTCA |
| | CTGCCCCTCA | GTCCGTTGAT | ACCTACTTGC | TTTATCTGTC | TAGGCGACTCT | ATCCACGGAG | TGACTAATTC | GTAACCATTG | ACAGTCTGGT | TCAAATGAGT |
| | | | | | | CoE1 ori | | | | |
| 7601 | TATATACTTT | AGATTGATTT | AAAACTTCAT | TTTTAATTTA | AAAGGATCTA | GGTGAAGATC | CTTTTTGATA | ATCTCATGAC | CAAAATCCCT | TAACGTGAGT |
| | ATATGAGAAA | TCTAACTAAA | TTTTGAAGTA | AAAATTAAAT | TTTCCTAGAT | CCACTTCTAG | GAAAAACTAT | TAGAGTACTG | GTTTTAGGGA | ATTGCACTCA |
| | | | | | | CoE1 ori | | | | |
| 7701 | TTTCGTTCCA | CTGAGCGTCA | GACCCCGTAG | AAAAGATCAA | AGGATCTTCT | TGAGATCCTT | TTTTTCTGCG | CGTAATCTGC | TGCTTGCAAA | CAAAAAAACC |
| | AAAGCAAGGT | GACTCGCAGT | CTGGGGCATC | TTTTCTAGTT | TCCTAGAAGA | ACTCTAGGAA | AAAAAGACGC | GCATTAGACG | ACGAACGTTT | GTTTTTTTGG |
| | | | | | | CoE1 ori | | | | |
| 7801 | ACCGCTACCA | GCGGTGGTTT | GTTTGCCGGA | TCAAGAGCTA | CCAACTCTTT | TTCCGAAGGT | AACTGGCTTC | AGCAGAGCGC | AGATACCAAA | TACTGTTCTT |
| | TGGCGATGGT | CGCCACCAAA | CAAACGGCCT | AGTTCTCGAT | GGTTGAGAAA | AAGGCTTCCA | TTGACCGAAG | TCGTCTCGCG | TCTATGGTTT | ATGACAAGAA |
| | | | | | | CoE1 ori | | | | |
| 7901 | CTAGTGTAGC | CGTAGTTAGG | CCACCACTTC | AAGAACTCTG | TAGCACCGCC | TACATACCTC | GCTCTGCTAA | TCCTGTTACC | AGTGGCTGCT | GCCAGTGGCG |
| | GATCACATCG | GCATCAATCC | GGTGGTGAAG | TTCTTGAGAC | ATCGTGGCGG | ATGTATGGAG | CGAGACGATT | AGGACAATGG | TCACCGACGA | CGGTCACCGC |
| | | | | | | CoE1 ori | | | | |
| 8001 | ATAAGTCGTG | TCTTACCGGG | TTGGACTCAA | GACGATAGTT | ACCGGATAAG | GCGCAGCGGT | CGGGCTGAAC | GGGGGGTTCG | TGCACACAGC | CCAGCTTGGA |
| | TATTCAGCAC | AGAATGGCCC | AACCTGAGTT | CTGCTATCAA | TGGCCTATTC | CGCGTCGCCA | GCCCGACTTG | CCCCCCAAGC | ACGTGTGTCG | GGTCGAACCT |
| | | | | | | CoE1 ori | | | | |
| 8101 | GCGAACGACC | TACACCGAAC | TGAGATACCT | ACAGCGTGAG | CTATGAGAAA | GCGCCACGCT | TCCCGAAGGG | AGAAAGGCGG | ACAGGTATCC | GGTAAGCGGC |
| | CGCTTGCTGG | ATGTGGCTTG | ACTCTATGGA | TGTCGCACTC | GATACTCTTT | CGCGGTGCGA | AGGGCTTCCC | TCTTTCCGCC | TGTCCATAGG | CCATTCGCCG |
| | | | | | | CoE1 ori | | | | |
| 8201 | AGGGTCGGAA | CAGGAGAGCG | CACGAGGGAG | CTTCCAGGGG | GAAACGCCTG | GTATCTTTAT | AGTCCTGTCG | GGTTTCGCCA | CCTCTGACTT | GAGCGTCGAT |
| | TCCCAGCCTT | GTCCTCTCGC | GTGCTCCCTC | GAAGGTCCCC | CTTTGCGGAC | CATAGAAATA | TCAGGACAGC | CCAAAGCGGT | GGAGACTGAA | CTCGCAGCTA |
| | | | | | | CoE1 ori | | | | |

FIG. 7 (Continued)

```
8301  TTTTGTGATG CTCGTTCAGGG GGGCGGAGCC TATGGAAAAA CGCCAGCAAC GCCCTTTTGC TGGCCTTTTG CTCACATGTT
      AAAACACTAC GAGCAGTCCC CCCGCCTCGG ATACCTTTTT GCGGTCGTTG CGGGTCGTTG ACCGGAAAAC GAGTGTACAA
         CoE1 ori 8401  CTTTCCTGCG TTATCCCCTG ATTCTGTGGA TAACCGTATT ACCGCCTTTG AGTGAGCTGA TACCGCTCGC CGCAGCCGAA
      GAAAGGACGC AATAGGGGAC TAAGCACACCT ATTGGCATAA TGGCGGAAAC TCACTCGACT ATGGCGAGCG GCGTCGGCTT GCTGGCTCGC GTCGCTCAGT 8501  GTGAGCGAGG AAGCGGAAGA GCGCCCAATA CGCAAACCGC CTCTCCCCGC GCGTTGGCCG ATTCATTAAT GCAGCAGGTT CCCGACTGGA
      CACTCGCTCC TTCGCCTTCT CGCGGGTTAT GCGTTTGGCG GAGAGGGGCG CGCAACCGGC TAAGTAATTA CGTCGTCCAA GGGCTGACCT 8601  AAGCGGGCAG TGAGCGCAAC GCAATTAATG TGAGTTAGCT CACTCATTAG GCACCCCAGG CTTTACACTT TATGCTTCCG GCTCGTATGT TGTGTGGAAT
      TTCGCCCGTC ACTCGCGTTG CGTTAATTAC ACTCAATCGA GTGAGTAATC CGTGGGGTCC GAAATGTGAA ATACGAAGGC CGAGCATACA ACACACCTTA 8701  TGTGAGCGGA TAACAATTTC ACACAGGAAA CAGCTATGAC CATGATTACG AATTAACCCT CACTAAAGGG AACAAAAGCT GGAGCTCCAC
      ACACTCGCCT ATTGTTAAAG TGTGTCCTTT GTCGATACTG GTACTAATGC TTAATTGGGA GTGATTTCCC TTGTTTTCGA CCTCGAGGTG 8801  CGCGGTGGCG GCCTCGAGGT CGAGATCCGG TCGACCAGCA ACCATAGTCC CGCCCCTAAC TCCGCCCATC CCGCCCCTAA CTCCGCCCAG TTCCGCCCAT
      GCGCCACCGC CGGAGCTCCA GCTCTAGGCC AGCTGGTCGT TGGTATCAGG GCGGGGATTG AGGCGGGTAG GGCGGGGATT GAGGCGGGTC AAGGCGGGTA
                                                    SV40

8901  TCTCCGCCCC ATGGCTGACT AATTTTTTTT ATTTATGCAG AGGCCGAGGC CGCCTCGGCC TCTGAGCTAT TCCAGAAGTA GTGAGGAGGC TTTTTTGGAG
      AGAGGCGGGG TACCGACTGA TTAAAAAAAA TAAATACGTC TCCGGCTCCG GCGGAGCCGG AGACTCGATA AGGTCTTCAT CACTCCTCCG AAAAAACCTC
        SV40                                                                     CMV

9001  GCCTAGGCTT TTGCAAAAAG CTTCGACGGT ATCGATTGGC TCATGTCCAA CATTACCGCC ATGTTGACAT TGATTATTGA CTAGTTATTA ATAGTAATCA
      CGGATCCGAA AACGTTTTTC GAAGCTGCCA TAGCTAACCG AGTACAGGTT GTAATGGCGG TACAACTGTA ACTAATAACT GATCAATAAT TATCATTAGT
                                                                  CMV

9101  ATTACGGGGT CATTAGTTCA TAGCCCATAT ATGGAGTTCC GCGTTACATA ACTTACGGTA AATGGCCCGC CTGGCTGACC GCCCAACGAC CCCCGCCCAT
      TAATGCCCCA GTAATCAAGT ATCGGGTATA TACCCTCAAGG CGCAATGTAT TGAATGCCAT TTACCGGGCG GACCGACTGG CGGGTTGCTG GGGGCGGGTA
                                                                  CMV

9201  TGACGTCAAT AATGACGTAT GTTCCCATAG TAACGCCAAT AGGGACTTTC CATTGACGTC AATGGGTGGA GTATTTACGG TAAACTGCCC ACTTGGCAGT
      ACTGCAGTTA TTACTGCATA CAAGGGTATC ATTGCGGTTA TCCCTGAAAG GTAACTGCAG TTACCCACCT CATAAATGCC ATTTGACGGG TGAACCGTCA
                                                                  CMV

9301  ACATCAAGTG TATCATATGC CAAGTACGCC CCCTATTGAC GTCAATGACG GTAAATGGCC CGCCTGGCAT TATGCCCAGT ACATGACCTT ATGGGACTTT
      TGTAGTTCAC ATAGTATACG GTTCATGCGG GGGATAACTG CAGTTACTGC CATTTACCGG GCGGACCGTA ATACGGGTCA TGTACTGGAA TACCCTGAAA
                                                                  CMV

9401  CCTACTTGGC AGTACATCTA CGTATTAGTC ATCGCTATTA CCATGGTGAT GCGGTTTTGG CAGTACATCA ATGGGCGTGG ATAGCGGTTT GACTCACGGG
      GGATGAACCG TCATGTAGAT GCATAATCAG TAGCGATAAT GGTACCACTA CGCCAAAACC GTCATGTAGT TACCCGCACC TATCGCCAAA CTGAGTGCCC
                                                                  CMV

9501  GATTTCCAAG TCTCCACCCC ATTGACGTCA ATGGGAGTTT GTTTTGGCAC CAAAATCAAC GGGACTTTCC AAAATGTCGT AACAACTCCG CCCATTGAC
      CTAAAGGTTC AGAGGTGGGG AGAGCTGCAGT TACCCTCAAA CAAAACCGTG GTTTTAGTTG CCCTGAAAGG GTTTTACAGCA TTTTACAGCA TTGTTGAGGC GGGTAACTG
```

FIG. 7 (Continued)

9601 GCAAATGGGC GGTAGGCGTG TACGGAATTC GGAGTGGCGA GCCCTCAGAT CCTGCATATA AGCAGCTGCT TTTTGCCTGT ACTGGGTCTC TCTG
     CGTTTACCCG CCATCCGCAC ATGCCTTAAG CCTCACCGCT CGGGAGTCTA GGACGTATAT TCGTCGACGA AAAACGGACA TGACCCAGAG AGAC

FIG. 7 (Continued)

```
  1 GTTAGACCAG ATCTGAGCCT GGGAGCTCTC TGGCTAACTA GGGAACCCAC TGCTTAAGCC TCAATAAAGC TTGCCTTGAG TGCTTCAAGT AGTGTGTGCC
    CAATCTGGTC TAGACTCGGA CCCTCGAGAG ACCGATTGAT CCCTTGGGTG ACGAATTCGG AGTTATTTCG AACGGAACTC AGAAGTTCA TCACACACGG
101 CGTCTGTTGT GTGACTCTGG TAACTAGAGA TCCCTCAGAC CCTTTTAGTC AGTGTGGAAA ATCTCTAGCA GTGGCGCCCG AACAGGGACT TGAAAGCGAA
    GCAGACAACA CACTGAGACC ATTGATCTCT AGGGAGTCTG GGAAAATCAG TCACACCTTT TAGAGATCGT CACCGCGGGC TTGTCCCTGA ACTTTCGCTT
201 AGGGAAACCA GAGGAGCTCT CTCGACGCAG GACTCGGCTT GCTGAAGCGC GCACGGCAAG CGGCGACTGG TGAGTACGCC AAAAATTTTG
    TCCCTTTGGT CTCCTCGAGA GAGCTGCGTC CTGAGCCGAA CGACTTCGCG CGTGCCGTTC CCGCTGACC ACTCATGCGG TTTTTAAAAC
                    psi
301 ACTAGCGGAG GCTAGAAGGA GAGAGATGGG TCAGTATTAA GCGGGGGAGA ATTAGATCGA TGGGAAAAAA TTCGGTTAAG GCCAGGGGGA
    TGATCGCCTC CGATCTTCCT CTCTCTACCC AGTCATAATT CGCCCCCTCT TAATCTAGCT ACCCTTTTTT AAGCCAATTC CGGTCCCCCT
401 AAGAAAAAAT ATAAATTAAA ACAGCTACAA TGGAGCAAGA GGGAGCTAGA ACGATTCGCA GTTAATCCTG GCCTGTTAGA AACATCAGAA GGCTGTAGAC
    TTCTTTTTTA TATTTAATTT TGTATATCAT CCCTCGTTCT TGCTAAGCGT CAATTAGGAC CGGACAATCT TTGTAGTCTT CCGACATCTG
501 AAATACTGGG ACAGCTACAA CCATCCCTTC AGAAGAGGAT CCTTCCTTAG AGATCATTAT AGATCATTTA TATTGTGTGC ATCAAAGGAT
    TTTATGACCC TGTCGATGTT GGTAGGGAAG TCTGTCCCTA GGAAGGAATC TCTAGTAATA TCTAGTAATA TATTATGTCA AGGACACAGC TAGTTTCCTA
601 AGAGATAAAA GACACCAAGG AAGCTTTAGA CAAGATAGAG GAAGAGCAAA ACAAAAGTAA GAAAAAAGCA CAGCTGACAC AGGACACAGC
    TCTCTATTTT CTGTGGTTCC TTCGAAATCT GTTCTATCTC CTTCGTCGTT TGTTTTCATT CTTTTTTCGT GTCGTCTGTC TCCTGTGTCG
701 AATCAGGTCA GCCAAAATTA CCCTATAGTG CAGAACATCC AGGGGCAAAT GGTACATCAG GCCATATCAC CTAGAACTTT AAATGCATGG GTAAAGTAG
    TTAGTCCAGT CGGTTTTAAT GGGATATCAC GTCTTGTAGG TCCCCGTTTA CCATGTAGTC GGTCTATAGTG GATCTTGAAA TTTACGTACC CATTTTCATC
801 TAGAAGAGAA GGCTTTCAGC CCAGAAGTAA TACCCATGTT TTCAGCATTA TCAGAAGGAG CCACCCCACA AGATTTAAAC ACCATGCTAA ACACAGTGGG
    ATCTTCTCTT CCGAAAGTCG GGTCTTCACT ATGGGTACAA AAGTCGTAAT AGTCTTCCTC GGTGGGGTGT TCTAAATTTG TGGTACGATT TGTGTCACCC
                                                                                          RRE
901 GGGACATCAA GCAGCCATGC AAATGTTAAA AGAGACCATC AATGAGGAAG CTGCAGGCAA AGAGAAGAGT GGTGCAGAGA GAAAAAAGAG CAGTGGGAAT
    CCCTGTAGTT CGTCGGTACG TTTACAATTT TCTCTGGTAG TTACTCCTTC GACGTCCGTT TCTCTTCTCA CCACGTCTCT CTTTTTTCTC GTCACCCTTA
                                                    RRE
1001 AGGAGCTTTG TTCCTTGGGT TCTTGGGAGC AGCAGGAAGC ACTATGGGCG CAGCGTCAAT GACGCTGACG GTACAGGCCA GACAATTATT GTCTGGTATA
     TCCTCGAAAC AAGGAACCCA AGAACCCTCG TCGTCCTTCG TGATACCCGC GTCGCAGTTA CTGCGACTGC CATGTCCGGT CTGTTAATAA CAGACCATAT
                                                                flap
1101 GTGCAGCAGC AGAACAATTT GCTGAGGGCT ATTGAGGCGC AACAGCATCT GTTGCAACTC ACAGTCTGGG GCATCAAGCA GCTCCAGGCA AGAATCCTGG
     CACGTCGTCG TCTTGTTAAA CGACTCCCGA TAACTCCGCG TTGTCGTAGA CAACGTTGAG TGTCAGACCC CGTAGTTCGT CGAGGTCCGT TCTTAGGACC
                                                                                                      flap
1201 CTGTGGAAAG ATACCTAAAG GATCAACAGC TCCTGGGGAT TTGGGGTTGC TCTGGAAAAC TCATTTGCAC CACTGCTGTG CCTTGGATCT ACAAATGGCA
     GACACCTTTC TATGGATTTC CTAGTTGTCG AGGACCCCTA AACCCCAACG AGACCTTTTG AGTAAACGTG GTGACGACAC GGAACCTAGA TGTTTACCGT
          RRE
1301 GTATTCATCC ACAATTTTAA AGGAAAAAGG GGGATTGGGG GGTACAGTGC AGGGGAAAGA ATAGTAGACA TAATAGCAAC TCATTTGCAC ACTAAAGAAT
     CATAAGTAGG TGTTAAAATT TCCTTTTTCC CCCTAACCCC CCATGTCACG TCCCCTTTCT TATCATCTGT ATTATCGTTG AGTAAACGTG TGATTTCTTA
```

FIG. 9

```
                                        flap
1401  TACAAAAACA AATTACAAAA ATTTCAAAATT TTCGGGTTTA TTACAGGGAC AGCAGAGATC CAGTTTGGGG ATCAATTGCA TGAAGAATCT GCTTAGGGTT
      ATGTTTTTGT TTAATGTTTT TAAGTTTTAA AAGCCCAAAT AATGTCCCTG TCGTCTCTAG GTCAAACCCC TAGTTAACGT ACTTCTTAGA CGAATCCCAA
                                                                           EF1p
1501  AGCCGTTTTG CGGTGCTTCG CGAGGATCCG TTTTCGTTTC CGATCGCTCC GGTGCCCGTC AGTGGGCAGA GCGCACATCG CCCACAGTCC CCGAGAAGTT
      TCCGCAAAAC GCCACGAAGC GCTCCTAGGC AAAAGCAAAG GCTAGCGAGG CCACGGGCAG TCACCCGTCT CGCGTGTAGC GGGTGTCAGG GGCTCTTCAA
                                                 EF1p
1601  GTCGGCAATT GAACCGGTGC CTAGAGAAGG TGGCGCGGGG TAAACTGGGA AAGTGATGTC GTGTACTGGC TCCGCCTTTT TCCCGAGGGT GGGGAGAAC
      CAGCCGTTAA CTTGGCCACG GATCTCTTCC ACCGCGCCCC ATTTGACCCT TTCACTACAG CACATGACCG AGGCGGAAAA AGGGCTCCCA CCCCCTCTTG
                                                 EF1p
1701  CGTATATAAG TGCAGTAGTC GCCGTGAACG TTCTTTTTTC CAACGGGTTT GCCGCCAGAA GCTTCGAGGG GCTCGCATCT CTCCTTCACG
      GCATATATTC ACGTCATCAG CGGCACTTGC AAGAAAAAAG GTTGCCCAAA CGGCGGTCTT CGAAGCTCCC CGAGCGTAGA GAGGAAGTGC
                                                 EF1p
1801  CGCCCCGCGC CCTACCTAGA GCCGCCATCC ACGCCGGTTG AGTCGCGTTC TGCCGCCTCC CGCCTCCTGT GCCTGTGGGT CGTGGTCCGC CGTCTAGGTA
      GCGGGGCGCG GGATGGACTC CGGCGGTAGG TGCGGCCAAC TCAGCGCAAG ACGGCGGAGG GCGGAGGACA CGGACACCA GCACCAGGCG GCAGATCCAT
1901  AGTTAAAGC TCAGGTCGAG AGTCCAGCTC ACCGGGCCTT TGTCCGCGC TCCCTTGGAG CCTACCTAGA CTCAGCCGGC TCTCCACGCT TTGCCTGACC CTGCTGCTC
      TCAAATTTCG AGTCCAGCTC TGGCCCGCAA ACAGGCCGCG AGGGAACCTC GGATGGATCT GAGTCGGCCG AGAGGTGCCA AACGGACTGG GACGAACGAG
                                                                                                    CE7R scFv
2001  AACTCTACGT CTTTGTTTCG TGCGCCGTTA CAGATCCAAG CTGTGACCGG CGCCTACCGG TAGCGCCGCC ACCATGCTGC TGCTGGTGAC
      TTGAGATGCA GAAACAAAGC ACGCGGCAAT GTCTAGGTTC GACACTGGCC GCGGATGGCC ATCGGCGGCG TGGTACGACG ACGACCACTG
                                                  CE7R scFv
2101  CAGCCCTGCT CTGTGCCAGC TGCCCCACCC CGGCCTTTCTG CTGATCCCCC AGTTGCAGCT GCAGCAGCCT GGGGCCGAGC TGGTGAAGCC AGGGGCCAGC
      GTCGGGACGAC GACACGGTCG ACGGGGTGGG GCCGGAAAGAC GACTAGGGGG TCCAACGTCGA CGTCGTCGGA CCCCGGCTCG ACCACTTCGG TCCCCGGTCG
                                                 CE7R scFv
2201  GTCAAGCTGT CCTGCAAGGC CAGCGGCTAC ACCTTCACCG GCTACTGGAT GCACTGGGTG AAGCAGAGAC CCGGCCACGG CCTGGAATGG ATCGGCCAGA
      CAGTTCGACA GGACGTTCCG GTCGCCGATG TGGAAGTGGC CGATGACCTA CGTGACCCAC TTCGTCTCTG GGCCGGTGCC GGACCTTACC TAGCCGGTCT
                                                  CE7R scFv
2301  TCAACCCCAG CAACGGCCGG ACCAACTACA ACGAGCAGAAG TTCAAGAGCAA GGCCGCCCTGA CCGTGGACAA GAGCAGCACC ACCGCCTTCA TGCAGCTGTC
      AGTTGGGGTC GTTGCCGGCC TGGTTGATGT TGCTCGTCGTTC AAGTTCTCGTT CCGGCGGGACT GGCACCTGTT CTCGTCGTGG TGGCGGAAGT ACGTCGACAG
                                                 CE7R scFv
2401  CGGCCCTGAC AGCCAGGACA GCGCCGTGTA CTTCTGCGCC AGGGACTACT ACGGCACCAG CTACAACTTC GACTACTGGG GCCAGGGCAC CACACTGACC
      GCCGGGACTG TCGGTCCTGT CGCGGCACAT GAAGACGCGG TCCCTGATGA TGCCGTGGTC GATGTTGAAG CTGATGACCC CGGTCCCGTG GTGTGACTGG
```

FIG. 9 (Continued)

```
                                                                                                CE7R scFv
2501 GTGAGCAGCG GCGGAGGGGG CTCTGGCGGC GGAGGATCTG GGGGAGGGGG CAGCGACATC CAGATGACCC AGAGCAGCAG CAGCTTCAGC GTGAGCCTGG
     CACTCGTCGC CGCCTCCCCC GAGACCGCCG CCTCCTAGAC CCCCTCCCCC GTCGCTGTAG GTCTACTGGG TCTCGTCGTC GTCGAAGTCG CACTCGGACC
                                                                                                CE7R scFv
2601 CGGCCGGGGT GACCATCACC TGTAAGGCCA TGTAGCCA ACGAGGACAT CTGGCCTGGT ATCAGCAGAA CCCCGGCAAC AGCCCCAAGC TGCTGATCAG
     GCCTGGCCCA CTGGTAGTGG ACATTCCGGT TGCTCCTGTA TGCTCCTGTA GACCGGACCA TAGTCGTCTT GGGGCCGTTG TCGGGGTTCG ACGACTAGTC
                                                                                                                CE7R scFv
2701 CGGCGGCACC AACCTGGTGA CCCGGCTGCC CAGCCGGTTT AGCGGCAGCG GCTCCGGCAA GGACTACACC CTGACCATCA CAAGCCTGCA GGCCGAGGAC
     GCCGCCGTGG TTGGACCACT GGGCCGACGG GTCGGCCAAA TCGCCGTCGC CGAGGCCGTT CCTGATGTGG GACTGGTAGT GTTCGGACGT CCGGCTCCTG
                                                                                                IgG4 Hinge
2801 TTCGCCACCT ACTACTGCCA GCAGTACTGG TCCACCCCCT TCACCTTCGG CCAGGGCACC GAGCTGGAAA TCAAAGAATC TAAGTACGGA CCCGCCCTGC
     AAGCGGTGGA TGATGACGGT CGTCATGACC AGGTGGGGGA AGTGGAAGCC GGTCCCGTGG CTCGACCTTT AGTTTCTTAG ATTCATGCCT GGGCGGGACGG
                                                                                                                    4-1BB
                             CD28tm
2901 CCCCTTGCCC TATGTTCTGG GTGCTGGTGG TGGTCGGAGG TGCTACAGCC TGCTGGTCAC CGTGGGCCTT ATCATCTTTT GGGTGAAACG GGGTCGGAAG
     GGGGAACGGG ATACAAGACC CACGACCACC ACCAGCCTCC ACGATGTCGG ACGACCAGTG GCACCCGGAA TAGTAGAAAA CCCACTTGC ACGAGGCTTC
                          4-1BB
3001 GGGCAGAAAG AAACTCCTGT ATATATTCAA ACAACCATTT ATGAGACCAG TACAAACTAC TCAAGAGGAA GATGGCTGTA GCTGCCGATT TCCAGAAGAA
     CCCGTCTTTC TTTGAGGACA TATATAAGTT TGTTGGTAAA TACTCTGGTC ATGTTTGATG AGTTCTCCTT CTACCGACAT CGACGGCTAA AGGTCTTCTT
                                                                                 Zeta
        4-1BB
3101 GAAGAAGGAG GATGTGAACT GCGGGTGAAG TTCAGCAGAA AGTCGTCTTC AGGGCCGACGC CCCTGCCTAC CAGCAGGGCC AGAATCAGCT GTACAACAGC CTGAACCTGG
     CTTCTTCCTC CTACACTTGA CGCCCACTTC AAGTCGTCTT TCAGCAGAAG TCCGGCTGCG GGGACGGATG GTCGTCCCGG TCTTAGTCGA CATGTTGCTC GACTTGGACC
3201 GCAGAGGGA AGAGTACGAC GTCCTGGATA AGCGGAGAGG CCGGGACCCT GAGATGGGCG GCAAGCCTCG CGTTCGGAGC CGCCTTCTTG GGGTCCTTC CGGACATATT
     CGTCTTCCCT TCTCATGCTG CAGGACCTAT TCGCCTCTCC GGCCCTGGGA CTCTACCCGC CGTTCGGAGC GCGGAAGAAC CCCAGGAAGC GCAAGCGGTAT TCAGGGCCTG
                             Zeta                                                                              T2A
3301 CGAACTGCAG AAAGACAAGA TGGCCGAGGC ATCAGCGAGA TGGCGAGCG AGGGCGAGCG CTCCGCCTCG AAGGCCACG ACGGCCTGTA TCAGGGCCTG
     GCTTGACGTC TTTCTGTTCT ACCGGCTCCG TAGTCGCTCT ACCGCTCGC GAGGCGGAGC CTCCGCCTCG TTCCCGGTGC TGCCGGACAT AGTCCCGGAC
                  Zeta
3401 TCCACCGCCA CCAAGGATAC CTACGACGCC CTGCACATGC AGGCCCTGCC CCCAAGGCTC GAGGGCGGCG GAGAGGGCAG AGGAAGTCTT CTAACATGCG
```

```
             AGGTGGCCGGT GGTTCCTATG GATGCTGCGG GACGTGTACG TCCCGGGACGG GGGTTCCGAG CTCCCGCCGC CTCTCCCGTC TCCTTCAGAA GATTGTACGC
                         T2A                                         ~~~~~~~~~~~~~~~~~~~~~~~~~~~~~~~~~~~~~~~~~~~~~~~~~~~~~~~~~~
                                                                                        EGFRt
3501  GTGACGTGGA GGAGAATCCC GGCCCTAGGA TGCTTCTCCT GGTTGCACAAGC CTTTCTGCTCT GTGAGTTACC ACACCCAGCA TTCCCTCCTGA TCCCACGCAA
      CACTGCACCT CCTCTTAGGG CCGGGATCCT ACGAAGAGAA CCACTGTTCG GAAGACGAGA CACTTCAATGG TGTGGGTCGT AAGGAGGACT AGGGTGCGTT
                                                 ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                                              EGFRt
3601  AGTGTGTAAC GGAATAGGTA TTGGTGAATT TAAAGACTCA CTCTCCATAA ATGCTACGAA TATTAAACAC TTCAAAAACT GCACCTCCAT CAGTGGCGAT
      TCACACATTG CCTTATCCAT AACCACTTAA ATTTCTGAGT GAGAGGTATT TACGATGCTT ATAATTTGTG AAGTTTTTGA CGTGGAGGTA GTCACCGCTA
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                EGFRt
3701  CTCCACATCC TGCCGGTGGC ATTTAGGGGT GACTCCTTCA CACATACTCC TCCTCTGGAT CCACAGGAAC TGGATATTCT GAAAACCGTA AAGGAAATCA
      GAGGTGTAGG ACGGCCACCG TAAATCCCCA CTGAGGAAGT GTGTATGAGG AGGACACCTA GGTGTCCTTG ACCTATAAGA CTTTTGGCAT TTCCTTTAGT
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                EGFRt
3801  CAGGGTTTTT GCTGATTCAG GCTTGGCCTG AAAACAGGAC GGACCTCCAT GCCTTTGAGA ACCTAGAAAT CATACGCGGC AGGACCAAGC AACATGGTCA
      GTCCCAAAAA CGACTAAGTC CGAACCGGAC TTTTGTCCTG CCTGGAGGTA CGGAAACTCT TGGATCTTTA GTATGCGCCG TCCTGGTTCG TTGTACCAGT
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                EGFRt
3901  GTTTTCTCTT GCAGTCGTCA GCCTGAACAT AACATCCTTG GGATTACGCT CCCTCAAGGA GATAAGTGAT GGAGATGTGA TAATTTCAGG AAACAAAAAT
      CAAAGAGAA CGTCAGCAGT CGGACTTGTA TTGTAGGAAC CCTAATGCGA GGGAGTTCCT CTATTCACTA CCTCTACACT ATTAAAGTCC TTTGTTTTTA
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                EGFRt
4001  TTGTCCTATG CAAATACAAT AAACTGTTTG GGACCCTCCG TCAGAAAACC AAAATTATAA GCAACAGAGG TGAAAACAGC TGCAAGGCCA
      AACACGATAC GTTTATGTTA TTTGACAAAC CCTGGAGGGC AGTCTTTTGG TTTTAATATT CGTTGTCTCC ACTTTTGTCG ACGTTCCGGT
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                EGFRt
4101  CAGGCCAGGT CTGCCATGCC TTGTGCTCCC CCGAGGGCTG CTGGGGCCCG ACTCTGAGTG GAGCCCAGGT ACTGCGTCTC TTGCCGGAAT GTCAGCCGAG GCCTGCCTCA GGCCATGAAC
      GTCCGGTCCA GACGGTACGG AACACGAGGG GGCTCCCGAC GACCCCGGGC CTCGGGTCCA CTCGGGTCCA TGACCGCAGAG AACGGCCTTA CAGTCGGCTC CGGACGGAGT CCGGTACTTG
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                EGFRt
4201  CGTGGACAAG TGCAACCTTC TGGAGGGTGA GCCAAGGGAG TTTTGTGGAGA ACTCTGAGACT CATTGACGGC CACACAGTGC CCCCACTGCG TCAAGGACCTG GCCTGCCTCA GGCCATGAAC
      GCACCTGTTC ACGTTGGAAG ACCTCCCACT CGGTTCCCTC AAACACCTCT TGAGACTCA CGGGTTTGAC GTAACTGCCG ACACGGGTAG GTTTGACGTC CGGACGGAGT CCGGTACTTG
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                EGFRt
4301  ATCACCTGCA CAGGACAGG TGCCTGGTCTGG AAGTACGCAG ACGCCGGCCA TGTGTGCCCA CGGCCGGCCA ACGCCGGCCA TGCCTGCCAC CTACGGATGC ACTGGGCCAG GTCATGGGAG
      TAGTGGACGT GTCCTGGTC CACGGACCC TTCATCGCTC TGCGGCCGGT ACACACGGGT TGCGGCCGGT TGCGGCCGGT ACGGACGGTG GATGCCTACG GGACCCGGTC CAGTACCCTC
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                EGFRt
4401  AAAACACAAC CCTGGTCTGG AAGTACGCAG ACGCCGGCCA TGTGTGCCCA CGGCCGGCCA ACGCCGGCCA TGCCTGCCAC CTACGGATGC ACTGGGCCAG GTCATGGGAG
      TTTTGTTGTG GGACCAGACC TTCATGCGTC TGCGGCCGGT ACACACGGGT TGCGGCCGGT TGCGGCCGGT ACGGACGGTG GATGCCTACG GGACCCGGTC CAGTACCCTC
       ~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
                                                EGFRt
4501  CTGTCCAACG AATGGGCCTA AGATCCCGTC CATCGCCACT GGGATGGTGG GGGCCCTCCT GTGGTGCCC CTTGCTGCTG GGGGATCCG GTCTTGAAGG CCTCTTCATG
      GACAGGTTGC TTACCCGGAT TCTAGGGCAG GTAGCGGTGA CCCTACCACC CCCGGGGAGGA ACCCCGGGAG GAACCTAGCC GTAGCCTCGG CCAGAACTTCC GGAGAAGTAC

FIG. 9 (Continued)
```

```
       EGFRt                                                                    WPRE
4601   TGAGCGGCCG CTCTAGACCC GGGCTGCAGG AATTCGATAT CAAGCTTATC GATAATCAAC CTCTGGATTA CAAAATTTGT GAAAGATTGA CTGGTATTCT
       ACTCGCCGGC GAGATCTGGG CCCGACGTCC TTAAGCTATA GTTCGAATAG CTATTAGTTG GAGACCTAAT GTTTTAAACA CTTTCTAACT GACCATAAGA

4701   TAACTATGTT GCTCCTTTTA CGCTATGTGG ATACGCTGCT TTAATGCCTT TGTATCATGC CGTATGGCTT TATTGCTTCC TCATTTTCTC CTCCTTGTAT
       ATTGATACAA CGAGGAAAAT GCGATACACC TATGCGACGA AATTACGGAA ACATAGTACG GCATACCGAA ATAACGAAGG AGTAAAAGAG GAGGAACATA

4801   AAATTCCTGGT TGCTGTCTCT TTATGAGGAG TTGTGGCCCG TTGTCAGGCA ACGTGGCGTG GTGTGCACTG TGTTTGCTGA CGCAACCCCC ACTGGTTGGG
       TTTAGGACCA ACGACAGAGA AATACTCCTC AACACCGGGC AACAGTCCGT TGCACCGCAC CACACGTGAC ACAAACGACT GCGTTGGGGG TGACCAACCC

4901   GCATTGCCAC CACCTGTCAG CTCCTTTCCG GGACTTTCGC TTTCCCCCTC CCTATTGCCA CGGCGGAACT CATCGCCGCC TGCCTTGCCC GCTGCTGGAC
       CGTAACGGTG GTGGACAGTC GAGGAAAGGC CCTGAAAGCG AAAGGGGGAG GGATAACGGT GCCGCCTTGA GTAGCGGCGG ACGGAACGGG CGACGACCTG

5001   AGGGGCTCGG CTGTTGGGCA CTGACAATTC CGTGGTGTTG TCGGGGAAAT CATCGCCGTC TTCCTTGGCTC CTCGCCTGTG TTGCCACCTG GATTCTGCGC
       TCCCCGAGCC GACAACCCGT GACTGTTAAG GCACCACACA AGCCCCTTTA GTAGCAGCAG AAGGAACCGAC AGGAACCGAG GAGCGGACAC CTAAGACGCG

5101   GGGACGTCCT TCTGCTACGT CCCTTCGGGC CTGACCTTCC TTTCCCCTCC TCGCTGCCGG CTGCTGCCGG GACGACGCCC TCTTCCGCCTT CTTCGCCTTC
       CCCTGCAGGA AGACGATGCA GGGAAGCCCG GACTGGAAGG AAAGGGGAGG AGCGACGGCC GACGACGGCC CTGCTGCGGG AGAAGGCGCA GAAGCGGAAG
                                       WPRE                                                                           del U3
5201   GCCCCTCAGAC GAGTCGGATC TCCCTTTGGG CCGCCTCCCC GCATCGGATAC CGTCGACTAC ACTTACAAGG CAGCTTGTAGA
       CGGGAGTCTG CTCAGCCTAG AGGGAAACCC GGCGGAGGGG CGTAGCCTATG GCAGCTGATC GGCATGGAAA TTCTGGTTAC TGAATGTTCC GTCGACATCT
                                                del U3                                                                          R
5301   TCTTAGCCAC TTTTTAAAAG AAAAGGGGGG ACTGGAAGGG CTAATTCACT CCCAAAGAAG ACAAGATCTG CTTTTTTGCCT GTACTGGGTC TCTCTGGTTA
       AGAATCGGTG AAAAATTTTC TTTTCCCCCC TGACCTTCCC GATTAAGTGA GGGTTTCTTC TGTTCTAGAC GAAAAACGGA CATGACCCAG AGAGACCAAT
                  R                                                                                 U5
5401   GACCAGATCT GAGCCTGGGA GCTCTCTGGC TAACTAGGGA ACCCACTGCT TAAGCCTCAA TAAAGCTTGC CTTGAGTGCT TCAAGTAGTG TGTGCCCGTC
       CTGGTCTAGA CTCGGACCCT CGAGAGACCG ATTGATCCCT TGGGTGACGA ATTCGGAGTT ATTTCGAACG GAACTCACGA AGTTCATCAC ACACGGGCAG 5501   TGTTGTGTGA CTCTGGTAAC TAGAGATCCC TCAGACCCTT TTAGTCAGTG TGGAAAATCT CTAGCAGAAT TGGCAGTACT GCTTATCGAT ACCGTCGACC
       ACAACACACT GAGACCATTG ATCTCTAGGG AGTCTGGGAA AATCAGTCAC ACCTTTTAGA GATCGTCTTA CCGTCATGA CGAATAGCTA TGGCAGCTGG 5601   TCGAGGGGGG GCCCGGTACC CAATTCGCCC TATAGTGAGT CGTATTACAA TTCACTGGCC GTCGTTTTAC AACGTCGTGA CTGGGAAAAC CCTGGCGTTA
       AGCTCCCCCC CGGGCCATGG GTTAAGCGGG ATATCACTCA GCATAATGTT AAGTGACCGG CAGCAAAATG TTGCAGCACT GACCCTTTTG GGACCGCAAT 5701   CCCAACTTAA TCGCCTTGCA GCACATCCCC CTTTCGCCAG CTGGCGTAAT AGCGAAGAGG CCCGCACCGA TCGCCCTTCC CAACAGTTGC GCAGCCTGAA
       GGGTTGAATT AGCGGAACGT CGTGTAGGGG GAAAGCGGTC GACCGCATTA TCGCTTCTCC GGGCGTGGCT AGCGGGAAGG GTTGTCAACG CGTCGGACTT
```

FIG. 9 (Continued)

```
5801 TGGCGAATGG AAATTGTAAG CGTTAATATT TTGTTAAAAT TCGCGTTAAA ATCAGCTCAT TTTTTAACCA ATAGGCCGAA ATCGGCAAAA
     ACCGCTTACC TTTAACATTC GCAATTATAA AACAATTTTA AGCGCAATTT AGTCGAGTA AAAAATTGGT TATCCGGCTT TAGCCGTTTT
5901 TCCCTTATAA ATCAAAAGAA TAGACCCGAGA TAGGGTTGAG TGTTGTTCCA GTTTGGAACA AGAGTCCACT ATTAAAGAAC ACGTCAAAGG
     AGGGAATATT TAGTTTTCTT ATCTGGCTCT ATCCCAACTC ACAACAAGGT CAAACCTTGT TCTCAGGTGA CACCTGAGGT TGCAGTTTCC
6001 GCGAAAAACC GTCTATCAGG GCGATGGCCC GCCTACCGGG ACTACGTGAA CCATCACCCT AGGTGCCCTA AGCACTAAA TCGGAACCCT
     CGCTTTTTGG CAGATAGTCC CAGATTTAG GCGATGCACTT TGATGCACTT GGTAGTGGA TTAGTTCAAA AAACCCCAGC TTCGTGATTT AGCCTTGGGA
6101 AAAGGGAGCC CCCGATTTAG GGCTAAATC TCGAACTGCC GTAACCACCA CACCCGCGCC GGGAAGAGC CGAAAGAAAG CGGCGCTAGG GCGCTGGCAA
     TTTCCCTCGG CACGCTGCGC GTAACCACCA CACCCGCGCC GTAATGCC CCCTCTTCCT GGTCACTTT CGGGGAAATG TGCGCGAAC
6201 GTGTAGCGGT CACGCTGCGC GTAACCACCA CACCCGCGCC GTTAATGCC CCGCTACAGG GCGCGTCAGG TGGCACTTT CGGGGAAATG TGCGCGAAC
     CACATCGCCA GTCGGACGCG CATTGGTGGT GTGGGCGGGG CGAATTACGC CGGCAGTCC ACCGTGAAAA GCCCCTTTAC ACGGCCTTG
                                                                                                    Ampr
6301 CCCTATTTGT TTATTTTTCT AAATACATTC AAATATGTAT CCGCTCATGA GACAATAACC CTGATAAATG ATTGAAAAAG GAAGAGTATG
     GGGATAAACA AATAAAAAGA TTTATGTAAG TTTATACATA GGCGAGTACT CTGTTATTGG GACTATTTAC CTTCAATAAT CTTCTCATAC
6401 AGTATTCAAC ATTTCCGTGT CGCCCTTATT CCCTTTTTTG CGGCATTTTG CCTTCCTGTT TTTGCTCACC CAGAAACGCT GGTGAAAGTA AAAGATGCTG
     TCATAAGTTG TAAAGGCACA GCGGGAATAA GGGAAAAAAC GCCGTAAAAC GGAAGGACAA AAACGAGTGG GTCTTTGCCA CCACTTTCAT TTTCTACGAC
                                         Ampr
6501 AAGATCAGTT GGGTGCACGA GTGGGTTACA TCGAACTGGA TCTCAACAGC GGTAAGATCC TTGAGAGTTT TCGCCCCGAA GAACGTTTTC CAATGATGAG
     TTCTAGTCAA CCCACGTGCT CACCCAATGT AGCTTGACCT AGAGTTGTCG CCATTCTAGG AACTCTCAAA AGCGGGGGCTT CTTGCAAAAG GTTACTACTC
                             Ampr
6601 CACTTTTAAA GTTCTGCTAT GTGGCGCGGT ATTATCCCGT ATTGACGCCG GGCAAGAGCA ACTCGGTCGC CGCATACACT ATTCTCAGAA TGACTTGGTT
     GTGAAAATTT CAAGACGATA CACCGCGCCA TAATAGGGCA TAACTGCGGC CCGTTCTCGT TGAGCCAGCG GCGTATGTGA TAAGAGTCTT ACTGAACCAA
                                     Ampr
6701 GAGTACTCAC CAGTCACAGA AAAGCATCTT ACGGATGGCA TGACAGTAAG AGAATTATGC AGTGCTGCCA TAACCATGAG TGATAACACT GCGGCCAACT
     CTCATGAGTG GTCAGTGTCT TTTCGTAGAA TGCCTACCGT ACTGTCATTC TCTTAATACG TCACGACGGT ATTGGTACTC ACTATTGTGA CGCCGGTTGA
                                                  Ampr
6801 TACTTCTGAC AACGATCGGA GGACCGAAGG AGCTAACCGC TTTTTTGCAC AACATGGGGG ATCATGTAAC TCGCCTTGAT CGTTGGGAAC CGGAGCTGAA
     ATGAAGACTG TTGCTAGCCT CCTGGCTTCC TCGATTGGCG AAAAAACGTG TTGTACCCCC TAGTACATTG AGCGGAACTA GCAACCCTTG GCCTCGACTT
                                          Ampr
6901 TGAAGCCATA CCAAACGACG AGCGTGACAC CACGATGCCT GTAGCAATGG CAACAACGTT GCGCAAACTA TTAACTGGCG AACTACTTAC TCTAGCTTCC
     ACTTCGGTAT GGTTTGCTGC TCGCACTGTG GTGCTACGGA CATCGTTACC CGTTGTTGCAA CGGCGTTTGAT AATTGACCGC TTGATGAATG AGATCGAAGG
                                      Ampr
7001 CGGCAACAAT TAATAGACTG GATGGAGGCG GATAAAGTTG CAGGACCACT TCTGCGCTCG GCCCTTCCCG CTGGCTGGTT TATTGCTGAT AAATCTGGAG
     GCCGTTGTTA ATTATCTGAC CTACCTCCGC CTATTTCAAC GTCCTGGTGA AGACGCGAGC CGGGAAGGGC GACCGACCAA ATAACGACTA TTTAGACCTC
                                      Ampr
7101 CCGGTGAGCG TGGGTCTCGC GGTATCATTG CAGCACTGGG GCCAGATGGT AAGCCCTCCC GTATCGTAGT TATCTACACG ACGGGGAGTC AGGCAACTAT
     GGCCACTCGC ACCCAGAGCG CCATAGTAAC GTCGTGACCC CGGTCTACCA TTCGGGAGGG CATAGCATCA ATAGATGTGC TGCCCCTCAG TCCGTTGATA
```

```
      GTGTCCTTTG TCGATACTGG TACTAATGCG GTTCGAGCTT TAATTGGGAG TGATTTCCCT TGTTTTCGAC CTCGAGGTGG CGCCACCGCC GGAGCTCCAG
                                                          Sv40
 8501 GAGATCCGGT CGACCAGCAA CCATAGTCCC GCCCCATCC CGCCCTAACT CCGCCCATCC CGCCCCCAGT TCCGCCCCCA TGGCTGACTA
      CTCTAGGCCA GCTGGTCGTT GGTATCAGGG CGGGGATTGA GGCGGGATTG AGGCGGGGTCA AGGCGGGGT ACCGACTGAT
                                                          Sv40
 8601 ATTTTTTTTA TTTATGCAGA GGCCGAGGCC GCCTCGGCCT CTGAGCTATT CCAGAAGTAG TGAGGAGGCT TTTTTTGGAGG CCTAGGCTTT TGCAAAAAGC
      TAAAAAAAAT AAATACGTCT CCGGCTCCGG CGGAGCCGGA GACTCGATAA GGTCTTCATC ACTCCTCCGA AAAAACCTCC GGATCCGAAA ACGTTTTTCG
                                                          CMV
 8701 TTCGACGGTA TCGATTGGCT CATGTCCAAC ATTACCGCCA TGTTGACATT GATTATTGAC TAGTTATTAA TAGTAATCAA TTACGGGGTC ATTAGTTCAT
      AAGCTGCCAT AGCTAACCGA GTACAGGTTG TAATGGCGGT ACAACTGTAA CTAATAACTG ATCAATAATT ATCATTAGTT AATGCCCCAG TAATCAAGTA
                                                          CMV
 8801 AGCCCATATA TGGAGTTCCG CGTTACATAA CTTACGGTAA ATGGCCCGCC TGGCTGACCG CCCAACGACC CCCGCCCATT GACGTCAATA ATGACGTATG
      TCGGGTATAT ACCTCAAGGC GCAATGTATT GAATGCCATT TACCGGGCGG ACCGACTGGC GGGTTGCTGG GGGCGGGTAA CTGCAGTTAT TACTGCATAC
                                                          CMV
 8901 TTCCCATAGT AACGCCAATA GGGACTTTCC ATTGACGTCA ATGGGTGGAG TATTTACGGT AAACTGCCCA CTTGGCAGTA CATCAAGTGT ATCATATGCC
      AAGGTATCA TTGCGGTTAT CCCTGAAAGG TAACTGCAGT TACCCACCTC ATAAATGCCA TTTGACGGGT GAACCGTCAT GTAGTTCACA TAGTATACGG
                                                          CMV
 9001 AAGTACGCCC CCTATTGACG TCAATGACGG TAAATGGCCC GCCTGGCATT ATGCCCAGTA CATGACCTTA TGGGACTTTC CTACTTGGCA GTACATCTAC
      TTCATGCGGG GGATAACTGC AGTTACTGCC ATTTACCGGG CGGACCGTAA TACGGGTCAT GTACTGGAAT ACCCTGAAAG ATGAACCGT CATGTAGATG
                                                          CMV
 9101 GTATTAGTCA TCGCTATTAC CATGGTGATG CGGTTTTGGC AGTACATCAA TGGGCGTGGA TAGCGGTTTG ACTCACGGGG ATTTCCAAGT CTCCACCCCA
      CATAATCAGT AGCGATAATG GTACCACTAC GCCAAAACCG TCATGTAGTT ACCCGCACCT ATCGCCAAAC TGAGTGCCCC TAAAGGTTCA GAGGTGGGGT
                                                          CMV
 9201 TTGACGTCAA TGGGAGTTTG TTTTGGCACC AAAATCAACG GGACTTTCCA AAATGTCGTA ACAACTCCGC CCCATTGACG CAAATGGGCG GTAGGCGTGT
      AACTGCAGTT ACCCTCAAAC AAAACCGTGG TTTTAGTTGC CCTGAAAGGT TTTACAGCAT TGTTGAGGCG GGGTAACTGC GTTTACCCGC CATCCGCACA
                                                          CMV
 9301 ACGGAATTCG GAGTGGCCAG CCCTCAGATC CTGCATATAA GCAGCTGCTT TTTGCCTGTA CTGGGTCTCT CTG
      TGCCTTAAGC CTCACCGGTC GGGAGTCTAG GACGTATATT CGTCGACGAA AAACGGACAT GACCCAGAGA GAC
```

FIG. 9 (Continued)

```
   1 GTTAGACCAG ATCTGAGCCT GGGAGCTCTC TGGCTAACTA GGGAACCCAC TGCTTAAGCC TCAATAAAGC TTGCCTTGAG TGCTTCAAGT AGTGTGTGCC
     CAATCTGGTC TAGACTCGGA CCCTCGAGAG ACCGATTGAT CCCTTGGGTG ACGAATTCGG AGTTATTTCG AACGGAACTC ACGAAGTTCA TCACACACGG
 101 CGTCTGTTGT GTGACTCTGG TAACTAGAGA TCCCTCAGAC CCTTTTAGTC AGTGTGGAAA ATCTCTAGCA GTGGCGCCCG AACAGGGACT TGAAAGCGAA
     GCAGACAACA CACTGAGACC ATTGATCTCT AGGGAGTCTG GGAAAATCAG TCACACCTTT TAGAGATCGT CACCGCGGGC TTGTCCCTGA ACTTTCGCTT
 201 AGGGAAACCA GAGGAGTCTC CTCGACGCAG GACTCGGCTT GCTGAAGCGC GCACGGCAAG AGGCGAGGGG CGGCGACTGG TGAGTACGCC AAAAATTTTG
     TCCCTTTGGT CTCCTCAGAG GAGCTGCGTC CTGAGCCGAA CGACTTCGCG CGTGCCGTTC TCCGCTCCCC GCCGCTGACC ACTCATGCGG TTTTTAAAAC
                 psi                  psi
 301 ACTAGCGGAG GCTAGAAGGA GAGAGATGGG TGCGAGAGCG TCAGTATTAA GCGGGGGAGA ATTAGATCGA TGGGAAAAAA TTCGGTTAAG GCCAGGGGGA
     TGATCGCCTC CGATCTTCCT CTCTCTACCC ACGCTCTCGC AGTCATAATT CGCCCCCCTCT TAATCTAGCT ACCCTTTTTT AAGCCAATTC CGGTCCCCCT
 401 AAGAAAAAAT ATAAATTAAA ACATATAGTA TGGGCAAGCA GGGAGCTAGA ACGATTCGCA GTTAATCCTG GCCTGTTAGA AACATCAGAA GGCTGTAGAC
     TTCTTTTTTA TATTTAATTT TGTATATCAT ACCCGTTCGT CCCTCGATCT TGCTAAGCGT CAATTAGGAC CGGACAATCT TTGTAGTCTT CCGACATCTG
 501 AAATACTGGG ACAGCTACAA CCATCCCTTC AGACAGGATC TCGTCCTTAT AGTGCAGAAC ATCCAGGGGG AGCAACCCTC TATTGTGTGC ATCAAAGGAT
     TTTATGACCC TGTCGATGTT GGTAGGGAAG TCTGTCCTAG AGCAGGAATA TCACGTCTTG TAGGTCCCCC TCGTTGGGAG ATAACACACG TAGTTTCCTA
 601 AGCATATAAA GACACCAAGG AAGCTTTAGA CAAGATAGAG GAAGAGCAAA ACAAAAGTAA CAAAAAAGCA CAGCAAGCAG CAGCTGACAC AGGACACAGC
     TCGTATATTT CTGTGGTTCC TTCGAAATCT GTTCTATCTC CTTCTCGTTT TGTTTTTCATT GTTTTTTCGT GTCGTTCGTC GTCGACTGTG TCCTGTGTCG
 701 AATCAGGTCA GCCAAAATTA CCCTATAGTG CAGAACATCC AGGGGCAAAT GGTACATCAG GCCATATCAG AAGAACTTGAA GATCTTGAAG GTAAAAGTAG
     TTAGTCCAGT CGGTTTTAAT GGGATATCAC GTCTTGTAGG TCCCCGTTTA CCATGTAGTC CGGTATAGTC TTCTTGAACT CTAGAACTTC CATTTTCATC
 801 TAGAAGAGAA GGCTTTCAGC CCAGAAGTAA AGCTTATTGAT ATGGGTACAA TACCCATGTT TTCAGCATTA TCAGAAGGAG CCACCCCACA AGATTTAAGA
     ATCTTCTCTT CCGAAAGTCG GGTCTTCACT TACCCATGTT ATGGGTACAA ATGGGTACAA AGTCGTAAT AGTCTTCCTC GGTGGGGTGT TCTAAATTTG
                                                                                      RRE
 901 GGGACATCAA GCAGCCATGC AAATGTTAAA AGAGACCATC AATGAGGAAG CTGCAGGCAA GGTGCAGAGT AGAGAAGAGT GAAAAAGAG CAGTGGGAAT
     CCCGTAGTT CGTCGGTACG TTTACAATTT TCTCTGGTAG TTACTCCTTC GACGTCCGTT CCACGTCTCA TCTCTTCTCA CTTTTTTCTC GTCACCCTTA
                                                  RRE
1001 AGAGCTTTG TTCCTTGGGT TCTTGGGAGC AGCAGGAAGC ACTATGGGCG CAGCGTCAAT GACGCTGACG CAGCTACAGG CA GACAATTATT GTCTGGTATA
     TCCTCGAAAC AAGGAACCCA AGAACCCTCG TCGTCCTTCG TGATACCCGC GTCGCAGTTA CTGCGACTGC GTCGATGTCC GT CTGTTAATAA CAGACCATAT
1101 GTGCAACAGC AGAACAATTT GCTGAGGGCT ATTGAGGCGC AACAGCATCT GTTGCAACTC ACAGTCTGGG GCATCAAGCA GCTCCAGGCA AGAATCCTGG
     CACGTTGTCG TCTTGTTAAA CGACTCCCGA TAACTCCGCG TTGTCGTAGA CAACGTTGAG TGTCAGACCC CGTAGTTCGT CGAGGTCCGT TCTTAGGACC
     RRE                                                                                                flap
1201 CTGTGGAAAG ATACCTAAAG GATCAACAGC TCCTGGGGAT TTGGGGTTGC TCTGGAAAAC TCATTTGCAC CACTGCTGTG CCTTGGATCT ACAAATGGCA
     GACACCTTTC TATGGATTTC CTAGTTGTCG AGGACCCCTA AACCCCAACG AGACCTTTTG AGTAAACGTG GTGACGACAC GGAACCTAGA TGTTTACCGT
                                                                                           flap
```

FIG. 11

```
1301  GTATTCATCC ACAATTTTAA AAGAAAAGGG GGGATTGGGG GGTACAGTGC AGGGGAAGA GGTACAGTGC AGGGGAAGA ATAGTAGACA TAATAGCAAC AGACATACAA ACTAAAGAAT
      CATAAGTAGG TGTTAAAATT TTCTTTTCCC CCCTAACCCC CCATGTCACG TCCCCTTTCT TATCATCTGT ATTATCGTTG TCTGTATGTT TGATTTCTTA
                                                        flap
1401  TACAAAAACA AATTACAAAA ATTCAAAATT TTCGGGTTTA TTACAGGGAC AGCAGAGATC CAGTTTGGGG ATCAATTGCA TGAAGAATCT GCTTAGGGTT
      ATGTTTTTGT TTAATGTTTT TAAGTTTTAA AAGCCCAAAT AATGTCCCTG TCGTCTCTAG GTCAAACCCC TAGTTAACGT ACTTCTTAGA CGAATCCCAA
                                                                                              EF1p
1501  AGGGCTTTTG CGCTGCTTCG CGAGGATCTG CGATCGCTCC GGTGCCCGTC AGTGGGCAGA GGGCACATCG CCCACAGTCC CCGAGAAGTT GGGGGAGGG
      TCCGCAAAAC GCGACGAAGC GCTCCTAGAC GCTAGCGAGG CCACGGGCAG TCACCCGTCT CCGTGTAGC GGGGTGTCAGG GGCTCTTCAA CCCCCTCCC
                                                                                 EF1p
1601  GTCGGCAATT GAACCCGGTG CTAGAGAAGG TGGGCGCGGG TAAACTGGGA AAGTGATGTC TCCGCCTTTT TCCCGAGGGT GGGGGAGAAC
      CAGCCGTTAA CTTGGCCACG GATCTCTTCC ACCGCGCCCC ATTTGACCCT TTCACTACAG AGGGCGGAAAA AGGGGTCCCA CCCCCTCTTG
                                                                                      EF1p
1701  CGTATATAAG TGCAGTAGTC GCCGTGAACG TTCTTTTTCG CAACGGGTTT GCCGCCAGAA GCTTCGAGGG GCTCGCCATCT CTCCTTCACG
      GCATATATTC ACGTCATCAG CGGCACTTGC AAGAAAAAGC GTTGCCCAAA CGGCGGTCTT CGAAGCTCCC CGAGCGGTAGA GAGGAAGTGC
                                                                                      EF1p
1801  CGCCCGCCGC CCTACTCGAG GCCGCCATCC ACGCCCGTTG AGTCGCGTTC TGCCGCGTTC GCCTGCCTGGT GCCTCCTGAA CTGCCTCCGC CGTCTAGGTA
      GCGGGCGGCG GGATGGACTC CGGCGGTAGG TGCGGGCAAC TCAGCGCAAG ACGGCGGAGG CGGAGGACTT GACCGGAGCC GCAGATCCAT
                                                                                  EF1p
1901  AGTTTAAAGC TCAGGTCGAG ACCGGGCCTT TGTCCGGCGC TCCCTTGGAG CCTACTTAGA CTCAGCCGGC TCTCCACGCT TTGCCTGACC CTGCTTGCTC
      TCAAATTTCG AGTCCAGCTC TGGCCCGGAA ACAGGCCGCG AGGGAACCTC GGATGGATCT GAGTCGGCCG AGAGGTGCGA AACGGACTGG GACGAACGAG
                                                                                                   CE7R scFv
2001  AACTCTACGT CTTTGTTTCG TTTTCTGTTC TGCCGCGTTA CAGATCCAAG CTGTGACCGG CGCCTACCGC ACCATGCGGC TGCTGGTGAC
      TTGAGATGCA GAAACAAAGC AAAAGACAAG ACGGCGCAAT GTCTAGGTTC GACACTGGCC GCGGATGCCG TGGTACGACG ACGACCACTG
                                                                       CE7R scFv
2101  CAGCCTGCTG CTGTGGCCGG TGCCCACCC CGCCTTTCTG CTGATCCCCC AGGTGCAGCT GGTGCAGCCT TGGTGAAGCC AGGGCCCAGC
      GTCGGACGAC GACACGGCCC ACGGGGTGGG GCGGAAAGAC GACTAGGGGG TCCACGTCGA CCACGTCGGA ACCACTTCGG TCCGGGTCG
                                                                       CE7R scFv
2201  GTGAAGCTGT CCTGCAAGGC CAGCGGGTAC ACCTTCACCG GCTACTGGAT GCACTGGGTG AAGCAGAGAC CCGGCCACGG ATCGGCGAGA
      CACTTCGACA GGACGTTCCG GTCGCCCATG TGGAAGTGGC CGATGACCTA CGTGACCCAC TTCGTCTCTG GGCCGGTGCC TAGCCGCTCT
                                                                      CE7R scFv
2301  TCAACCCCAG CAACGGCCGG ACCAACTACA ACGAGCAAG GCCACCCTGA CCGTGGACAA GAGCAGCAGC ACCGCCTTCA TGCAGCTGTC
      AGTTGGGGTC GTTGCCGGCC TGGTTGATGT TGCTCGTCGTT CGGTGGGACT GGCACCTGTT CTCGTCGTCG TGGCGGAAGT ACGTCGACAG
                                                                      CE7R scFv
2401  CGGCCTGACC AGCGAGGACA GCGCCGTGTA CTTCTGCGCC AGGGACTACT ACGGCACCAG CTACAACTTC GACTACTGGG GCCAGGGCAC CACACTGACC
      GCCGGACTGG TCGCTCCTGT CGCGGCACAT GAAGACGCGG TCCCTGATGA TGCCGTGGTC GATGTTGAAG CTGATGACCC CGGTCCCGTG GTGTGACTGG
                                                                      CE7R scFv
```

FIG. 11 (Continued)

```
2501  GTGAGCAGCCG GCCGGAGGGGG CTCTGGCGGC GGAGGATCTG GGGGAGGGGG CAGATGACCC AGAGCAGCAG CAGCTTCAGC GTGAGCCTGG
      CACTCGTCGC CGGCCTCCCC CGAGACCGCC CCTCCTAGAC CCCCTCCCCC GTCGCTGTAG GTCCGTCGTC TCGGAAGTCG CACTCGGACC
                                                CE7R scFv
2601  GCGACCGGGT GACCATCACC TGTAAGGCCA ACGAGGACAT CAACAACCGG CTGGCCTGGT ATCAGCAGAC CCCCGGCAAC AGCCCCAGGC TGCTGATCAG
      CGCTGGCCCA CTGGTAGTGG ACATTCCGGT TGCTCCTGTA GTTGTTGGCC GACCGGACCA TAGTCGTCTG GGGGCCGTTG TCGGGGTCCG ACGACTAGTC
                                                CE7R scFv
2701  CGGCGCCACC AACCTGGTGA CCGGGGTGCC CAGCCGGTTT AGCGGCAGCG GCTCCGGCAA GGACTACACC CTGACCATCA GCAGCCTGCA GGCCGAGGAC
      GCCGCGGTGG TTGGACCACT GGCCCCACGG GTCGGCCAAA TCGCCGTCGC CGAGGCCGTT CCTGATGTGG GACTGGTAGT CGTCGGACGT CCGGCTCCTG
                                                CE7R scFv                                                  IgG4 Hinge
2801  TTTGCCACCT ACTACTGCCA GCAGTACTGG TCCACCCCCT TCAACTTCGG CAGCGGCACC GAGCTGGAAA TCAAAGAATC TAAGTACGGA CCGCCCTGCC
      AAGCGGTGGA TGATGACGGT CGTCATGACC AGGTGGGGGA AGTTGAAGCC GTCGCCGTGG CTCGACCTTT AGTTTCTTAG ATTCATGCCT GGCGGGACGG
              IgG4 Hinge                                                                                    CD28gg
2901  CCCCTTGCCC TATGTTCTCG GTGCTGGTGG TGGTCGGAGG CGTGCTGGCC TGCTACAGCC CGTGGCCTTC ATCATCTTTT GGGTCCGCAG
      GGGGAACGGG ATACAAGAGC CACGACCACC ACCAGCCTCC GCACGACCGG ACGATGTCGG GCACCGGAAG TAGTAGAAAA CCCAGGCGTC
        CD28gg                                                                   CD28tm
3001  CAAGCGGAGC AGAGGCGGGC ACAGCGGACTA CATGAACATG GACCTGCGGC CACCAGAAAG CCTACGCGCC CCTACGGCCC TCCCCGGGAC
      GTTCGCCTCG TCTCCGCCCG TGTCGCCTGAT GTACTTGTAC CCGGACGCCG GTGGTCTTTC GGATGCGCGG GGATGCCGGG AGGGGCCCTG
        CD28gg                                                                           4-1BB
3101  TTTGCCGGCCT ACAGAAGCAA ACGGGGCAGA AAGAAACTCC TGTATATATT CAAACAACCA CAGTACAAAC TACTCAAGAG GAAGATGGCT
      AAACGGCCGGA TGTCTTCGTT TGCCCCGTCT TTCTTTGAGG ACATATATAA GTTTGTTGGT GTCATGTTTG ATGAGTTCTC CTTCTACCGA
         4-1BB                                                                       Zeta
3201  GTAGCGGCCG ATTTCCAGAA GAAGAAGAAG GAGGATGTGA ACTGCGGGTG AAGTTCAGCA CGCCCCTGCC TACCAGCAGG GCCAGAATCA
      CATCGACGGC TAAAGGTCTT CTTCTTCTTC CTCCTACACT TGACGCCCAC TTCAAGTCGT GCGGGGACGG ATGGTCGTCC CGGTCTTAGT
                                                Zeta
3301  GCTGTACAAC GAGCTGAACC TGGGCAGAAG GGAAGAGTAC GACGTCCTGG ATAAGCGGAG AGGCCGGGAC CCTGAGATGG GCGGCAAGCC TCGGCGGAAG
      CGACATGTTG CTCGACTTGG ACCCGTCTTC CCTTCTCATG CTGCAGGACC TATTCGCCTC TCCGGCCCTG GGACTCTACC CGCCGTTCGG AGCCGCCTTC
                                                        Zeta
3401  AACCCCCAGG AAGGCCTGTA TAACGAACTG CAGAAGGACA AGATGGCCGA GGCCTACAGC GAGATCGGCA TGAAGGGCGA GCGGAGGCGG GGCAAGGGCC
      TTGGGGGTCC TTCCGGACAT ATTGCTTGAC GTCTTCCTGT TCTACCGGCT CCGGATGTCG CTCTAGCCGT ACTTCCCGCT CGCCTCCGCC CCGTTCCCGG
                                                            Zeta                                               T2A
```

FIG. 11 (Continued)

```
                     Zeta
3501 ACGACGGGCCT GTATCAGGGC CTGGTCCACCG CCACCAAGGA TACCTACGAC GCCCTGCACA TGCAGGCCCT GCCCCCAAGG CTCGAGGGCG GCGGAGAGGG
     TGCTGCCCGGA CATAGTCCCG GACCAGGTGGC GGTGGTTCCT ATGGATGCTG CGGGACGTGT ACGTCCGGGA CGGGGGTTCC GAGCTCCCGC CGCCTCTCCC
                                    T2A                                                        EGFRt
3601 CAGAGGAAGT CTTCTAACAT GCGGTGACGT GGAGAGAAT CCCGGCCCTA GGATGCTTCT CCTGGTGACA AGCCTTCTGC TCTGTGAGTT ACCACACCCA
     GTCTCCTTCA GAAGATTGTA CGCCACTGCA CCTCCTCTTA GGGCCGGGAT CCTACGAAGA GGACCACTGT TCGGAAGACG AGACACTCAA TGGTGTGGGT 3701 GCATTCCTCC TGATCCCACG CAAAGTGTGT GTATTGGTGA ATTTAAAGAC TCACTCTCCA TAAATGCTAC GAATATTAAA CACTTCAAAA
     CGTAGGAGG  ACTAGGGTGC GTTTCACACA CATAACCACT TAAATTTCTG AGTGAGAGGT ATTTACGATG CTTATATAATT GTGAAGTTTT 3801 ACTGCACCTC CATCAGTGGC GATCTCCACA TCCTGCCGGT GGCATTTAGG GGTGACTCCT TCACACATAC TCCTCCTCTG GATCCACAGG AACTGGATAT
     TGACGTGGAG GTAGTCACCG CTAGAGGTGT AGGACGGCCA CCGTAAATCC CCACTGAGGA AGTGTGTATG AGGAGGAGAC AGTAGGTGTCC TTGACCTATA 3901 TCTGAAAACC GTAAAGGAAA TCACAGGGTT TTTGCTGATT CAGGCTTGGC CTGAAAACAG GACGGACCTC CATGCCTTTG AGAACCTAGA AATCATACGC
     AGACTTTTGG CATTTCCTTT AGTGTCCCAA AAACGACTAA GTCCGAACCG GACTTTTGTC CTGCCTGGAG GTACGGAAAC TCTTGGATCT TTAGTATGCG 4001 GGCAGGACCA AGCAACATGG TCAGTTTTCT CTTGCAGTCG TCAGCCTGAA CATAACATCC TTGGGATTAC GCTCCCTCAA GGAGATAAGT GATGGAGATG
     CCGTCCTGGT TCGTTGTACC AGTCAAAAGA GAACGTCAGC AGTCGGACTT GTATTGTAGG AACCCTAATG CGAGGGAGTT CCTCTATTCA CTACCCTCAC
                                                                                                   EGFRt
4101 TGATAATTTC AGGAACATGG AATTGTGCT ATGCAAATAC AAAAAACTGT TTGGACCTC CGGTCAGAAA ACCAAAATTA TAAGCAACAG
     ACTATTAAAG TCCTTGTATT TTAAACACGA TACGTTTATG TTATTTGACC AAACCCTGGAG GCCAGTCTTT TGGTTTTAAT ATTCGTTGTC
                                                                                                   EGFRt
4201 AGGTGAAAAC AGCTGCAAGG CCACAGGCCA ATGCGTGACG GGTCTGTGCT GCCCCGAGGG CTGCTGGGGC CCGGAGCCCA GGGACTGCCT CTCTTGCCGG
     TCCACTTTTG TCGACGTTCC GGTGTCCGGT TACGCACTGC CCAGACGTCA CGAGACACGA CGGGGCTCCC GACGACCCCG GGCCTCGGGT GAGAACGGCC
                                                                                                   EGFRt
4301 AATGTCAGCC GAGGCAGGGA CTCCGTGCGG AAGCCAACC TTCTGGAGGG TGAGCCAAGG AGTTTGTGG AGAACTCTGA GTGCATACAG TGCCACCCAG
     TTACAGTCGG CTCCGTCCCT GAGGCACGCC TTCGGTTGG AAGACCTCCC ACTCGGTTCC TCAAACACC TCTTGAGACT CACGTATGTC ACGGTGGGTC
                                                                                                   EGFRt
4401 AGTGCCTGCC TCAGGACGCC ACCACATCACT GGGACCAGACG AACTGTATCC AGTGTGCCCA CTACATTGAC GGCCCCACT GCGTCAAGAC CGCAGTTCTG
     TCACGGACGG AGTCCGGTAC TTGTAGTGGA CCCTGGTCCT TGTCCTGCTC AGTACATAGG TCACACGGGT GATGTAACTG CCGGGGTGA CGCAGTTCTG
                                                                                                   EGFRt
4501 CTGCCCGGCA GGAGTCATGG GAGAAACAA CACCCTGGTC TGGAAGTACG CAGACGCCGG CCATGTGTGC CACCTGTGCC ATCCAAACTG CACCTACGGA
     GACGGGCCGT CCTCAGTACC CTCTTTGTT GTGGGACCAG ACCTTCATGC GTCTGCGGCC GGTACACACG GTGGACACGG TAGGTTTGAC GTGGATGCCT
                                                                                                   EGFRt
```

```
5701  CAAGCTTATC GATACCGTCG ACCTCGAGGG GGGGCCCGGT ACCCAATTCG CCCTATAGTG AGTCGTATTA CAATTCACTG GCCGTCGTTT TACAACGTCG
      GTTCGAATAG CTATGGCAGC TGGAGCTCCC CCCCGGGCCA TGGGTTAAGC GGGATATCAC CCCTTTTCGC AGTCGTATTA CAATTCACTG GCCGTCGTTT ATGTTGCAGC
5801  TGACTGGGAA AACCCTGGCG TTACCCAACT TAATCGCCTT GCAGCACATC CCCTTTCGC  CAGCTGGCGT AATAGCGAAG CGGCAGCAAA CGATCGCCCT
      ACTGACCCCT TTGGGACCGC AATGGGTTGA ATTAGCGGAA CGTCGTGTAG GGGGAAAGCG GTCGACCGCA TTATCGCTTC AAATTTTTGT TAAATCAGCT CATTTTTTAA
5901  TCCCAACAGT TGCCGCAGCT GAATGGCGAA TGGCGCCTGA ACCTTTAACA TTCGCAGTTT AAGCGTTAAT TTTAAAAACA TTTAAAAACA TTTAAAAACA GTAAAAAATT
      AGGGTTGTCA ACGGCGTCGA CTTACGCCTT ACCTTTAGGT TCGGCAGTT  GAATAGACCG AGTGTTGTT  TTTAAAAACA TTTAAAAACA ACAAGAGTCC ACTATTAAAG
6001  CCAATAGGCC GAAATCGGCA AAATCCCTTA TTTAGGGAAT CTTATCTGGC CCAGTGTGTT CCAGTTTGGA GGTCAAACCT TGTTCTCAGG TGATAATTTC
      GGTTATCCGG CTTTAGCCGT CCAACGTCAA AGGGCGAAAA ACCGTCTATC AGGGCGATGG TCTACAACAA CCTAATCAAG TTTTTGGGG  TCGAGGTGCC
6101  AACGTGGACT CCAACGTCAA GGTTGCAGTT TCCCGCTTTT TGGCAGATAG TCCCGCTACC GGGTGATGCA CTTGGTAGTG GGATTAGTTC AAAAACCCC  AGCTCCACGG
      TTGCACCTGA GGTTGCAGTT AAATCGGAAC CCTAAAGGGA GCCCCGATT  TAGAGCTTGA CGGCGAACGT CGGCGAAAGC GAAGGAAGA  AAGCGAAAGG
6201  GTAAAGCACT TTTAGCCTTG GGATTTCCCT CGGGCTAA   ATCTCGAACT CGGGTAACCA CACACCCGC  GCCCTTTCG  CCGCTCTTTC TTCGCTTTCC
      CATTTTCGTGA AGGGCGCT   AGGGCGCCTG GGTCACGCTG CCAGTGCGAC CCAGTTGT   CGCCGTAAT  GCCCGCTTAT ACGGCCGTC  AGGTGGCACT
6301  ACGGGCCCGA TCCCGGCCGA AGGGGCGCT  AGGGCGCCTG GGTCACGCTG CCAGTGCGAC CCAGTTGT   GGTGTGGGCG TGCCGCCAG  TCCACCGTGA
      TCGCCCCGGA ATGTGCGGG  TCCCGGCCGA GTTCACATCG CCAGTGCGAC GCGATTGGT  TTCAAATATG GCGCGAATTA CGGGGCGATG TCCCGCGGGAG
6401  TTCTGGGGAA ATGTGCGCGG AACCCTATT  TGTTTATTT  TCTAAATACA TATCCGCTCA TGAGACAATA ACCCTGATAA ATGCTTCAAT
      AAAGCCCTT  TACACGCGCC TTGGGGATAA ACAAATAAAA AGATTTATGT AAGTTGTTAT ACTTCGTTAT ATAGGCGAGT TGGGACTATT TACGAAGTTA
                                                                                   Ampr
6501  AATATTGAAA AAGGAAGAGT ATGAGTATTC AACATTTCCG TGTCGCCCTT ATTCCCTTT  TTTGCGCATT GTTTTTGCTC ACCCAGAAAC
      TTATAACTTT TTCCTTCTCA TACTCATAAG TTGTAAAGGC ACAGCGGGAA TAAGGGAAAA AAGGGAAA   AACGCCGTAA CAAAACGAG  TGGGTCTTTG
                            Ampr
6601  GCTGGTGAAA GTAAAAGATG CTGAAGATCA GTTGGGTGCA CGAGTGGGTT ACATCGAACT GGATCTCAAC AGCGGTAAGA TCCTTGAGAG TTTTCGCCCC
      CGACCACTTT CATTTTCTAC GACTTCTAGT CAACCCACGT GCTCACCCAA TGTAGCTTGA CCTAGAGTTG TCGCCATTCT AGGAACTCTC AAAAGCGGGG
                            Ampr
6701  GAAGAACGTT TTCCAATGAT GAGCACTTTT AAAGTTCTGC TATGTGGCGC GGTATTATCC CGTATTGACG CCGGGCAAGA GCAACTCGGT CGCCGCATAC
      CTTCTTGCAA AAGGTTACTA CTCGTGAAAA TTTCAAGACG ATACACCGCG CCATAATAGG GCATAACTGC GGCCCGTTCT CGTTGAGCCA GCGGCGTATG
                            Ampr
6801  ACTATTCTCA GAATGACTTG GTTGAGTACT CACCAGTACT CAGAAAAGCAT CTTACGGATG GCATGACAGT AAGAGAATTA TGCAGTGCTG CCATAACCAT
      TGATAAGAGT CTTACTGAAC CAACTCATGA GTGGTCATGA TCTTTTCGTA GAATGCCTAC CGTACTGTCA TTCTCTTAAT ACGTCACGAC GGTATTGGTA
                            Ampr
6901  GAGTGATAAC ACTGCGGCCA ACTTACTTCT GACAACGATC GGAGGACCGA AGGAGCTAAC CGCTTTTTTG CACACACATG GGGATCATGT AACTCGCCTT
      CTCACTATTG TGACGCCGGT TGAATGAAGA CTGTTGCTAG CCTCCTGGCT TCCTCGATTG GCGAAAAAAC GTGTGTACC  CCCTAGTACA TTGAGCGGAA
                            Ampr
7001  GATCGTTGGG AACCGGAGCT GAATGAAGCC ATACCAAACG ACGAGCGTGA CACCACGATG CCTGTAGCAA TGGCAACAAC GTTGCGCAAA CTATTAACTG
      CTAGCAACCC TTGGCCTCGA CTTACTTCGG TATGGTTTGC TGCTCGCACT GTGGTGCTAC GGACATCGTT ACCGTTGTTG CAACGCGTTT GATAATTGAC
                            Ampr
7101  GCGAACTACT TACTCTAGCT TCCCGGCAAC AATTAATAGA CTGGATGGAG GCGGATAAAG TTGCAGGACC ACTTCTGCGC TCGGCCCTTC CGGCTGGCTG
      CGCTTGATGA ATGAGATCGA AGGGCCGTTG TTAATTATCT TTAATTATCT GACCTACCTC CGCCTATTTC AACGTCCTGG TGAAGACGCG AGCCGGGAAG GCCGACCGAC
```

FIG. 11 (Continued)

```
                          Ampr
7201  GTTTATTGCT GATAAATCTC GAGCCGGTGA GCGTGGGTCT CGCGGTATCA TTGCAGCACT GGGGCCAGAT GGTAAGCCCT CCCGTATCGT AGTTATCTAC
      CAAATAACGA CTATTTAGAG CTCGGCCACT CGCACCCAGA GCGCCATAGT AACGTCGTGA CCCCGGTCTA CCATTCGGGA GGGCATAGCA TCAATAGATG
                    Ampr
7301  ACGACGGGGA GTCAGGCAAC TATGGATGAA CGAAATAGAC AGATCGCTGA GATAGGTGCC TCACTGATTA AGCATTGGTA ACTGTCAGAC CAAGTTTACT
      TGCTGCCCCT CAGTCCGTTG ATACCTACTT GCTTTATCTG TCTAGCGACT CTATCCACGG AGTGACTAAT TCGTAACCAT TGACAGTCTG GTTCAAATGA
                                                                           CoE1 Ori
7401  CATATATACT TTAGATTGAT TTAAAACTTC ATTTTTAATT TAAAAGGATC TAGGTGAAGA TCCTTTTTGA TAATCTCATG ACCAAATCCC CTTAACGTGA
      GTATATATGA AATCTAACTA AATTTTGAAG TAAAAATTAA ATTTTCCTAG ATCCACTTCT AGGAAAAACT ATTAGAGTAC TGGTTTAGGG GAATTGCACT
                                                                CoE1 Ori
7501  GTTTTCGTTC CACTGAGCGT CAGACCCCGT AGAAAAGATC AAAGGATCTT CTTGAGATCC TTTTTTTCTG CGCGTAATCT GCTGCTTGCA AACAAAAAAA
      CAAAAGCAAG GTGACTCGCA GTCTGGGGCA TCTTTTCTAG TTTCCTAGAA GAACTCTAGG AAAAAAAGAC GCGCATTAGA CGACGAACGT TTGTTTTTTT
                                                               CoE1 Ori
7601  CCACCGCTAC CAGCGGTGGT TTGTTTGCCG GATCAAGAGC TACCAACTCT TTTTCCGAAG GTAACTGGCT TCAGCAGAGC GCAGATACCA AATACTGTTC
      GGTGGCGATG GTCGCCACCA AACAAACGGC CTAGTTCTCG ATGGTTGAGA AAAAGGCTTC CATTGACCGA AGTCGTCTCG CGTCTATGGT TTATGACAAG
                                                               CoE1 Ori
7701  TTCTAGTGTA GCCGTAGTTA GGCCACCACT TCAAGAACTC TGTAGCACCG CCTACATACC TCGCTCTGCT AATCCTGTTA CCAGTGGCTG CTGCCAGTGG
      AAGATCACAT CGGCATCAAT CCGGTGGTGA AGTTCTTGAG ACATCGTGGC GGATGTATGG AGCGAGACGA TTAGGACAAT GGTCACCGAC GACGGTCACC
                                                               CoE1 Ori
7801  CGATAAGTCG TGTCTTACCG GGTTGGACTC AAGACGATAG TTACCGGATA AGGCGCAGCG GTCGGGCTGA ACGGGGGGTT CGTGCACACA GCCCAGCTTG
      GCTATTCAGC ACAGAATGGC CCAACCTGAG TTCTGCTATC AATGGCCTAT TCCGCGTCGC CAGCCCGACT TGCCCCCCAA GCACGTGTGT CGGGTCGAAC
                                                               CoE1 Ori
7901  GAGCGAACGA CCTACACCGA ACTGAGATAC CTACAGCGTG AGCTATGAGA AAGCGCCACG CTTCCCGAAG GGAGAAAGGC GGACAGGTAT CCGGTAAGCG
      CTCGCTTGCT GGATGTGGCT TGACTCTATG GATGTCGCAC TCGATACTCT TTCGCGGTGC GAAGGGCTTC CCTCTTTCCG CCTGTCCATA GGCCATTCGC
                                                               CoE1 Ori
8001  GCAGGGTCGG AACAGGAGAG CGCACGAGGG AGCTTCCAGG GGGAAACGCC TGGTATCTTT ATAGTCCTGT CGGGTTTCGC CACCTCTGAC TTGAGCGTCG
      CGTCCCAGCC TTGTCCTCTC GCGTGCTCCC TCGAAGGTCC CCCTTTGCGG ACCATAGAAA TATCAGGACA GCCCAAAGCG GTGGAGACTG AACTCGCAGC
                                                               CoE1 Ori
8101  ATTTTTGTGA TGCTCGTCAG GGGGGCGGAG CCTATGGAAA AACGCCAGCA ACGCGGCCTT TTTACGGTTC CTGGCCTTTT GCTGGCCTTT TGCTCACATG
      TAAAAACACT ACGAGCAGTC CCCCCGCCTC GGATACCTTT TGCGGTCGT TGCGCCGGAA AAATGCCAAG GACCGGAAAA CGACCGGAAA ACGAGTGTAC
                                                               CoE1 Ori
8201  TTCTTTTCCTG CGTTATCCCC TGATTCTGTG GATAACCGTA TTACCGCCTT TGAGTGAGCT GATACCGCTC GCCGCAGCCG AACGACCGAG CGCAGCGAGT
      AAGAAAAGGAC GCAATAGGGG ACTAAGACAC CTATTGGCAT AATGGCGGAA ACTCACTCGA CTATGGCGAG CGGCGTCGGC TTGCTGGCTC GCGTCGCTCA
        CoE1 Ori
8301  CAGTGAGCGA GGAAGCGGAA GAGCGCCCAA TACGCAAACC GCCTCTCCCC GCGCGTTGGC CGATTCATTA ATGCAGCTGG CACGACAGGT TTCCCGACTG
      GTCACTCGCT CCTTCGCCTT CTCGCGGGTT ATGCGTTTGG CGGAGAGGGG CGCGCAACCG GCTAAGTAAT TACGTCGACC GTGCTGTCCA AAGGGCTGAC
8401  GAAAGCGGGC AGTGAGCGCA ACGCAATTAA TGTGAGTTAG CTCACTCATT AGGCACCCCA GGCTTTACAC TTTATGCTTC CGGCTCGTAT GTTGTGTGGA
      CTTTCGCCCG TCACTCGCGT TGCGTTAATT ACACTCAAATC GAGTGAGTAA TCCGTGGGGT CCGAAATGTG AAATACGAAG GCCGAGCATA CAACACACCT
```

FIG. 11 (Continued)

```
8501  ATTGTGAGCG GATAACAATT TCACACAGGA AACAGCTATG ACCATGATTA CGCCAAGCTC GAAATTAACC CTCACTAAAG GGAACAAAAG CTGGAGCTCC
      TAACACTCGC CTATTGTTAA AGTGTGTCCT TTGTCGATAC TGGTACTAAT GCGGTTCGAG CTTTAATTGG GAGTGATTTC CCTTGTTTTC GACCTCGAGG
                                                                     SV40

8601  ACCGCGGTGG CGGCCTCGAG GTCGAGATCC GGTCGACCAG CAACCATAGT CCCGCCCCTA ACTCCGCCCA TCCCGCCCCT AACTCCGCCC AGTTCCGCCC
      TGGCGCCACC GCCGGAGCTC CAGCTCTAGG CCAGCTGGTC GTTGGTATCA GGGCGGGGAT TGAGGCGGGT AGGGCGGGGA TTGAGGCGGG TCAAGGCGGG
                                                              SV40

8701  ATTCTCCGCC CCATGGCTGA CTAATTTTTT TTATTTATGC AGAGGCCGAG GCCGCCTCGG CCTCTGAGCT ATTCCAGAAG TAGTGAGGAG GCTTTTTTGG
      TAAGAGGCGG GGTACCGACT GATTAAAAAA AATAAATACG TCTCCGGCTC CGGCGGAGCC GGAGACTCGA TAAGGTCTTC ATCACTCCTC CGAAAAAACC
              SV40                                                                          CMV

8801  AGGCCTAGGC TTTTGCAAAA AGCTTCGACG GTATCGATTG GCTCATGTCC AACATTACCG CCATGTTGAC ATTGATTATT GACTAGTTAT TAATAGTAAT
      TCCGGATCCG AAAACGTTTT TCGAAGCTGC CATAGCTAAC CGAGTACAGG TTGTAATGGC GGTACAACTG TAACTAATAA CTGATCAATA ATTATCATTA
                                                                 CMV

8901  CAATTACGGG GTCATTAGTT CATAGCCCAT ATATGGAGTT CCGCGTTACA TAACTTACGG TAAATGGCCC GCCTGGCTGA CCGCCCAACG ACCCCCGCCC
      GTTAATGCCC CAGTAATCAA GTATCGGGTA TATACCTCAA GGCGCAATGT ATTGAATGCC ATTTACCGGG CGGACCGACT GGCGGGTTGC TGGGGGCGGG
                                                                 CMV

9001  ATTGACGTCA ATAATGACGT ATGTTCCCAT AGTAACGCCA ATAGGGACTT TCCATTGACG TCAATGGGTG GAGTATTTAC GGTAAACTGC CCACTTGGCA
      TAACTGCAGT TATTACTGCA TACAAGGGTA TCATTGCGGT TATCCCTGAA AGGTAACTGC AGTTACCCAC CTCATAAATG CCATTTGACG GGTGAACCGT
                                                                 CMV

9101  GTACATCAAG TGTATCATAT GCCAAGTACG CCCCCTATTG ACGTCAATGA CGGTAAATGG CCCGCCTGGC ATTATGCCCA GTACATGACC TTATGGGACT
      CATGTAGTTC ACATAGTATA CGGTTCATGC GGGGGATAAC TGCAGTTACT GCCATTTACC GGGCGGACCG TAATACGGGT CATGTACTGG AATACCCTGA
                                                                 CMV

9201  TTCCTACTTG GCAGTACATC TACGTATTAG TCATCGCTAT TACCATGGTG ATGCGGTTTT GGCAGTACAT CAATGGGCGT GGATAGCGGT TTGACTCACG
      AAGGATGAAC CGTCATGTAG ATGCATAATC AGTAGCGATA ATGGTACCAC TACGCCAAAA CCGTCATGTA GTTACCCGCA CCTATCGCCA AACTGAGTGC
                                                                 CMV

9301  GGGATTTCCA AGTCTCCACC CCATTGACGT CAATGGGAGT TTGTTTTGGC ACCAAAATCA ACGGGACTTT CCAAAATGTC GTAACAACTC CGCCCCATTG
      CCCTAAAGGT TCAGAGGTGG GGTAACTGCA GTTACCCTCA AACAAAACCG TGGTTTTAGT TGCCCTGAAA GGTTTTACAG CATTGTTGAG GCGGGGTAAC
             CMV

9401  ACGCAAATGG GCGGTAGGCG TGTACGGTGG GAGGTCTATA TAAGCAGCTG ATCCTGCATA TAAGCAGCTG CTTTTTGCCT GTACTGGGTC TCTCTG
      TGCGTTTACC CGCCATCCGC ACATGCCACC CTCCAGATAT ATTCGTCGAC TAGGACGTAT ATTCGTCGAC GAAAAACGGA CATGACCCAG AGAGAC
```

FIG. 11 (Continued)

CD3,Ki67,Caspase 3,Hoechst

FIG. 14F1

Cd3, Ki67, Caspase 3, Hoechst

FIG. 14F2

Panel A

Panel B

METHOD AND COMPOSITIONS FOR CELLULAR IMMUNOTHERAPY

RELATED APPLICATIONS

The present application is a U.S. National Phase Application of PCT International Application Number PCT/US2015/024882, filed on Apr. 8, 2015, designating the United States of America and published in the English language which claims the benefit of priority to U.S. Provisional Patent Application No. 61/977,751, filed Apr. 10, 2014, U.S. Provisional Patent Application No. 61/986,479, filed Apr. 30, 2014, U.S. Provisional Patent Application No. 62/058,973, filed Oct. 2, 2014, U.S. Provisional Patent Application No. 62/088,363, filed Dec. 5, 2014, U.S. Provisional Patent Application No. 62/089,730 filed Dec. 9, 2014, and U.S. Provisional Patent Application No. 62/090,845, filed Dec. 11, 2014. The entire disclosures of the aforementioned applications are expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SCRI065NPSUBSEQLIST.TXT, the date of creation of the ASCII text file is Oct. 10, 2019, and the size of the ASCII text file is about 68 kb.

FIELD OF THE INVENTION

The present application relates to the field of biomedicine and specifically methods and compositions for use in cellular immunotherapy, including those useful for cancer therapy. In particular, alternatives of the invention relate to methods and compositions for carrying out cellular immunotherapy comprising T cells modified with tumor targeting receptors.

BACKGROUND OF THE INVENTION

Approaches to cancer immunotherapy, whereby T cells are genetically modified to express synthetic chimeric antigen receptors (CARs), are the subject of considerable early phase human clinical trials. Whereas dramatic anti-tumor potency is observed in patients treated with CD19-specific or CD19-targeting CAR T cells for B cell lineage malignancies, such as acute lymphoblastic leukemia and non-Hodgkin lymphomas, the challenges to achieve similar responses in patients harboring solid tumors are considerable. At present, the development and clinical testing of CAR redirected T cell adoptive therapy in cancer patients is largely empiric and constrained by a variety of technical parameters that impact feasibility of executing clinical phase I trials involving heavily pretreated patients with bulky refractory tumors. Two parameters related to cell products that can be defined with greater precision are T lymphocyte subset composition and the tuning of CAR signaling for functional outputs that maximize their anti-tumor activity. In some alternatives, the therapeutic activity of CAR-expressing central memory T cells has been examined and shown that a stable antigen-experienced component of the T cell repertoire having stem cell like features has the capacity to repopulate long lived functional memory niches following adoptive transfer. Anti-CD19 CAR-expressing cells have been produced, following enrichment for $CD45RO^+$ $CD62L^+$ $T_{CM}$ cells using immunomagnetic selection, and assessed in the clinic.

Moving beyond the targeting of CD19 expressing B cell malignancies, a challenge for the field can be identifying and vetting of cell surface target molecules on tumor cells that are amenable to CAR T cell recognition with tolerable "on" target "off" tumor reactivity. Once identified, however, approaches to tune new CARs for signaling outputs that are compatible with CD4 and CD8 T cell activation have not been entirely satisfactory. Parameters that are generally perceived as central to CAR development are the affinity of the target molecule CAR antigen binding domain, typically but not exclusively an antibody scFv, and the signaling modules of the cytoplasmic domain.

There is a need to identify methods for determining elements of chimeric receptor design that are important for therapeutic activity, and to enhance or improve chimeric receptors for targeting specific antigens, and cell populations to genetically modify and adoptively transfer that provide enhanced survival and efficacy in vivo. Among the provided alternatives are those addressing such needs.

SUMMARY OF THE INVENTION

Despite the therapeutic efficacy of chimeric antigen receptor (CAR) redirected T cell immunotherapy in leukemia and lymphoma patients, methods and compositions are needed to achieve similar clinical responses in solid tumors. CAR development can in some cases be biased towards selecting constructs that elicit the highest magnitude of T cell functional outputs, for example, based on in vitro readouts. Different CAR extracellular spacers and cytoplasmic signaling domain variants can be combined to tune the magnitude of CD8+ CTL activation for tumor cell cytolysis and cytokine secretion. In studies described herein, CAR constructs that displayed the highest activity in such in vitro assays also displayed the lowest anti-tumor activity in vivo, whereas CARs tuned for moderate signaling potency mediated tumor inactivation and/or eradication. It was observed that recursive CAR triggering can have rendered CTLs expressing hyperactive CARs highly susceptible to activation induced cell death (AICD) possibly as a result of augmented FasL expression. CAR tuning using combinations of extracellular spacers and cytoplasmic signaling modules, e.g., by varying properties of such portions independently, in order to limit AICD, can promote enhanced or improved clinical activity against solid tumors. Described herein are impacts of features of the extracellular spacer joining the antigen binding and transmembrane domains, such as length of the spacer, in contributing to CAR T cell performance. In some alternatives, CAR spacers are selected in order to adjust and/or enhance or improve the biophysical synapse distance between the CAR-expressing cell, e.g., T cell, and targeted cell, e.g., tumor cell, for example, to achieve a synapse distance compatible with and/or optimal for immune cell, e.g., T cell, activation.

The alternatives described herein relate to the respective contributions of both extracellular spacer length and cytoplasmic signaling moiety selection on the performance of a CAR that can target and/or is specific for a tumor selective epitope on CD171 (L1-CAM) that is recognized by monoclonal antibody CE7 and has been tested as a first generation CAR in a clinical pilot study. Using in vitro functional assays for CAR redirected effector potency, a quantitative hierarchy of effector outputs based on spacer dimension in the context of second and third generation cytoplasmic signaling domains was observed. In one alternative, a striking discordance in CAR T cell performance in vitro versus in vivo due to activation induced cell death (AICD) of the most functionally potent CAR formats was shown. These alternatives reveal clinically relevant parameters for inspection in the development of CAR T cell immunotherapy for solid tumors. Given that each new scFv and target molecule defines a unique distance from the tumor cell plasma membrane, the adjustment of CAR spacers are unique to each construct and derive via empiric testing of libraries of spacer length variants.

In one aspect, the present disclosure relates to methods and compositions to confer and/or augment immune responses mediated by cellular immunotherapy, such as by adoptively transferring tumor-specific, genetically modified populations of immune cells, such as genetically modified subsets of CD8+ or CD4+ T cells alone, or in combination. The disclosure provides for chimeric receptor nucleic acids, and vectors and host cells including such nucleic acids, as well as chimeric receptors encoded thereby. The nucleic acid sequence that encodes such a chimeric receptor generally links together a number of modular components that can be excised and replaced with other components in order to customize a chimeric receptor that can target and/or is specific for efficient cell activation and recognition of a specific target molecule or an epitope on the target molecule.

Adoptive immunotherapy using chimeric antigen receptor (CAR) expressing cells can be useful for treating, ameliorating, and/or inhibiting proliferation of a cancer. In some alternatives, a CAR directed to an epitope of the antigen CD171 (L1CAM) is used. Such CAR constructs are useful to treat, ameliorate, or inhibit any disease or disorder or malignancy in which cells express CD171. In some alternatives, the disease or disorder is a cancer or tumor that expresses CD171 (L1CAM). In some alternatives, the cancer that expresses CD171 is neuroblastoma (NB). CD171 is expressed in 100% of high risk NB. Other cancers that express CD171 include melanoma, cervical carcinoma, ovarian cancer, uterine carcinoma, pancreatic cancer, colon carcinoma, renal carcinoma, and glioblastoma.

CD171, also known as L1CAM, is a 200-kDa transmembrane glycoprotein. It is a neuronal cell adhesion molecule involved in axon guidance and cell migration, with a strong implication in treatment-resistant cancer. CD171 belongs to the immunoglobulin superfamily of recognition molecules, and participates in heterophilic interactions with other adhesion molecules such as laminin, integrins, proteoglycans and CD24. In some alternatives, CD171 comprises, consists essentially of or consists of an epitope that is predominantly found on tumor cells. In some alternatives, the epitope is found on the extracellular domain of a glycosylated CD171 and not found on unglycosylated CD171. In some alternatives, the epitope is referred to as CE7 or the epitope recognized by the antibody deemed CE7.

Neuroblastoma is the most common extracranial solid tumor that arises during infancy. It is an embryonal malignancy of the sympathetic nervous system arising from neuroblasts (pluripotent sympathetic cells). In the developing embryo, these cells invaginate, migrate along the neuraxis, and populate the sympathetic ganglia, adrenal medulla, and other sites. The patterns of distribution of these cells correlate with the sites of primary neuroblastoma presentation. Age, stage, and biological features encountered in tumor cells are important prognostic factors and are used for risk stratification and treatment assignment. The differences in outcome for patients with neuroblastoma are striking. Patients with low-risk and intermediate-risk neuroblastoma have excellent prognosis and outcome. However, those with high-risk disease continue to have very poor outcomes despite intensive therapy. Unfortunately, approximately 70-80% of patients older than 18 months present with metastatic disease, usually in the lymph nodes, liver, bone, and bone marrow. Less than half of these patients are cured, even with the use of high-dose therapy followed by autologous bone marrow or stem cell rescue. Thus, the CAR transduced lymphocytes described herein are useful in the treatment, amelioration, or inhibition of neuroblastoma in subjects.

In some alternatives, a CAR directed to CD171 comprises components that enhance the in vivo activity and/or survival and/or persistence of the CAR or cells expressing the same. In some alternatives, a ligand binding domain comprises an antibody or antigen binding fragment, which specifically binds and/or targets an epitope of CD171, such as one found more often on tumor cells than healthy cells. In other alternatives, a spacer region is included, which is a short extracellular spacer. In some alternatives, an intracellular signaling domain contains a single co-stimulatory domain and a single intracellular signaling domain, and excludes other signaling domains.

Some alternatives relate to a chimeric receptor nucleic acid that comprises a polynucleotide coding for a ligand binding domain, and/or chimeric receptors encoded by the same, wherein the ligand is a molecule expressed on cancer or tumor cells, a polynucleotide encoding a polypeptide spacer, a polynucleotide encoding a transmembrane domain; and a polynucleotide encoding an intracellular signaling domain. In some alternatives, the spacer joins or is found between the ligand binding domain and the transmembrane domain. In some alternatives, the polypeptide spacer comprises a hinge region, such as a hinge region from an antibody molecule, such as a hinge region containing an amino acid sequence $X_1PPX_2P$ (SEQ ID NO: 1). Such a hinge region may be linked to other amino acid sequences, including one or more constant regions of an antibody, including but not limited to CH2 and CH3 regions, e.g., CH3 only sequences, of the Ig Fc. It has been surprisingly found that the length of the spacer region can be customized for individual target molecules, for better tumor or target cell recognition and/or effector function and/or persistence of cells expressing the receptor, especially in vivo.

In some alternatives, the length of the spacer is less than or is at 229, 200, 150, 120, 119, 100, 50, 40, 30, 20, 19, 18, 17, 16, 15, 14, 13, or 12 amino acids in length (but not less than 2 or 1 amino acids in length) or a length within a range defined by any two of the aforementioned lengths. In some alternatives, the spacer length is at 15 or at 12 amino acids in length. In some alternatives, the spacer length is short, intermediate (also referred to herein as "medium"), or long. In some alternatives, the short, intermediate, or long spacer is the short, intermediate, or long spacer as shown in Tables 7 and 8.

In some alternatives, the length of the linker is determined or influenced by the distance of the epitope of the antigen to which the chimeric receptor binds, relative to the surface plasma membrane of the cell being targeted, such as the tumor cell.

In some alternatives, a CAR directed to CD171 comprises a polynucleotide encoding a short spacer region having 15 amino acids or less (but not less than 1 or 2 amino acids), such as 15, 14, 13, or 12 amino acids, or 15, 14, 13, 12, 11, 10, 9, 8, 7, 6, 5, 4, 3, or 2 amino acids or a length within a range defined by any two of the aforementioned lengths. In some alternatives, the short spacer comprises, consists essentially of, or consists of an amino acid sequence of X$_1$PPX$_2$P (SEQ ID NO: 1). In some alternatives, a CAR directed to an epitope of CD171 recognized by CE7, or an epitope having a similar distance on CD171 with respect to the surface plasma membrane, comprises a spacer region less than 100, 50, 40, 20, 15, or 12 amino acids in length, such as a short spacer region having 15 amino acids or less (but not less than 1 or 2 amino acids), such as 15, 14, 13, or 12 amino acids, or 11, 10, 9, 8, 7, 6, 5, 4, 3, or 2 amino acids or a length within a range defined by any two of the aforementioned lengths.

Another aspect of the disclosure provides an isolated chimeric receptor nucleic acid comprising: a polynucleotide coding for a ligand binding domain, wherein the ligand is a tumor specific antigen, or any other molecule expressed on a target cell population that is suitable to mediate recognition, inactivation and/or elimination by a lymphocyte; a polynucleotide coding for a polypeptide spacer, wherein the polypeptide spacer is of a customized length, wherein the spacer is optimized; a polynucleotide coding for a transmembrane domain; and a polynucleotide coding for one or more intracellular signaling domains. The disclosure includes expression vectors and host cells comprising the isolated chimeric receptor as described herein, as well. In some alternatives, the spacer is optimized for increased T cell proliferation and/or cytokine production in response to the ligand as compared to a reference chimeric receptor. In some alternatives, the host cell is a precursor T cell. In some alternatives, the host cell is a hematopoietic stem cell.

Another aspect of the disclosure provides a chimeric receptor polypeptide comprising a ligand binding domain, wherein the ligand is a tumor specific antigen or any other molecule that is expressed on a target cell population and can be targeted to mediate recognition and elimination by lymphocytes; a polypeptide spacer wherein the polypeptide spacer is 15 amino acids or less (but not less than 1 or 2 amino acids), such as 15, 14, 13, 12, 11, 10, 9, 8, 7, 6, 5, 4, 3, or 2 amino acids or a length within a range defined by any two of the aforementioned lengths; a transmembrane domain; and one or more intracellular signaling domains. In some alternatives, the polypeptide spacer comprises a hinge region containing the amino acid sequence X$_1$PPX$_2$P (SEQ ID NO: 1).

In another aspect, the present disclosure provides compositions to confer and/or augment immune responses mediated by cellular immunotherapy, such as by adoptively transferring tumor-specific, subset specific genetically modified CD4+ expressing T cells, wherein the CD4+ expressing T cells confer and/or augment the ability of CD8+ expressing T cells to sustain anti-tumor reactivity and increase and/or maximize tumor-specific proliferation. In some alternatives, the CD4+ expressing T cells are genetically modified to express a chimeric receptor nucleic acid and/or chimeric receptor polypeptide, as described herein.

In another aspect, the present disclosure provides compositions to confer and/or augment immune responses mediated by cellular immunotherapy, such as by adoptively transferring tumor-specific, subset specific genetically modified CD8+ expressing T cells. In some alternatives, the CD8+ expressing T cells express a chimeric receptor nucleic acid and/or chimeric receptor polypeptide, as described herein.

In another alternative, aspects of the present invention provide an adoptive cellular immunotherapy composition having a genetically modified CD8+ expressing cytotoxic T lymphocyte cell preparation to confer and/or augment immune responses, wherein the cytotoxic T lymphocyte cell preparation comprises CD8+ expressing T cells that express a chimeric receptor comprising a ligand binding domain for a ligand associated with the disease or disorder, a customized spacer region, a transmembrane domain; and an intracellular signaling domain of a T cell or other receptors, such as a co-stimulatory domain, and/or a genetically modified helper T lymphocyte cell preparation, wherein the helper T lymphocyte cell preparation has CD4+ expressing T cells that express a chimeric receptor comprising an antibody variable domain that can target and/or is specific for the ligand associated with the disease or disorder, a customized spacer region, a transmembrane domain; and one or more intracellular signaling domains.

In some alternatives, the present disclosure provides a method of treating, ameliorating, or inhibiting a cancer, such as NB, in a patient, a method of inhibiting or delaying progression and/or metastasis of a cancer, such as NB, in a patient, a method of inhibiting or reducing the presence of a tumor or cancer cell, such as NB, in a patient, and/or a method of inhibiting or reducing a target population of CD171 expressing cells in a patient in need thereof. Such methods involve administering to said subject or said patient a genetically modified cytotoxic T lymphocyte cell preparation that provides a cellular immune response, wherein the cytotoxic T lymphocyte cell preparation comprises CD8+ expressing T cells that have a chimeric receptor encoded by a polynucleotide coding for a ligand binding domain, wherein the ligand is a tumor specific antigen, or any other molecule expressed on a target cell population (e.g., CD171) that is suitable to mediate recognition and elimination by a lymphocyte; a polynucleotide coding for a polypeptide spacer, wherein the polypeptide spacer is of a customized length, wherein the spacer provides for enhanced T cell proliferation, enhanced in vivo cellular activities and/or cytokine production (e.g., in vivo) as compared to a reference chimeric receptor; a polynucleotide coding for a transmembrane domain; and a polynucleotide coding for one or more intracellular signaling domains.

In some alternatives, the ligand binding domain is an extracellular antibody variable domain that can target and/or is specific for a ligand associated with the disease or disorder. An alternative includes a genetically modified helper T lymphocyte cell preparation, wherein the helper T lymphocyte cell preparation comprises CD4+ expressing T cells that have a chimeric receptor comprising an a polynucleotide coding for a ligand binding domain, wherein the ligand is a tumor specific antigen or a tumor targeting antigen, or any other molecule expressed on a target cell population that is suitable to mediate recognition and elimination by a lymphocyte; a polynucleotide coding for a polypeptide spacer, wherein the polypeptide spacer is of a customized length, wherein the spacer provides for enhanced T cell proliferation, enhanced in vivo cellular activities and/or cytokine production as compared to a reference chimeric receptor; a polynucleotide coding for a transmembrane domain; and a polynucleotide coding for one or more intracellular signaling domains. In some alternatives, a ligand binding domain comprises an antibody or antigen binding fragment thereof, which can target and/or specifically bind an epitope of CD171 more often found on tumor cells rather than healthy cells. In other alternatives, a spacer region comprises a short extracellular spacer. In some alternatives, a signaling domain contains a single signaling domain and excludes other signaling domains.

In some alternatives, the genetically modified CD8+ and genetically modified CD4+ expressing T cell populations are co-administered. In some alternatives, the T cells are autologous or allogeneic T cells. Various modifications of the methods described herein are possible. For example, the chimeric receptor that is expressed by the CD4+ expressing T cell and the CD8+ expressing T cell can be the same or different.

Another alternative relates to a method of manufacturing an adoptive immunotherapy composition by obtaining a chimeric receptor modified tumor-specific or tumor-targeting CD8+ expressing cytotoxic T lymphocyte cell preparation that elicits a cellular immune response and expresses an antigen-reactive chimeric receptor, wherein the modified cytotoxic T lymphocyte cell preparation comprises CD8+ expressing T cells that have a chimeric receptor comprising a ligand binding domain, wherein the ligand is a tumor specific antigen or tumor targeting antigen, or any other molecule expressed on a target cell population that is suitable to mediate recognition and elimination by a lymphocyte; a polypeptide spacer, wherein the polypeptide spacer is of a customized length, wherein the spacer provides for enhanced T cell proliferation, enhanced in vivo cellular activities and/or cytokine production, as compared to a reference chimeric receptor; a transmembrane domain; and one or more intracellular signaling domains; and/or obtaining a modified naïve or memory CD4+ expressing T helper cell, wherein the modified helper T lymphocyte cell preparation comprises CD4+ expressing cells that have a chimeric receptor comprising a ligand binding domain, wherein the ligand is a tumor specific antigen or a tumor targeting antigen, or any other molecule expressed on a target cell population that is suitable to mediate recognition and elimination by a lymphocyte; a polypeptide spacer, wherein the polypeptide spacer is of a customized length, wherein the spacer is optimized; a transmembrane domain; and one or more intracellular signaling domains. In some alternatives, the spacer is optimized for increased T cell proliferation and/or cytokine production in response to the ligand as compared to a reference chimeric receptor. In some alternatives, a ligand binding domain comprises an antibody or antigen binding fragment, which specifically binds and/or targets an epitope of CD171 more often found on tumor cells rather than healthy cells. In other alternatives, a spacer region comprises a short extracellular spacer, which can be 15 amino acids or less (but not less than 1 or 2 amino acids), such as 15, 14, 13, 12, 11, 10, 9, 8, 7, 6, 5, 4, 3, or 2 amino acids or a length within a range defined by any two of the aforementioned lengths. In some alternatives, a signaling domain contains a single signaling domain and excludes other signaling domains.

Some alternatives also relate to a nucleic acid encoding a chimeric receptor. In some alternatives, said nucleic acid comprises: a) a polynucleotide coding for a ligand binding domain, wherein the ligand binding domain binds to and/or targets CD171, b) a polynucleotide coding for a polypeptide spacer interposed between the ligand binding domain and a transmembrane domain, c) a polynucleotide coding for the transmembrane domain, and d) a polynucleotide coding for an intracellular signaling domain, wherein expression of the chimeric receptor in a population of immune cells results in increased survival and/or persistence of the immune cells over time, following encounter with CD171 and/or an increase in therapeutic efficacy, upon administration to a subject having a CD171-expressing tumor, said increase being relative to expression of said reference chimeric receptor having a longer polypeptide spacer. In some alternatives, the increased survival and/or persistence over time comprises a relative reduction in antigen-induced cell death as measured in an in vitro stress test assay, comprising exposing the cells expressing said chimeric receptor to cells expressing CD171 over multiple, successive rounds and/or the increased survival and/or persistence over time comprises an increase in persistence of the cells in vivo following administration to a subject having a CD171-expressing tumor and/or said longer polypeptide spacer is at least 2, 3, 4, 5, 6, 7, 8, 9, or 10 times greater in length. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer is less than or equal to 200, 150, 100, 50, or 20 amino acids in length (but not less than 1 or 2 amino acids) or a length within a range defined by any two of the aforementioned lengths.

Some alternatives relate to a chimeric receptor nucleic acid, wherein the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO: 17), ERKCCVECPPCP (SEQ ID NO: 18), ELKTPLGDTHTCPRCP (EPKSCDTPPPCPRCP)$_3$ (SEQ ID NO: 19), ESKYGPPCPSCP (SEQ ID NO: 20), ESKYGPPCPPCP (SEQ ID NO: 21), YGPPCPPCP (SEQ ID NO: 51), KYGPPCPPCP (SEQ ID NO: 52), or EVVKYGPPCPPCP (SEQ ID NO: 53). In some alternatives, the spacer consists of or consists essentially of ESKYGPPCPSCP (SEQ ID NO: 20), ESKYGPPCPPCP (SEQ ID NO: 21), YGPPCPPCP (SEQ ID NO: 51), KYGPPCPPCP (SEQ ID NO: 52), or EVVKYGPPCPPCP (SEQ ID NO: 53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, and NKG2C, B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence.

In some alternatives, a chimeric receptor nucleic acid is provided, wherein the chimeric receptor nucleic acid comprises a) a polynucleotide coding for a ligand binding domain, wherein the ligand binding domain binds to and/or targets CD171, b) a polynucleotide coding for a polypeptide spacer of a length, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence.

In some alternatives, a chimeric receptor polypeptide is provided, wherein the chimeric receptor polypeptide is coded for by a chimeric receptor nucleic acid. In some alternatives, the chimeric receptor nucleic acid comprises a) a polynucleotide coding for a ligand binding domain, wherein the ligand binding domain binds to and/or targets CD171, b) a polynucleotide coding for a polypeptide spacer of a length, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence.

In some alternatives, an expression vector comprising an isolated chimeric receptor nucleic acid is provided. In some alternatives, the chimeric receptor nucleic acid comprises a) a polynucleotide coding for a ligand binding domain, wherein the ligand binding domain binds to and/or targets CD171, b) a polynucleotide coding for a polypeptide spacer of a length, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence.

In some alternatives, a host cell comprising an expression vector is provided. In some alternatives, the expression vector comprises an isolated chimeric receptor nucleic acid. In some alternatives, the chimeric receptor nucleic acid comprises a) a polynucleotide coding for a ligand binding domain, wherein the ligand binding domain binds to and/or targets CD171, b) a polynucleotide coding for a polypeptide spacer of a length, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and CD8+. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and CD4+ and negative for CD45RO. In some alternatives, the host cell is a precursor T cell. In some alternatives, the host cell is a hematopoietic stem cell.

In some alternatives, a composition comprising a host cell in a pharmaceutically acceptable excipient is provided. In some alternatives, the host cell comprises an expression vector. In some alternatives, the expression vector comprises an isolated chimeric receptor nucleic. In some alternatives, the chimeric receptor nucleic acid comprises a) a polynucleotide coding for a ligand binding domain, wherein the ligand binding domain binds to and/or targets CD171, b) a polynucleotide coding for a polypeptide spacer of a length, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and CD8+. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and CD4+ and negative for CD45RO. In some alternatives, the host cell is a precursor T cell. In some alternatives, the host cell is a hematopoietic stem cell. In some alternatives, the composition comprises a CD8+ T cytotoxic lymphocyte cell selected from the group consisting of naïve CD8+ T cells, central memory CD8+ T cells, effector memory CD8+ T cells and bulk CD8+ T cells or a central memory T cell wherein the central memory T cell is positive for CD45RO+, CD62L+, and CD8+ and another host cell wherein the host cell is a central memory T cell wherein the central memory T cell is positive for CD45RO+, CD62L+, and CD8+ or a CD4+ T helper lymphocyte cell is selected from the group consisting of naïve CD4+ T cells, central memory CD4+ T cells, effector memory CD4+ T cells, and bulk CD4+ T cells or a naïve CD4+ T cell, wherein the naïve CD4+ T cell is positive for CD45RA+, CD62L+ and CD4+ and negative for CD45RO.

In some alternatives, a method for preparing a host cell is provided wherein the method comprises a) providing a library of nucleic acids coding for a chimeric receptor, wherein each of the plurality of nucleic acids code for a chimeric receptor that differs in length, b) introducing each of the plurality of the nucleic acids into a separate isolated T lymphocyte population and expanding each T lymphocyte population in vitro. c) administering each genetically modified T lymphocyte population into an animal model bearing a tumor and determining whether a genetically modified T lymphocyte population has anti-tumor efficacy and d) selecting a nucleic acid coding for the chimeric receptor that provides for anti-tumor efficacy. In some alternatives, the host cell comprises an expression vector. In some alternatives, the expression vector comprises an isolated chimeric receptor nucleic. In some alternatives, the chimeric receptor nucleic acid comprises a) a polynucleotide coding for a ligand binding domain, wherein the ligand binding domain binds to and/or targets CD171, b) a polynucleotide coding for a polypeptide spacer of a length, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and CD8+. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and CD4+ and negative for CD45RO. In some alternatives, the host cell is a precursor T cell. In some alternatives, the host cell is a hematopoietic stem cell. In some alternatives, the chimeric receptor nucleic acid comprises a) a polynucleotide coding for a ligand binding domain, wherein the ligand binding domain binds to and/or targets CD171, b) a polynucleotide coding for a polypeptide spacer of a length, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the method further comprises introducing the selected nucleic acid coding for the chimeric receptor into a host cell.

In some alternatives, a method for preparing a host cell of any one of claims is provided, wherein the method comprises a) introducing a nucleic acid or an expression vector into a lymphocyte population that has a CD45RA−, CD45RO+, and CD62L+ phenotype and b) culturing the cells in the presence of anti-CD3 and/or anti CD28, and at least one homeostatic cytokine until the cells expand sufficiently for use as a cell infusion. In some alternatives, the expression vector comprises an isolated chimeric receptor nucleic acid. In some alternatives, the chimeric receptor nucleic acid comprises a) a polynucleotide coding for a ligand binding domain, wherein the ligand binding domain binds to and/or targets CD171, b) a polynucleotide coding for a polypeptide spacer of a length, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and CD8+. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and CD4+ and negative for CD45RO. In some alternatives, the host cell is a precursor T cell. In some alternatives, the host cell is a hematopoietic stem cell. In some alternatives, the chimeric receptor nucleic acid further comprises a nucleic acid that codes for a marker sequence. In some alternatives, the lymphocyte is CD8+ or CD4+.

In some alternatives, a use of the host cell or a composition of claims is provided, wherein the use is for treatment of cancer or a solid tumor expressing CD171. In some alternatives, the host cell comprises an expression vector. In some alternatives, the expression vector comprises an isolated chimeric receptor nucleic acid. In some alternatives, the chimeric receptor nucleic acid comprises a) a polynucleotide coding for a ligand binding domain, wherein the ligand binding domain binds to and/or targets CD171, b) a polynucleotide coding for a polypeptide spacer of a length, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and CD8+. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and CD4+ and negative for CD45RO. In some alternatives, the host cell is a precursor T cell. In some alternatives, the host cell is a hematopoietic stem cell. In some alternatives, the composition comprises a host cell in a pharmaceutically acceptable excipient is provided. In some alternatives, the host cell comprises an expression vector. In some alternatives, the expression vector comprises an isolated chimeric receptor nucleic. In some alternatives, the chimeric receptor nucleic acid comprises a) a polynucleotide coding for a ligand binding domain, wherein the ligand binding domain binds to and/or targets CD171, b) a polynucleotide coding for a polypeptide spacer of a length, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and CD8+. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and CD4+ and negative for CD45RO. In some alternatives, the host cell is a precursor T cell. In some alternatives, the host cell is a hematopoietic stem cell. In some alternatives, the composition comprises a CD8+ T cytotoxic lymphocyte cell selected from the group consisting of naïve CD8+ T cells, central memory CD8+ T cells, effector memory CD8+ T cells and bulk CD8+ T cells or a central memory T cell wherein the central memory T cell is positive for CD45RO+, CD62L+, and CD8+ and another host cell wherein the host cell is a central memory T cell, wherein the central memory T cell is positive for CD45RO+, CD62L+, and CD8+ or a CD4+ T helper lymphocyte cell is selected from the group consisting of naïve CD4+ T cells, central memory CD4+ T cells, effector memory CD4+ T cells, and bulk CD4+ T cells or a naïve CD4+ T cell, wherein the naïve CD4+ T cell is positive for CD45RA+, CD62L+ and CD4+ and negative for CD45RO. In some alternatives, the cancer is a neuroblastoma. In some alternatives, the solid tumor is selected from the group consisting of a breast cancer, brain cancer, colon cancer, renal cancer, pancreatic cancer, and ovarian cancer.

In some alternatives, a method of performing cellular immunotherapy in a subject having cancer or a tumor is provided, wherein the method comprises administering a composition or a host cell to the subject. In some alternatives, the host cell comprises an expression vector. In some alternatives, the expression vector comprises an isolated chimeric receptor nucleic acid. In some alternatives, the chimeric receptor nucleic acid comprises a) a polynucleotide coding for a ligand binding domain, wherein the ligand binding domain binds to and/or targets CD171, b) a polynucleotide coding for a polypeptide spacer of a length, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and CD8+. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and CD4+ and negative for CD45RO. In some alternatives, the host cell is a precursor T cell. In some alternatives, the host cell is a hematopoietic stem cell. In some alternatives, the composition comprises a host cell in a pharmaceutically acceptable excipient is provided. In some alternatives, the host cell comprises an expression vector. In some alternatives, the expression vector comprises an isolated chimeric receptor nucleic. In some alternatives, the chimeric receptor nucleic acid comprises a) a polynucleotide coding for a ligand binding domain, wherein the ligand binding domain binds to and/or targets CD171, b) a polynucleotide coding for a polypeptide spacer of a length, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and CD8+. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and CD4+ and negative for CD45RO. In some alternatives, the host cell is a precursor T cell. In some alternatives, the host cell is a hematopoietic stem cell. In some alternatives, the composition comprises a CD8+ T cytotoxic lymphocyte cell selected from the group consisting of naïve CD8+ T cells, central memory CD8+ T cells, effector memory CD8+ T cells and bulk CD8+ T cells or a central memory T cell wherein the central memory T cell is positive for CD45RO+, CD62L+, and CD8+ and another host cell wherein the host cell is a central memory T cell wherein the central memory T cell is positive for CD45RO+, CD62L+, and CD8+ or a CD4+ T helper lymphocyte cell is selected from the group consisting of naïve CD4+ T cells, central memory CD4+ T cells, effector memory CD4+ T cells, and bulk CD4+ T cells or a naïve CD4+ T cell, wherein the naïve CD4+ T cell is positive for CD45RA+, CD62L+ and CD4+ and negative for CD45RO. In some alternatives, the cancer is neuroblastoma. In some alternatives, the tumor is selected from the group consisting of a breast cancer, brain cancer, colon cancer, renal cancer, pancreatic cancer, and ovarian cancer. In some alternatives, the spacer is optimized for increased T cell proliferation and/or cytokine production in response to the ligand as compared to a reference chimeric receptor.

Another alternative relates to a chimeric receptor polypeptide coded for by a chimeric receptor nucleic acid. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO: 20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the spacer provides for increased T cell proliferation and/or cytokine production in response to the ligand as compared to a reference chimeric receptor.

Another alternative relates to an expression vector comprising a chimeric receptor nucleic acid. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO: 20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the spacer provides for increased T cell proliferation and/or cytokine production in response to the ligand as compared to a reference chimeric receptor.

In some alternatives, a host cell comprising an expression vector is provided. In some alternatives, the expression vector comprises a chimeric receptor nucleic acid. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO: 20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the host cell is a CD8+ T cytotoxic lymphocyte cell. In some alternatives, the CD8+ cytotoxic T lymphocyte cell is a central memory T cell wherein the central memory T cell is positive for CD45RO, CD62L, and CD8. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA, CD62L and/or CD4 and/or negative for CD45RO. In some alternatives, the spacer provides for increased T cell proliferation and/or cytokine production in response to the ligand as compared to a reference chimeric receptor. In some alternatives, the host cell is a precursor T cell. In some alternatives, the host cell is a hematopoietic stem cell.

In some alternatives, a composition comprising host cells in provided. In some alternatives, the composition comprises host cells comprising an expression vector. In some alternatives, the host cell is a precursor T cell. In some alternatives, the host cell is a hematopoietic stem cell. In some alternatives, the expression vector comprises a chimeric receptor nucleic acid. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the host cell is a CD8+ T cytotoxic lymphocyte cell. In some alternatives of the composition, the said host cells comprise a population of CD8+ cells consisting essentially of, or having been enriched for naïve CD8+ T cells, central memory CD8+ T cells, effector memory CD8+ T cells or bulk CD8+ T cells. In some alternatives, the said population of CD8+ cells consists essentially of or has been enriched for CD8+ central memory T cells positive for CD45RO, CD62L, and CD8. In some alternatives, said host cells comprise a population of CD4+ cells consisting essentially of or having been enriched for CD4+ T helper lymphocytes selected from the group consisting of naïve CD4+ T cells, central memory CD4+ T cells, effector memory CD4+ T cells, and bulk CD4+ T cells. In some alternatives, said population of CD4+ cells consists essentially of or has been enriched for naïve CD4+ T cells positive for CD45RA, CD62L, and CD4 and negative for CD45RO. In some alternatives, the CD8+ cytotoxic T lymphocyte cell is a central memory T cell wherein the central memory T cell is positive for CD45RO, CD62L, and CD8. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA, CD62L and/or CD4 and/or negative for CD45RO. In some alternatives, the host cell is a precursor T cell. In some alternatives, the host cell is a hematopoietic stem cell.

In another alternative, a composition comprising host cell or composition of and a pharmaceutically acceptable excipient is provided. In some alternatives, the host cell comprises an expression vector. In some alternatives, the host cell is a precursor T cell. In some alternatives, the host cell is a hematopoietic stem cell. In some alternatives, the expression vector comprises a chimeric receptor nucleic acid. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the host cell is a CD8+ T cytotoxic lymphocyte cell. In some alternatives, the CD8+ cytotoxic T lymphocyte cell is a central memory T cell wherein the central memory T cell is positive for CD45RO, CD62L, and/or CD8. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA, CD62L, and/or CD4 and/or negative for CD45RO. In some alternatives, the composition comprises host cells comprising an expression vector. In some alternatives, the expression vector comprises a chimeric receptor nucleic acid. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the host cell is a CD8+ T cytotoxic lymphocyte cell. In some alternatives of the composition, the said host cells comprise a population of CD8+ cells consisting essentially of, or having been enriched for naïve CD8+ T cells, central memory CD8+ T cells, effector memory CD8+ T cells or bulk CD8+ T cells. In some alternatives, the said population of CD8+ cells consists essentially of or has been enriched for CD8+ central memory T cells positive for CD45RO, CD62L, and/or CD8. In some alternatives, said host cells comprise a population of CD4+ cells consisting essentially of or having been enriched for CD4+ T helper lymphocytes selected from the group consisting of naïve CD4+ T cells, central memory CD4+ T cells, effector memory CD4+ T cells, and bulk CD4+ T cells. In some alternatives, said population of CD4+ cells consists essentially of or has been enriched for naïve CD4+ T cells positive for CD45RA, CD62L and/or CD4 and/or negative for CD45RO. In some alternatives, the CD8+ cytotoxic T lymphocyte cell is a central memory T cell wherein the central memory T cell is positive for CD45RO, CD62L, and CD8. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA, CD62L and/or CD4 and/or negative for CD45RO. In some alternatives, the composition comprises a host cell wherein the host cell is a CD8+ T cytotoxic lymphocyte cell or the CD8+ cytotoxic T lymphocyte cell is a central memory T cell wherein the central memory T cell is positive for CD45RO, CD62L, and/or CD8, and another host cell wherein the host cell is a CD4+ T helper lymphocyte cell is selected from the group consisting of naïve CD4+ T cells, central memory CD4+ T cells, effector memory CD4+ T cells, and bulk CD4+ T cells or the CD4+ helper lymphocyte cell is a naïve CD4+ T cell, wherein the naïve CD4+ T cell is positive for CD45RA, CD62L and/or CD4 and/or negative for CD45RO. In some alternatives, the host cell is a precursor T cell. In some alternatives, the host cell is a hematopoietic stem cell.

In another alternative, an in vitro method for preparing a host cell is provided. In some alternatives, the host cell comprises an expression vector. In some alternatives, the expression vector comprises a chimeric receptor nucleic acid. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO: 20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the host cell is a CD8+ T cytotoxic lymphocyte cell. In some alternatives, the CD8+ cytotoxic T lymphocyte cell is a central memory T cell wherein the central memory T cell is positive for CD45RO, CD62L, and/or CD8. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA, CD62L and/or CD4 and/or negative for CD45RO. In some alternatives, the host cell is a CD8+ T cytotoxic lymphocyte cell. In some alternatives, the CD8+ cytotoxic T lymphocyte cell is a central memory T cell wherein the central memory T cell is positive for CD45RO, CD62L, and/or CD8. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA, CD62L and/or CD4 and/or negative for CD45RO. In some alternatives, the method comprises a) providing a library comprising a plurality of nucleic acids, each coding for a chimeric receptor, wherein each of a plurality of chimeric receptors coded by the plurality of nucleic acids differs in length, b) introducing each of the plurality of the nucleic acids into a separate lymphocyte population and expanding each T lymphocyte population in vitro, thereby generating a plurality of genetically modified T lymphocyte populations, c) administering each of the plurality of genetically modified T lymphocyte populations into an animal model bearing a tumor and has assessing a readout of anti-tumor efficacy and d) selecting a nucleic acid coding for a chimeric receptor exhibiting anti-tumor efficacy in vitro and/or in an animal model. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKY-GPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKY-GPPCPSCP (SEQ ID NO: 20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the plurality of nucleic acids code for an expression vector. In some alternatives, the expression vector comprises a chimeric receptor nucleic acid. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKY-GPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKY-GPPCPSCP (SEQ ID NO: 20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the method further comprises introducing the selected nucleic acid coding for the chimeric receptor into a host cell. In some alternatives, the host cell is a precursor T cell. In some alternatives, the host cell is a hematopoietic stem cell.

In some alternatives, an in vitro method for selecting a chimeric receptor for targeting an antigen is provided, wherein the method comprises incubating each of a plurality of cell populations with donor cells expressing the antigen in a series of sequential recursive rounds, wherein the plurality of cell populations comprises nucleic acids encoding a plurality of chimeric receptors of varying lengths, each chimeric receptor specifically binding to and/or targets the antigen and assessing expansion, activation, and/or survival of each of the plurality of cell populations, and selecting the chimeric receptor based on said assessment. In some alternatives, the series of sequential rounds comprises at least three rounds of incubation, wherein the cell populations are harvested between rounds. In some alternatives, the assessment is carried out by detecting survival or number or percentage of surviving cells of each population following the sequential rounds of incubation, wherein the selected chimeric receptor is expressed by a population for which survival or cell number or percentage is increased relative to another of the plurality of cell populations. In some alternatives, the cells of the populations and cells expressing the antigen are incubated at a ratio of 1:1 at the start of each round. In some alternatives, the chimeric receptors of varying lengths comprise spacers of different lengths, each spacer joining an antigen binding domain and a transmembrane domain of the chimeric receptor; and/or the chimeric receptors of varying lengths comprise chimeric receptors having varying numbers of intracellular costimulatory domains, each intracellular domain individually from a different natural costimulatory molecule. In some alternatives, the host cell is a precursor T cell. In some alternatives, the host cell is a hematopoietic stem cell.

In another alternatives, an in vitro method for preparing a host cell is provided, wherein the method comprises: introducing a nucleic acid, as set forth above, or an expression vector, as set forth above, into a lymphocyte population that has a CD45RA, CD45RO+, and/or CD62L+ phenotype and culturing the cells in the presence of anti-CD3 and/or anti CD28, and at least one homeostatic cytokine until the cells expand sufficiently for use as a cell infusion. In some alternatives, the host cell comprises an expression vector, as set forth above. In some alternatives, the expression vector comprises a chimeric receptor nucleic acid, as set forth above. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO: 20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the host cell is a CD8+ T cytotoxic lymphocyte cell. In some alternatives, the CD8+ cytotoxic T lymphocyte cell is a central memory T cell wherein the central memory T cell is positive for CD45RO, CD62L, and/or CD8. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA, CD62L and/or CD4 and/or negative for CD45RO. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO: 20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the lymphocyte is CD8+ or CD4+. In some alternatives, the host cell is a precursor T cell. In some alternatives, the host cell is a hematopoietic stem cell.

In some alternatives, a use of a host cell or composition in the treatment or inhibition of cancer or a solid tumor expressing CD171 is provided. In some alternatives, the cancer is a neuroblastoma. In some alternatives, the solid tumor is selected from the group consisting of a breast cancer, brain cancer, colon cancer, renal cancer, pancreatic cancer, and ovarian cancer. In some alternatives, the host cell comprises an expression vector, as set forth herein. In some alternatives, the expression vector comprises a chimeric receptor nucleic acid. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO: 20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the host cell is a CD8+ T cytotoxic lymphocyte cell. In some alternatives, the CD8+ cytotoxic T lymphocyte cell is a central memory T cell, wherein the central memory T cell is positive for CD45RO, CD62L, and/or CD8. In some alternatives, the host cell is a CD4+ T helper lymphocyte cell selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA, CD62L and/or CD4 and/or negative for CD45RO.

In some alternatives, a composition comprises host cells. In some alternatives, the composition comprises host cells comprising an expression vector, as set forth herein. In some alternatives, the expression vector comprises a chimeric receptor nucleic acid, as set forth herein. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)$_3$ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO: 20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the host cell is a CD8+ T cytotoxic lymphocyte cell. In some alternatives of the composition, the said host cells comprise a population of CD8+ cells consisting essentially of, or having been enriched for naïve CD8+ T cells, central memory CD8+ T cells, effector memory CD8+ T cells or bulk CD8+ T cells. In some alternatives, the said population of CD8+ cells consists essentially of or has been enriched for CD8+ central memory T cells positive for CD45RO, CD62L, and CD8. In some alternatives, said host cells comprise a population of CD4+ cells consisting essentially of or having been enriched for CD4+ T helper lymphocytes selected from the group consisting of naïve CD4+ T cells, central memory CD4+ T cells, effector memory CD4+ T cells, and bulk CD4+ T cells. In some alternatives, said population of CD4+ cells consists essentially of or has been enriched for naïve CD4+ T cells positive for CD45RA, CD62L and CD4 and negative for CD45RO. In some alternatives, the CD8+ cytotoxic T lymphocyte cell is a central memory T cell wherein the central memory T cell is positive for CD45RO, CD62L, and CD8. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA, CD62L and/or CD4 and/or negative for CD45RO. In some alternatives, the composition further comprises a pharmaceutically acceptable excipient. In some alternatives, the host cell is a precursor T cell. In some alternatives, the host cell is a hematopoietic stem cell.

In some alternatives, a method of performing cellular immunotherapy in a subject having cancer or a tumor is provided, wherein the method comprises: administering a composition or a host cell of claims to the subject. In some alternatives, the cancer is neuroblastoma. In some alternatives, the tumor is selected from the group consisting of a breast cancer, brain cancer, colon cancer, renal cancer, pancreatic cancer, and ovarian cancer. In some alternatives, the host cell comprises an expression vector, as set forth herein. In some alternatives, the expression vector comprises a chimeric receptor nucleic acid, as set forth herein. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)₃ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO: 20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the host cell is a CD8+ T cytotoxic lymphocyte cell. In some alternatives, the CD8+ cytotoxic T lymphocyte cell is a central memory T cell, wherein the central memory T cell is positive for CD45RO, CD62L, and/or CD8. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA, CD62L and/or CD4 and/or negative for CD45RO. In some alternatives, a composition comprises host cells. In some alternatives, the composition comprises host cells comprising an expression vector. In some alternatives, the expression vector comprises a chimeric receptor nucleic acid. In some alternatives, the chimeric receptor nucleic acid comprises: a) a polynucleotide coding for a ligand binding domain, which ligand binding domain specifically binds to and/or targets CD171, b) a polynucleotide coding for a polypeptide spacer of less than 100 amino acids in length (but not less than 1 or 2 amino acids), which spacer joins the ligand binding domain and a transmembrane domain of the chimeric receptor, c) a polynucleotide coding for the transmembrane domain of the chimeric receptor and a polynucleotide coding for an intracellular signaling domain of the chimeric receptor. In some alternatives, the spacer comprises an amino acid sequence of $X_1PPX_2P$ (SEQ ID NO: 1), in which $X_1$ and $X_2$, independently, are any amino acid. In some alternatives, $X_1$ and/or $X_2$ is cysteine. In some alternatives, the spacer is less than 15 amino acids in length (but not less than 1 or 2 amino acids). In some alternatives, the spacer is 12, 13, 14, or 15 amino acids in length or a length within a range defined by any two of the aforementioned lengths. In some alternatives, the spacer region comprises a portion of a hinge region of a human antibody. In some alternatives, the spacer comprises, consists of, or consists essentially of EPKSCDKTHTCPPCP (SEQ ID NO:17), ERKCCVECPPCP (SEQ ID NO:18), ELKTPLGDTHTCPRCP (EPKSCDTPPPCPRCP)₃ (SEQ ID NO:19), ESKYGPPCPSCP (SEQ ID NO:20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the spacer consists of or consists essentially of ESKYGPPCPSCP (SEQ ID NO: 20), ESKYGPPCPPCP (SEQ ID NO:21), YGPPCPPCP (SEQ ID NO:51), KYGPPCPPCP (SEQ ID NO:52), or EVVKYGPPCPPCP (SEQ ID NO:53). In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the intracellular signaling domain does not further comprise an intracellular portion of another costimulatory molecule and/or wherein the intracellular signaling domain does not comprise an intracellular signaling portion of a molecule selected from the group consisting of CD27, CD28, OX-40, CD30, CD40, PD-1, ICOS, LFA-1, CD2, CD7, NKG2C, and B7-H3, and/or wherein the intracellular signaling domain does not comprise an intracellular signaling portion of CD28. In some alternatives, the chimeric receptor nucleic acid further comprises a nucleic acid that codes for a marker sequence. In some alternatives, the host cell is a CD8+ T cytotoxic lymphocyte cell. In some alternatives of the composition, the said host cells comprise a population of CD8+ cells consisting essentially of, or having been enriched for naïve CD8+ T cells, central memory CD8+ T cells, effector memory CD8+ T cells or bulk CD8+ T cells. In some alternatives, the said population of CD8+ cells consists essentially of or has been enriched for CD8+ central memory T cells positive for CD45RO, CD62L, and/or CD8. In some alternatives, said host cells comprise a population of CD4+ cells consisting essentially of or having been enriched for CD4+ T helper lymphocytes selected from the group consisting of naïve CD4+ T cells, central memory CD4+ T cells, effector memory CD4+ T cells, and bulk CD4+ T cells. In some alternatives, said population of CD4+ cells consists essentially of or has been enriched for naïve CD4+ T cells positive for CD45RA, CD62L and/or CD4 and/or negative for CD45RO. In some alternatives, the CD8+ cytotoxic T lymphocyte cell is a central memory T cell wherein the central memory T cell is positive for CD45RO, CD62L, and/or CD8. In some alternatives, the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA, CD62L and/or CD4 and/or negative for CD45RO. In some alternatives, the composition further comprises a pharmaceutically acceptable excipient. In some alternatives, the host cell is a precursor T cell. In some alternatives, the host cell is a hematopoietic stem cell.

Figure 3A:
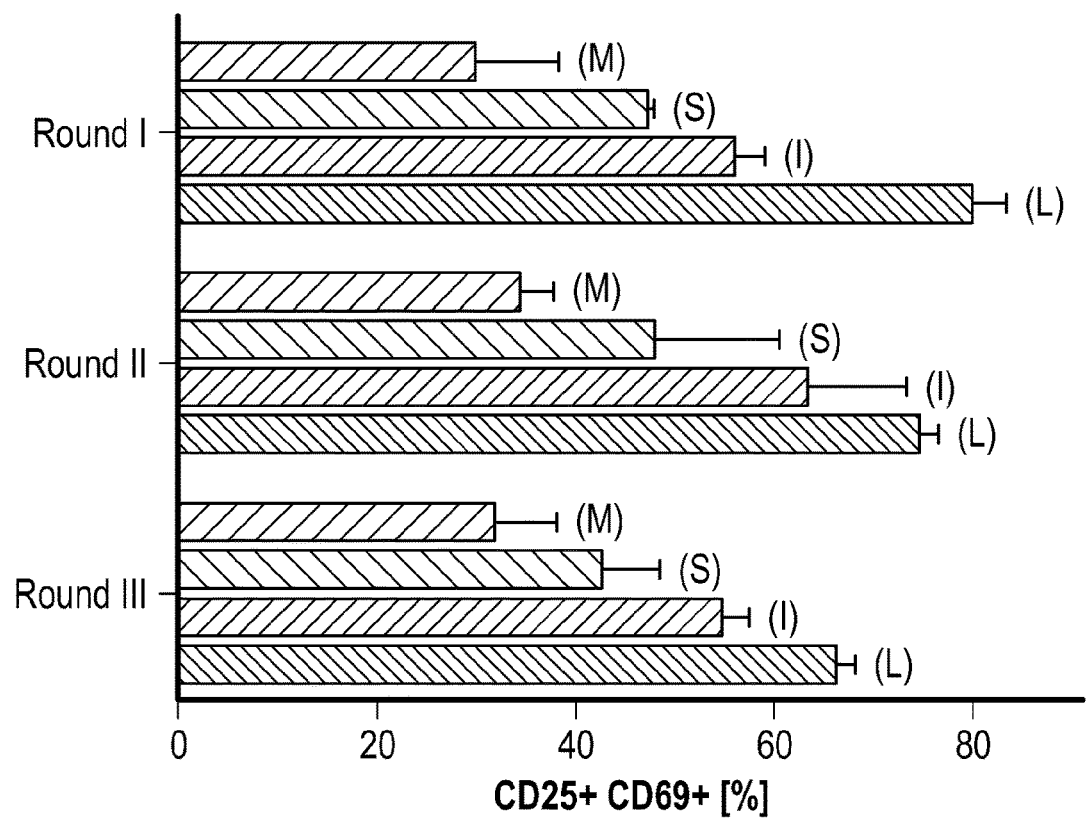
FIGS. 3A, 3B and 3C shows activation status and viability of transduced CAR T cells after exposure to tumor cells for 24 hours (round 1); T cells are then harvested from round 1 cell culture and transferred to a new culture for another 24 hours (round 2); and T cells are then harvested from round 2 cell culture and transferred to a new culture for another 24 hours round 3). Between the transfers the amount of viable T cells was kept the same between the different T cell lines.

FIG. 3A shows that CD8 cells transduced with a construct with a long spacer region (L) had a greater % of cells with activated cell surface markers CD25/CD69 as compared to those cells transduced with a construct with a short spacer(S) at each round of transfer.

Figure 3B:
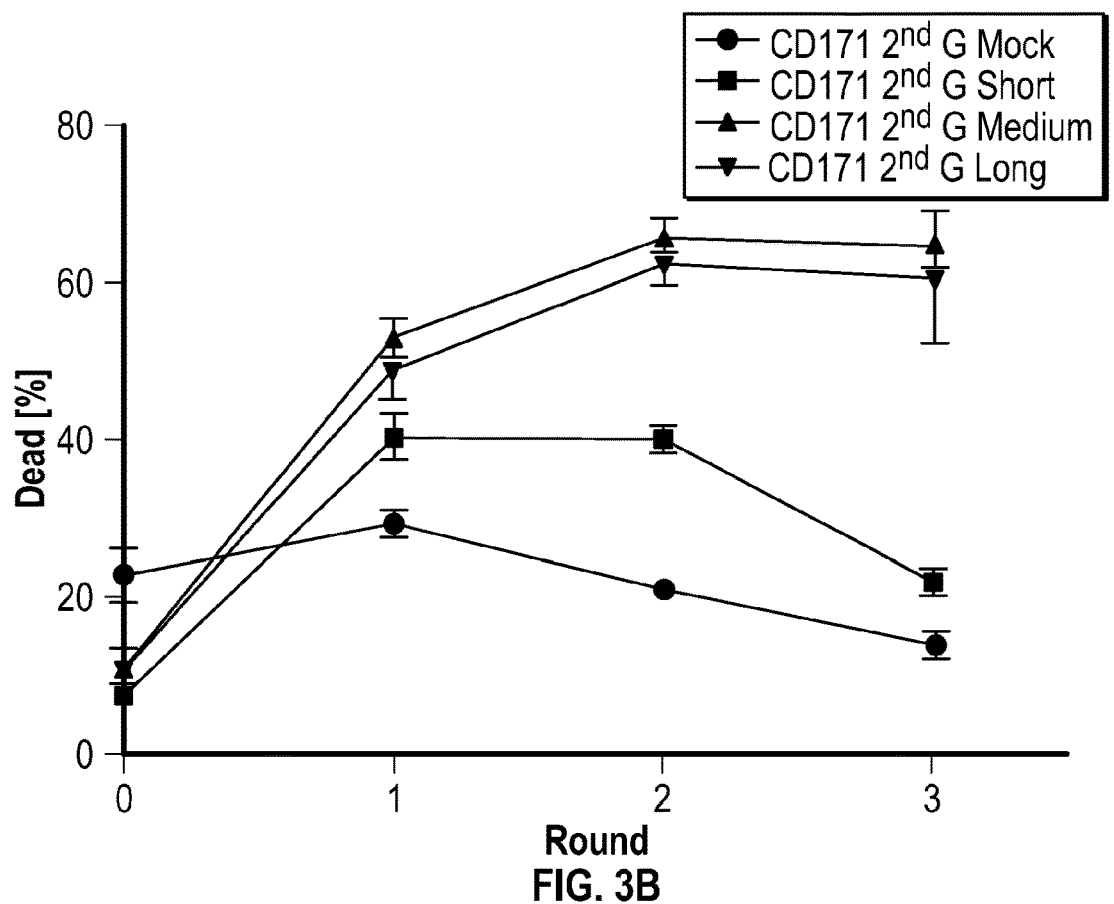

FIG. 3B shows that CD8 cells transduced with a construct with a long (▼) or intermediate spacer region (▲) had a greater % of dead cells (top 2 lines) as compared to those cells transduced with a construct with a short spacer (■).

Figure 3C:
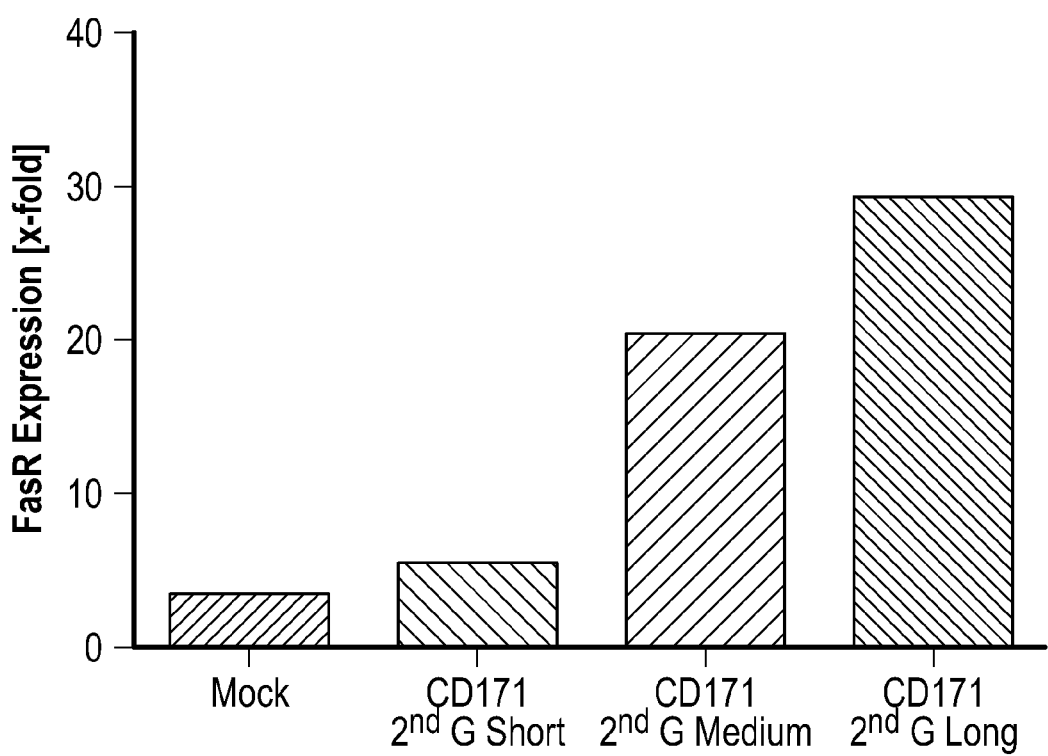

FIG. 3C shows that CD8 cells transduced with a construct with a long or intermediate spacer region caused greater expression of FasR expression in tumor cells compared to those cells transduced with a construct with a short spacer.

FIGS. 4A, 4B, 4C, 4D, 4E, and 4F shows CD8 central memory T cells transduced with a CAR construct with a short spacer region but having an additional intracellular signaling region from CD28 so that the construct includes costimulatory signaling regions from CD28 and 4-1BB together with the CD3 zeta signaling domain.

Figure 4A:
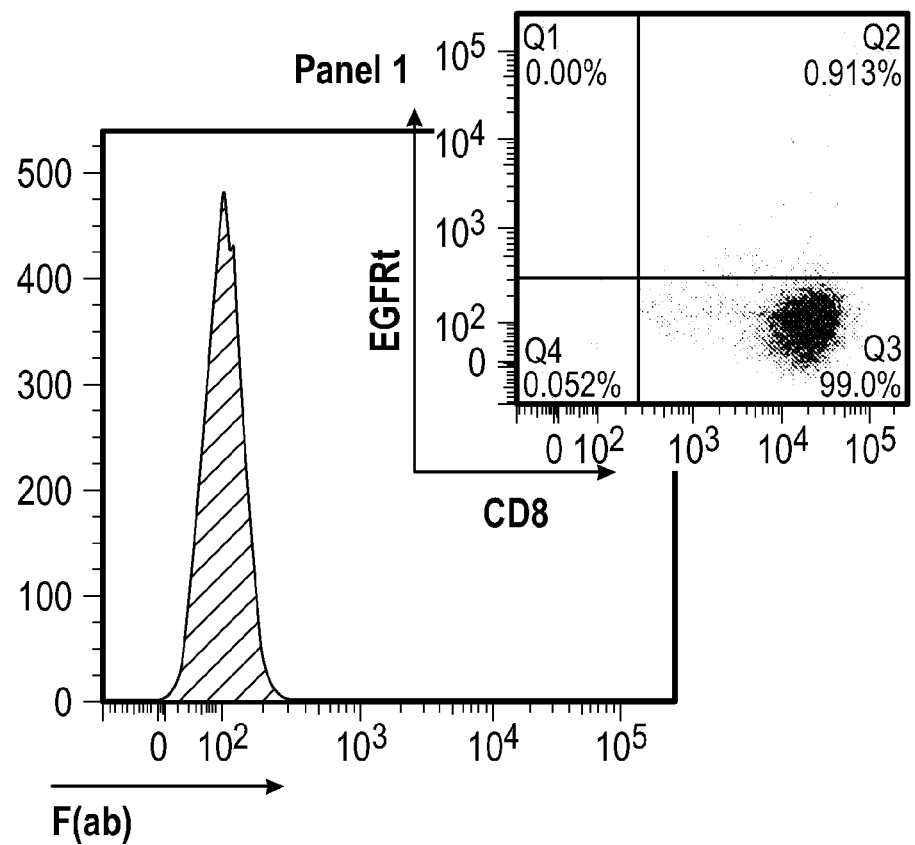
Figure 4A:
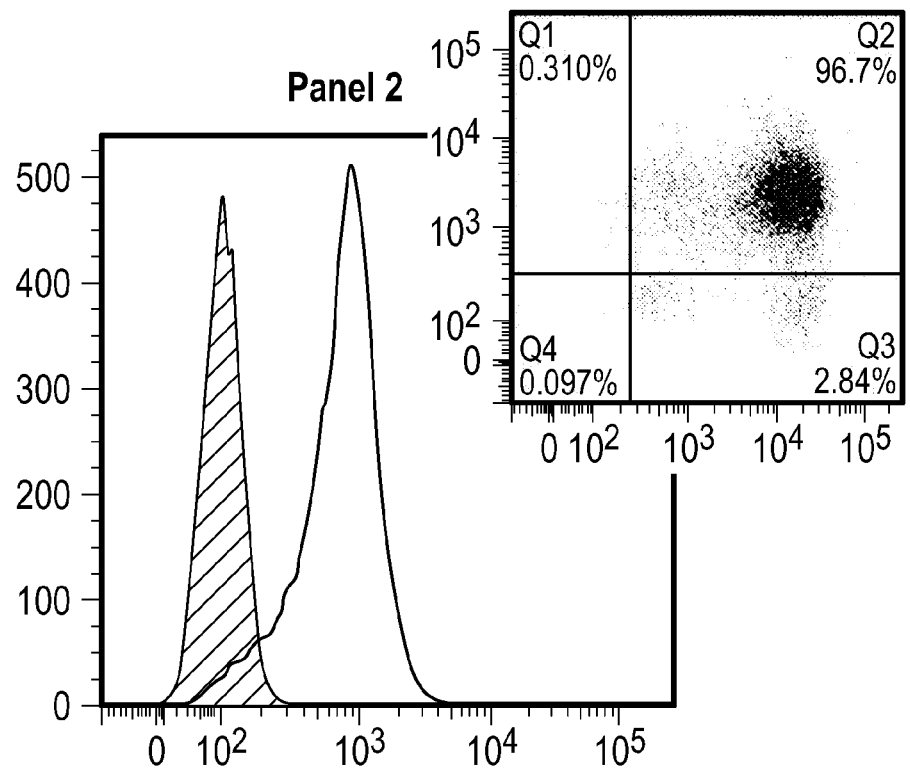
Figure 4A:
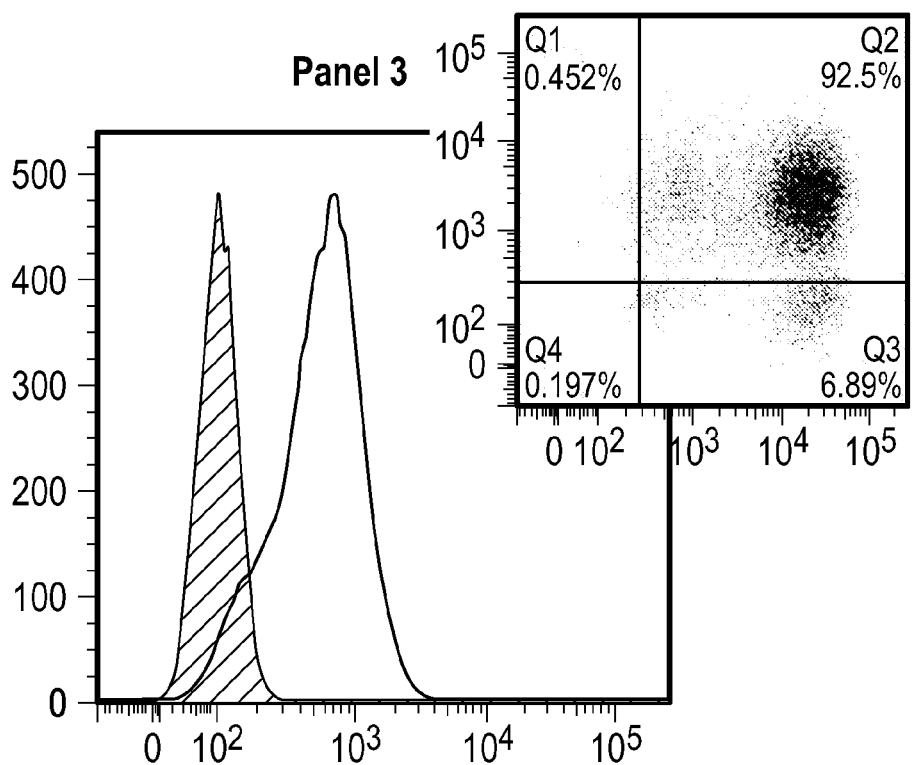

FIG. 4A shows flow cytometry profiles of CD8 central memory cells transduced with a CAR construct having a CD28cyto/4-1BB costimulatory domain and a construct having a 4-1BB costimulatory domain. The expression of anti-CD171 CAR is detected by an antibody that binds to a F(ab). The inset graphs for each panel shows the % of cells expressing CD8 and the truncated EGFR present in each construct in each cell population. Panel 1 is mock infected cells and exhibits no expression of F(ab) or EGFRt. Panel 2 shows expression of the short construct with the 4-1BB costimulatory domain as determined by expression of CD8, EGFRt, and F(ab). Panel 3 shows expression of the short construct with the a CD28cyto/4-1BB costimulatory domain as determined by expression of CD8, EGFRt, and F(ab). Expression of each of the constructs in CD8 cells is similar.

Figure 4B:
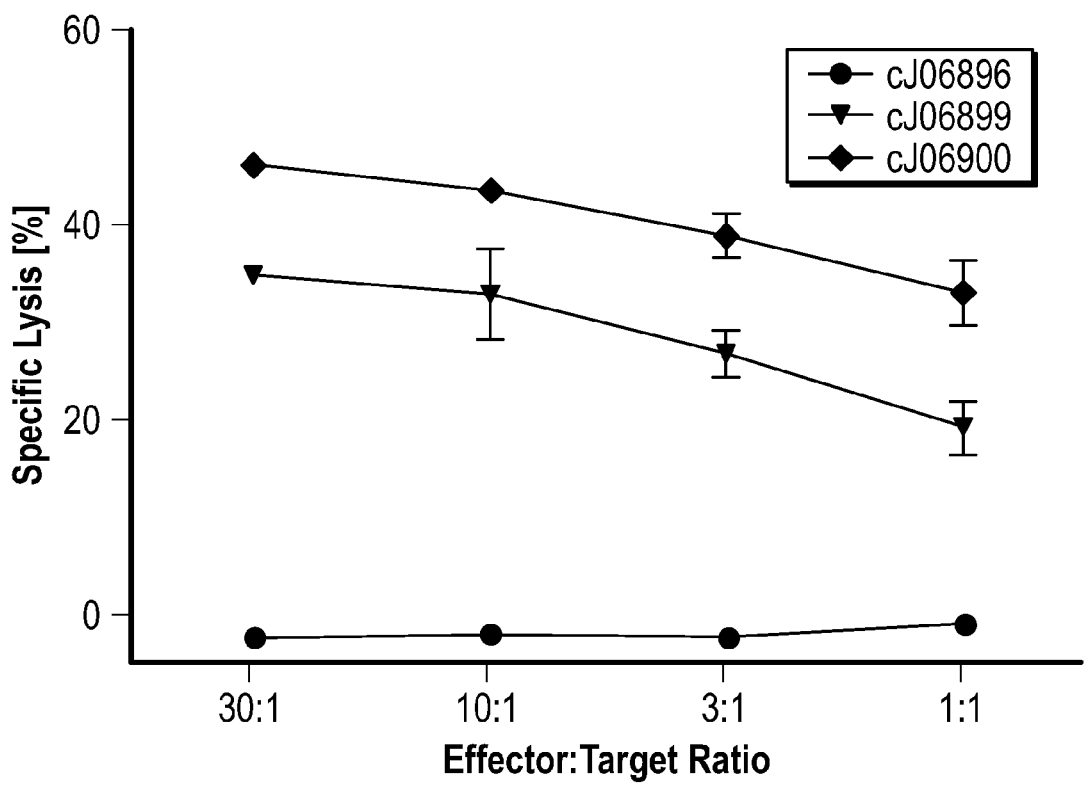

FIG. 4B shows cytolytic activity of CD8 cells transduced with a construct comprising a short spacer, costimulatory domain 4-1BB, and signaling domain CD3ζ and a construct comprising a short spacer, costimulatory domain CD28 cyto, costimulatory domain 4-1BB, and signaling domain CD3ζ against SK-N-BE 2 neuroblastoma cell line (Be2) The graph shows that the cells transduced with the construct with the costimulatory domain CD28cyto (top line ♦) are more effective at killing CD171 expressing neuroblastoma cells than the cells transduced with a construct lacking the CD28 cyto ($2^{nd}$ line from the top ▼))

Figure 4C:
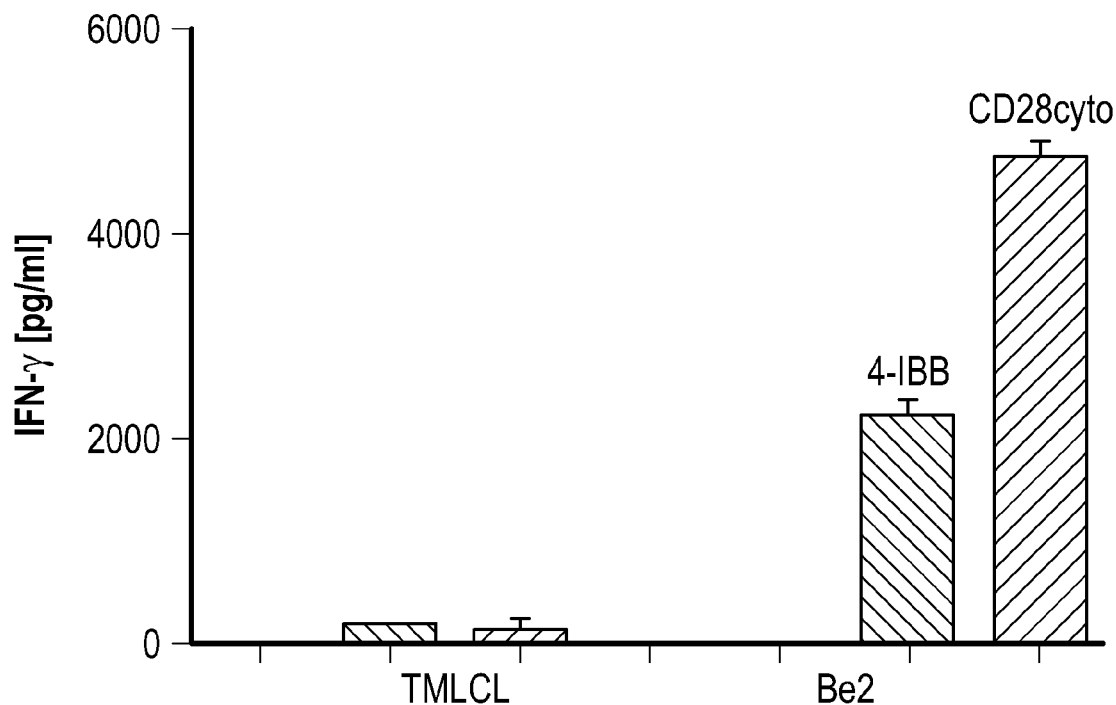

FIG. 4C shows cytokine production by transduced T cells when contacted with Be2 neuroblastoma cells or control TML. Be2 or TML cells are contacted with CD8 cells transduced with a construct comprising a short spacer, costimulatory domain 4-1BB, and signaling domain CD3ζ and a construct comprising a short spacer, costimulatory domain CD28 cyto, costimulatory domain 4-1BB, and signaling domain CD3ζ. The graph shows that CD8 transduced cells with the construct with the CD28cyto costimulatory domain (CD28cyto) in contact with Be2 cells produced more IFNγ than CD8 cells transduced with the construct without the CD28cyto costimulatory domain (4-1BB).

Figure 4D:
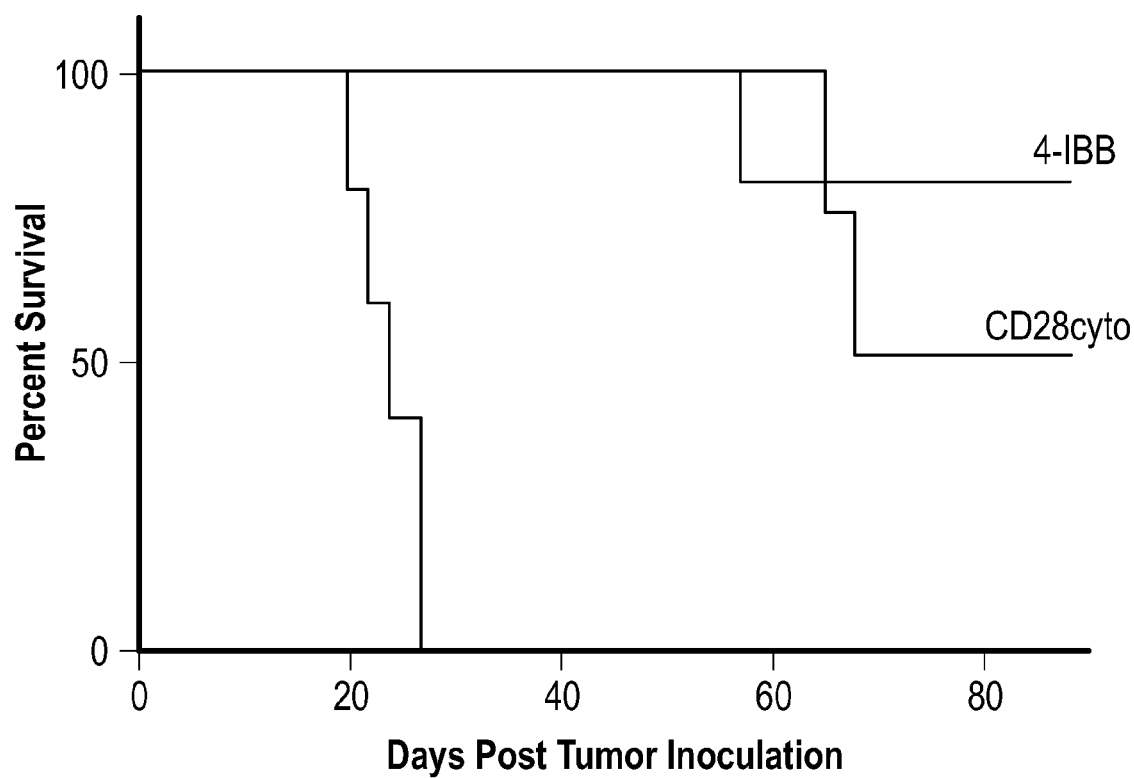

FIG. 4D shows tumor cell survival and proliferation of the intracranial neuroblastoma xenograft tumor model in NSG mice. The graph shows survival of mice having a xenograft neuroblastoma tumor treated with CD8 cells transduced with a construct comprising a short spacer, costimulatory domain 4-1BB, and signaling domain CD3ζ(4-1BB) and a construct comprising a short spacer, costimulatory domain CD28 cyto, costimulatory domain 4-1BB, and signaling domain CD3ζ (CD28 cyto). A greater percentage of mice treated with CD8 cells transduced with a construct without CD28cyto costimulatory domain(4-1BB) survived than mice treated with cells transduced with the construct with the CD28cyto costimulatory domain (CD28 cyto).

Figure 4E:
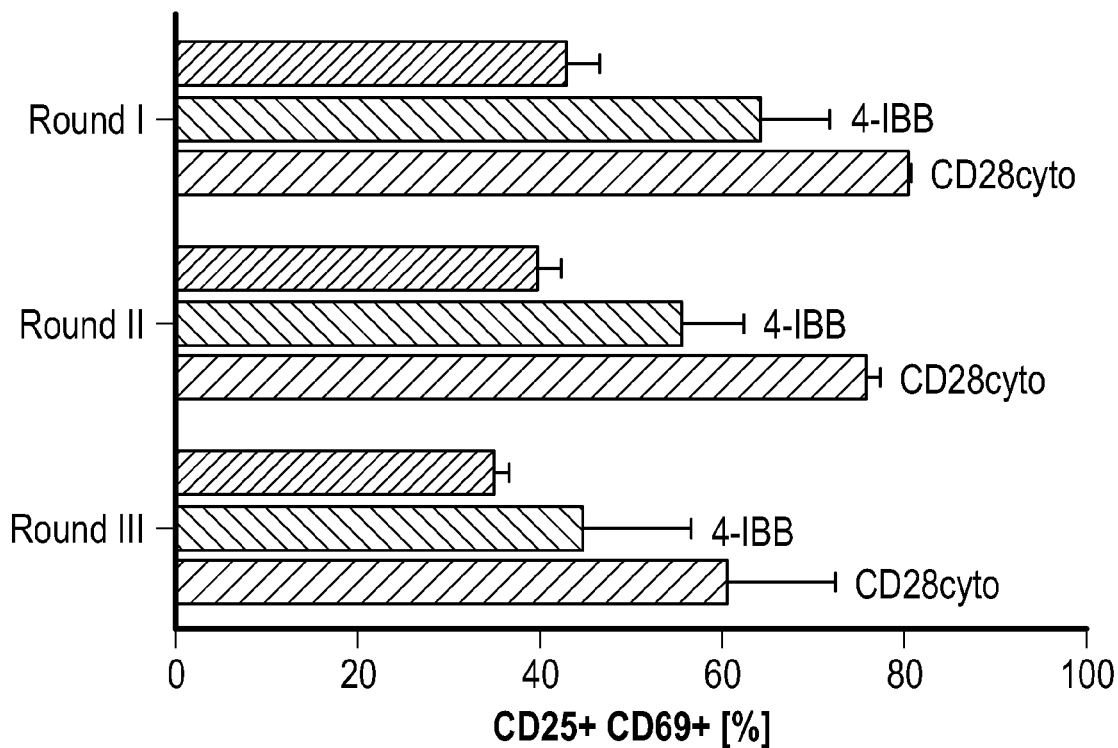

FIG. 4E shows activation status and viability of transduced CAR T cells after exposure to tumor cells for 24 hours (round 1), T cells are then harvested from round 1 cell culture and transferred to a new culture for another 24 hours (round 2) and T cells are then harvested from round 2 cell culture and transferred to a new culture for another 24 hours (round 3). The graph shows that CD8 cells transduced with a construct with CD28 cyto costimulatory domain (CD28 cyto) had a greater % of cells with activated cell surface markers CD25/CD69, as compared to those cells transduced with a construct without CD28 cyto costimulatory domain (4-1BB).

Figure 4F:
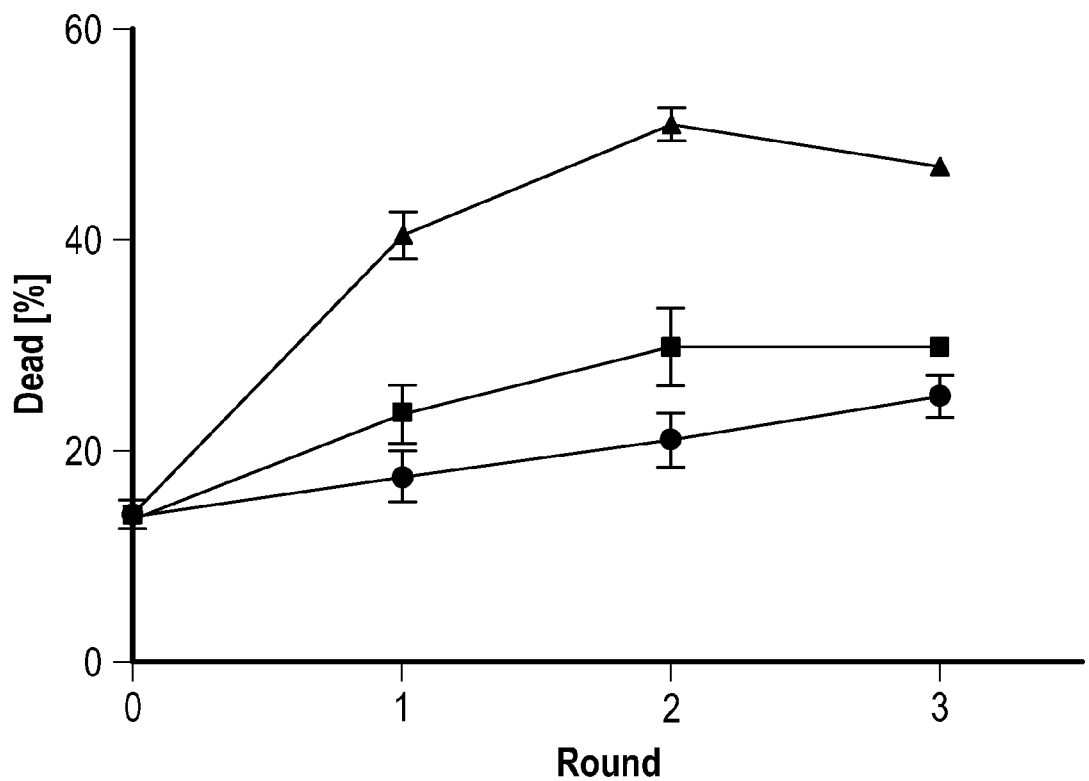

FIG. 4F shows that CD8 cells transduced with a construct with CD28cyto costimulatory domain (▲) had a greater % of dead cells as compared to those cells transduced with a construct without CD28cyto costimulatory domain (■).

Figure 5:
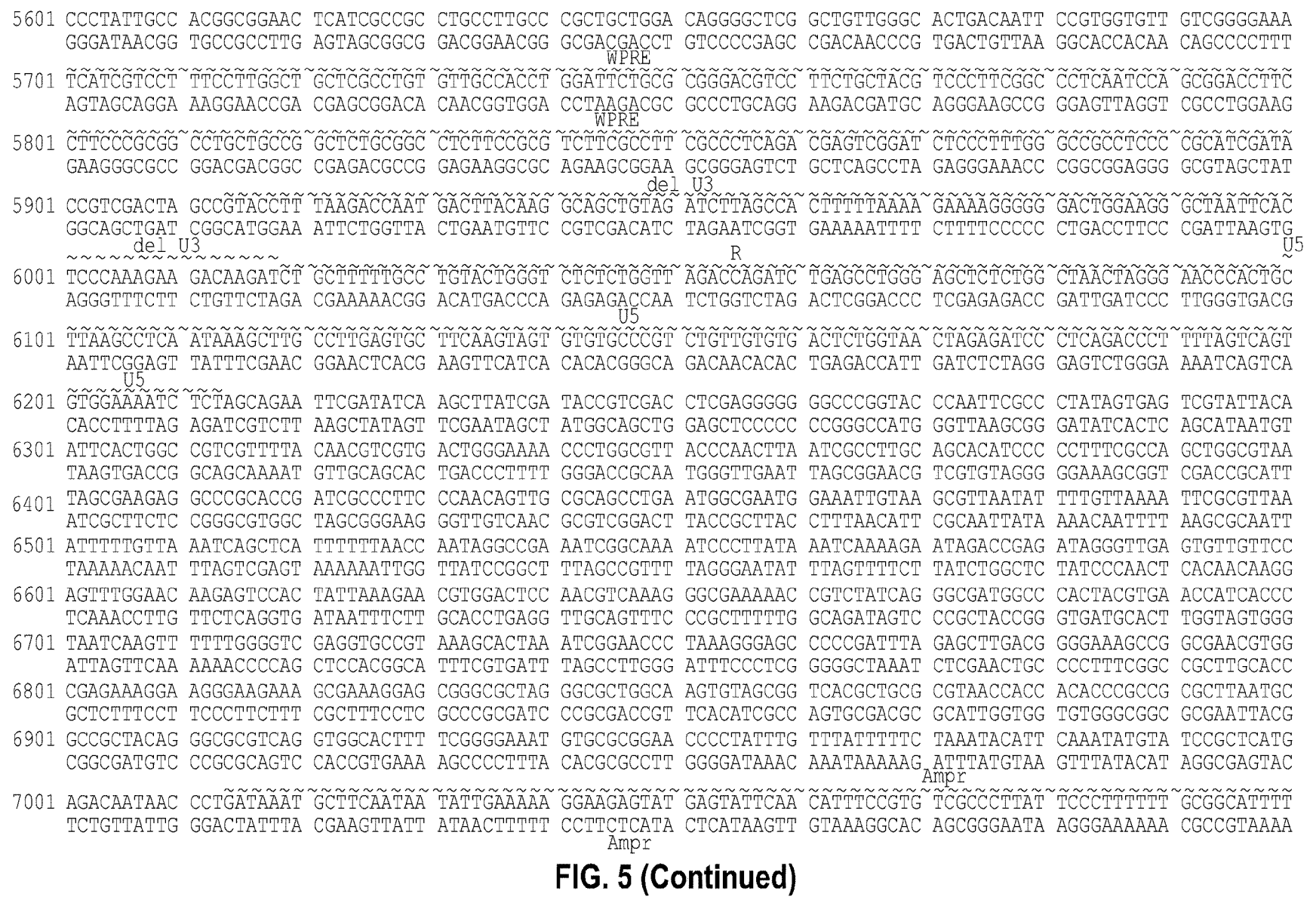
Figure 5:
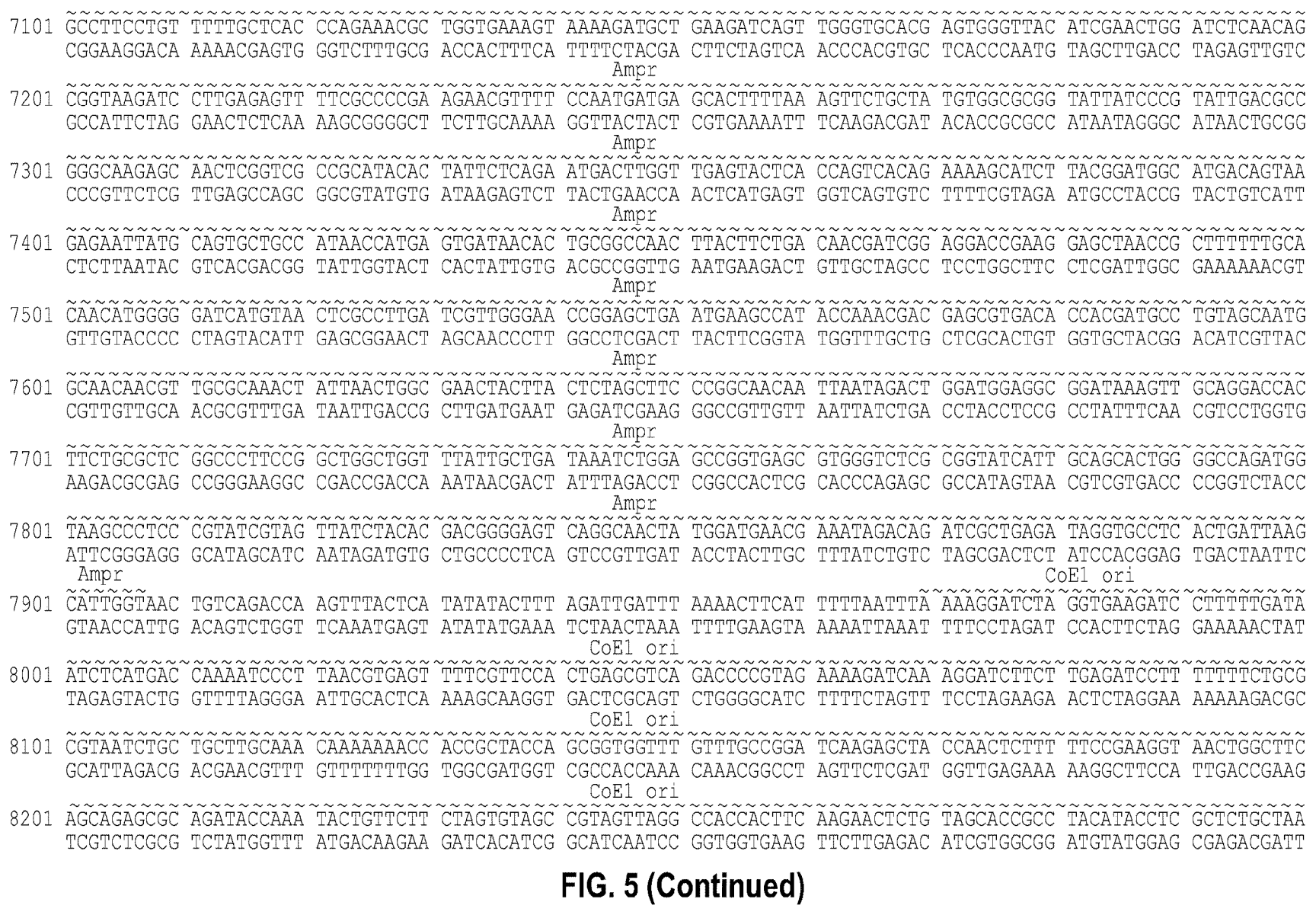

FIG. 5 shows the sequences for the Ce7scFv-IgG4hinge-CH2-CH3 CD28tm/4-1BB-zeta-T2A-EGFRt-epHIV7 (long construct) (SEQ ID NO: 54). Tildes show the beginning and end of the coding sequence for each component of the construct.

Figure 6:
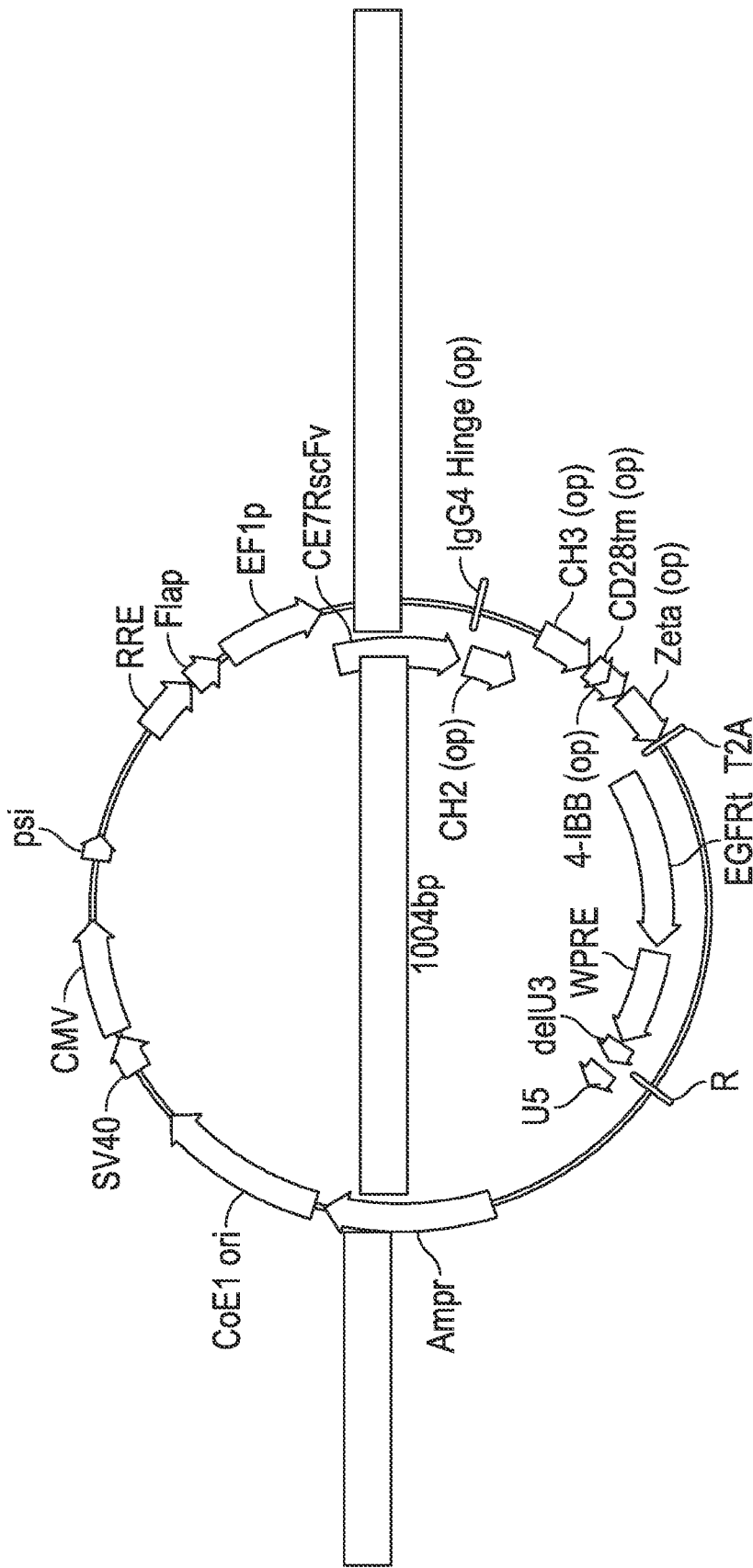

FIG. 6 shows the plasmid map including the sequences for the Ce7scFv-IgG4hinge-CH2-CH3-CD28tm/4-1BB-zeta-T2A-EGFRt-epHIV7 (long construct).

Figure 7:
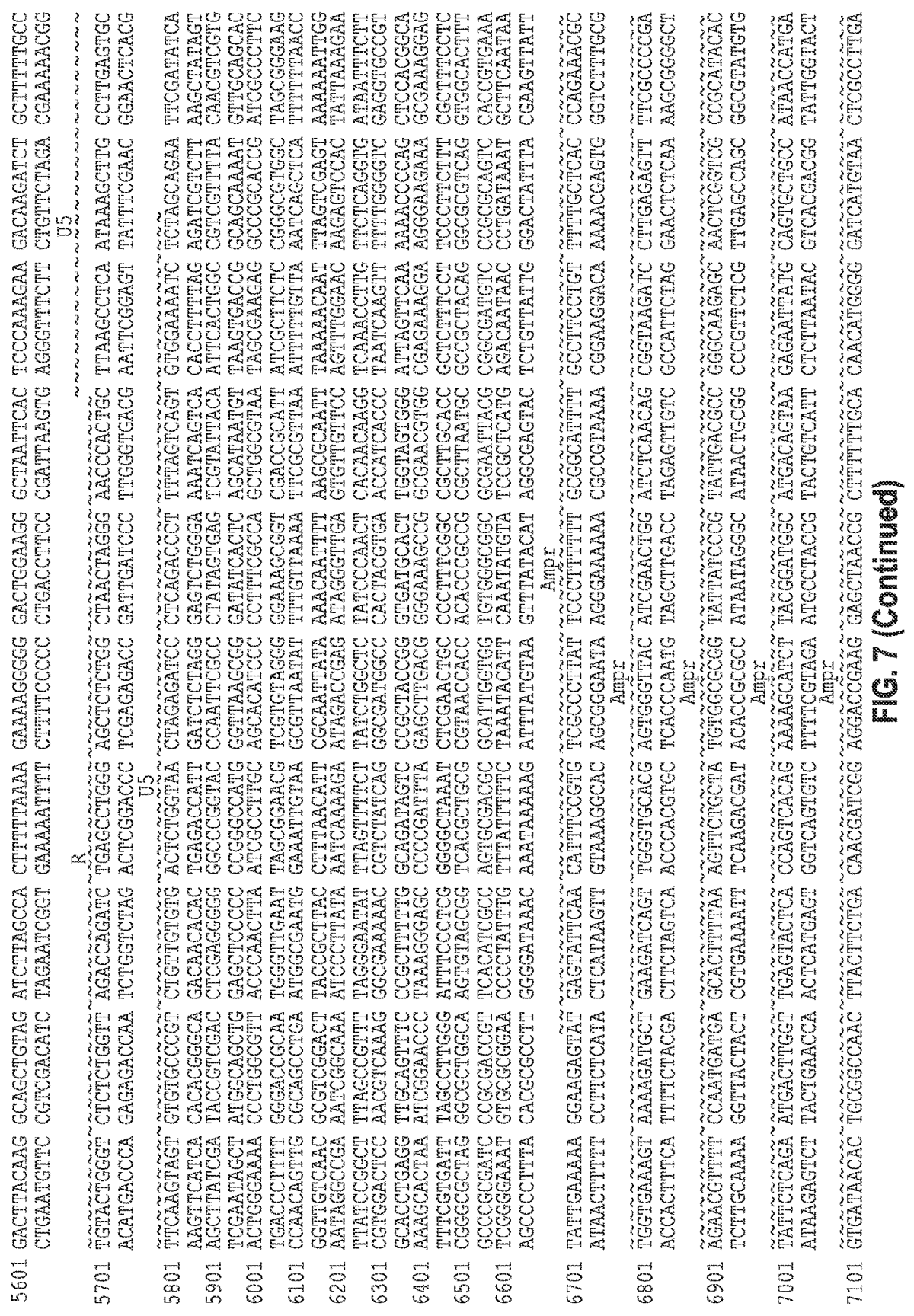

FIG. 7 shows the sequences for the CE7scFv-IgG4hinge-CH3-CD28tm/4-1BB-zeta-T2A-EGFRt-epHIV7 (intermediate) (SEQ ID NO: 55). Tildes show the beginning and end of the coding sequence for each component of the construct.

Figure 8:
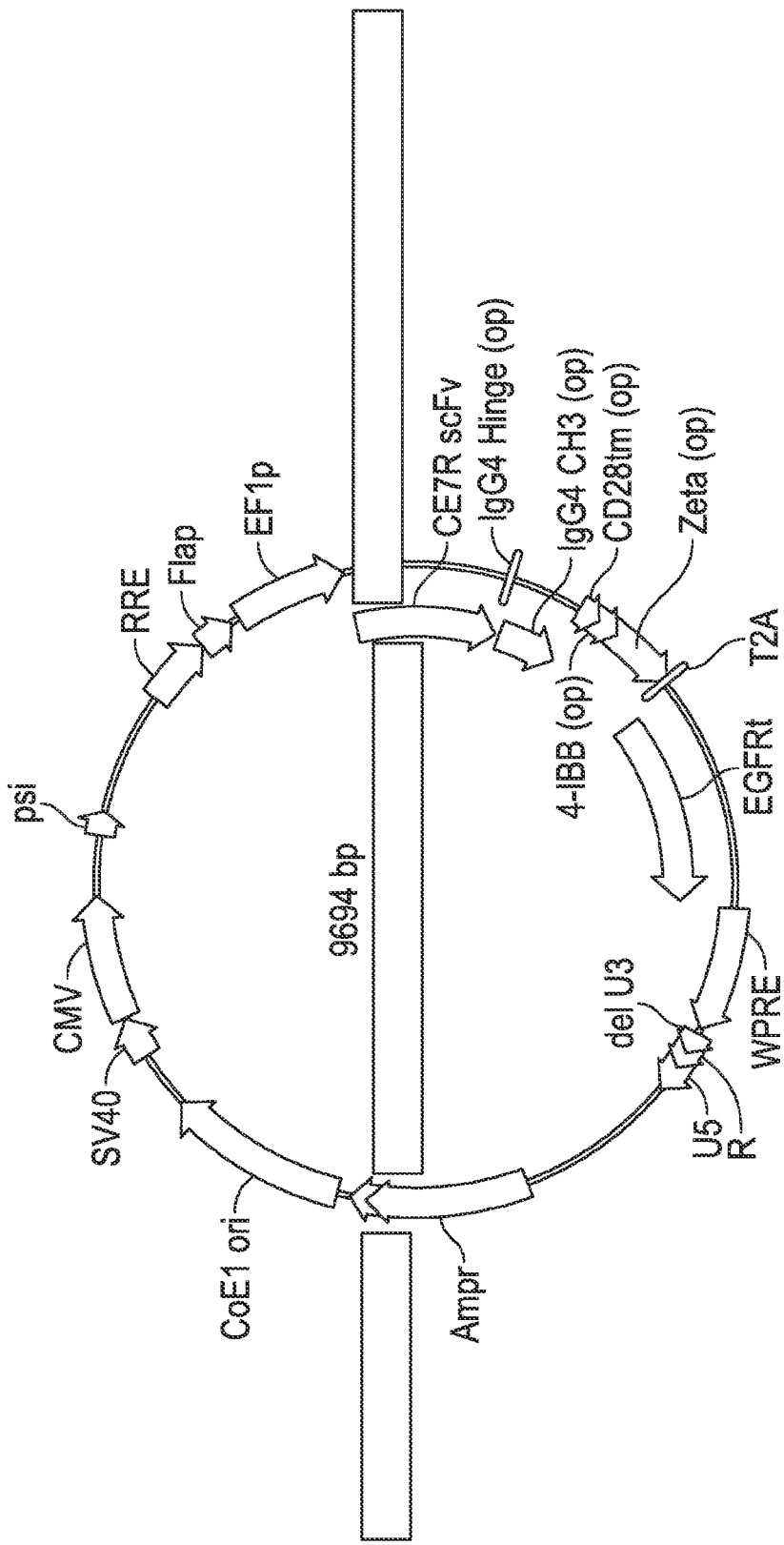

FIG. 8 shows the plasmid map including the sequences for the CE7scFv-IgG4hinge-CH3-CD28tm/4-1BB-zeta-T2A-EGFRt-epHIV7 (intermediate).

Figure 9:
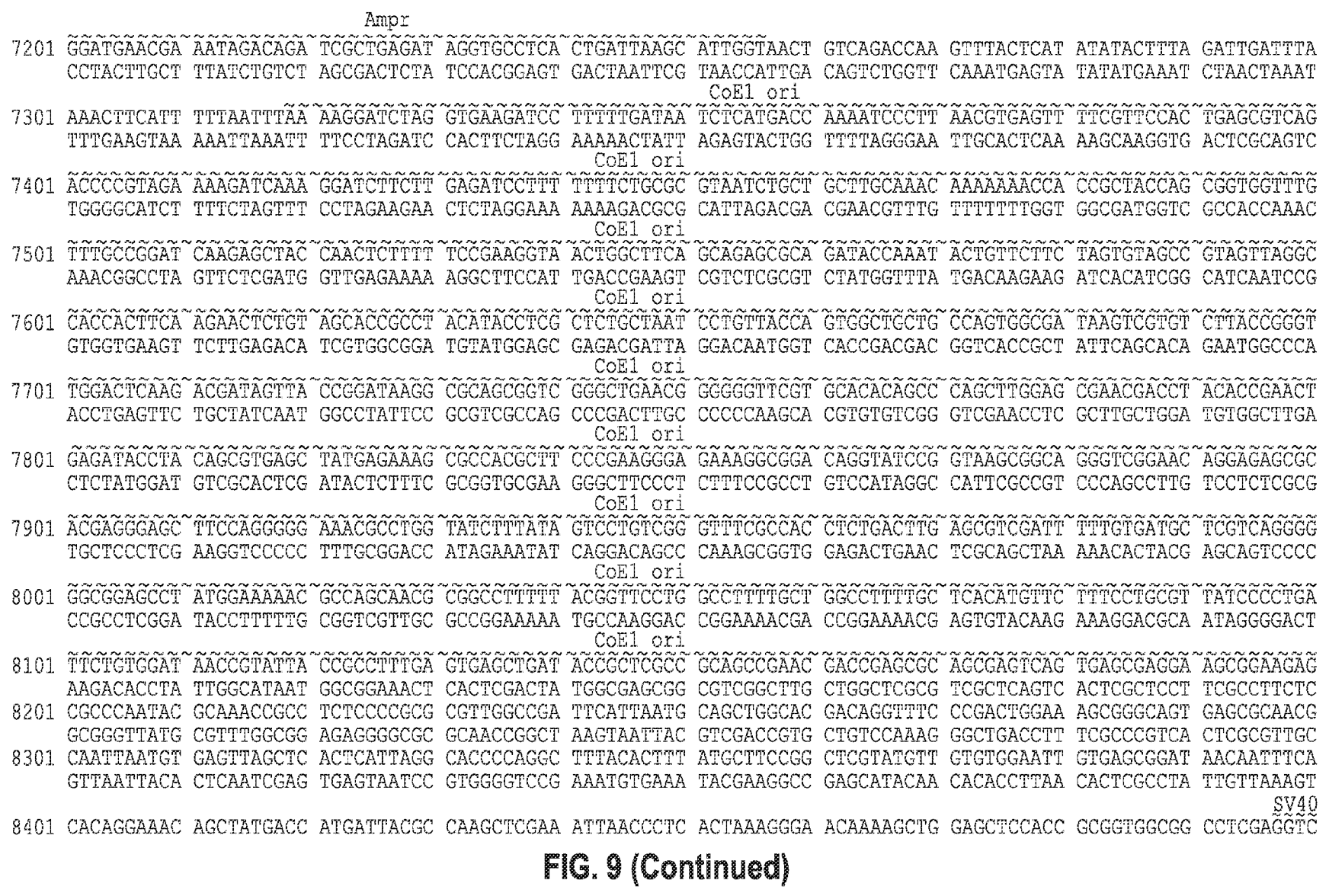

FIG. 9 shows the sequences for CE7scFv-IgG4hinge-CD28tm/4-1BB-zeta-T2A-EGFRt-epHIV7 (short) (SEQ ID NO: 56). Tildes show the beginning and end of the coding sequence for each component of the construct.

Figure 10:
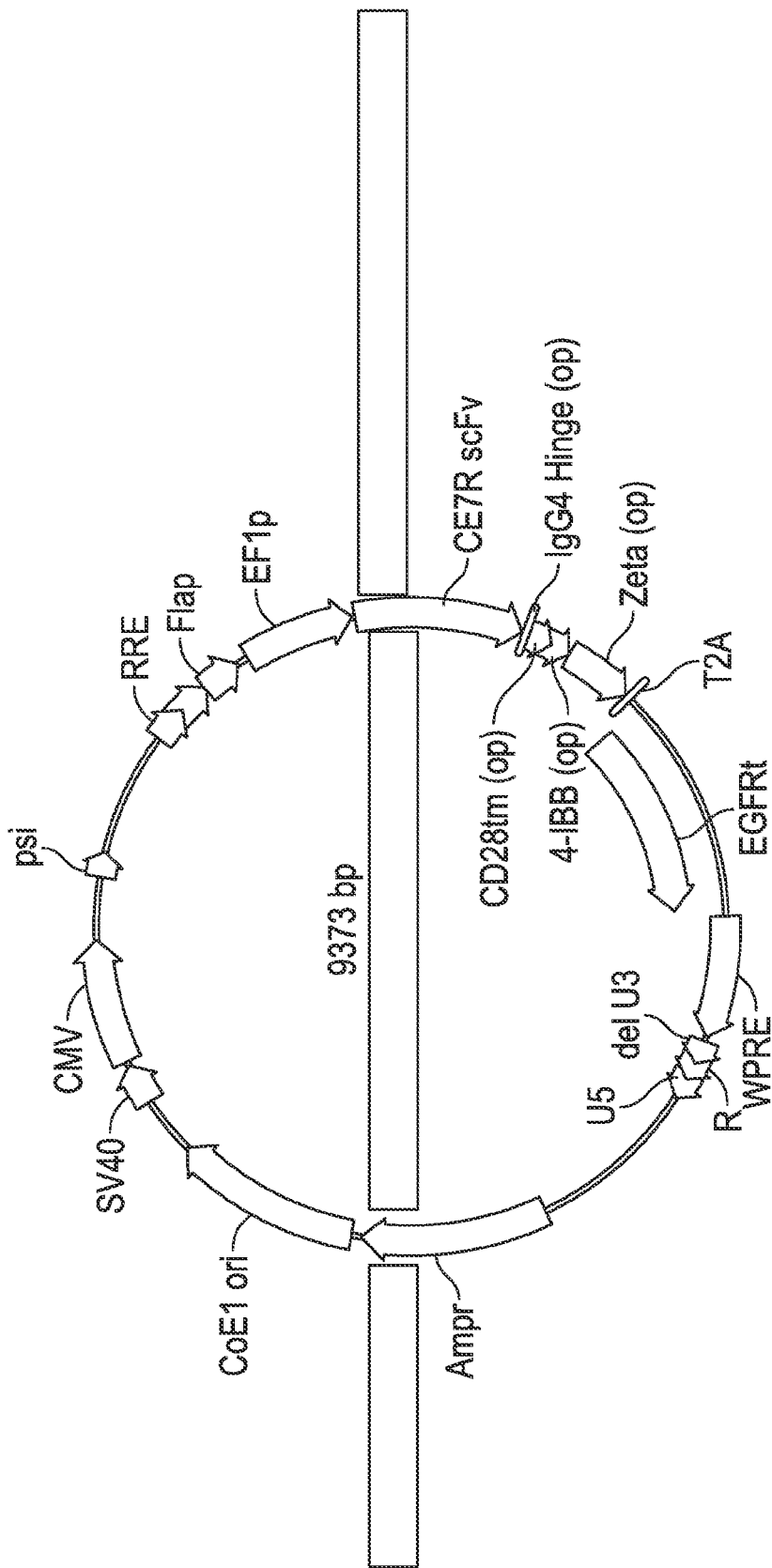

FIG. 10 shows the plasmid map for the sequences for CE7scFv-IgG4hinge-CD28tm/4-1BB-zeta-T2A-EGFRt-epHIV7 (short).

Figure 11:
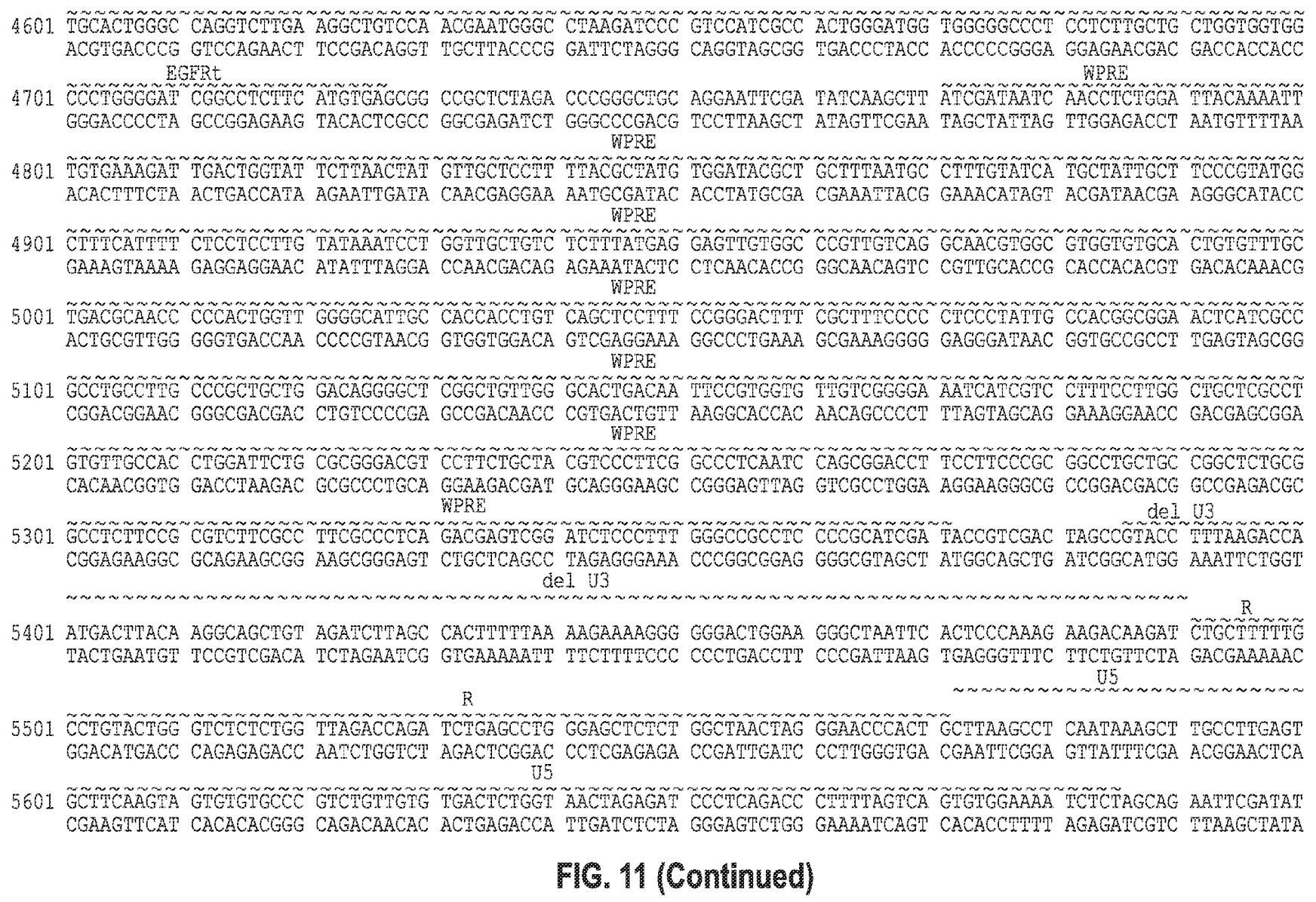

FIG. 11 shows the sequence for construct CE7scFv-IgG4hinge-CD28tm/cyto-4-1BB-zeta-T2A-EGFRt-epHIV7 (short) with two costimulatory domains (SEQ ID NO: 57). Tildes show the beginning and end of the coding sequence for each component of the construct.

Figure 12:
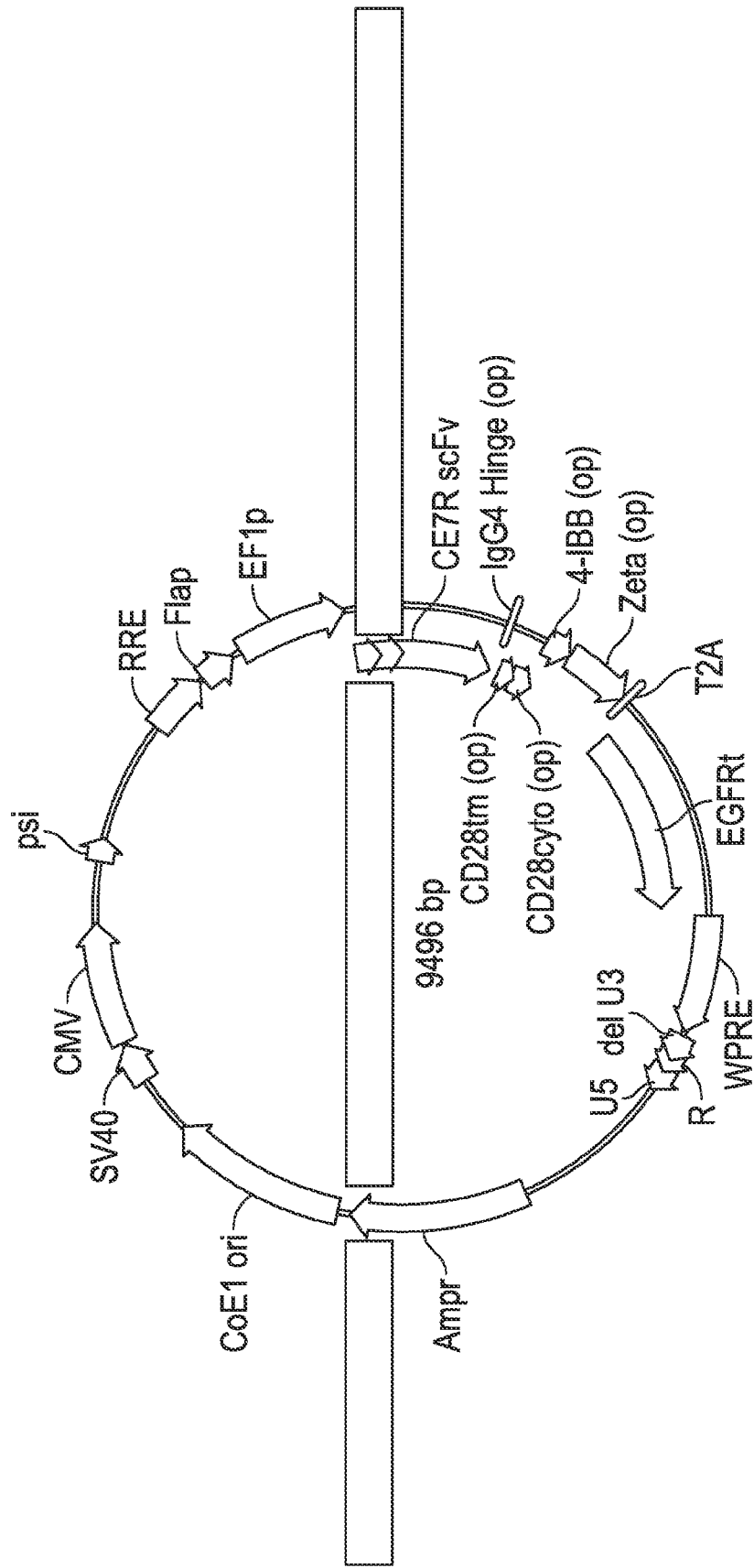

FIG. 12 shows the plasmid map including the sequence for construct CE7scFv-IgG4hinge-CD28tm/cyto-4-1BB-zeta-T2A-EGFRt-epHIV7 (short) with two costimulatory domains.

Figure 13A:
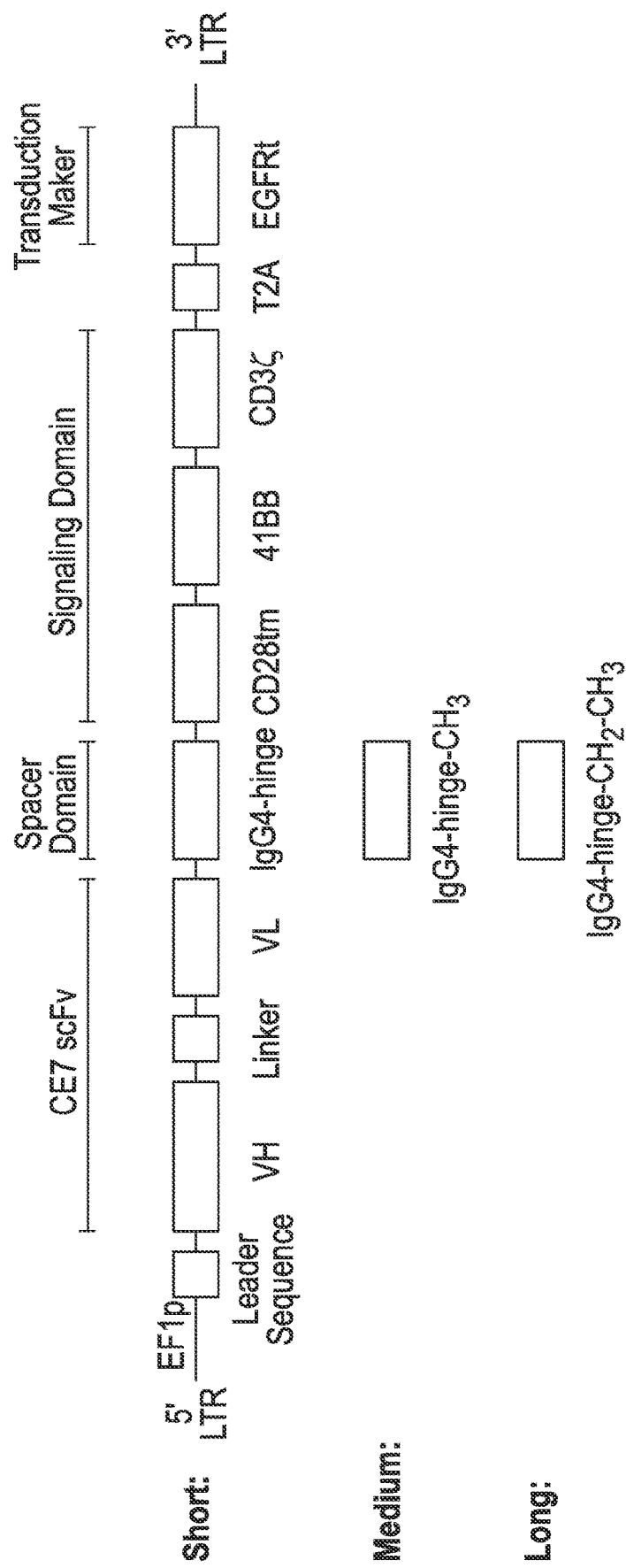
Figure 13B:
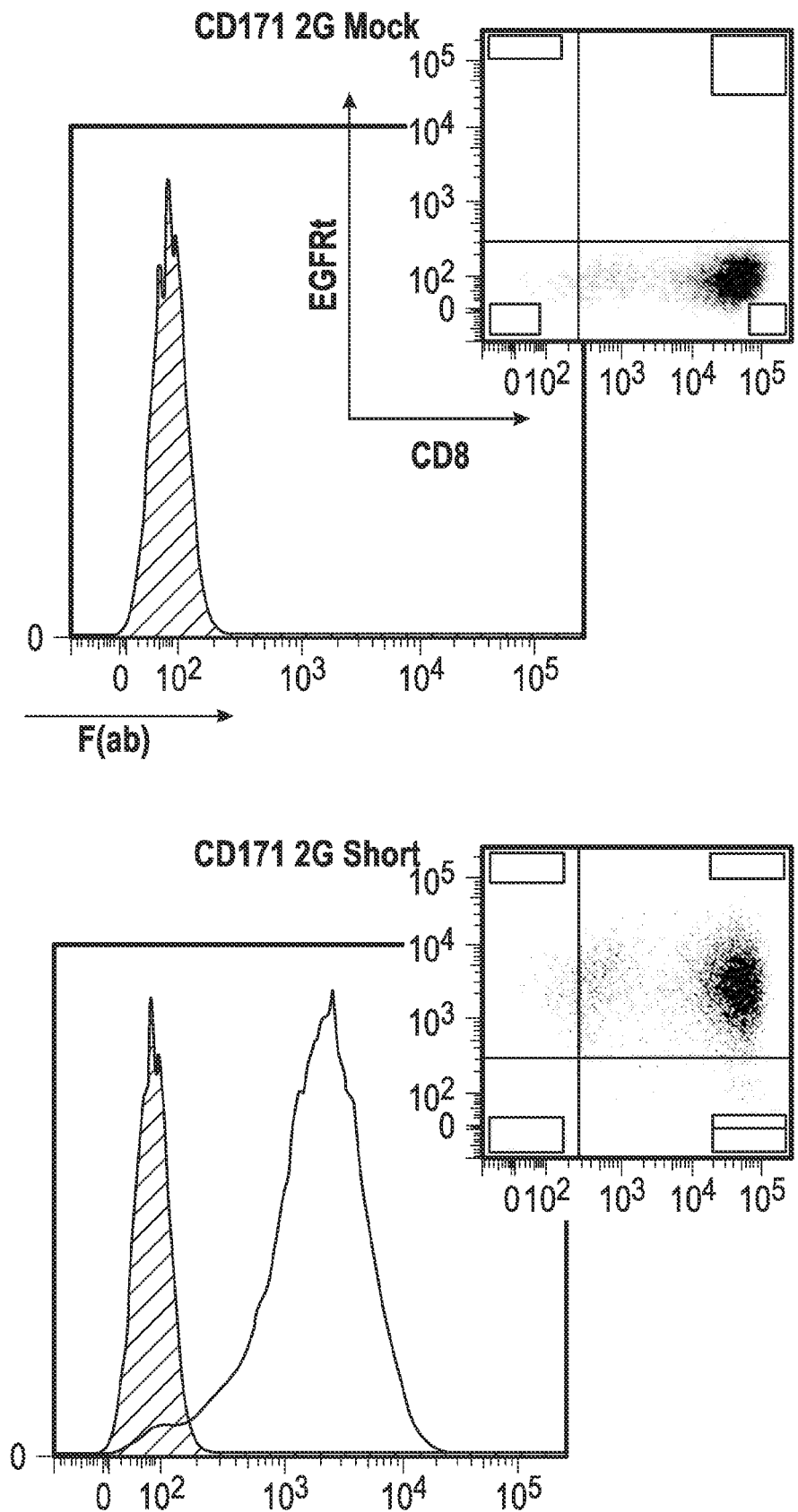
Figure 13B:
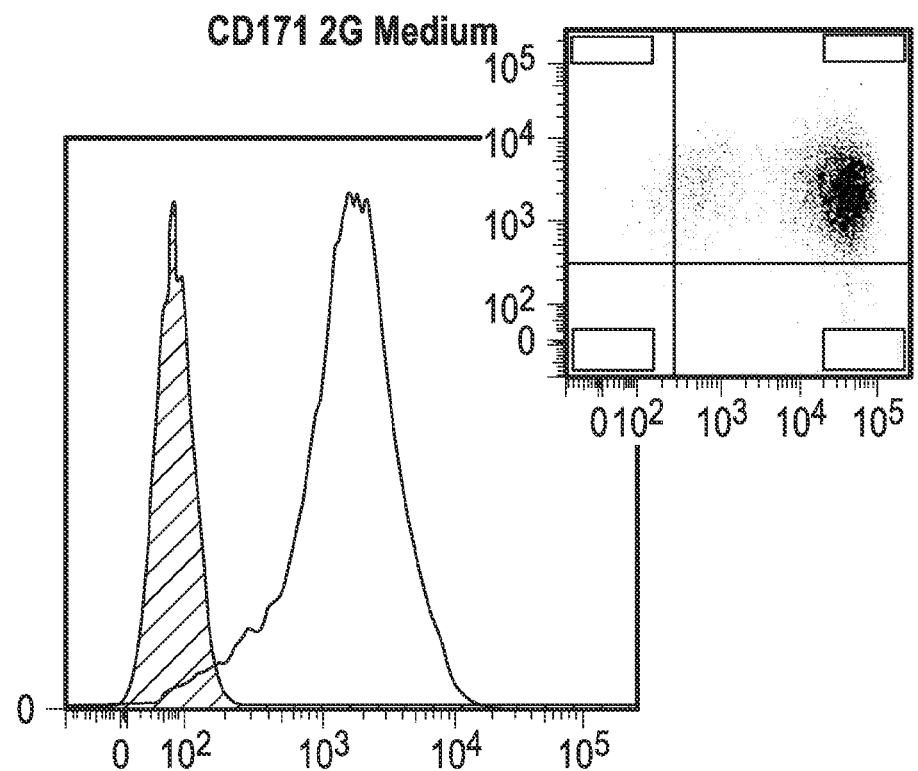
Figure 13B:
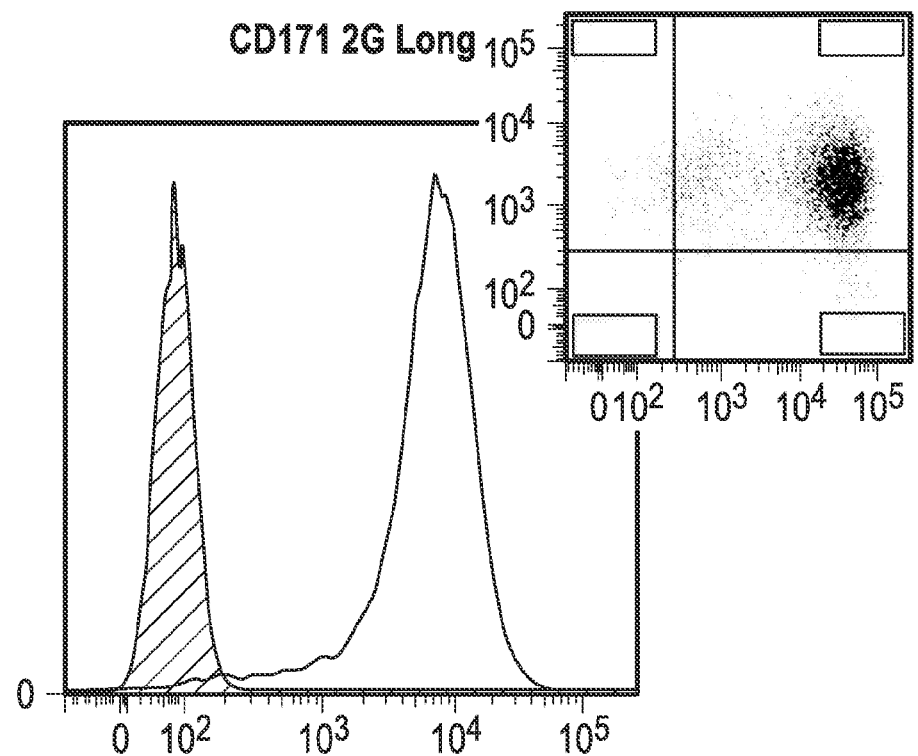
Figure 13C:
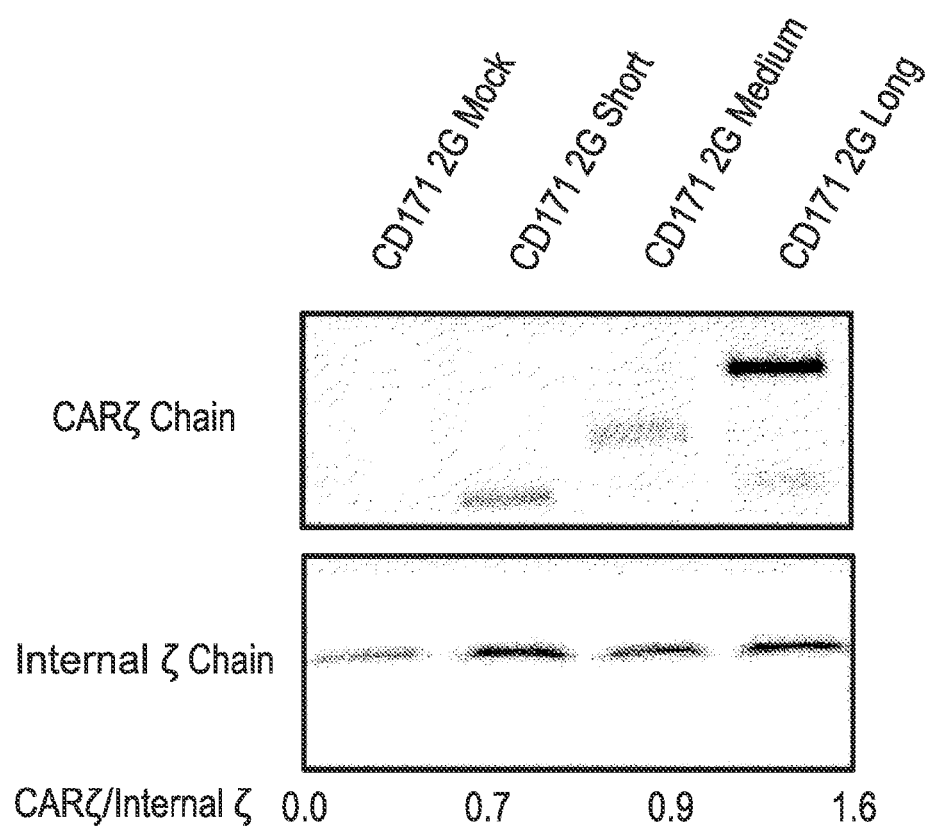
Figure 13D:
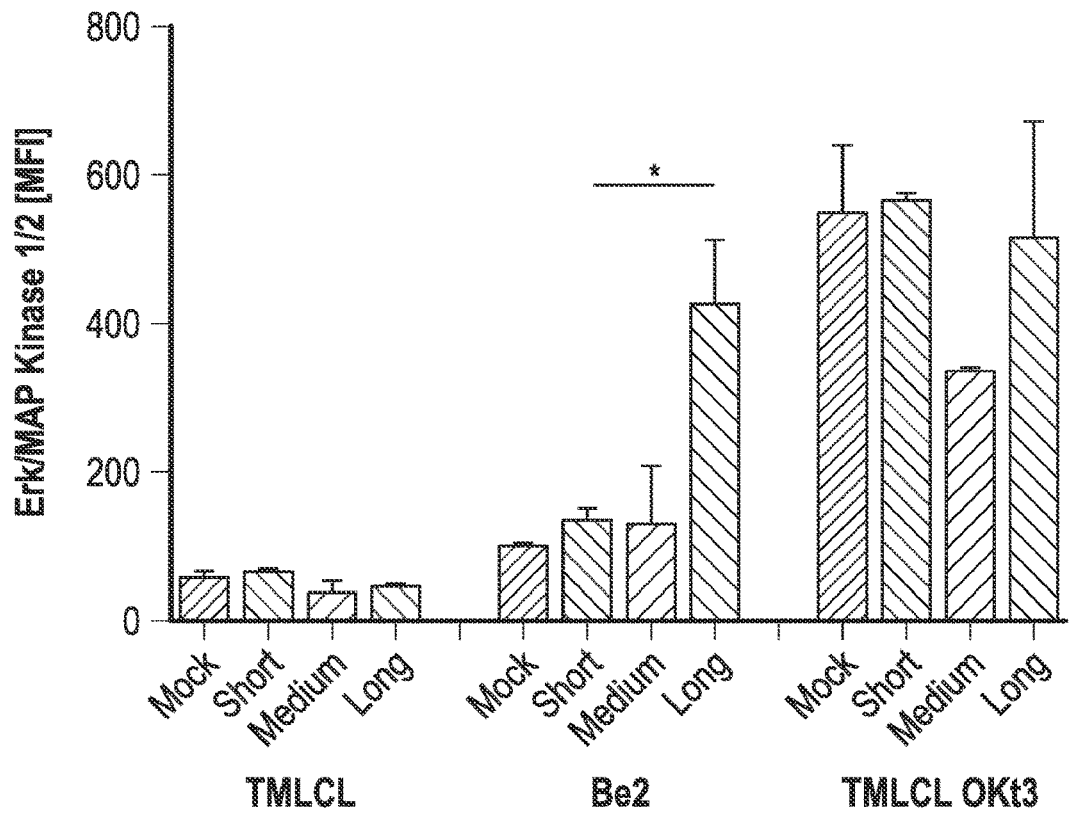
Figure 13E:
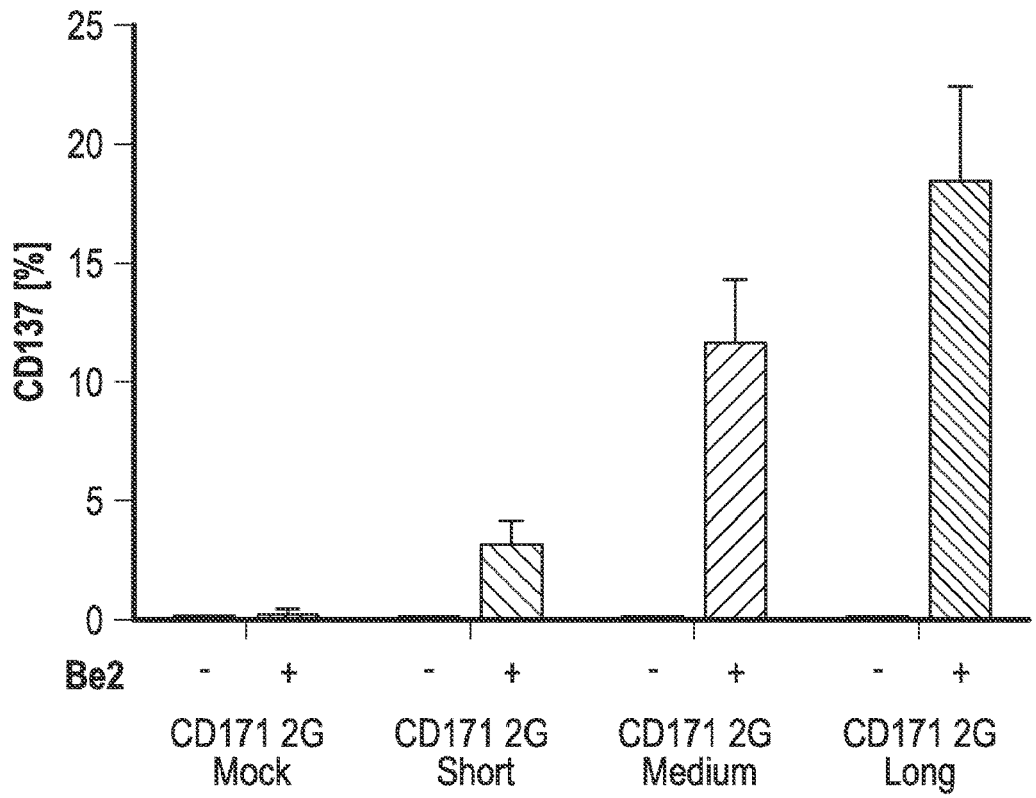
Figure 13F:
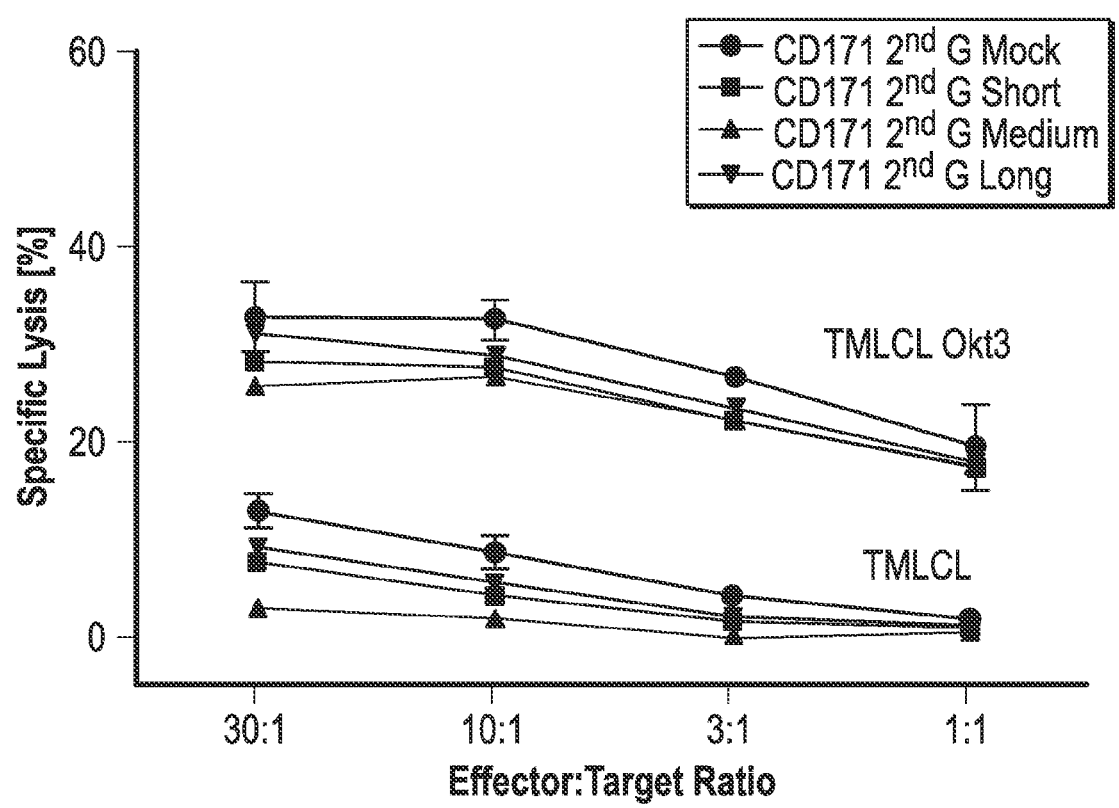
Figure 13F:
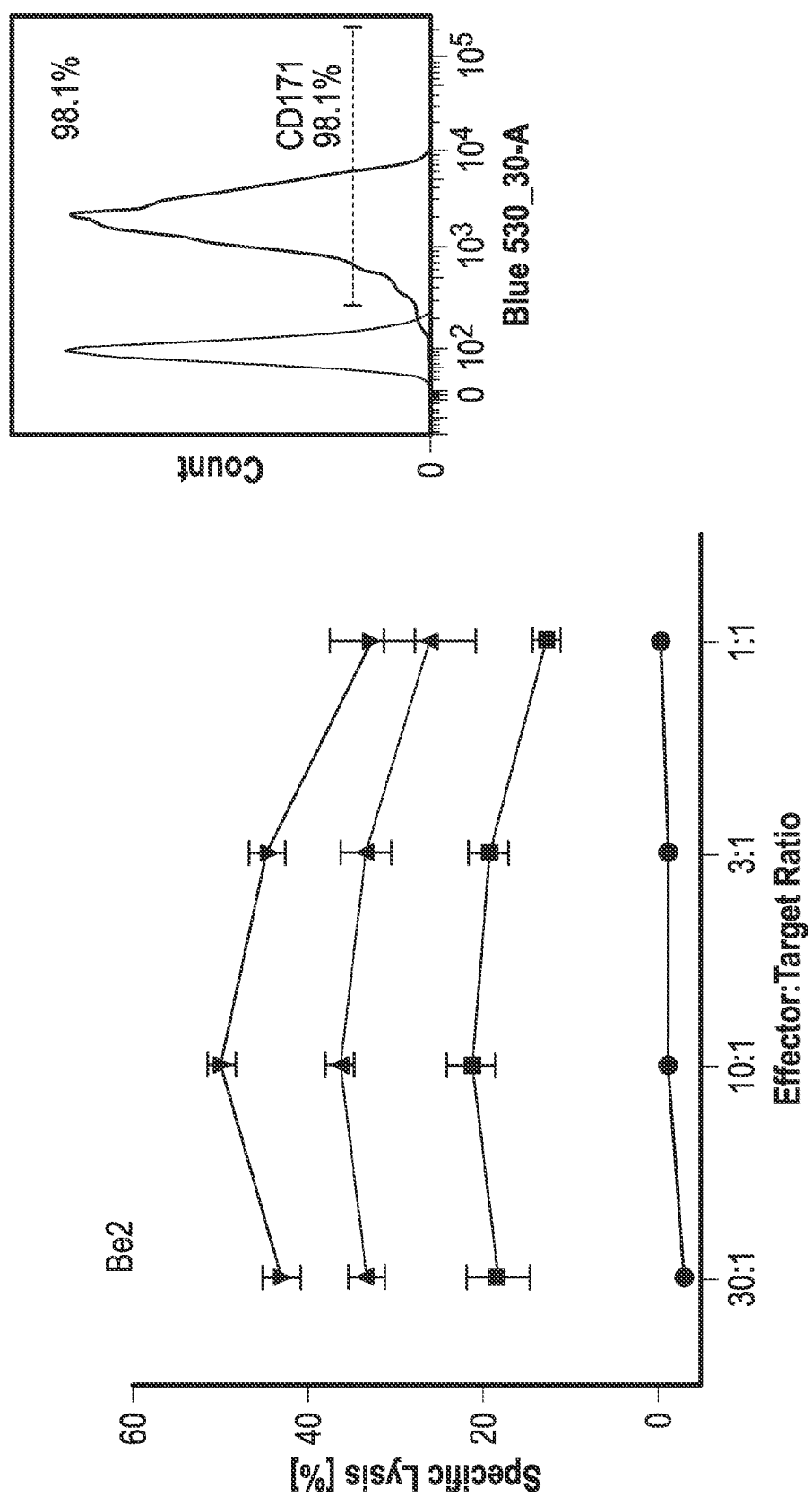
Figure 13F:
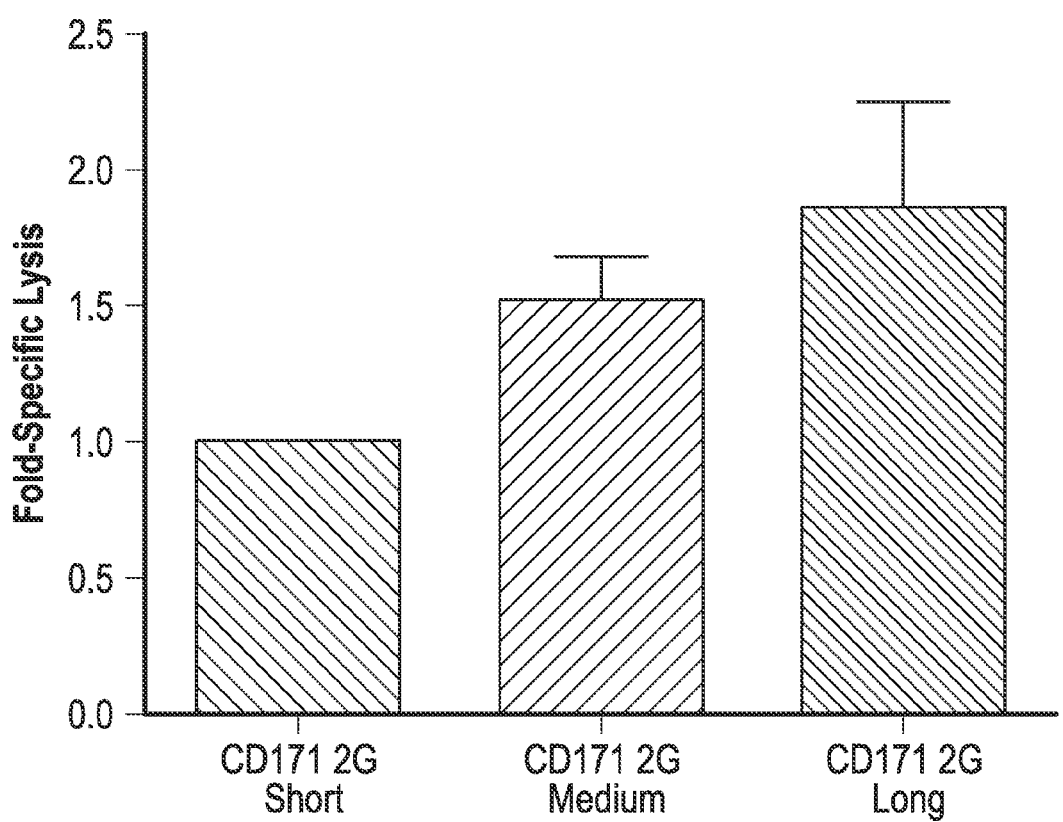
Figure 13G:
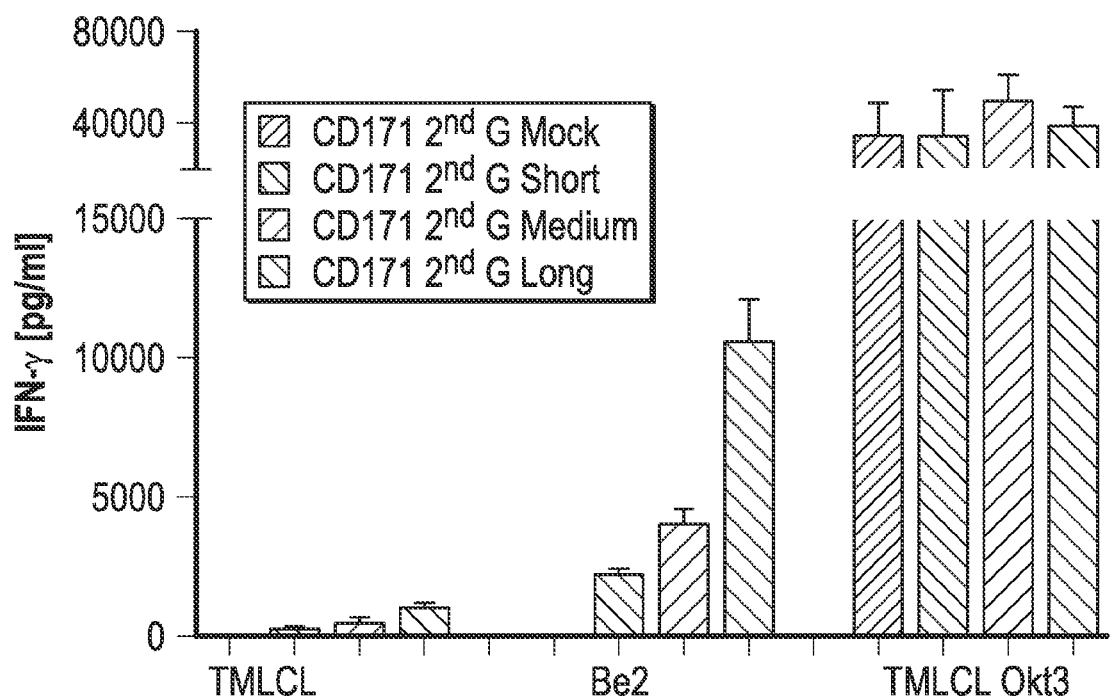
Figure 13G:
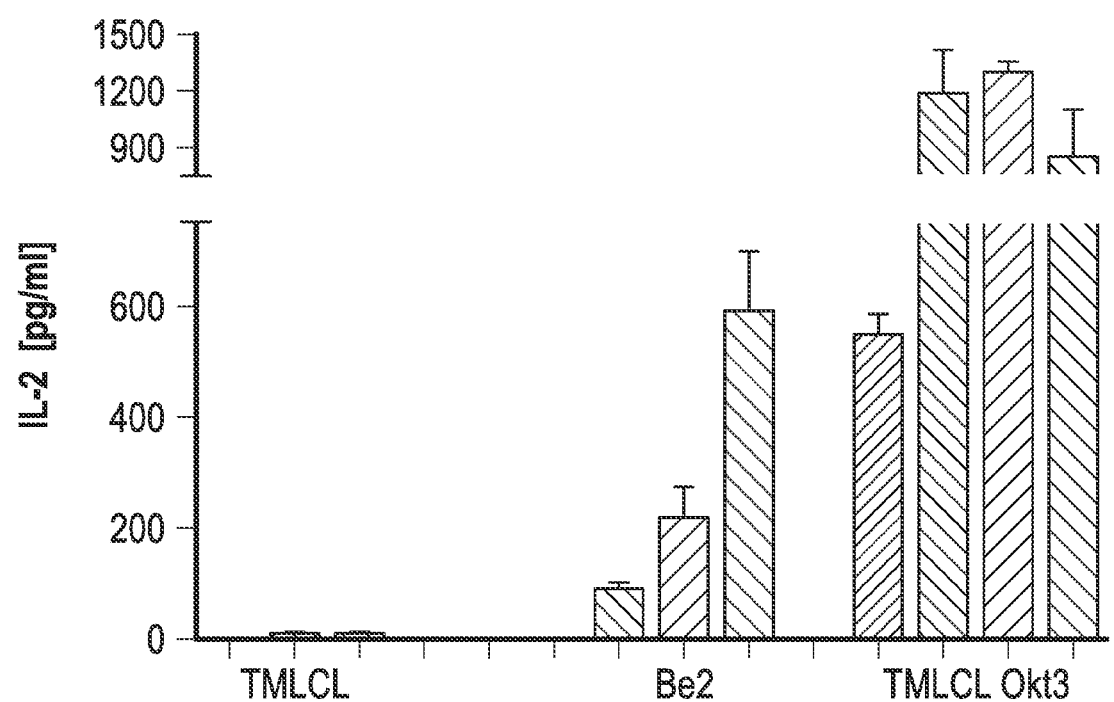
Figure 13G:
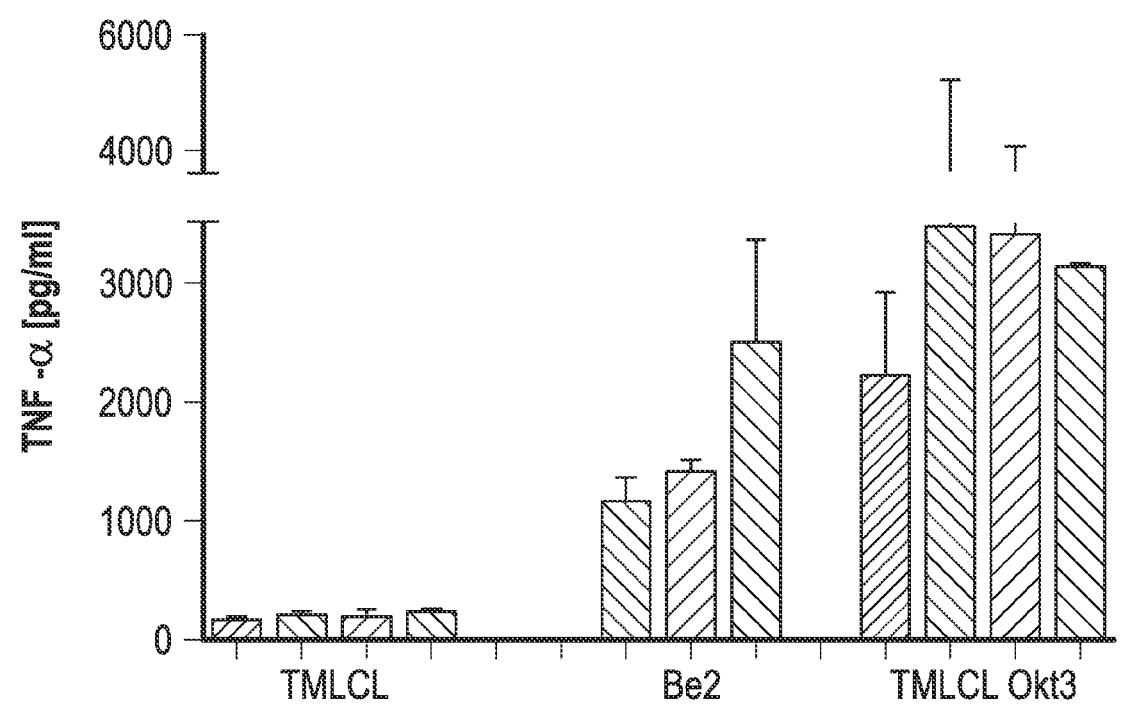
Figure 13H:
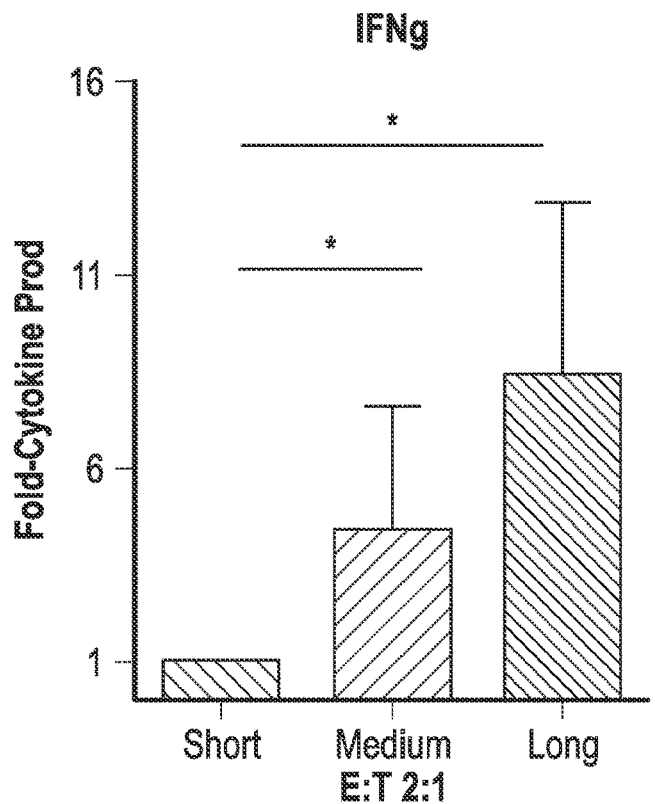
Figure 13H:
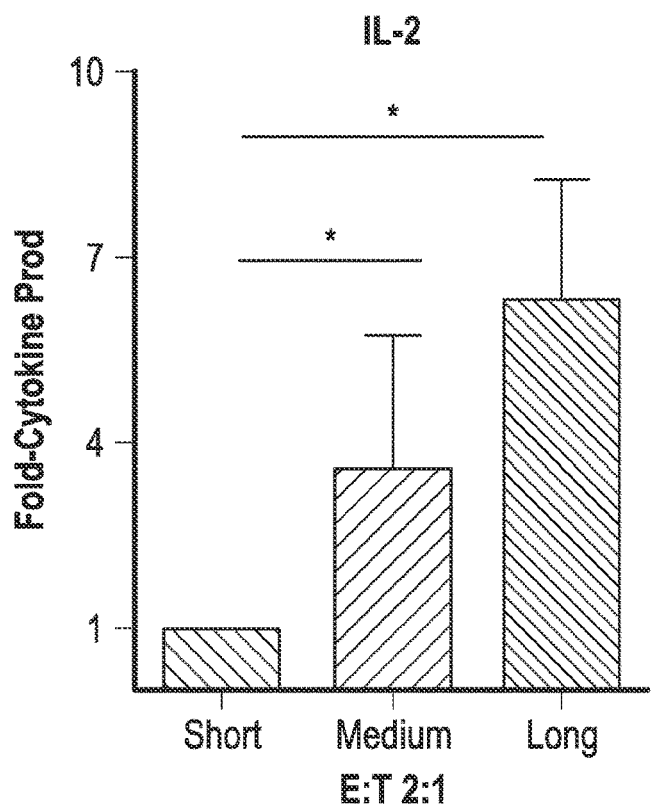
Figure 13H:
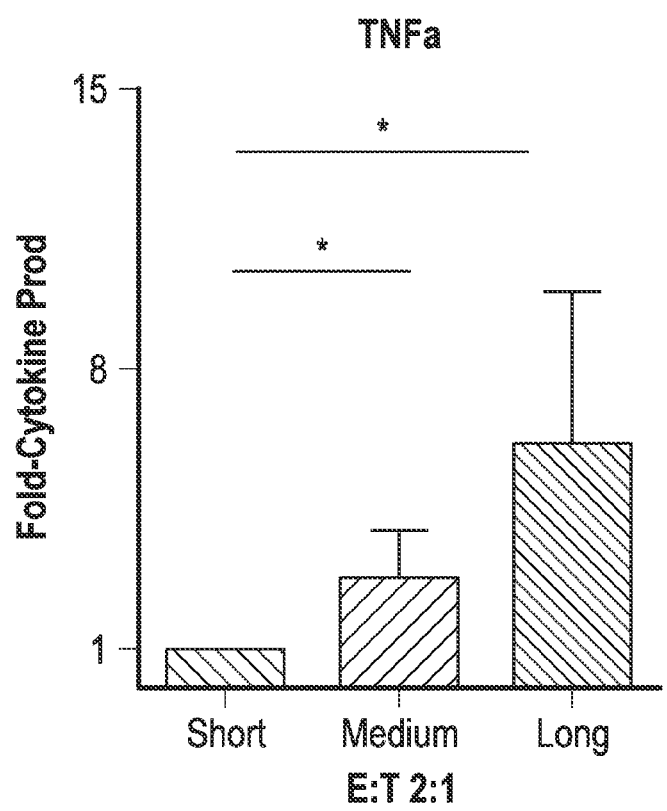

FIGS. 13A-13H shows the CAR extracellular spacer tunes anti-tumor effector outputs of CD8$^+$ expressing CTLs. FIG. 13A shows the schematic of CD171-specific and/or targeting 2G-CAR extracellular domain spacer variants. FIG. 13B shows the Human CD8$^+$ T$_{E(CM)}$ cell surface expression of 2G SS, MS or LS spacer variants and EGFRt detected with anti-murine FAB and cetuximab, respectively. FIG. 13C shows the 2G-CAR expression levels detected by a CD3-ζ specific Western Blot. FIG. 13D shows the 2G-CAR induced levels of phospho-ERK upon co-culture with CD171$^+$ Be2 neuroblastoma tumor cells at an E:T ratio of 1:1 (n≥3 per condition). FIG. 13E shows the 2G-CAR activation induced CD137 surface expression upon tumor co-culture as in FIG. 13D. FIG. 13F shows the Anti-tumor lytic activity of spacer variant 2G-CAR CTLs determined by 4-hour chromium release assay. Fold specific lysis of LS and MS spacers relative to SS 2G-CAR CTLs at an E:T ratio of 10:1. FIG. 13G shows the Stimulation of cytokine secretion in mixed 2G-CAR CTL mixed tumor (Be2) cultures (n≥5 per condition). Fold cytokine production comparison is relative to SS 2G-CAR, as in FIG. 13H.

Figure 1:
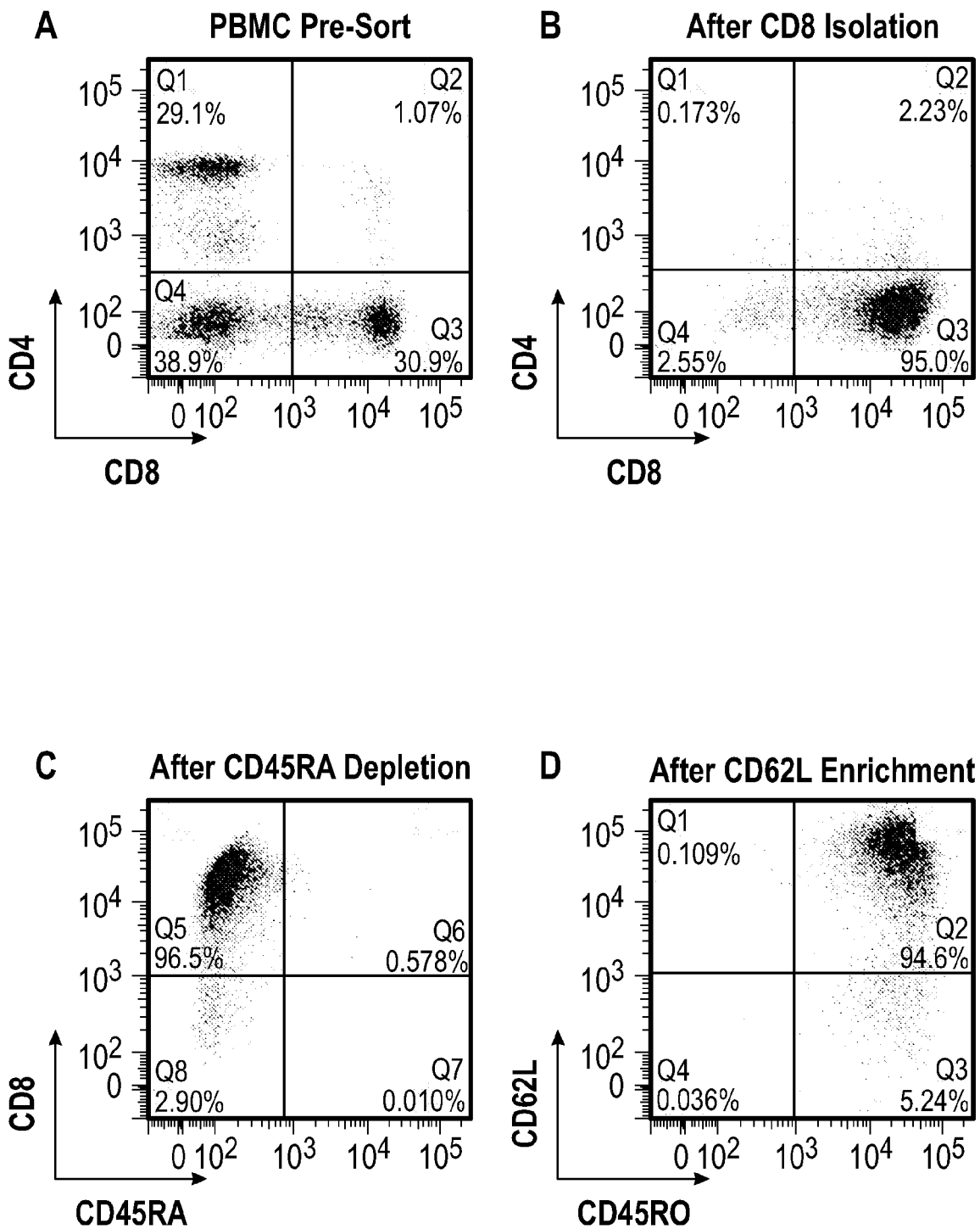
FIG. 1 shows isolation of central memory T cells from peripheral blood mononuclear cells. A) shows a flow cytometry profile of cells presorted for CD4 and CD8 markers. B) shows a flow cytometry profile of cells after sorting for the presence of CD8. C) shows a flow cytometry profile of cells after depletion of the CD8+ cell population for cells positive for CD45RA. D) shows a flow cytometry profile of a cell population enriched for CD8, depleted for CD45RA, enriched for CD45RO, and enriched for CD62L.
Figure 14A:
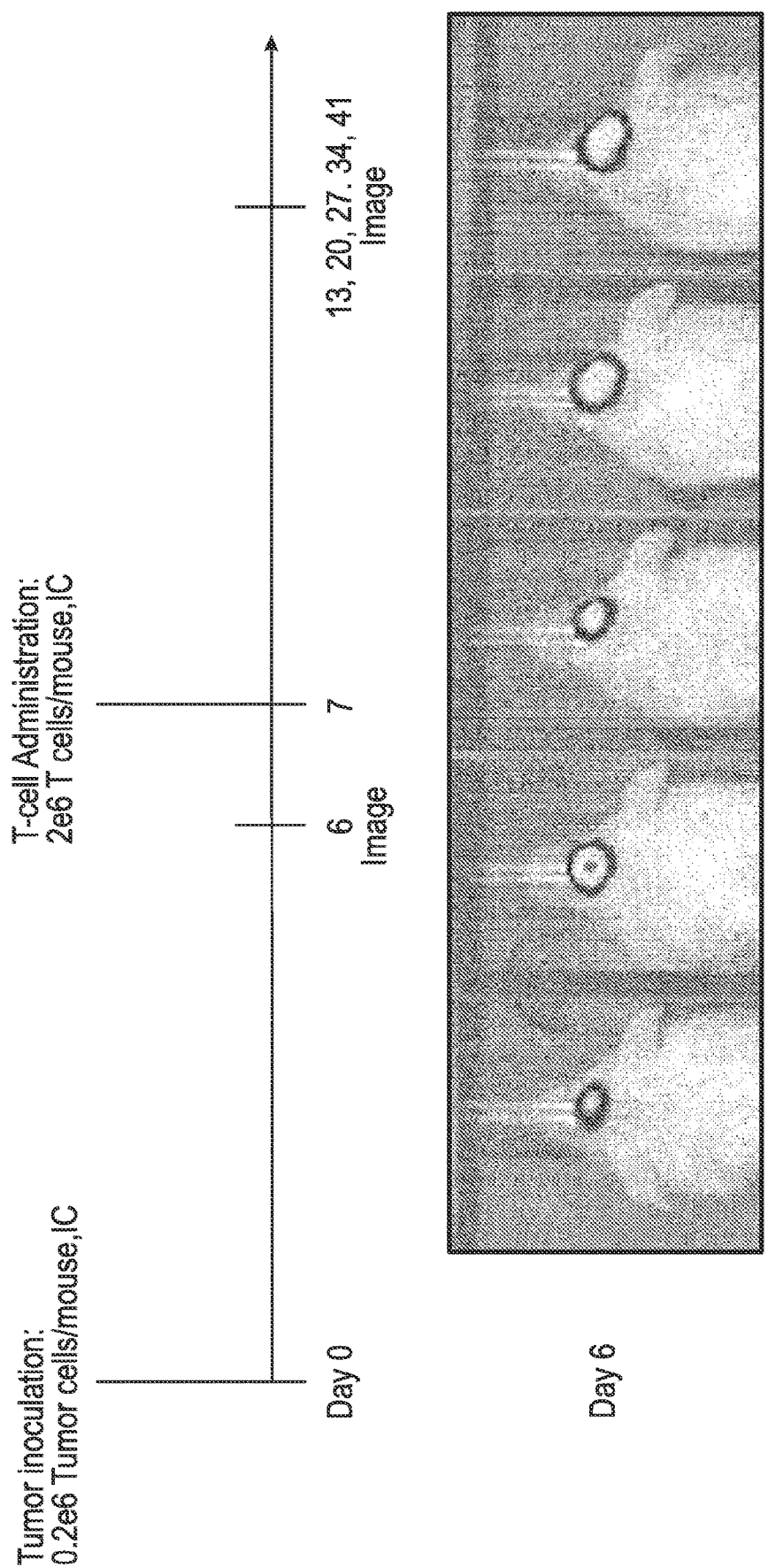
Figure 14B:
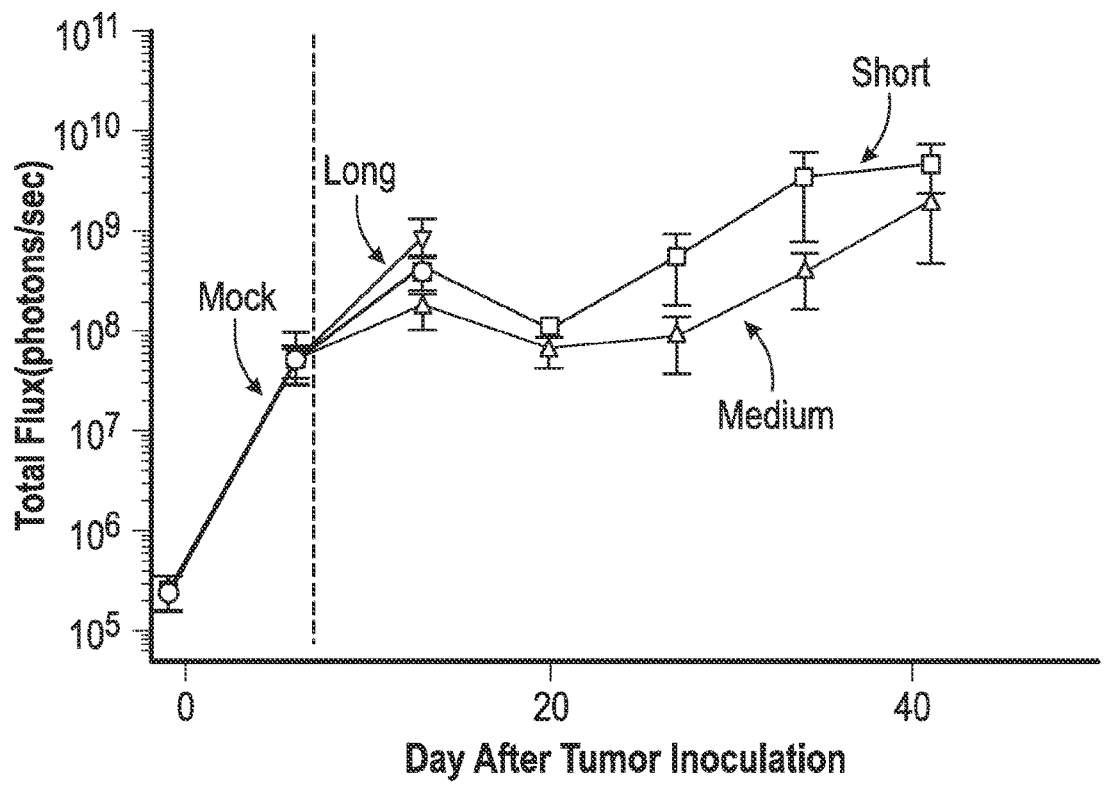
Figure 14C:
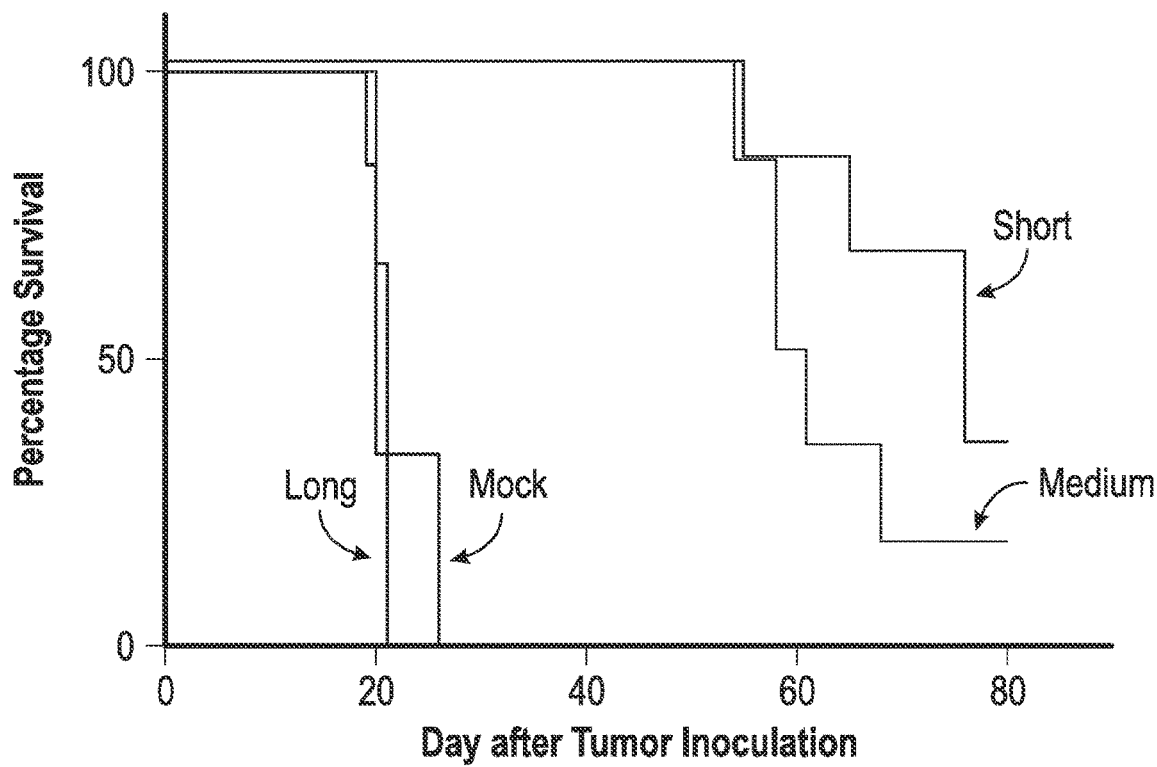
Figure 14D:
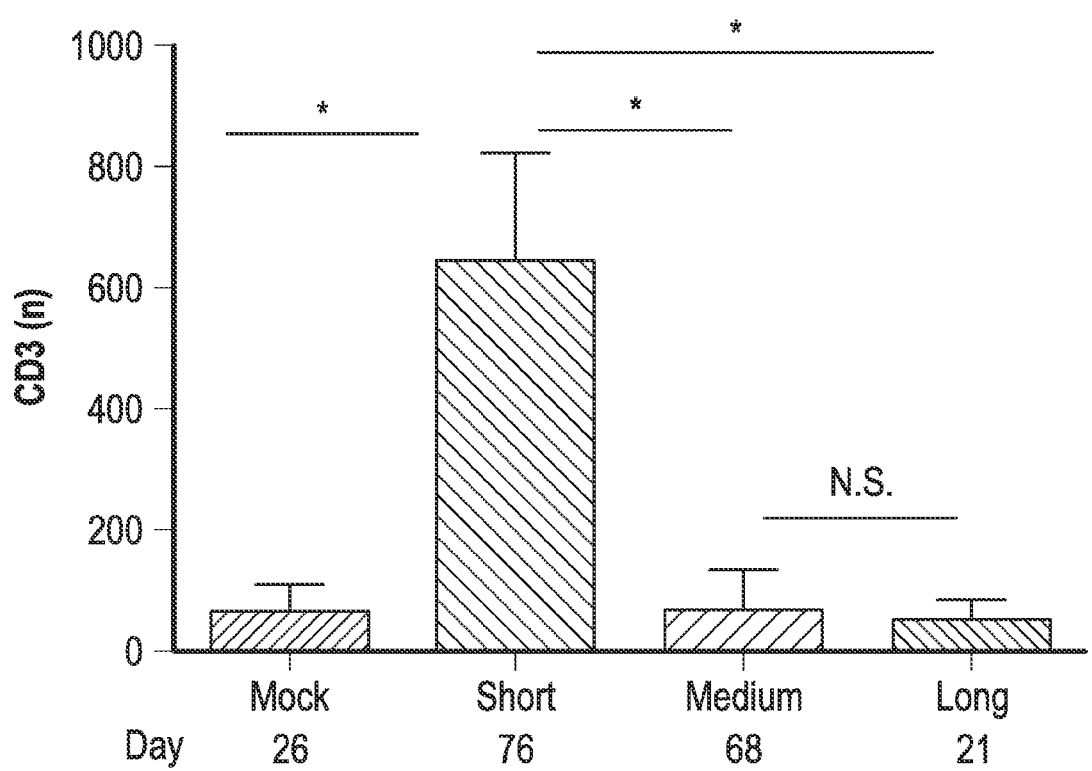
Figure 14E:
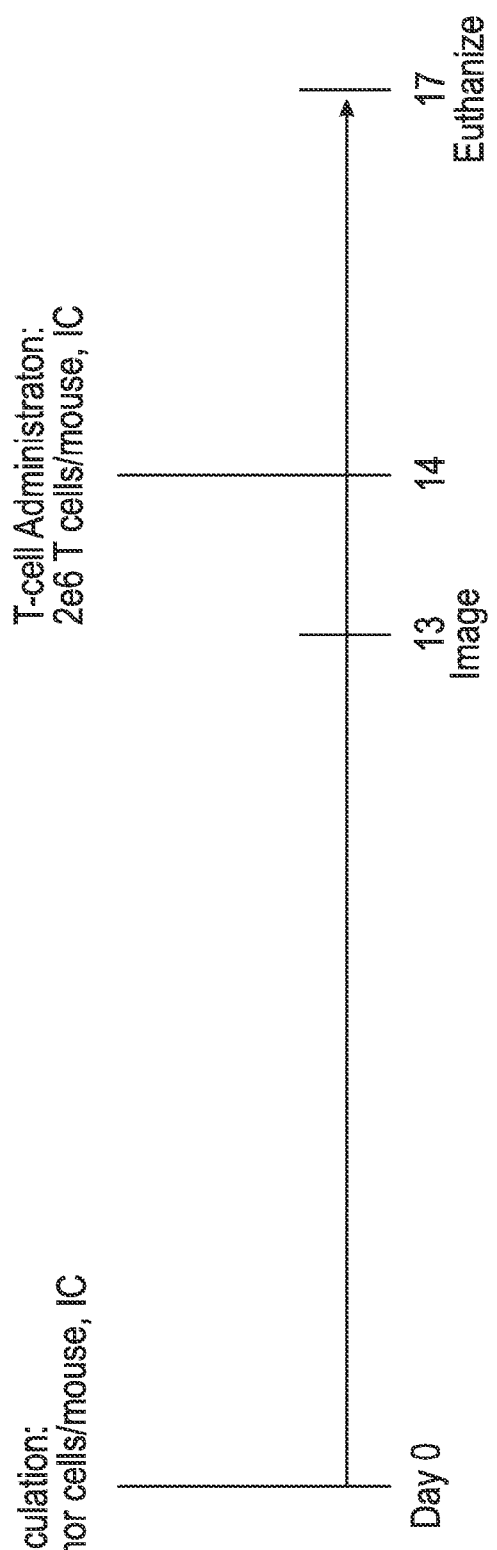
Figure 14G:
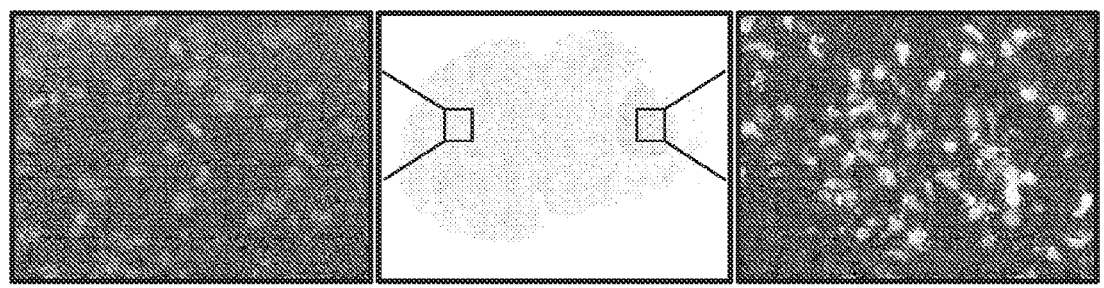
Figure 14G:
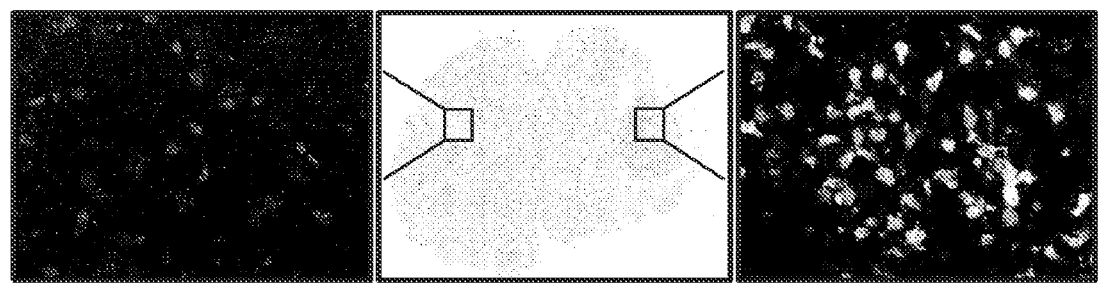
Figure 14G:
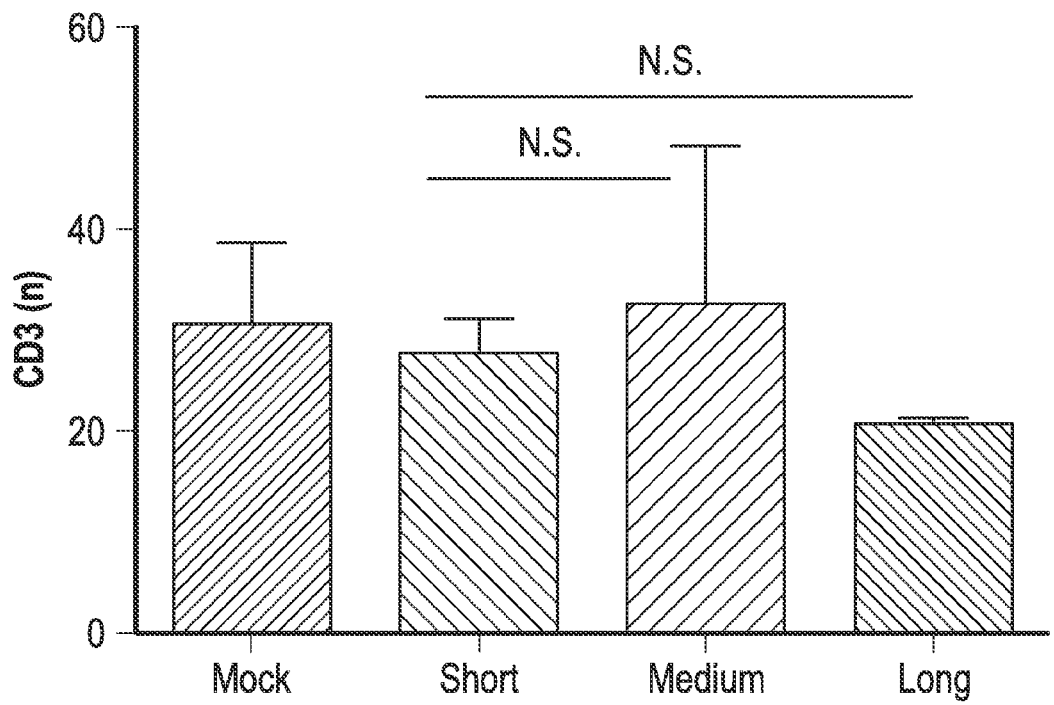
Figure 14H:
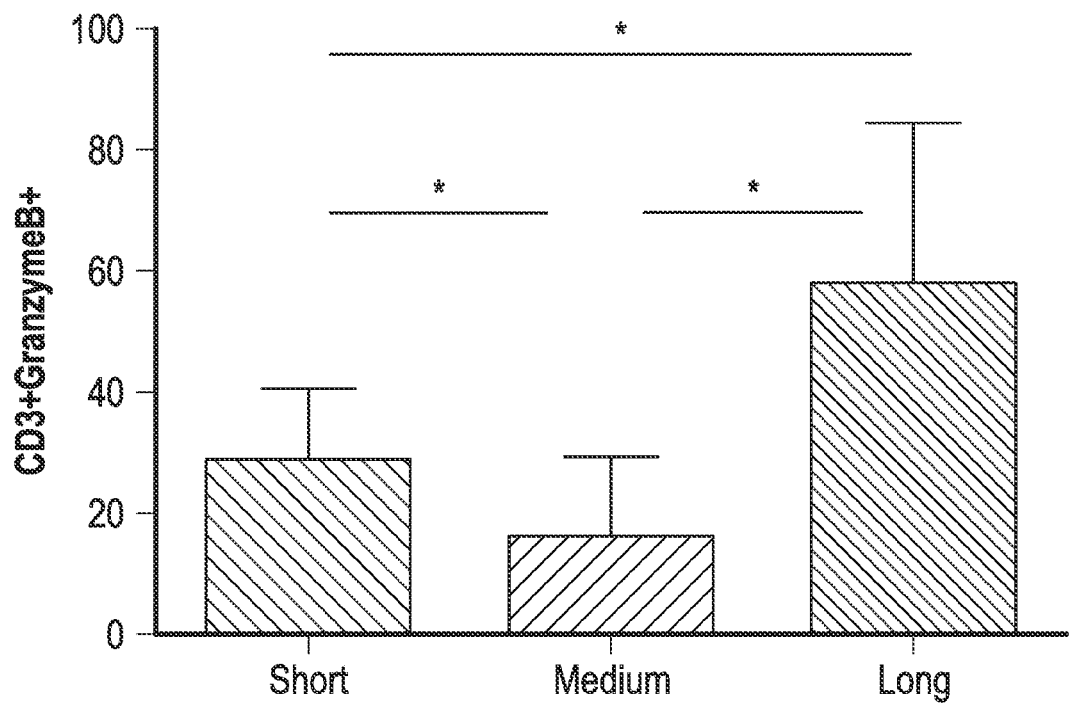
Figure 14H:
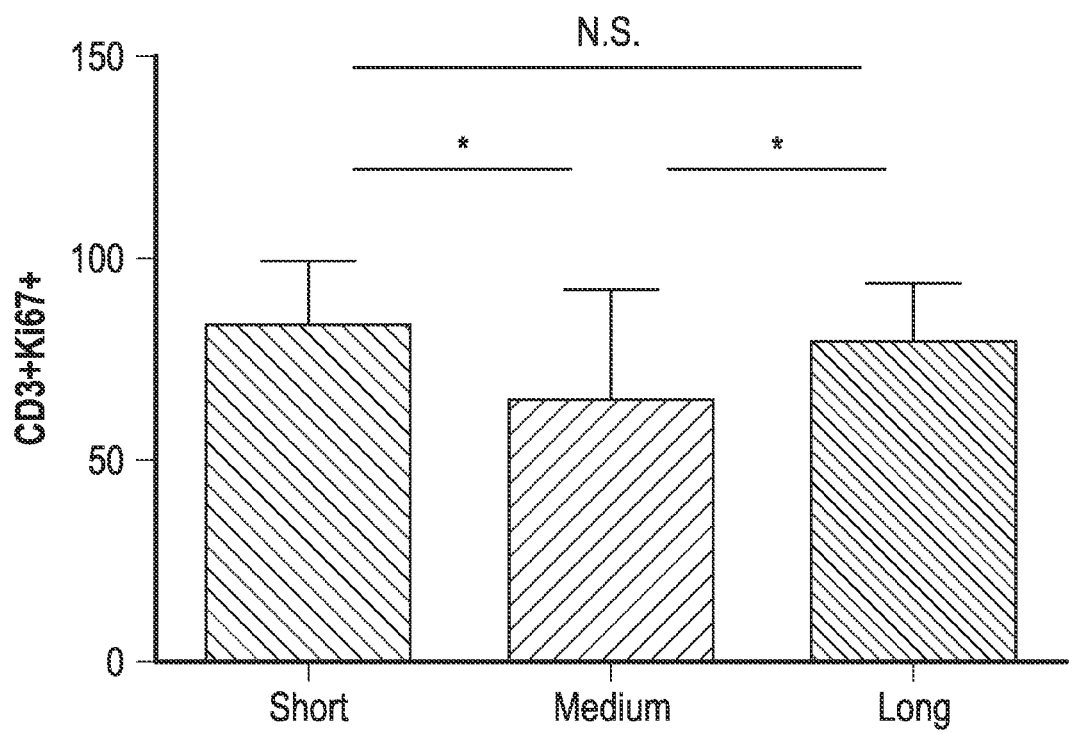
Figure 14H:
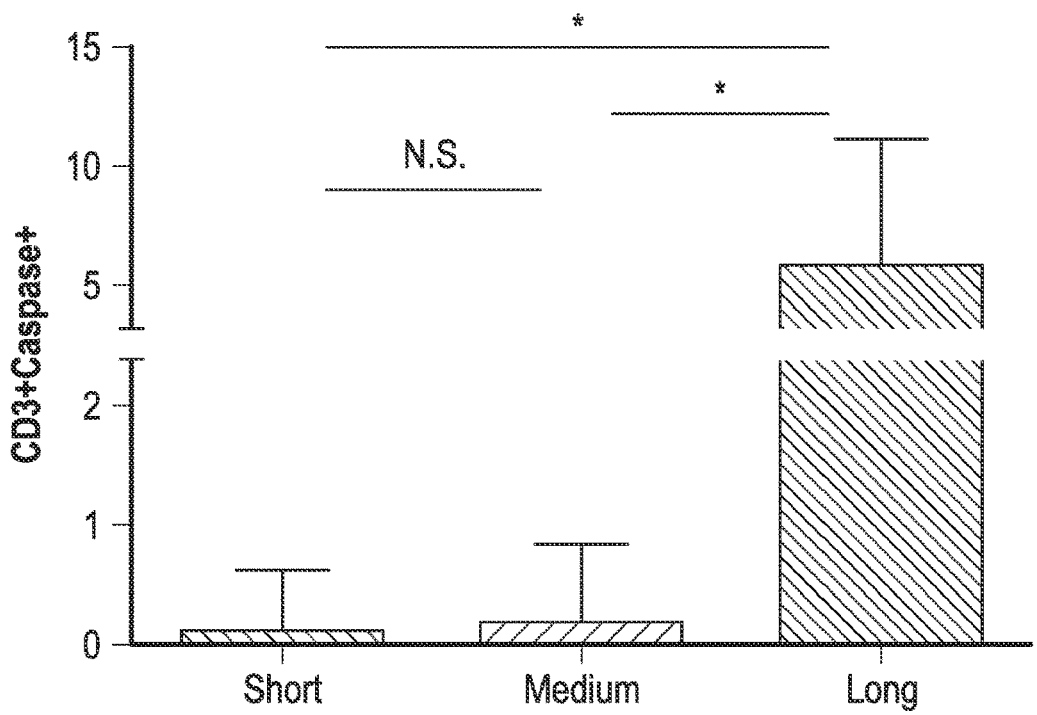

FIGS. 14A-14H shows the inverse correlation of CAR spacer-dependent CTL functional potency in vitro and anti-tumor activity in vivo. FIG. 14A shows the schema of intracranial NSG mouse neuroblastoma xenograft therapy model and biophotonic signal of ffLuc$^+$ Be2 tumors at day +6 following stereotactic implantation. FIG. 14B shows the Biophotonic Be2 tumor signal response to intratumorally infused 2G-CAR CD8$^+$ $T_{E(CM)}$ spacer variants (n=6 mice per group). LS 2G-CAR cohort was euthanized on day 20 due to tumor related animal distress. FIG. 14C shows the Kaplan Meier survival of treated cohorts from FIG. 14B. FIG. 14D shows the quantitation of intratumoral 2G-CAR T cells at time of symptomatic tumor progression. T cell density determined by counting human CD3+ cells and reported as total number per 40 hpf's (data representative of individual tumor analysis). FIG. 14E shows the timeline of tumor retrieval from NSG mice bearing Be2 i.c. xenografts and treated with 2G-CAR CTLs for subsequent IHC/IF inspection. FIGS. 14F1 and 14F2 shows the representative tumor and contralateral hemisphere IF images for co-staining of co-localized SS 2G-CAR CTLs for CD3, Ki67 and activated caspase 3. FIG. 14G shows the IF quantitation of persisting 2G-CAR spacer variant CTLs three days after intratumoral implantation. N=total human CD3+ cells per 40 hpf as in FIG. 14D. FIG. 14H shows the Percentage of CD3+ T cells that co-express granzyme B (left panel), Ki67 (middle panel), and activated caspase 3 (right panel) (n=ave. number cells/40hpf from analysis of two individual engrafted mice).

Figure 15A:
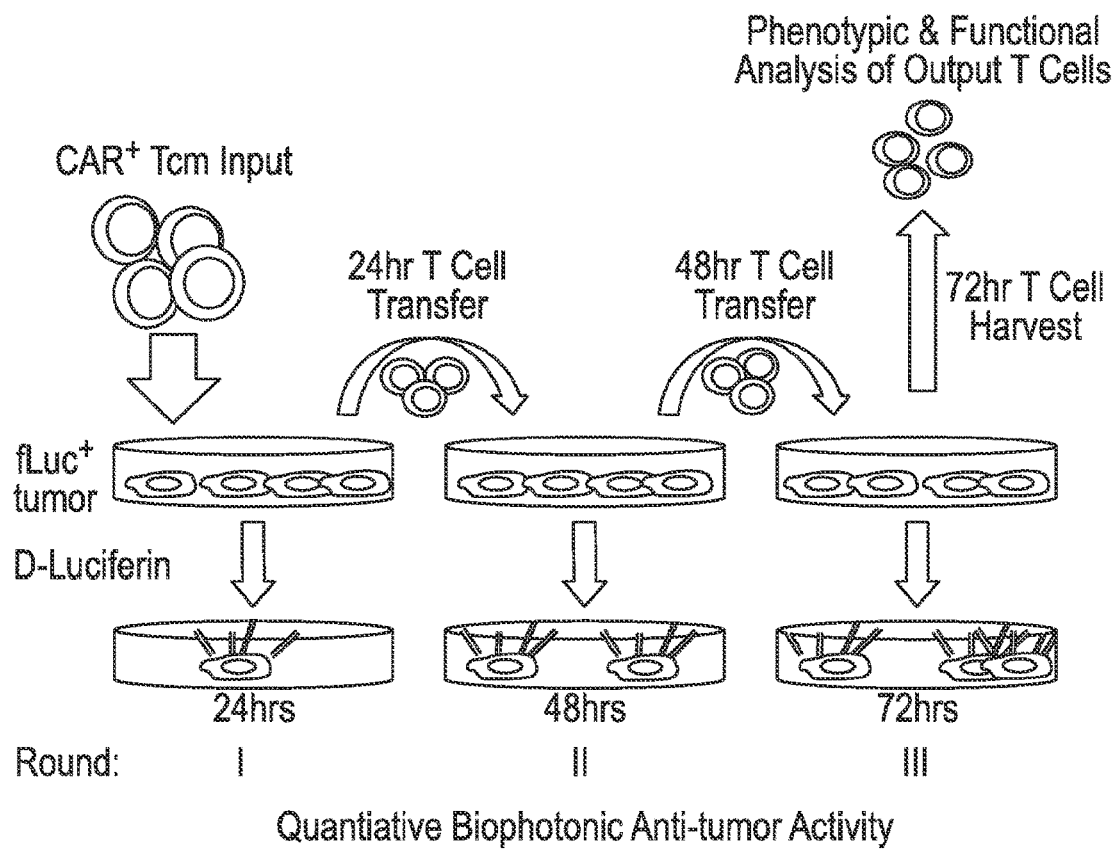
Figure 15B:
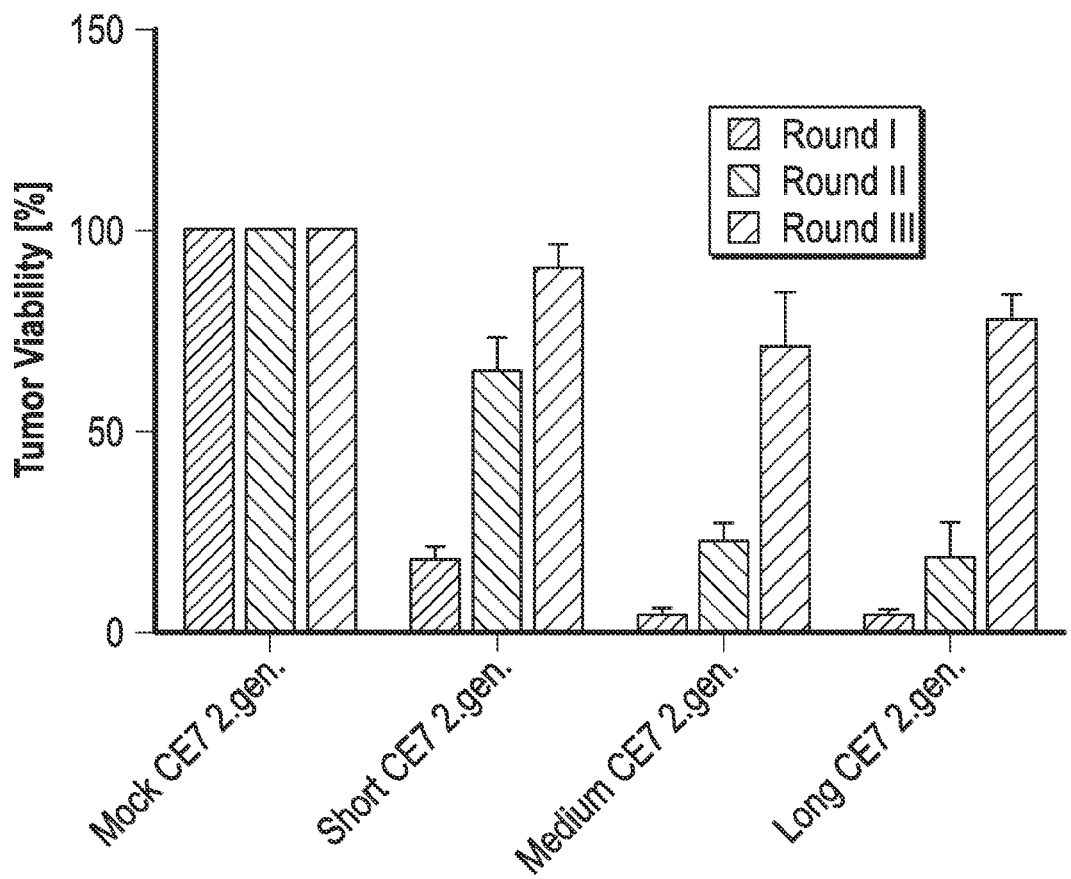
Figure 15C:
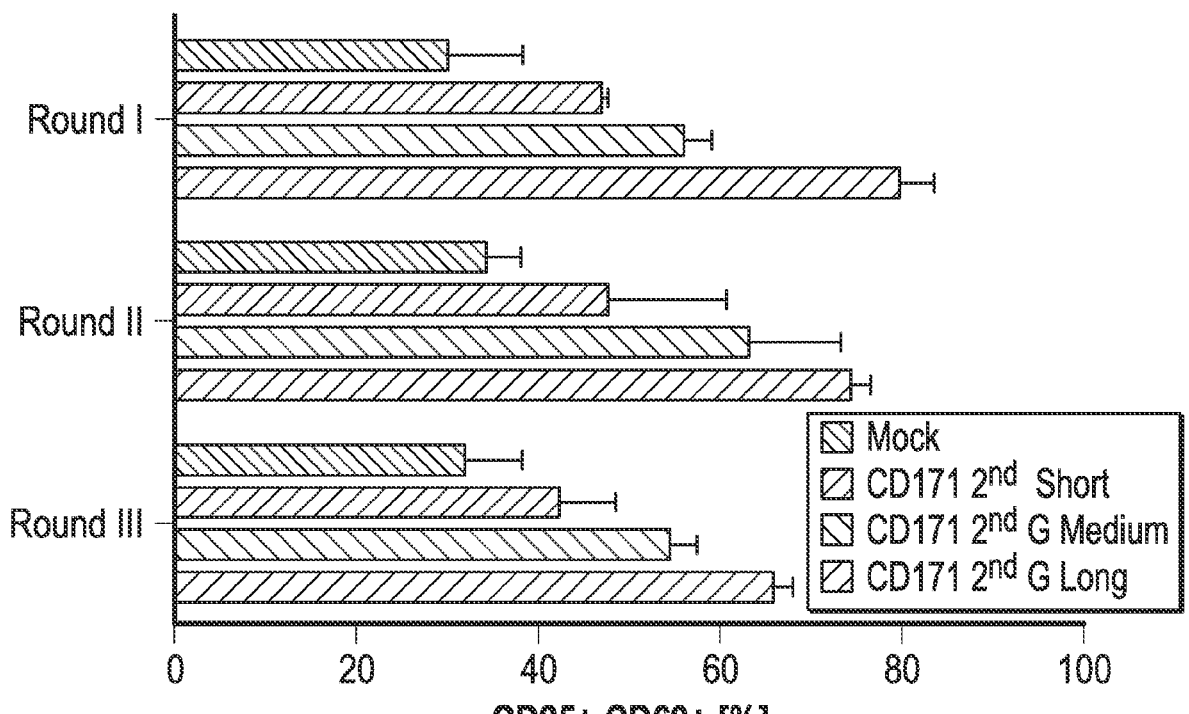
Figure 15D:
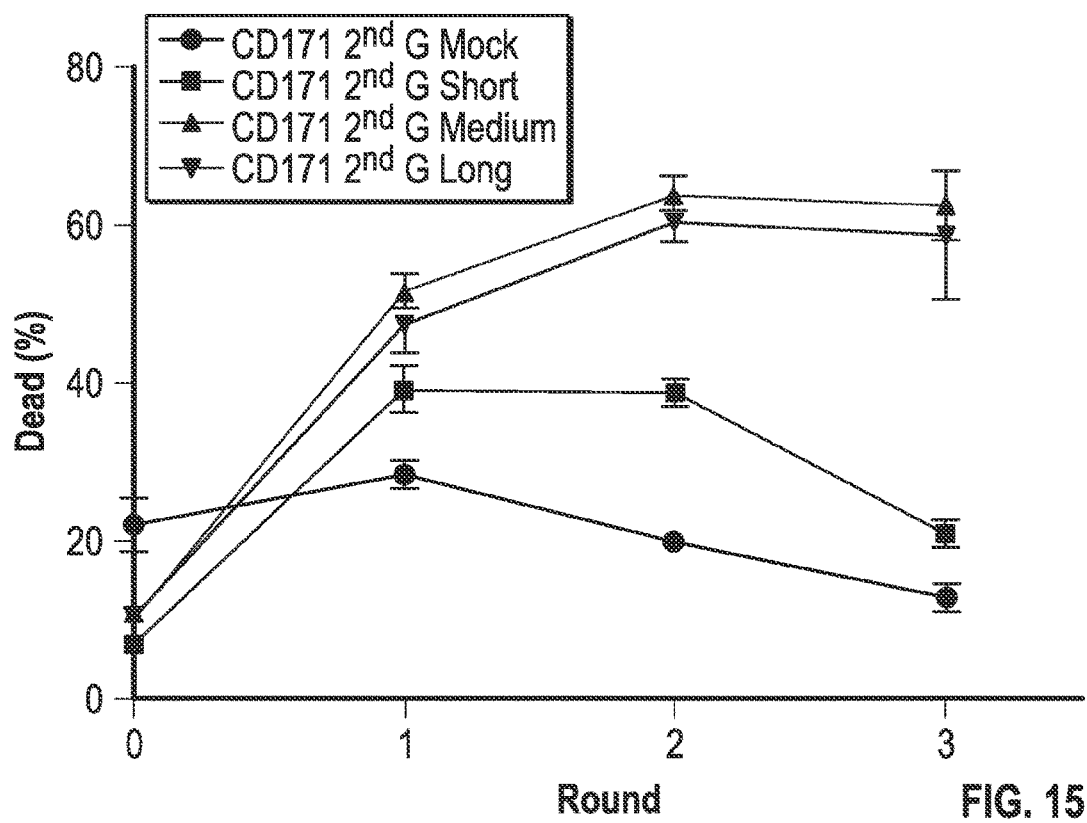
Figure 15E:
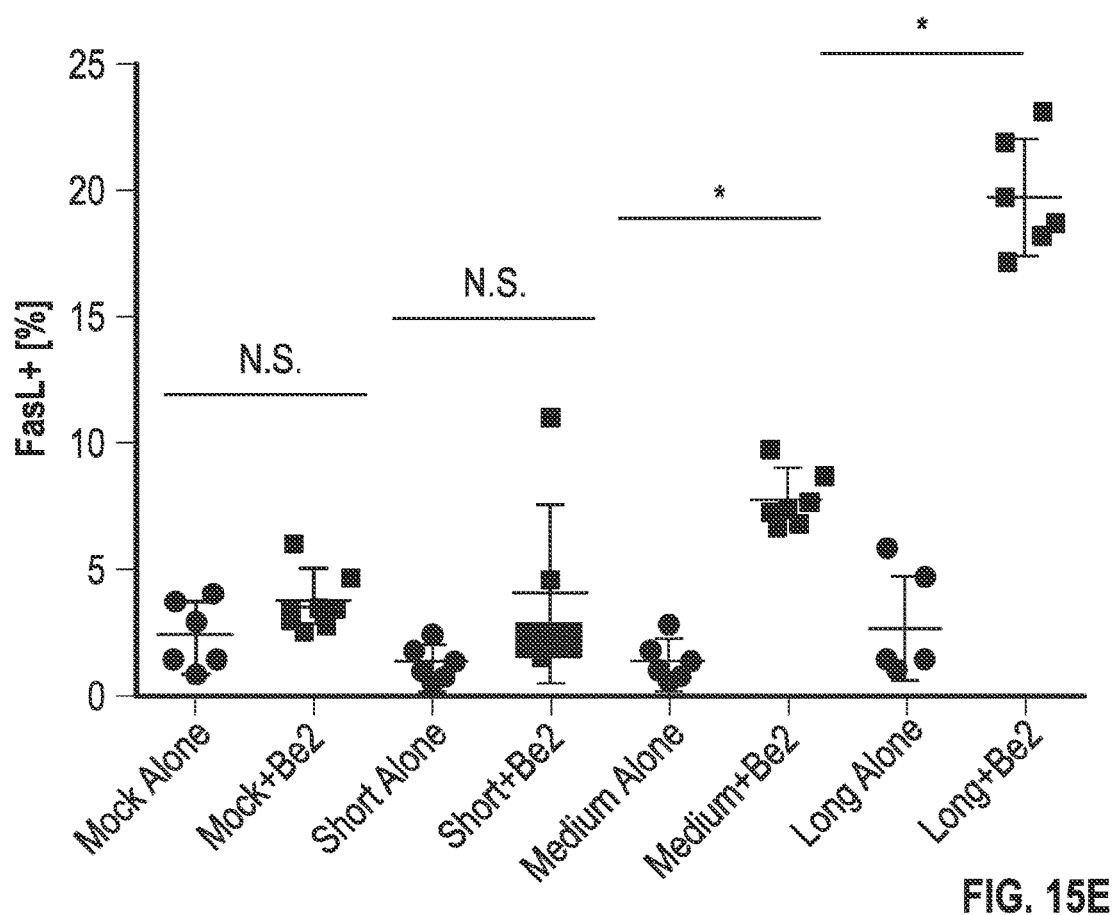
Figure 15F:
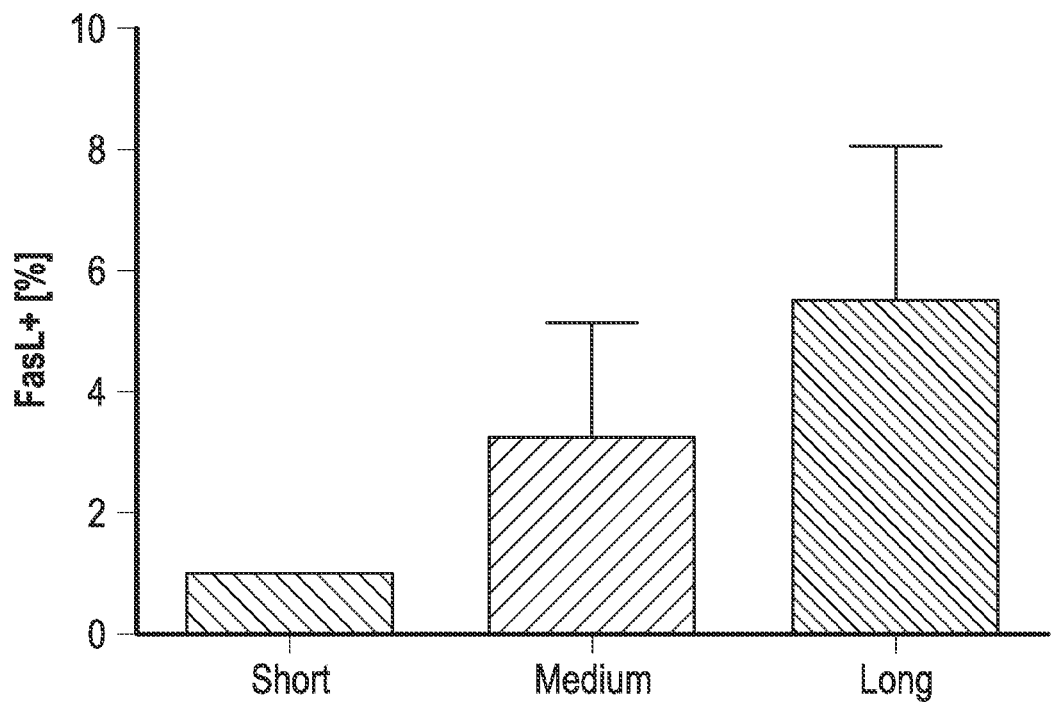
Figure 15G:
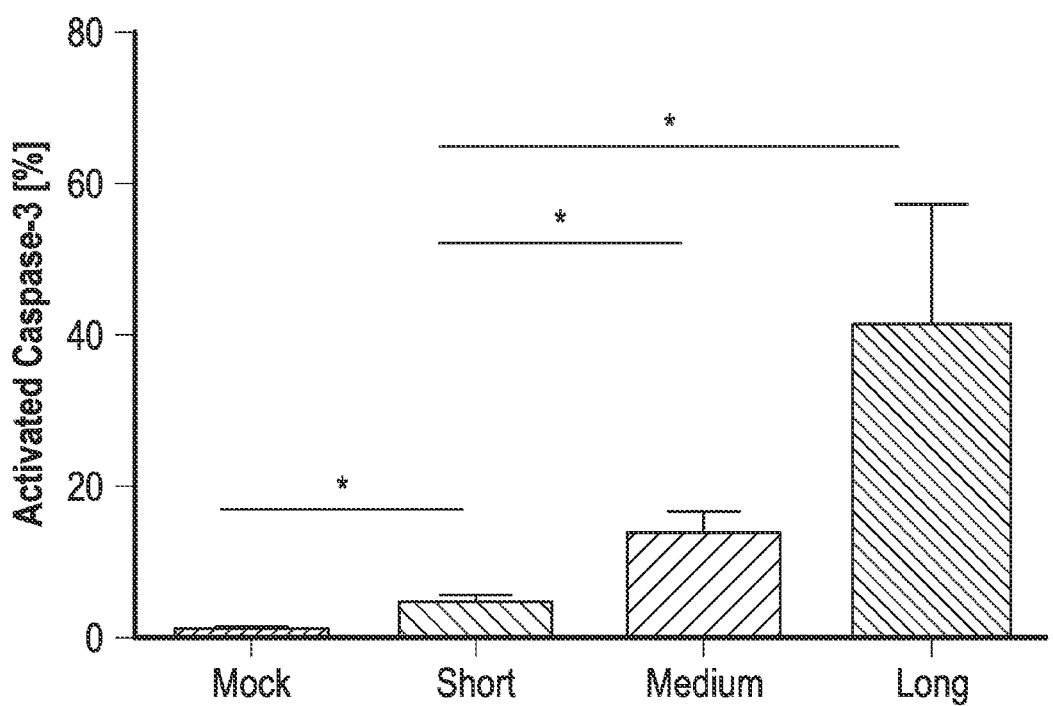
Figure 15H:
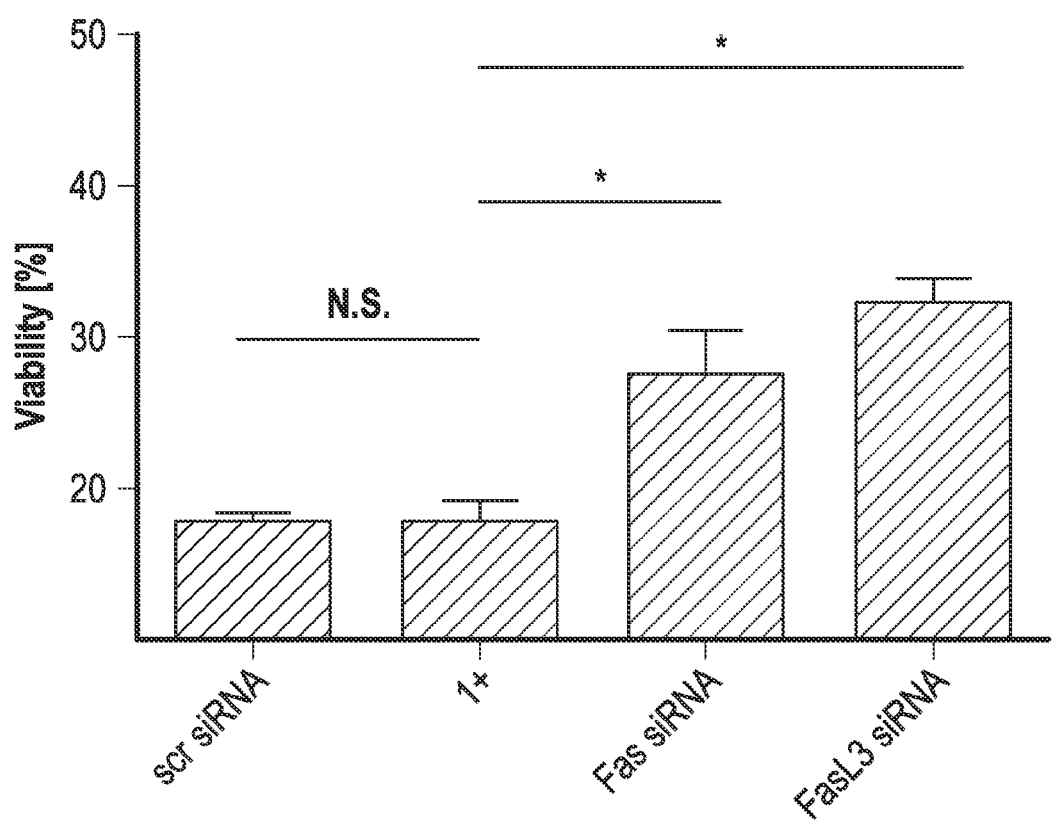

FIGS. 15A-15H shows the recursive antigen exposure in vitro results in differential FasL mediated AICD based on CAR spacer dimension. FIG. 15A shows the schema of in vitro stress test assay for analysis of CAR T cell functional status and viability upon repetitive stimulation with tumor cells. FIG. 15B shows the quantitation of residual viable fLuc$^+$Be2 tumor cells after successive rounds of 2G-CAR transfer (% tumor viability=average of 3 independent experiments). FIG. 15C shows the glow cytometric quantitation of CD25 and CD69 surface expression following successive rounds of co-culture with Be2 cells at an effector: stimulator (E:S) ratio of 1:1 (% CD25$^+$CD69$^+$ values=average of 2 independent experiments). FIG. 15D shows the 2G-CAR T cell viability determination by Guava Viacount assay after each round. % Dead T cells values derived as in FIG. 15C. FIG. 15E shows the frequency of FasL+2G-CAR CTLs before and after 8-hour co-culture with Be2 (E:S 1:1; each data point is derived from an independent experiment). FIG. 15F shows the Fold-induction of FasL mRNA transcription measured by rt-qPCR upon co-culture of MS and LS 2G-CAR spacer variants relative to SS 2G-CAR CTLs normalized to beta-actin (average of 5 independent experiments). FIG. 15G shows the Frequency of activated caspase 3$^+$2G-CAR CTLs following 16-hour co-culture with Be2 (E:S 1:1; values=average of 4 independent experiments). FIG. 15H shows the effect of siRNA knockdown of Fas or FasL on apoptosis induction in LS 2G-CAR CTLs after 3 rounds. Average viability determination by Guava Viacount assay performed in 3 independent experiments ("I+" condition is mock electroporated T cells, "scr" condition scrambled siRNA).

Figure 16A:
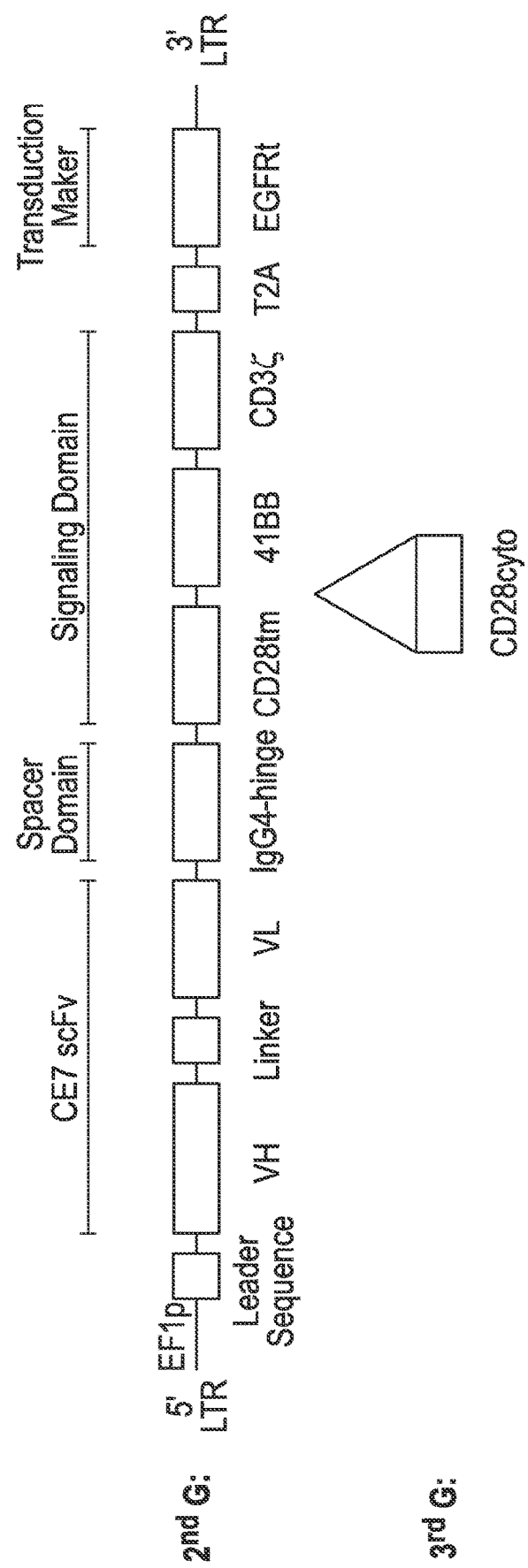
Figure 16B:
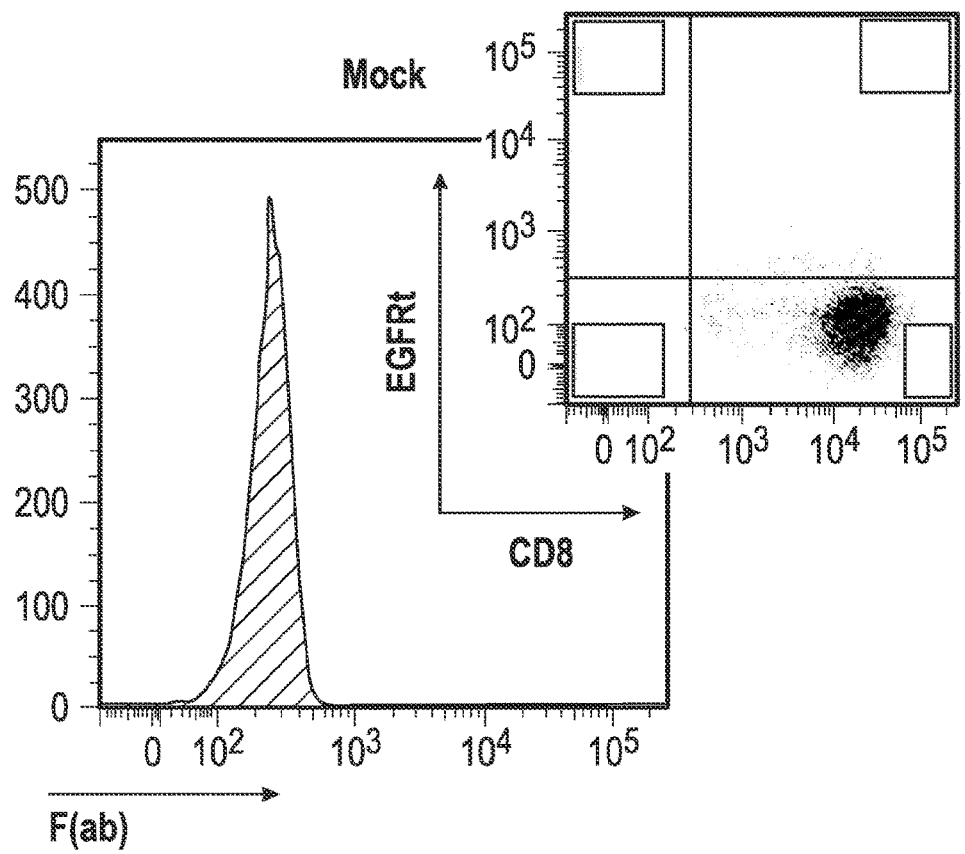
Figure 16B:
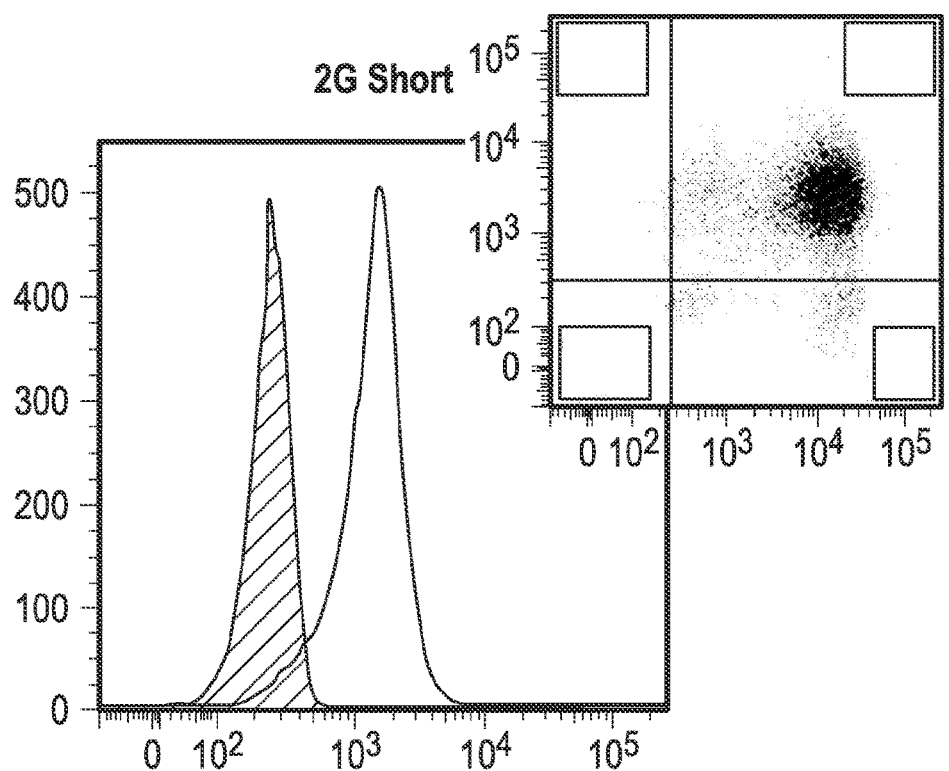
Figure 16B:
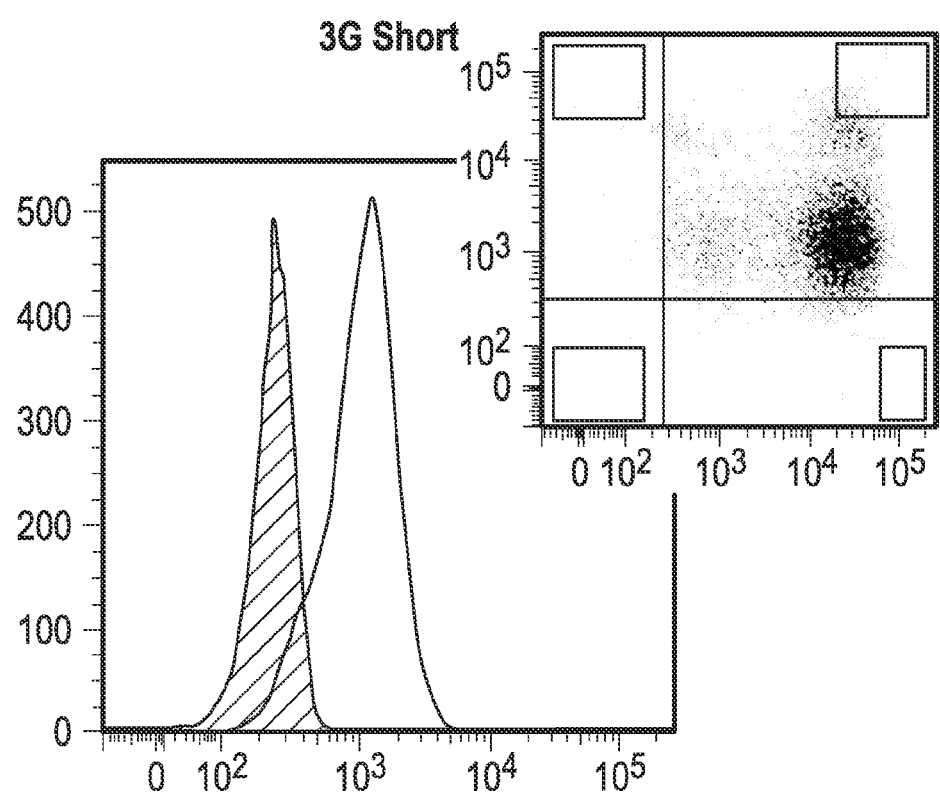
Figure 16C:
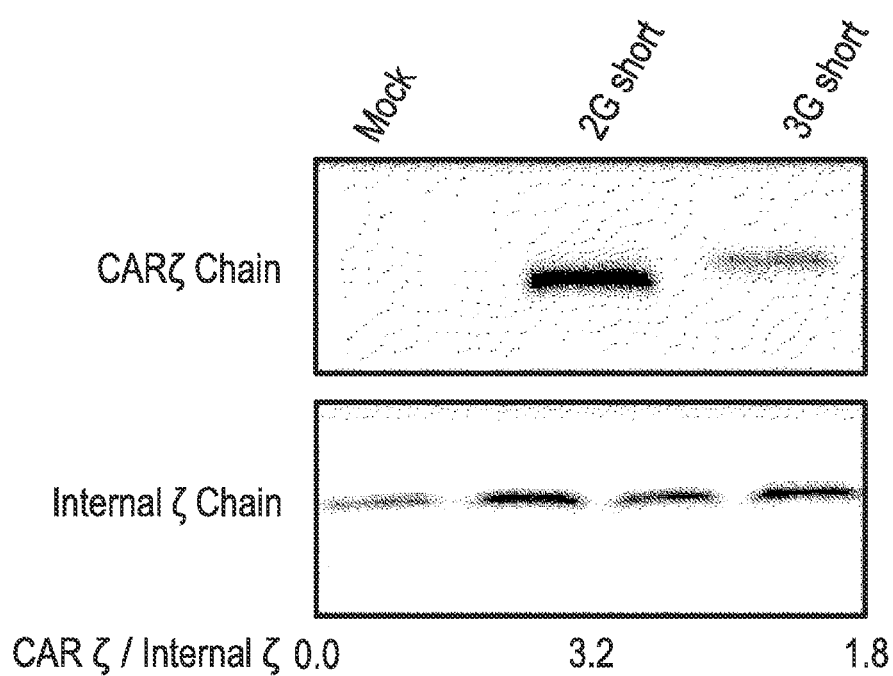
Figure 16D:
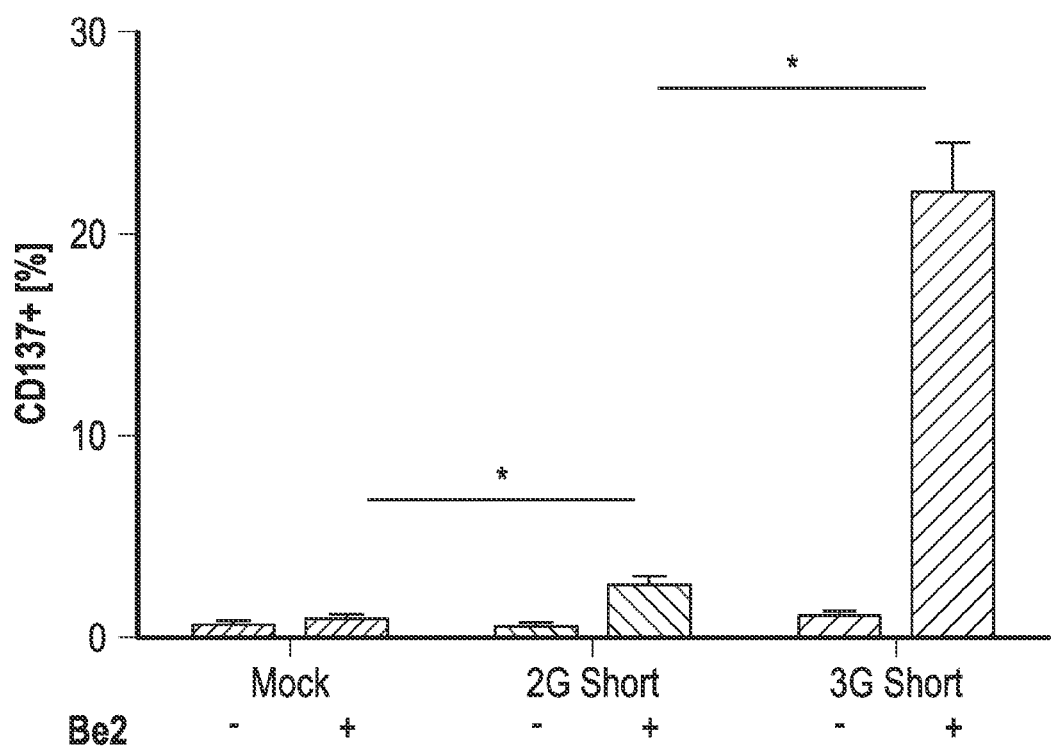
Figure 16E:
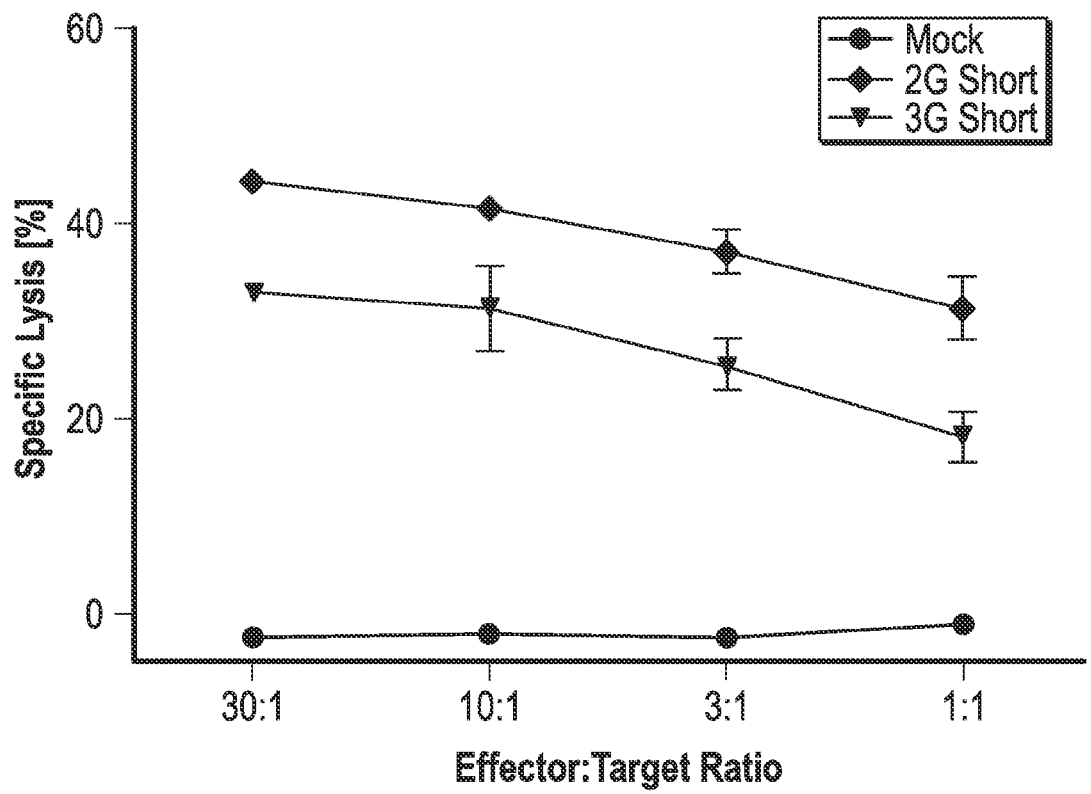
Figure 16E:
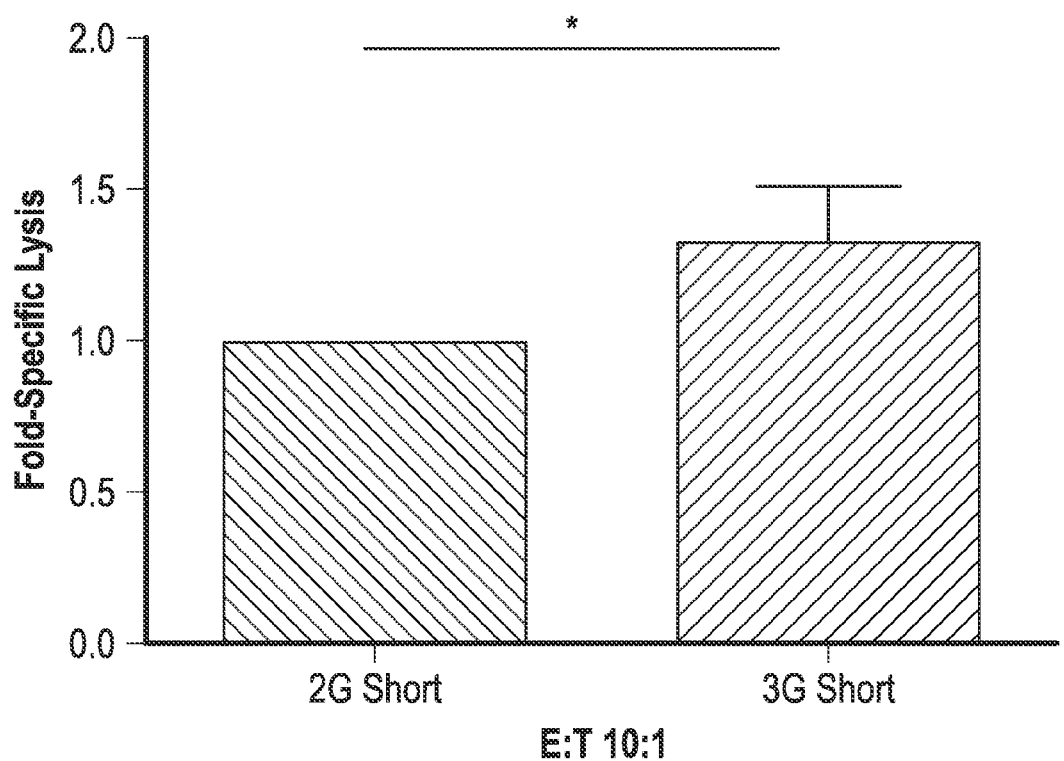
Figure 16F:
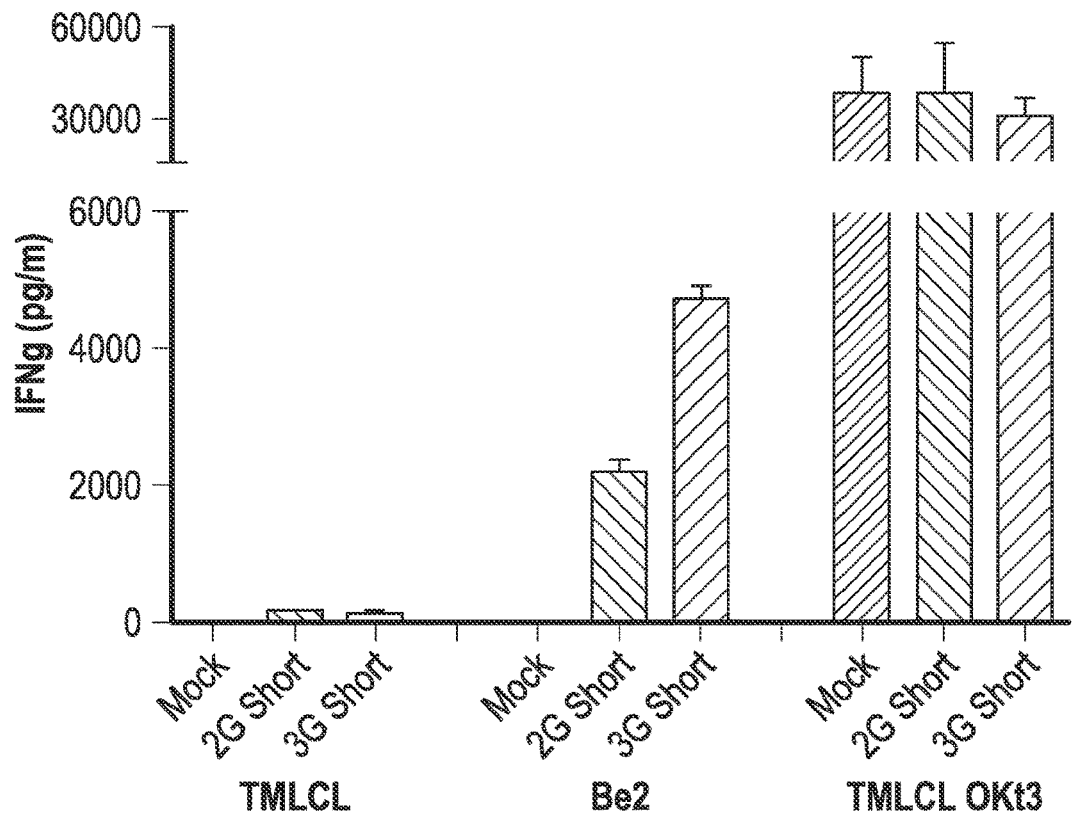
Figure 16F:
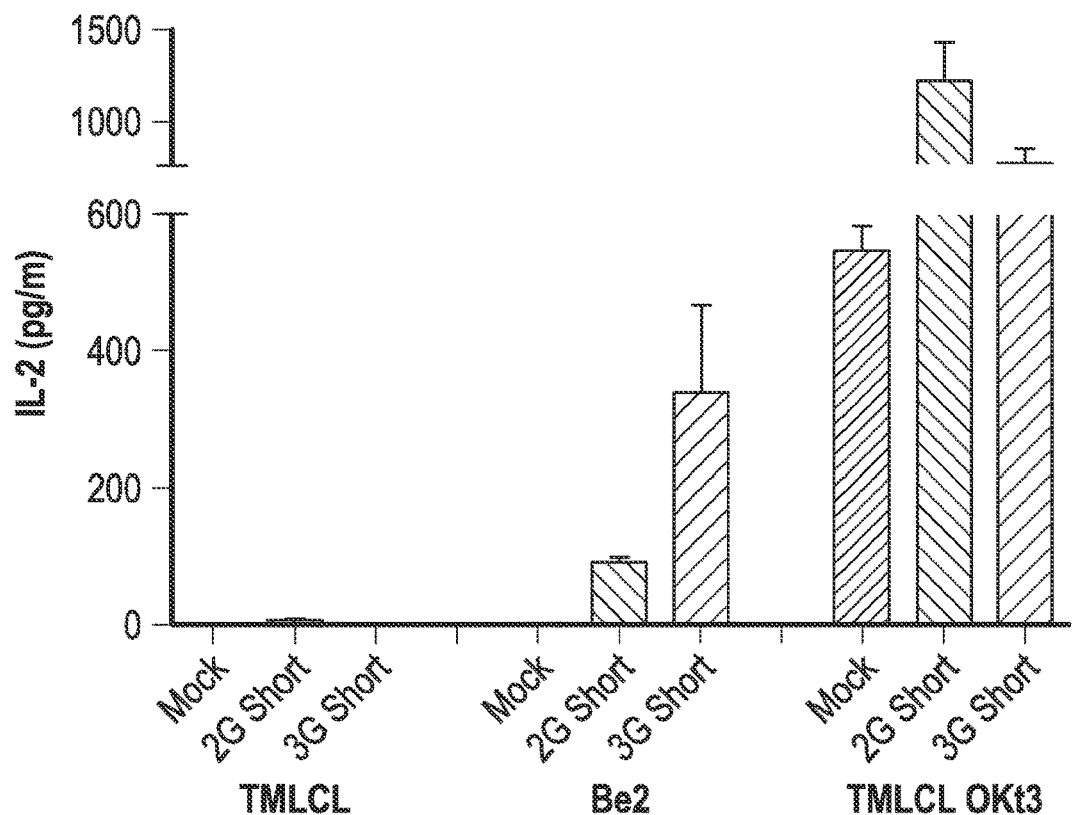
Figure 16F:
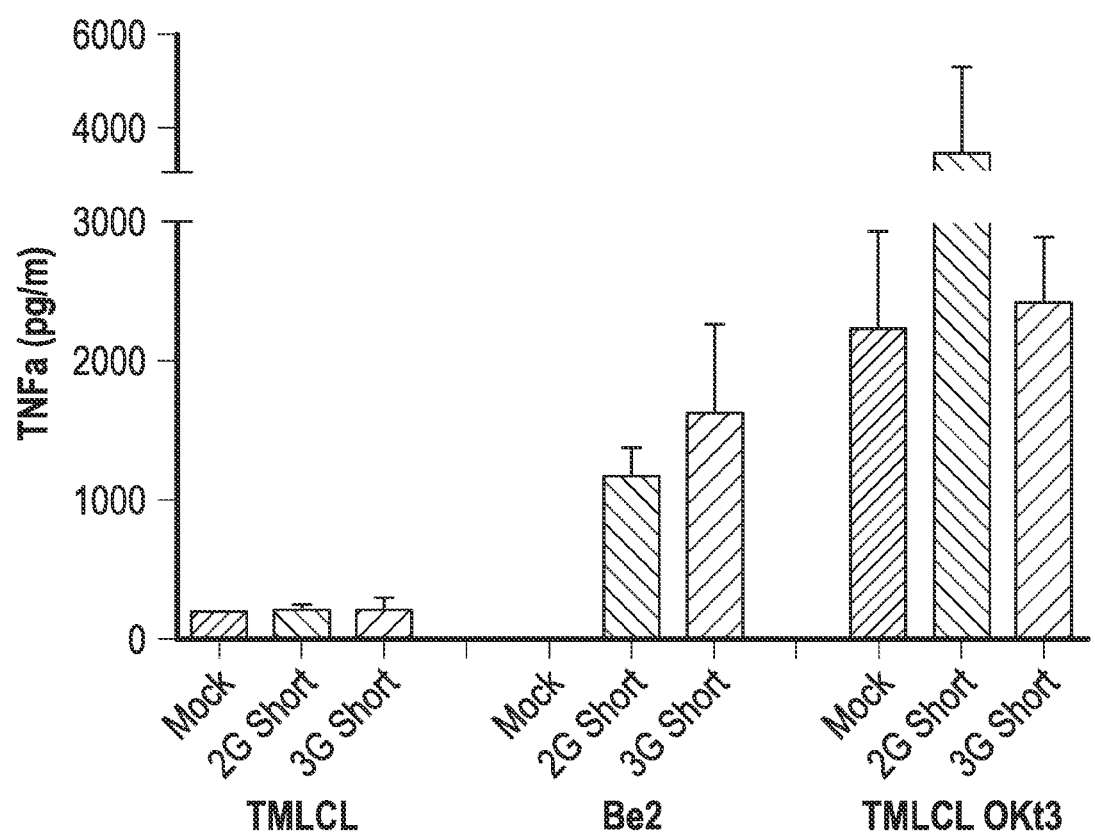
Figure 16F:
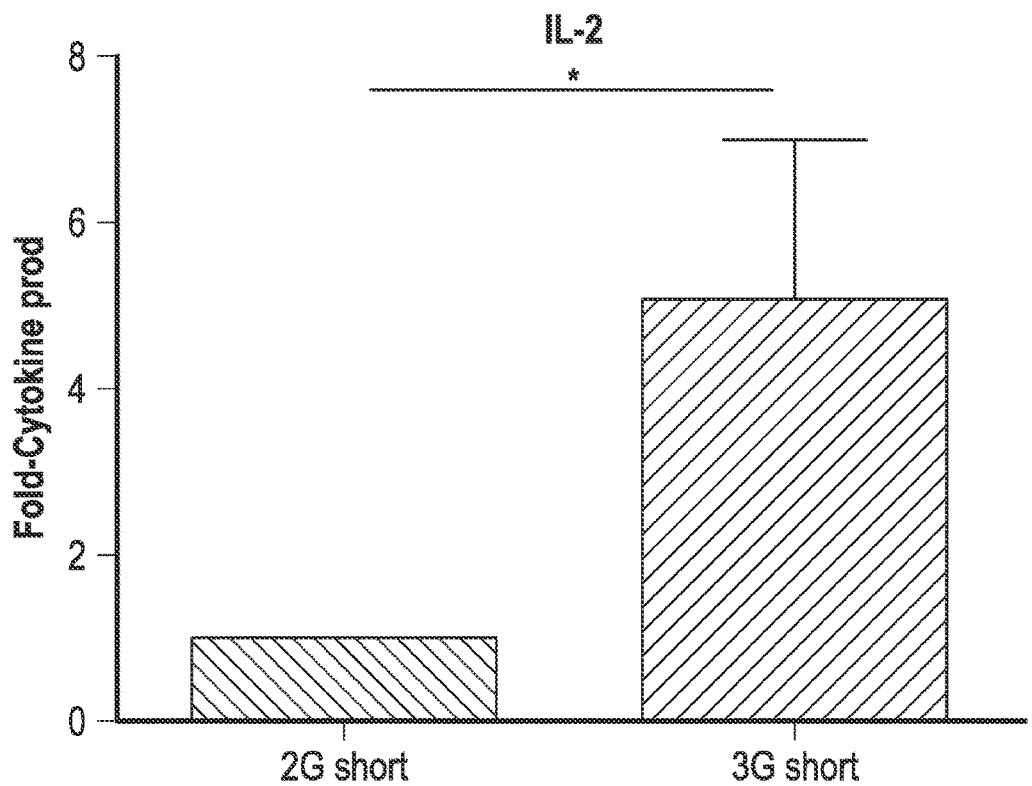
Figure 16F:
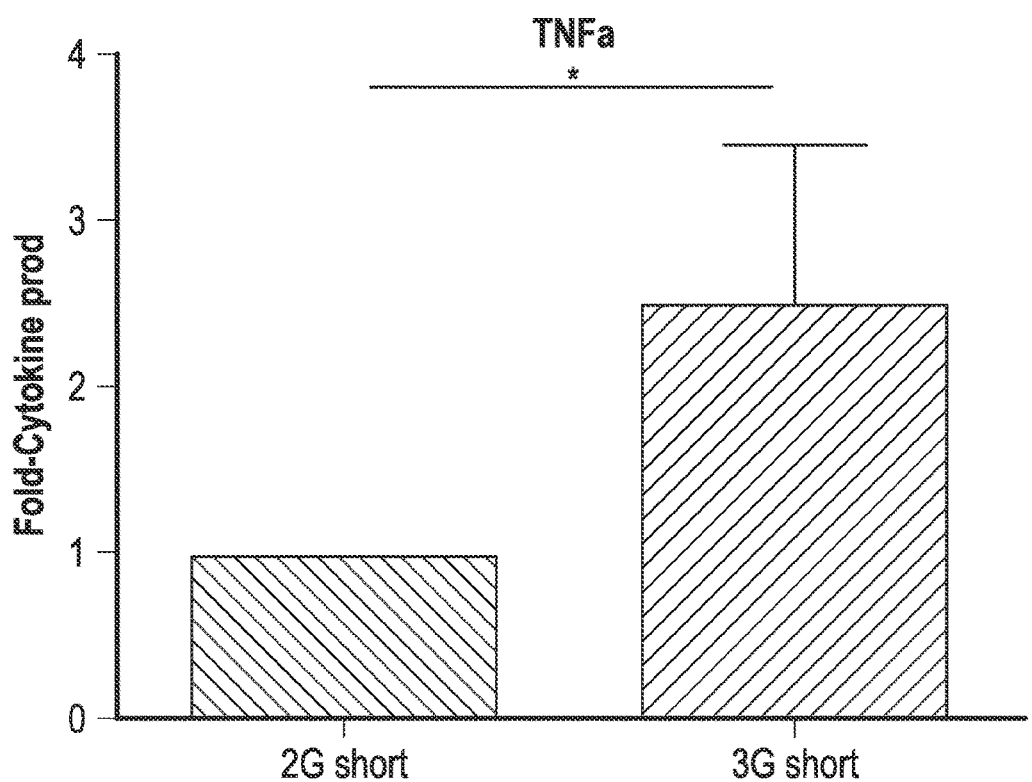

FIGS. 16A-16F shows the augmented co-stimulation via a third generation CD28:4-1BB:zeta cytoplasmic domain results in enhanced effector function outputs in vitro. FIG. 16A shows the schematic of 2G- versus 3G-CAR composition. FIG. 16B shows the human CD8$^+$ $T_{E(CM)}$ cell surface expression of 2G- versus 3G-CAR(SS) and EGFRt detected with anti-murine FAB and cetuximab, respectively. FIG. 16C shows the 2G- and 3G-CAR(SS) expression levels detected by of CD3-ζ specific Western Blot. FIG. 16D shows the 2G- versus 3G-CAR(SS) activation induced CD137 surface expression upon tumor co-culture. FIG. 16E shows the anti-tumor lytic activity of 2G- versus 3G-CAR (SS) CTLs determined by 4-hour chromium release assay. Fold specific lysis of SS-3G relative to SS-2G CTL at an E:T ratio of 10:1 (average of 3 independent experiments). FIG. 16F shows the stimulation of cytokine secretion in 2G- versus 3G-CAR(SS) CTL tumor (Be2) co-cultures (n≥6 per condition). Fold cytokine production comparison is relative to 2G-CAR(SS) as in (E).

Figure 17A:
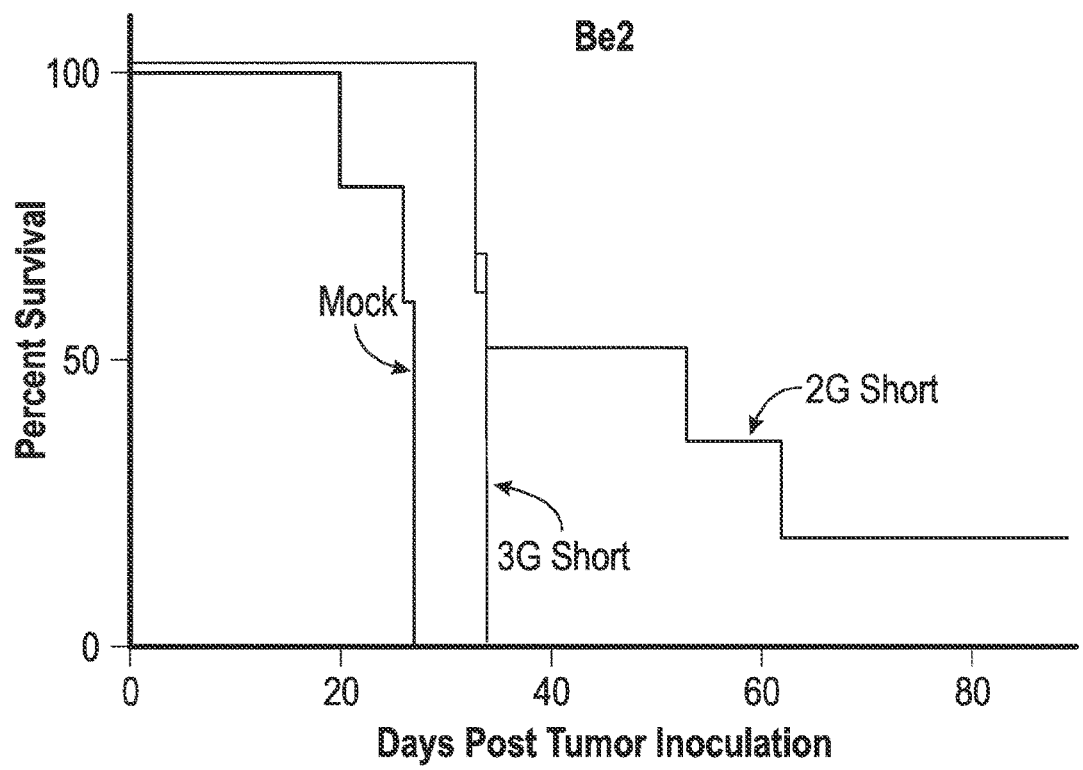
Figure 17B:
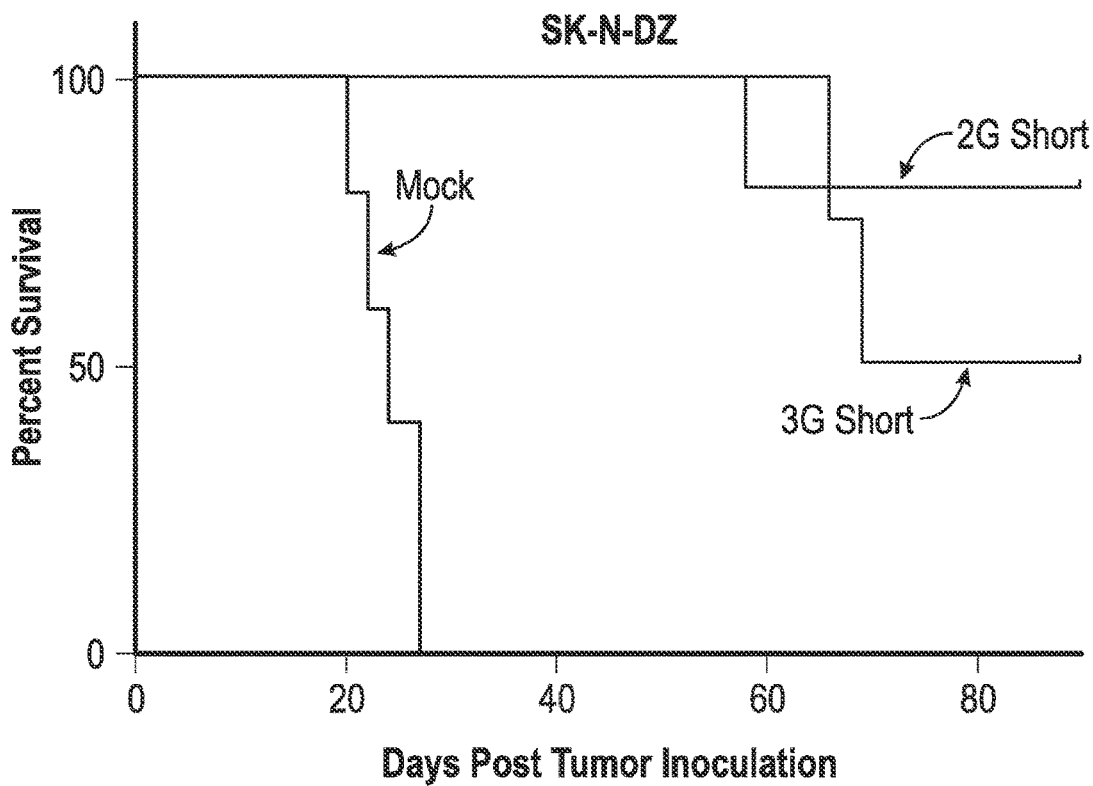
Figure 17C:
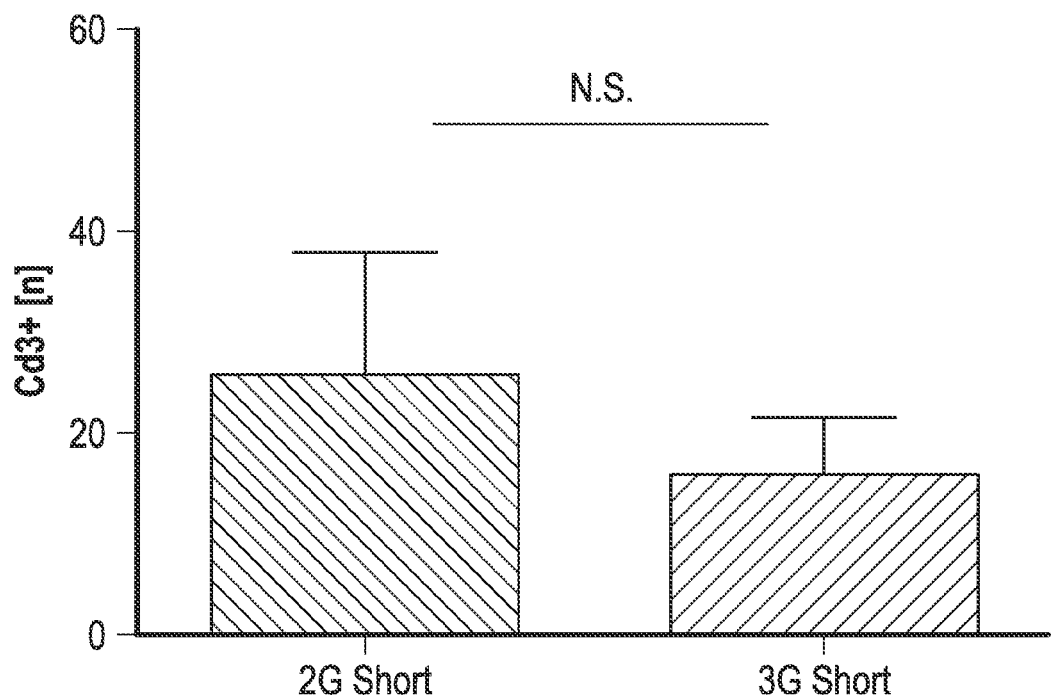
Figure 17C:
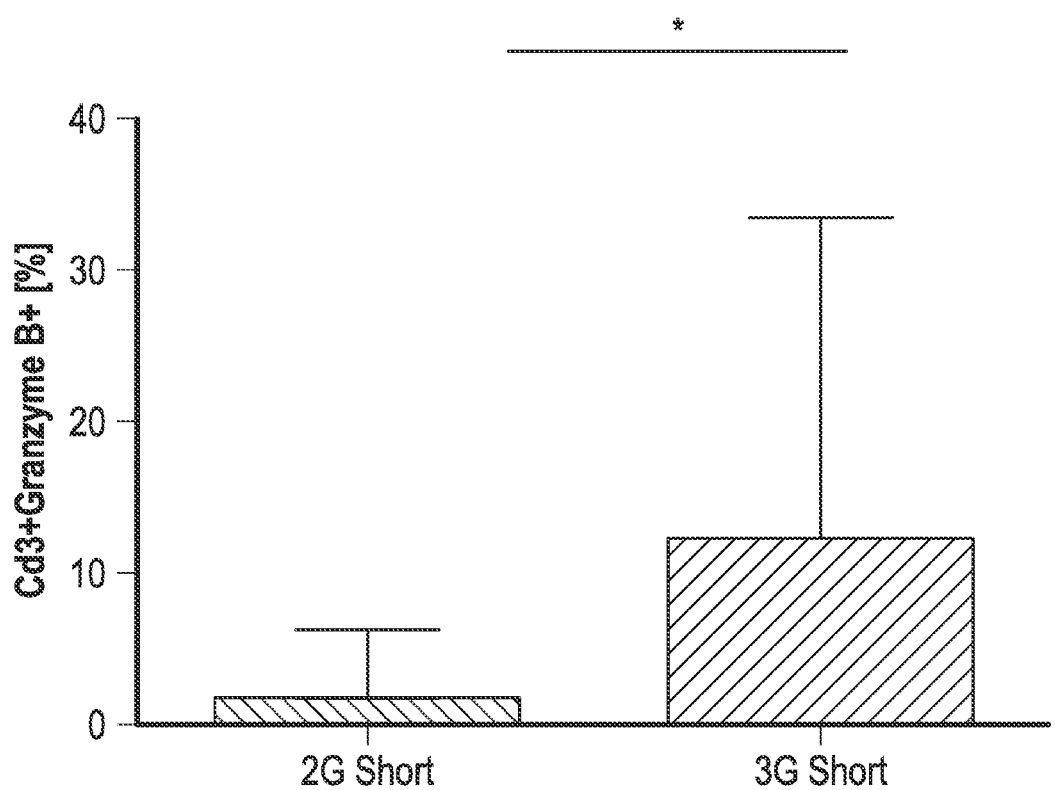
Figure 17C:
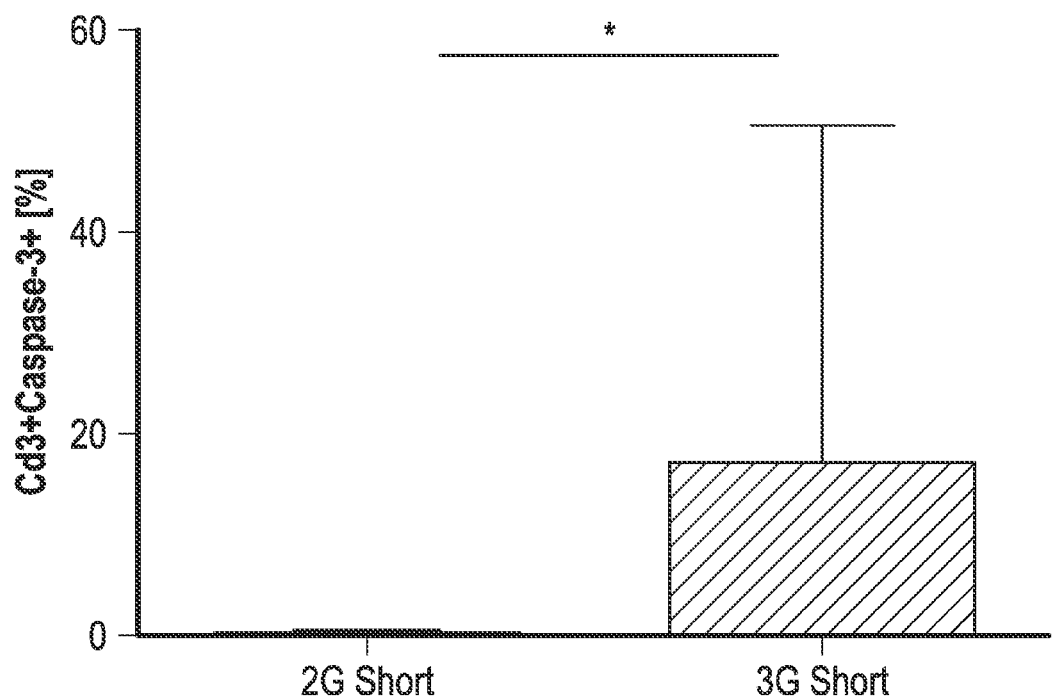
Figure 17D:
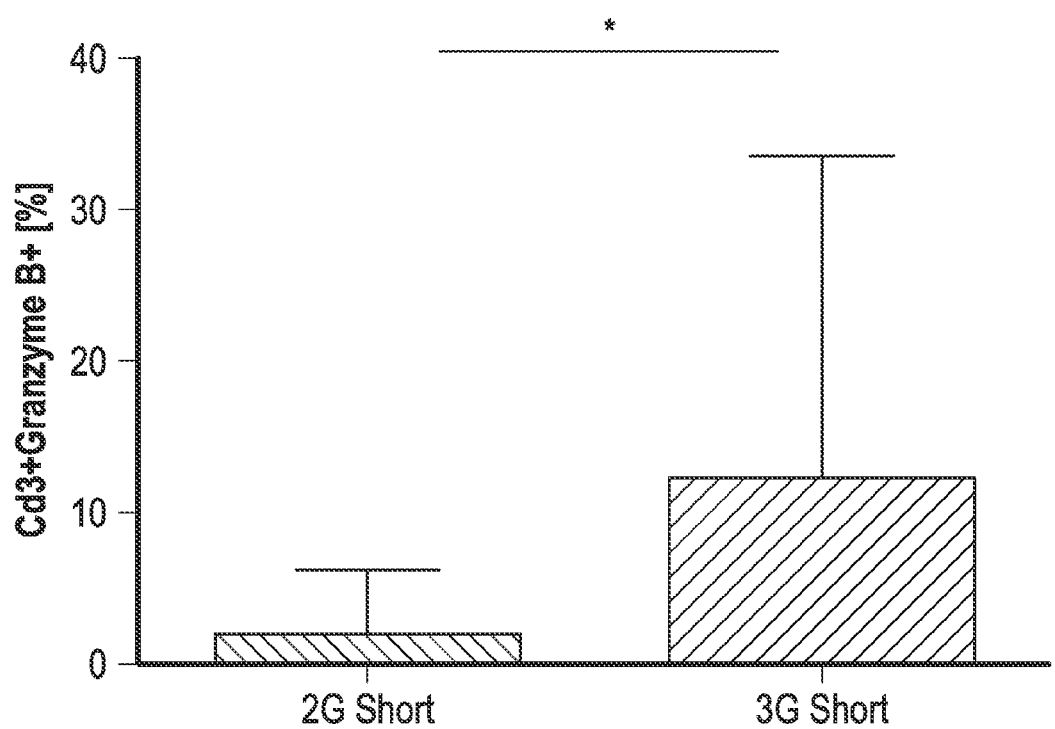
Figure 17D:
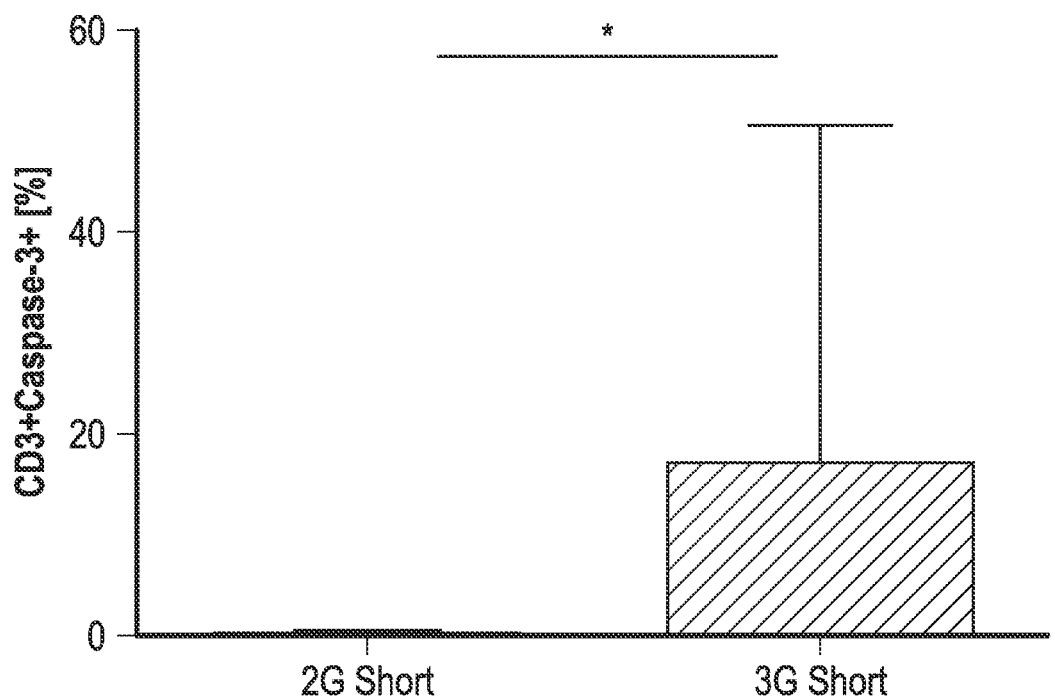

FIGS. 17A-17D shows that 3G-CAR(SS) CTLs do not exhibit enhanced anti-tumor activity in vivo. FIG. 17A shows the Kaplan Meier survival curves of Be2 engrafted NSG mice treated with 2G- versus 3G-CAR(SS) CTLs (n=5-6 per group, sham transduced CTL control in black). FIG. 17B shows the Kaplan Meier survival curves for SK-N-DZ engrafted mice treated as in FIG. 17A. FIG. 17C shows the 2G- versus 3G-CAR(SS) T cell intratumoral persistence 3 days following adoptive transfer. N=number of CD3$^+$ cells per 40hpf in two independently derived tumor specimens. FIG. 17D shows the IF detection of granzyme B (left panel) and activated caspase 3$^+$(right panel) CD3+ CTL as described in FIG. 17C.

Figure 18A:
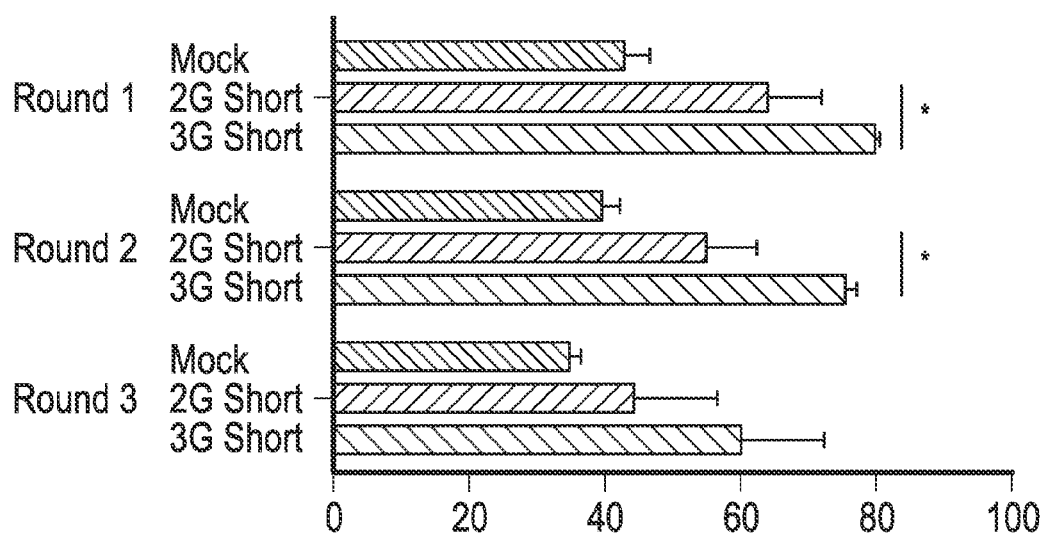
Figure 18B:
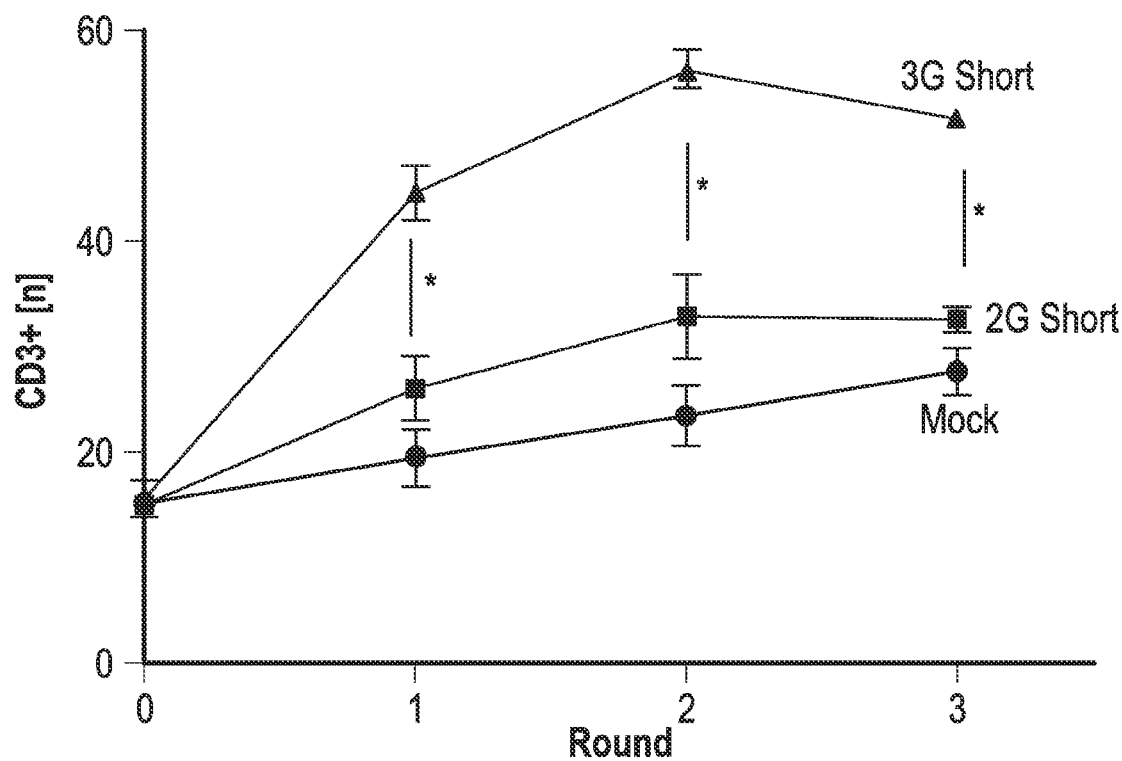
Figure 18C:
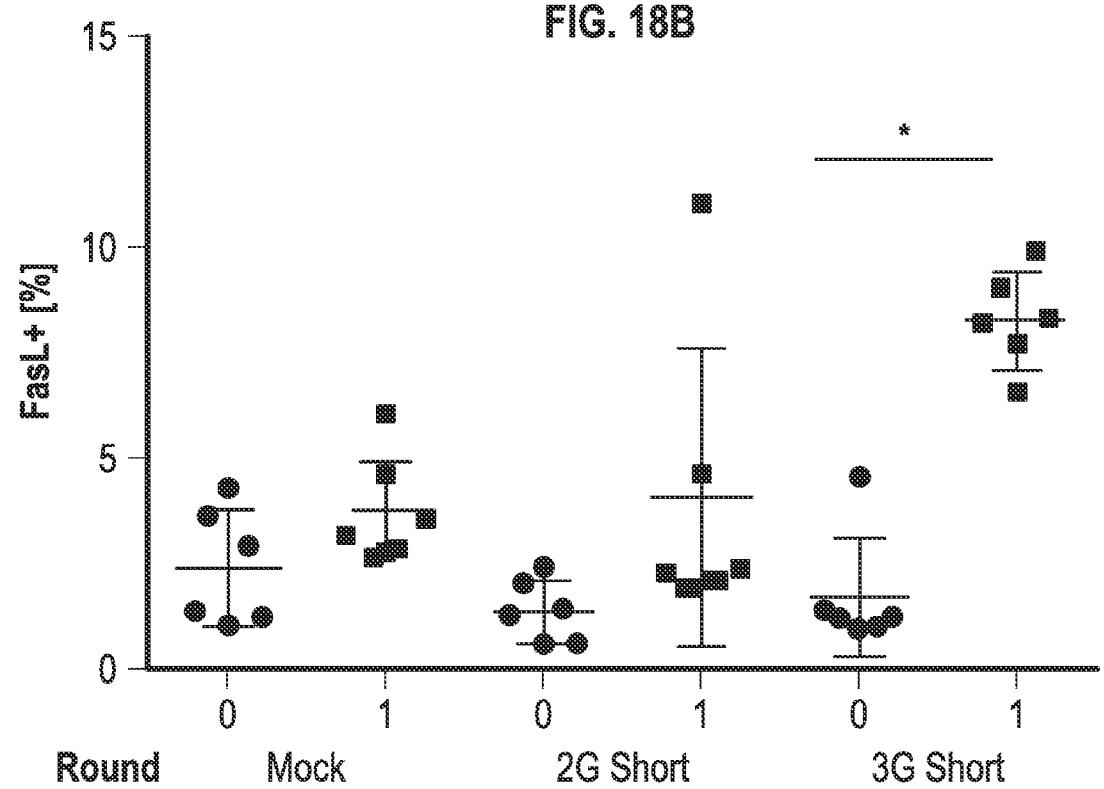
Figure 18D:
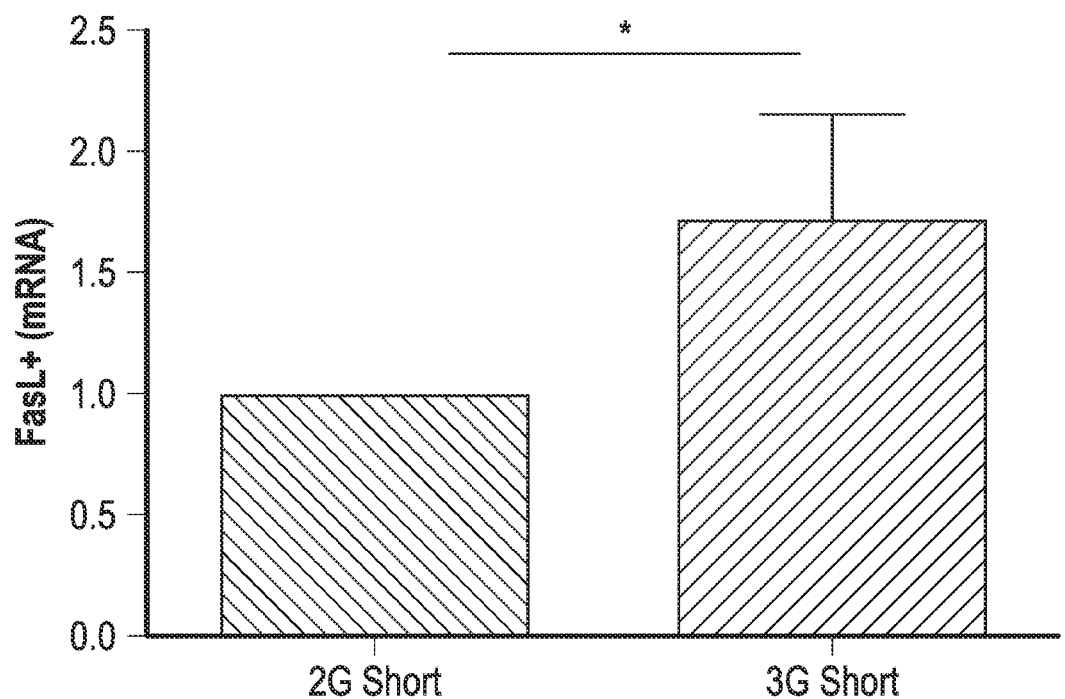
Figure 18E:
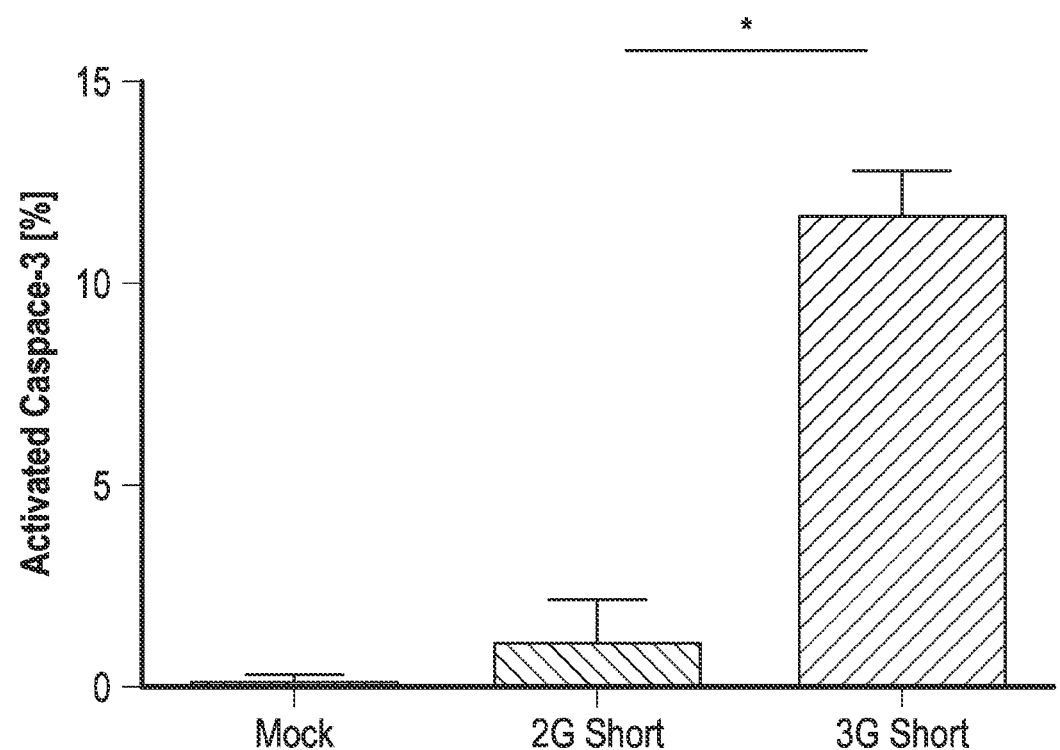

FIG. 18A-18E shows that the recursive antigen exposure in vitro results in differential FasL mediated AICD based on CAR cytoplasmic signaling in the context of a short spacer extracellular domain. FIG. 18A shows the flow cytometric quantitation of CD25 and CD69 surface expression by 2G- versus 3G-CAR(SS) CTLs following successive rounds of co-culture with Be2 cells at an E:S of 1:1 (% CD25$^+$CD69$^+$ values derived from average of two independent experiments). FIG. 18B shows 2G- versus 3G-CAR(SS) T cell viability determination by Guava Viacount assay after each round of tumor co-culture. % Dead T cells values derived as previously described. FIG. 18C shows the frequency of FasL$^+$2G- versus 3G-CAR(SS) CTLs before and after 8-hour co-culture with Be2 cells at an E:S ratio of 1:1 (each data point of 5 per 2G-CAR spacer variant is derived from an independently conducted experiment). FIG. 18D shows the fold induction of FasL mRNA transcription measured by rt-qPCR upon co-culture of 2G- versus 3G-CAR(SS) CTLs normalized to beta-actin (average results from 5 independently conducted experiments). FIG. 18E shows the frequency of cytosolic activated caspase 3$^+$2G- versus 3G-CAR(SS) CTLs following 16-hour co-culture with Be2 at an E:S ratio of 1:1 (values ave. of 4 independent experiments).+(FIG. 18D) and activated caspase 3+(FIG. 18E) CD3+ CTL as described in FIG. 18C.

Figure 19A:
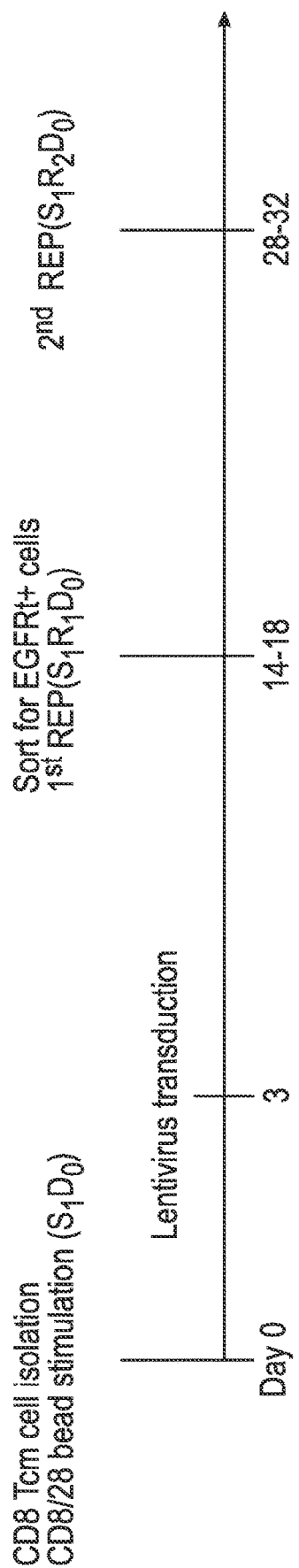
Figure 19B:
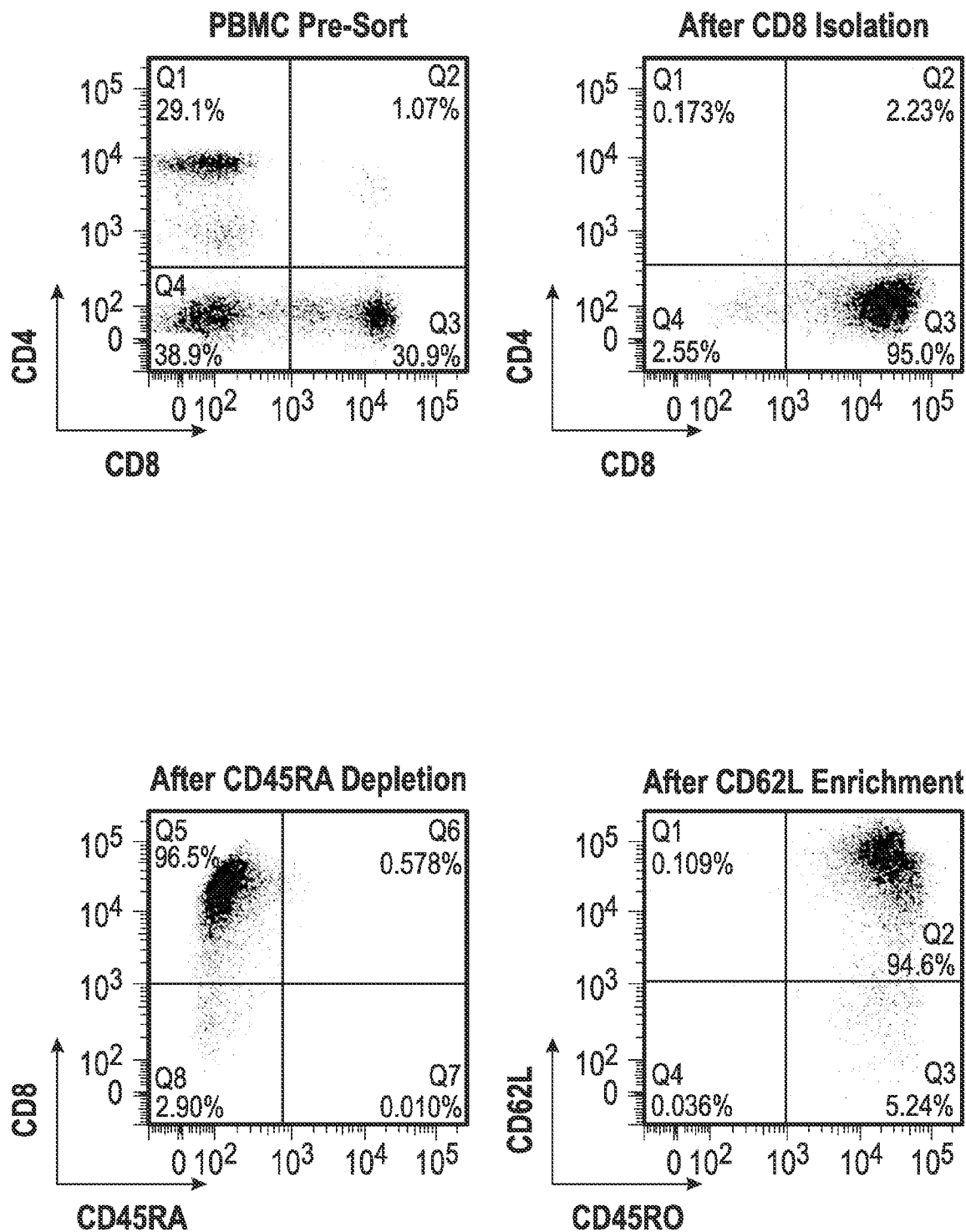
Figure 19C:
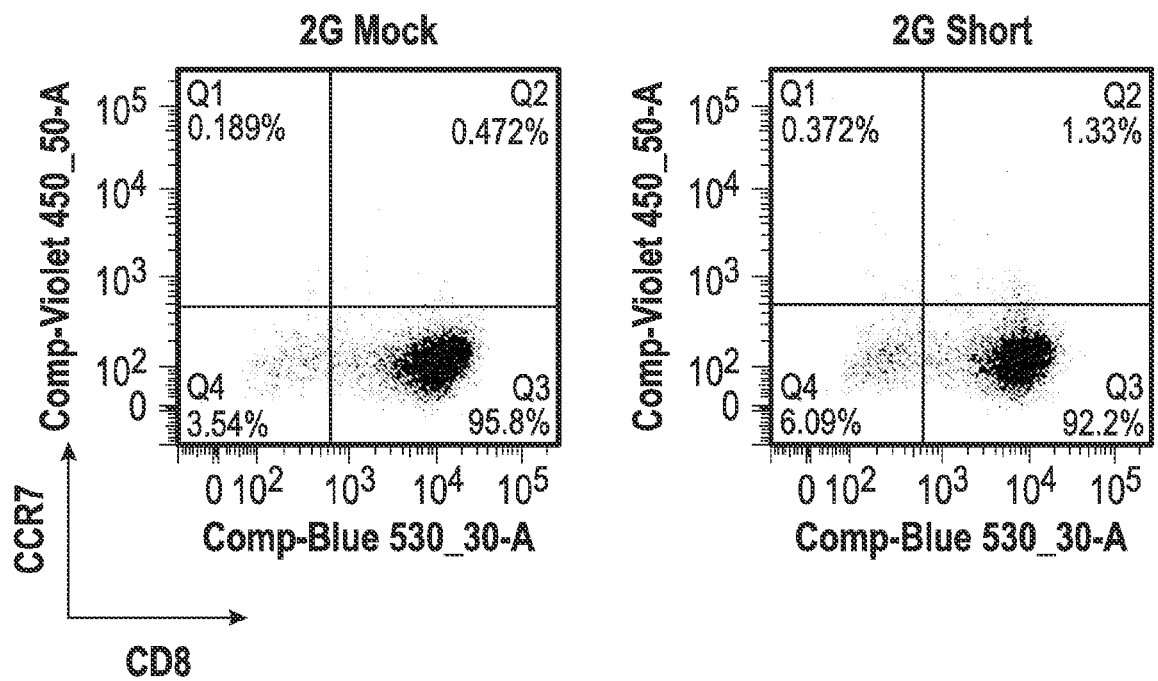
Figure 19C:
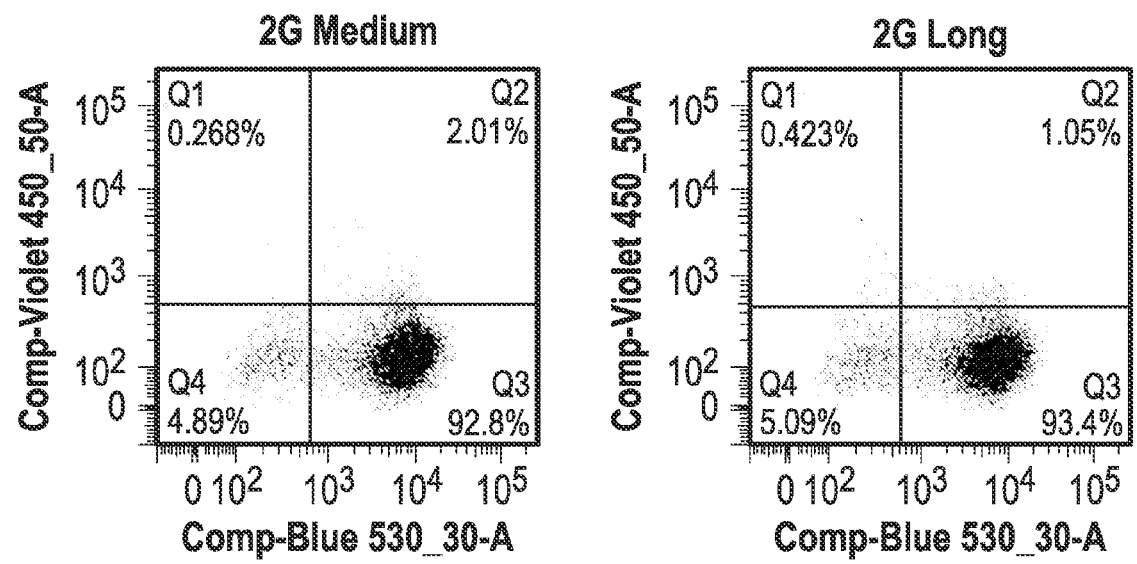
Figure 19C:
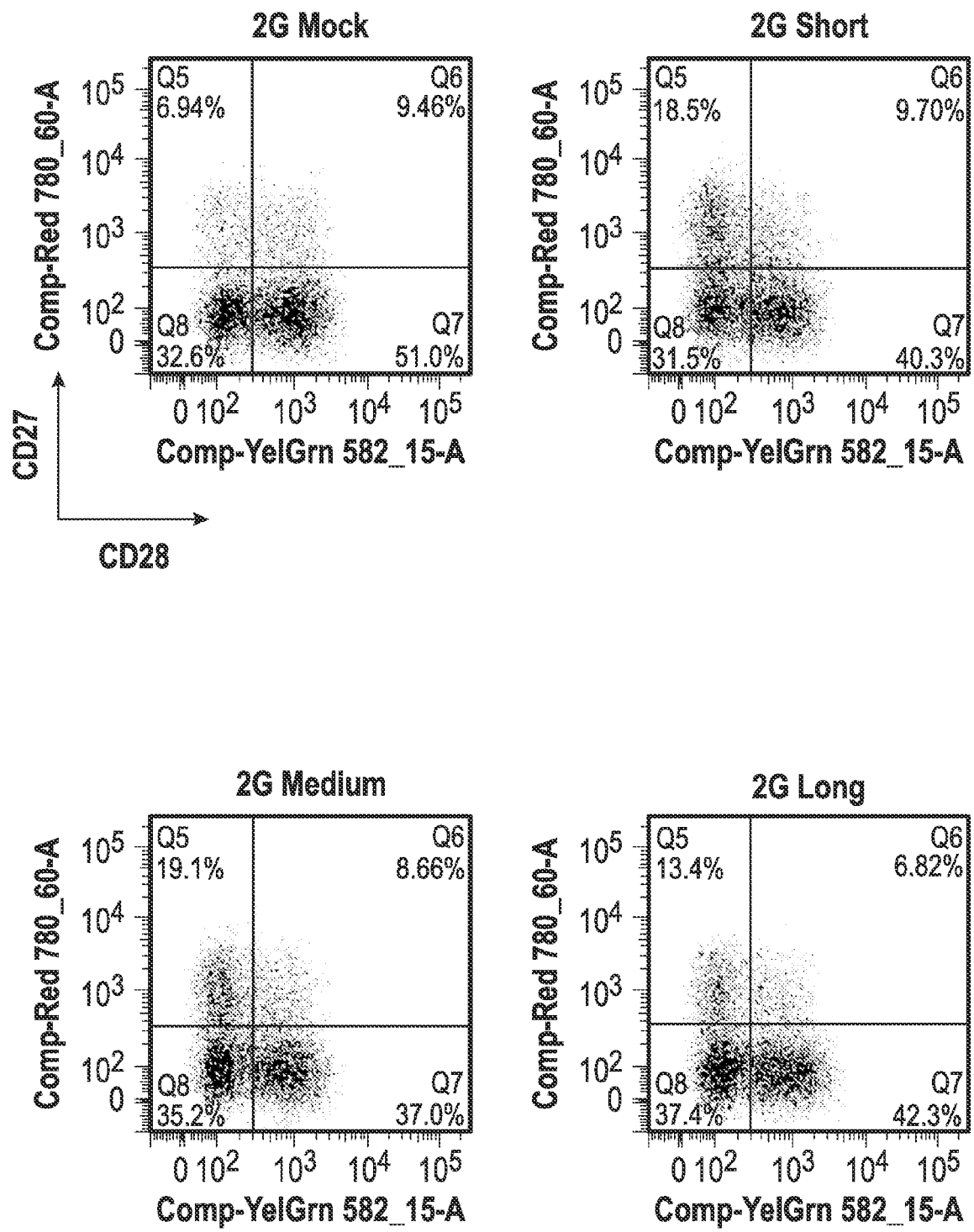
Figure 19C:
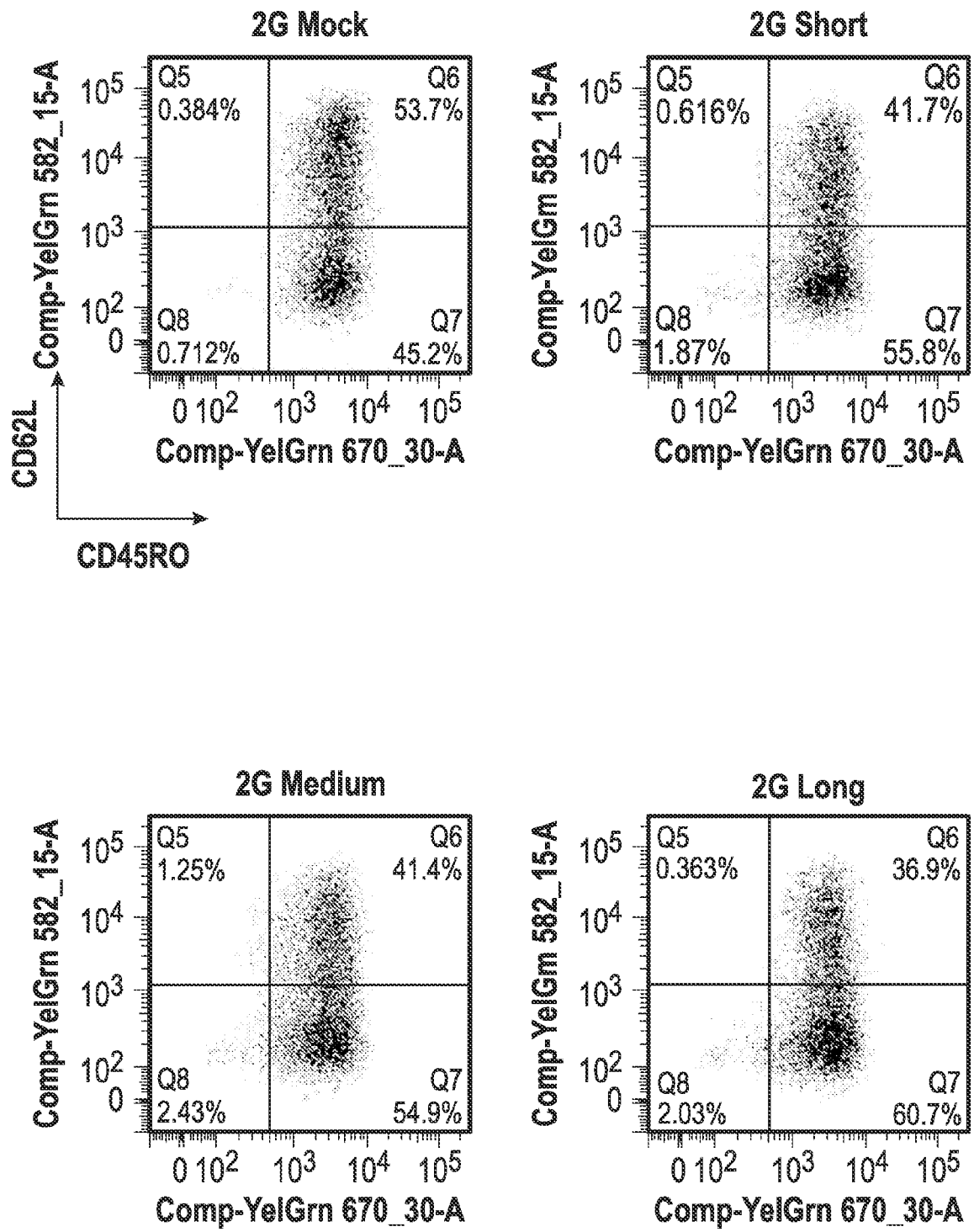

FIGS. 19A-19C shows phenotypic similarity between isolated CD45RO$^+$CD62L$^+$ human $T_{CM}$ expanded following lentiviral transduction with spacer variant 2G-CARs. FIG. 19A shows the timeline of CD8 $T_{CM}$ isolation, transduction and expansion prior to experimental use. FIG. 19B shows the Immunomagnetic isolation method and purity of CD8$^+$ $T_{CM}$ cells (CD45RO+CD62L+) from PBMC. FIG. 19C shows the phenotype of CD8+ T$_{E(CM)}$ transduced with different spacer variants of 2G-CAR at time of experimental use.

Figure 20A:
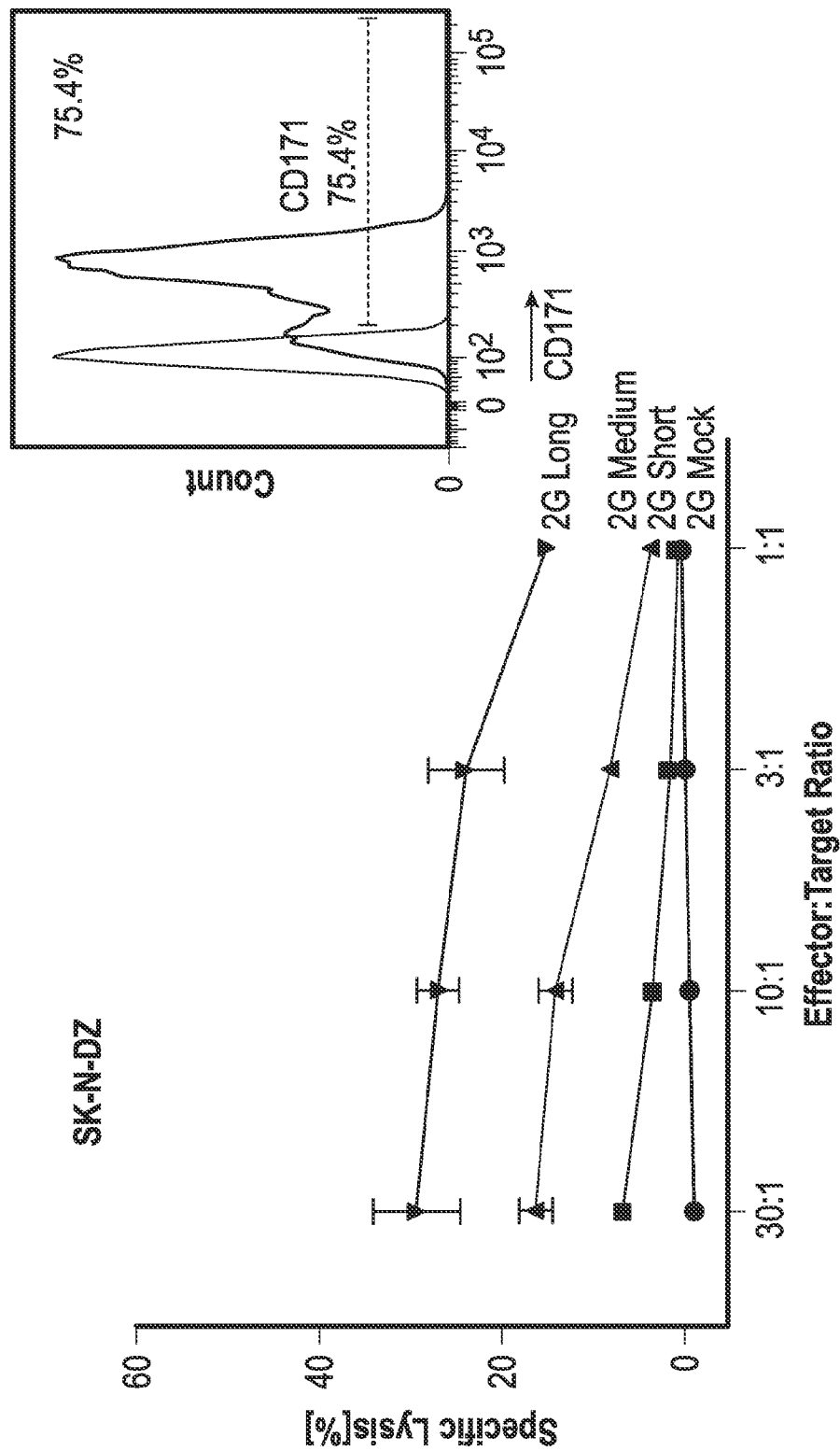
Figure 20B:
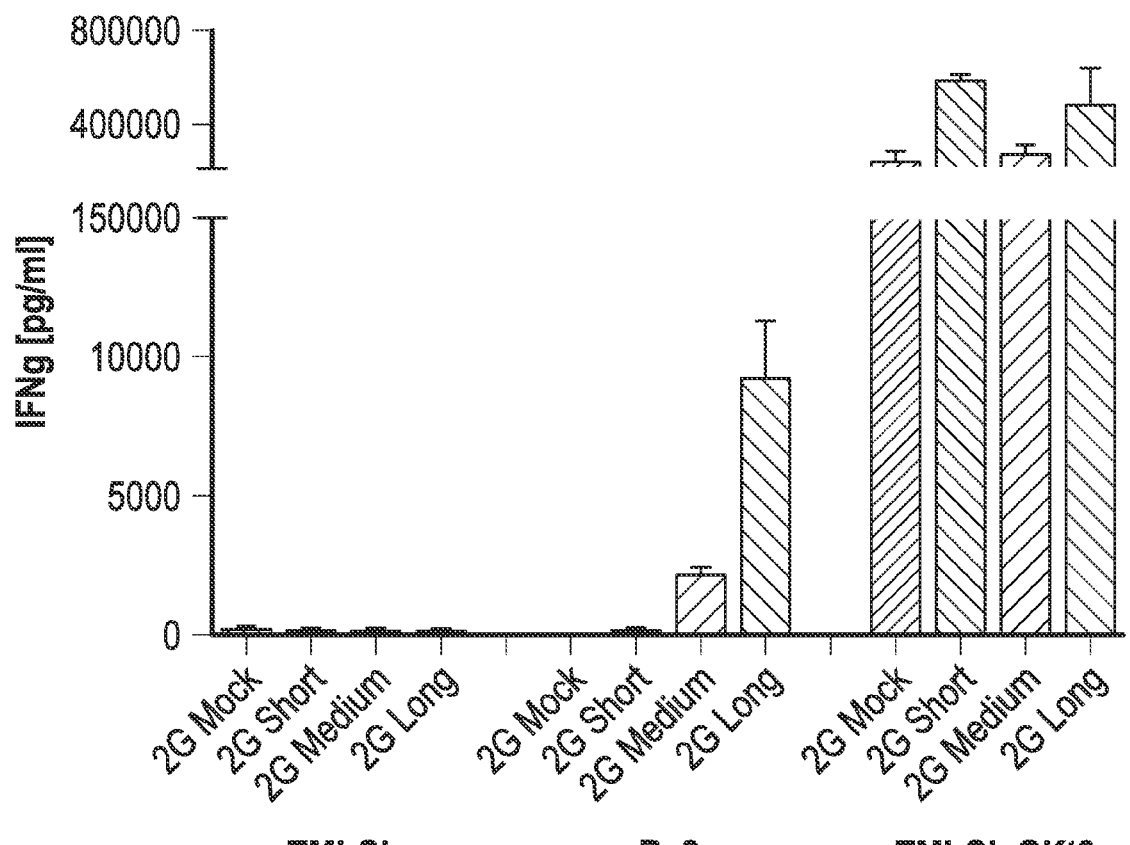
Figure 20C:
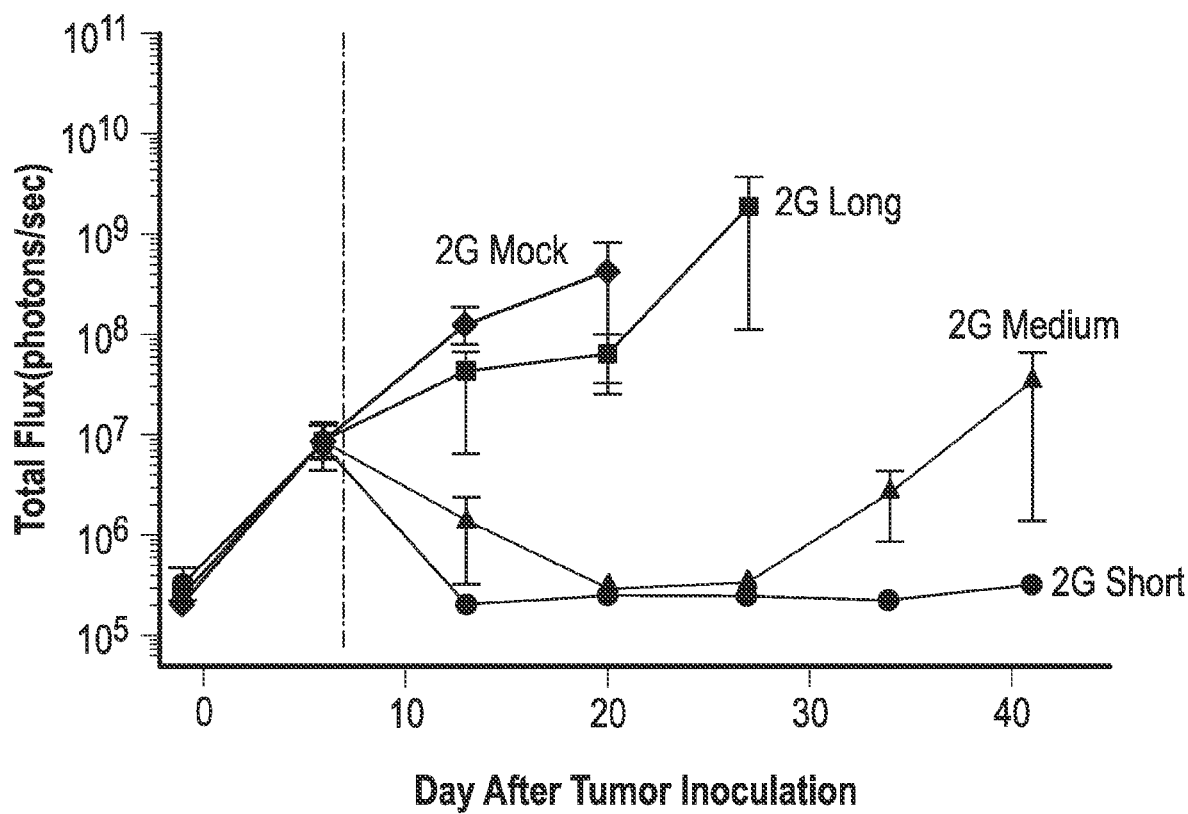
Figure 20D:
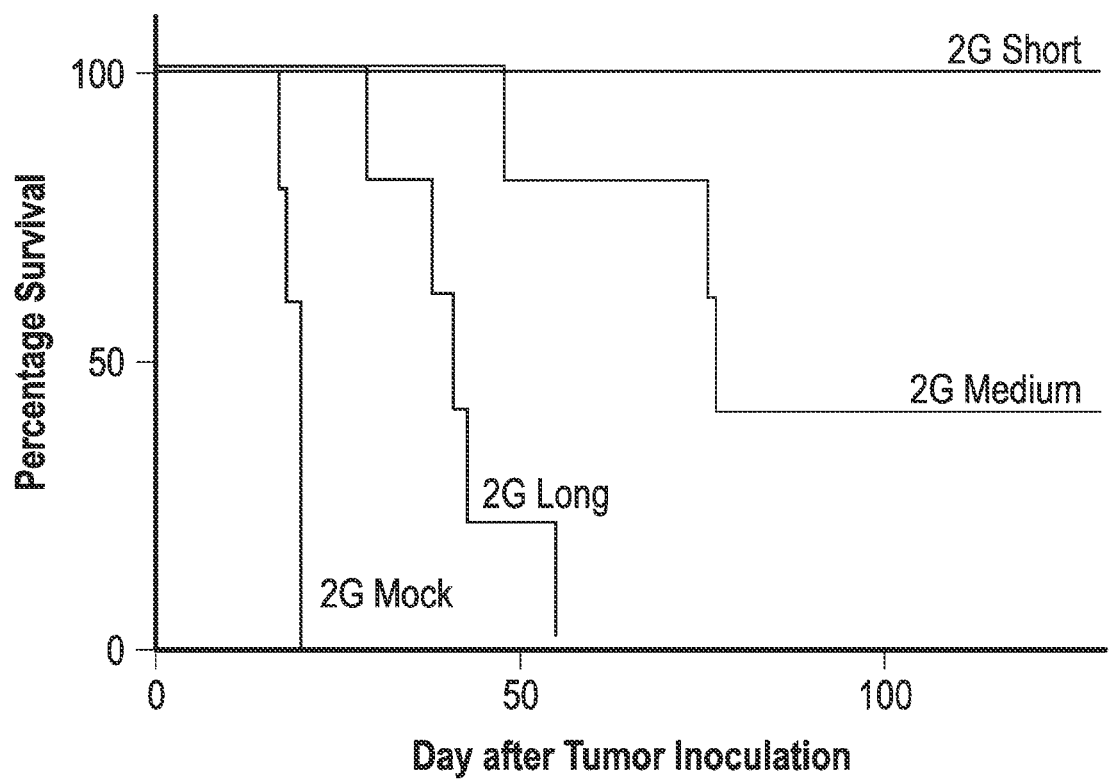

FIGS. 20A-20D shows the in vitro and in vivo anti-tumor activity of CD171-specific and/or targeting 2G-CAR spacer variant CD8$^+$ T$_{E(CM)}$ CLTs against CD171$^{low}$ SK-N-DZ human neuroblastoma xenografts. FIG. 20A shows the lytic potency of 2G-CAR spacer variants in 4-hour CRA against SK-N-DZ. FIG. 20B shows SK-N-DZ stimulation of IFNγ secretion by spacer variant 2G-CAR CTLs. FIG. 20C shows Biophotonic SK-N-DZ tumor signal response to intratumorally infused 2G-CAR(SS, MS or LS) CD8$^+$ T$_{E(CM)}$ (n=5 per group). FIG. 20D shows the Kaplan Meier survival of treated cohorts.

Figure 21:
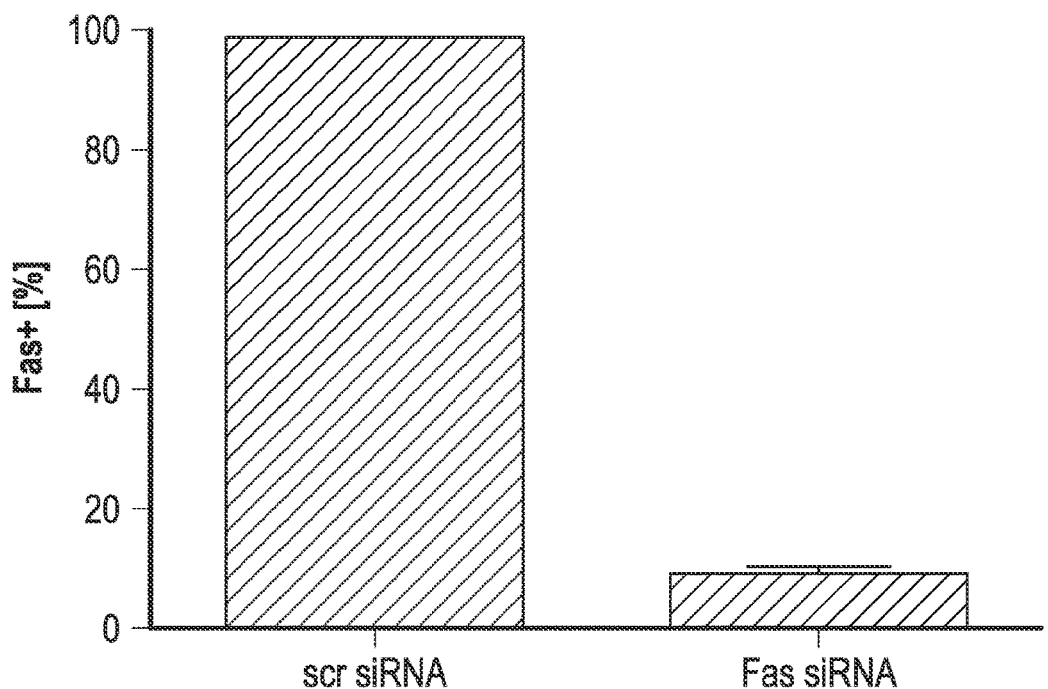
Figure 21:
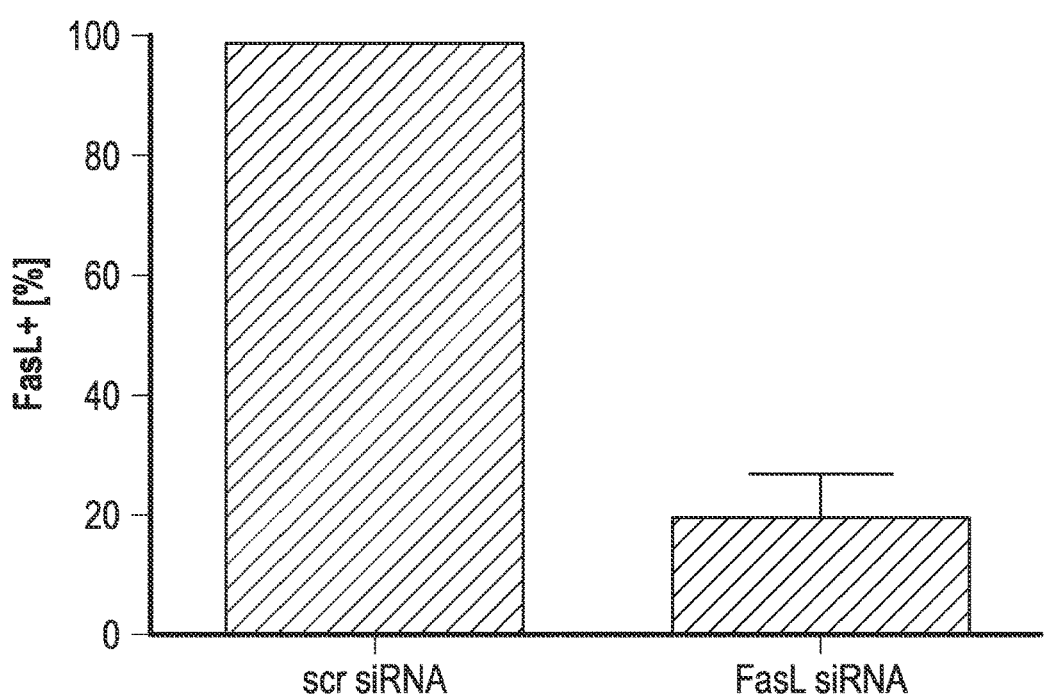

FIG. 21 shows the expression of Fas and FasL after siRNA knockdown. Panel A shows the frequency of Fas$^+$ LS 2G-CAR CTLs after siRNA knockdown of Fas relative to LS 2G-CAR CTLs treated with scr siRNA (% Fas$^+$ values derived from average of 4 independent experiments). Panel B shows the frequency of FasL$^+$ LS 2G-CAR CTLs after siRNA knockdown of FasL as described in Panel A.

DETAILED DESCRIPTION

Unless defined otherwise, all technical and scientific terms used herein have the same meaning as commonly understood by one of ordinary skill in the art to which the invention pertains.

"Activation", as used herein, refers to the state of a T cell that has been sufficiently stimulated to induce detectable cellular proliferation, cytokine production or expression of cell surface markers such as CD69 and CD25, or detectable effector functions.

"Activation Induced cell death" as used herein refers to a state of a T cell that is activated but is not able to proliferate for more than 2 generations and exhibits markers of apoptosis.

"Antigen" or "Ag" as used herein refers to a molecule that provokes an immune response. This immune response may involve either antibody production, or the activation of specific immunologically-competent cells, or both. It is readily apparent that an antigen can be generated synthesized, produced recombinantly or can be derived from a biological sample. Such a biological sample can include, but is not limited to a tissue sample, a tumor sample, a cell or a biological fluid.

"Anti-tumor effect" as used herein, refers to a biological effect, which can be manifested by a decrease in tumor volume, a decrease in the number of tumor cells, a decrease in the number of metastases, an increase in life expectancy, or a decrease of various physiological symptoms associated with the cancerous condition. An "anti-tumor effect" can also be manifested by a decrease in recurrence or an increase in the time before recurrence.

"Chimeric receptor" as used herein refers to a synthetically designed receptor comprising a ligand binding domain of an antibody or other protein sequence that binds to a molecule associated with the disease or disorder and is linked via a spacer domain to one or more intracellular signaling domains of a T cell or other receptors, such as a costimulatory domain. Chimeric receptor can also be referred to as artificial T cell receptors, chimeric T cell receptors, chimeric immunoreceptors, or chimeric antigen receptors (CARs). These CARs are engineered receptors that can graft an arbitrary specificity onto an immune receptor cell. Chimeric antigen receptors or "CARs" are considered by some investigators to include the antibody or antibody fragment, the spacer, signaling domain, and transmembrane region. However, due to the surprising effects of modifying the different components or domains of the CAR, such as the epitope binding region (for example, antibody fragment, scFv, or portion thereof), spacer, transmembrane domain, and/or signaling domain), in some contexts, in the present disclosure, the components of the CAR are described independently. The variation of the different elements of the CAR can, for example, lead to stronger binding affinity for a specific epitope.

"Co-stimulatory domain," as the term is used herein refers to a signaling moiety that provides to T cells a signal which, in addition to the primary signal provided by for instance the CD3 zeta chain of the TCR/CD3 complex, mediates a T cell response, including, but not limited to, activation, proliferation, differentiation, cytokine secretion, and the like. A co-stimulatory domain can include all or a portion of, but is not limited to, CD27, CD28, 4-1BB, OX40, CD30, CD40, ICOS, lymphocyte function-associated antigen-1 (LFA-1), CD2, CD7, LIGHT, NKG2C, B7-H3, and/or a ligand that specifically binds with CD83 and/or targets CD83. In some alternatives, the co-stimulatory domain is an intracellular signaling domain that interacts with other intracellular mediators to mediate a cell response including activation, proliferation, differentiation and cytokine secretion, and the like.

"Coding for," as used herein, refers to the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. A "nucleic acid sequence coding for a polypeptide" includes all nucleotide sequences that are degenerate versions of each other and that code for the same amino acid sequence.

"Cytotoxic T lymphocyte" (CTL) as used herein refers to a T lymphocyte that expresses CD8 on the surface thereof (e.g., a CD8$^+$ expressing T cell, also referred to as a CD8+ T cell or a CD8 T cell, all of which can be used interchangeably). In some alternatives such cells are preferably "memory" T cells (T$_M$ cells) that are antigen-experienced. In similar fashion, CD4+ expressing T cells may be referred to as CD4+ T cells or CD4 T cells interchangeably.

"Central memory" T cell (or "T$_{CM}$") as used herein refers to an antigen experienced CTL that expresses CD62L or CCR-7 and/or CD45RO on the surface thereof, and does not express or has decreased expression of CD45RA as compared to naive cells. In some alternatives, central memory cells are positive for expression of CD62L, CCR7, CD28, CD127, CD45RO, and/or CD95, and/or have decreased expression of CD54RA as compared to naïve cells.

"Effector memory" T cell (or "T$_{EM}$") as used herein refers to an antigen experienced T cell that does not express or has decreased expression of CD62L on the surface thereof as compared to central memory cells, and does not express or has decreased expression of CD45RA as compared to naïve cell. In some alternatives, effector memory cells are negative for expression of CD62L and/or CCR7, as compared to naïve cells or central memory cells, and have variable expression of CD28 and/or CD45RA.

"Naïve" T cells as used herein refers to a non-antigen experienced T lymphocyte that expresses CD62L and/or CD45RA, and/or does not express CD45RO– as compared to central or effector memory cells. In some alternatives, naïve CD8+ T lymphocytes are characterized by the expression of phenotypic markers of naïve T cells including CD62L, CCR7, CD28, CD127, and/or CD45RA.

"Effector $T_E$" T cells as used herein refers to a antigen experienced cytotoxic T lymphocyte cells that do not express or have decreased expression of CD62L, CCR7, CD28, and/or are positive for granzyme B and/or perforin, as compared to central memory or naïve T cells.

"T cell precursors" as described herein refers to lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8, and are therefore classed as double-negative (CD4−CD8−) cells. As they progress through their development, they become double-positive thymocytes (CD4+CD8+), and finally mature to single-positive (CD4+CD8− or CD4−CD8+) thymocytes that are then released from the thymus to peripheral tissues.

About 98% of thymocytes die during the development processes in the thymus by failing either positive selection or negative selection, whereas the other 2% survive and leave the thymus to become mature immunocompetent T cells.

The double negative (DN) stage of the precursor T cell is focused on producing a functional β-chain whereas the double positive (DP) stage is focused on producing a functional α-chain, ultimately producing a functional αβ T cell receptor. As the developing thymocyte progresses through the four DN stages (DN1, DN2, DN3, and DN4), the T cell expresses an invariant α-chain but rearranges the β-chain locus. If the rearranged β-chain successfully pairs with the invariant α-chain, signals are produced which cease rearrangement of the β-chain (and silence the alternate allele) and result in proliferation of the cell. Although these signals require this pre-TCR at the cell surface, they are dependent on ligand binding to the pre-TCR. These thymocytes will then express both CD4 and CD8 and progresses to the double positive (DP) stage where selection of the α-chain takes place. If a rearranged β-chain does not lead to any signaling (e.g. as a result of an inability to pair with the invariant α-chain), the cell may die by neglect (lack of signaling).

"Hematopoietic stem cells" or "HSC" as described herein, are precursor cells that can give rise to myeloid cells such as, for example, macrophages, monocytes, macrophages, neutrophils, basophils, eosinophils, erythrocytes, megakaryocytes/platelets, dendritic cells and lymphoid lineages (such as, for example, T-cells, B-cells, NK-cells). HSCs have a heterogeneous population in which three classes of stem cells exist, which are distinguished by their ratio of lymphoid to myeloid progeny in the blood (L/M).

"Targeting," "target" as described herein refers to an ability to bind to a ligand in which a molecule is specific for. "Specific" or "Specificity" can refer to the characteristic of a ligand for the binding partner or alternatively, the binding partner for the ligand, and can include complementary shape, charge and hydrophobic specificity for binding. Specificity for binding can include stereospecificity, regioselectivity and chemoselectivity.

"Enriched" and "depleted" as used herein to describe amounts of cell types in a mixture refers to the subjecting of the mixture of the cells to a process or step which results in an increase in the number of the "enriched" type and a decrease in the number of the "depleted" cells. Thus, depending upon the source of the original population of cells subjected to the enriching process, a mixture or composition may contain 60, 70, 80, 90, 95, or 99 percent or more (in number or count) of the "enriched" cells and 40, 30, 20, 10, 5 or 1 percent or less (in number or count) of the "depleted" cells.

"Epitope" as used herein refers to a part of an antigen or molecule that is recognized by the immune system including antibodies, T cells, and/or B cells. Epitopes usually have at least 7 amino acids and can be linear or conformational.

"Isolated," when used to describe the various polypeptides disclosed herein, means polypeptide or nucleic acid that has been identified and separated and/or recovered from a component of its natural environment. Preferably, the isolated polypeptide or nucleic acid is free of association with all components with which it is naturally associated. Contaminant components of its natural environment are materials that would typically interfere with diagnostic or therapeutic uses for the polypeptide or nucleic acid, and may include enzymes, hormones, and other proteinaceous or non-proteinaceous solutes.

"Intracellular signaling domain" as used herein refers to all or a portion of one or more domains of a molecule (here the chimeric receptor molecule) that provides for activation of a lymphocyte. Intracellular domains of such molecules mediate a signal by interacting with cellular mediators to result in proliferation, differentiation, activation and other effector functions. In some alternatives, such molecules include all or portions of CD28, CD3, or 4-1BB, or combinations thereof. Intracellular signaling domains include costimulatory domains.

"Ligand" as used herein refers to a substance that binds specifically to another substance to form a complex and/or targets another substance. Examples of ligands include epitopes on antigens, molecules that bind to receptors, substrates, inhibitors, hormones, and activators. "Ligand binding domain" as used herein refers to substance or portion of a substance that binds to a ligand. Examples of ligand binding domains include antigen binding portions of antibodies, extracellular domains of receptors, and active sites of enzymes.

"Operably linked" as used herein refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Percent (%) amino acid sequence identity" with respect to the chimeric receptor polypeptide sequences identified herein is defined as the percentage of amino acid residues in a candidate sequence that are identical with the amino acid residues in the reference sequence for each of the ligand binding domain, spacer, transmembrane domain, and/or the lymphocyte activating domain, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software.

Those skilled in the art can determine appropriate parameters for measuring alignment, including any algorithms needed to achieve maximal alignment over the full-length of the sequences being compared. For example, % amino acid sequence identity values generated using the WU-BLAST-2 computer program [Altschul et al., Methods in Enzymology, 266:460-480 (1996)] uses several search parameters, most of which are set to the default values. Those that are not set to default values (i.e., the adjustable parameters) are set with the following values: overlap span=1, overlap fraction=0.125, word threshold (T)=11 and scoring matrix=BLOSUM62. A % amino acid sequence identity value is determined by dividing (a) the number of matching identical amino acid residues between the each or all of the polypeptide amino acid sequence of the reference chimeric receptor sequence provided in Table 2 and the comparison amino acid sequence of interest as determined by WU-BLAST-2 by (b) the total number of amino acid residues of the polypeptide of interest.

"Chimeric receptor variant polynucleotide" or "chimeric receptor variant nucleic acid sequence" as used herein refers to a polypeptide-encoding nucleic acid molecule as defined below having at least 80%, 85%, 90%, 91%, 92%, 93%, 94%, 95%, 96%, 97%, 98%, or 99% nucleic acid sequence identity with the polynucleotide acid sequence shown in FIG. 5, 7, 9, or 11 or a specifically derived fragment thereof, such as polynucleotide coding for an antigen binding domain, a polynucleotide encoding a spacer domain, a polynucleotide coding for a transmembrane domain and/or a polynucleotide coding for a lymphocyte stimulatory domain. Ordinarily, a chimeric receptor variant of polynucleotide or fragment thereof will have at least 80%, 85%, 90%, 91%, 92%, 93%, 94%, 95%, 96%, 97%, 98%, or 99% nucleic acid sequence identity, more preferably at least 81% nucleic acid sequence identity, more preferably at least 82% nucleic acid sequence identity, more preferably at least 83% nucleic acid sequence identity, more preferably at least 84% nucleic acid sequence identity, more preferably at least 85% nucleic acid sequence identity, more preferably at least 86% nucleic acid sequence identity, more preferably at least 87% nucleic acid sequence identity, more preferably at least 8% nucleic acid sequence identity, more preferably at least 89% nucleic acid sequence identity, more preferably at least 90% nucleic acid sequence identity, more preferably at least 91% nucleic acid sequence identity, more preferably at least 92% nucleic acid sequence identity, more preferably at least 93% nucleic acid sequence identity, more preferably at least 94% nucleic acid sequence identity, more preferably at least 95% nucleic acid sequence identity, more preferably at least 96% nucleic acid sequence identity, more preferably at least 97% nucleic acid sequence identity, more preferably at least 98% nucleic acid sequence identity and yet more preferably at least 99% nucleic acid sequence identity with the nucleic acid sequence as shown in FIG. 5, 7, 9, or 11 or a derived fragment thereof. Variants do not encompass the native nucleotide sequence. In this regard, due to the degeneracy of the genetic code, one of ordinary skill in the art will immediately recognize that a large number of chimeric receptor variant polynucleotides having at least 80%, 85%, 90%, 91%, 92%, 93%, 94%, 95%, 96%, 97%, 98%, or 99% nucleic acid sequence identity to the nucleotide sequence of FIG. 5, 7, 9, or 11.

"Substantially purified" refers to a molecule that is essentially free of other molecule types or a cell that is essentially free of other cell types. A substantially purified cell also refers to a cell, which has been separated from other cell types with which it is normally associated in its naturally occurring state. In some instances, a population of substantially purified cells refers to a homogenous population of cells.

"Not substantially found" when used in reference the presence of a tumor antigen or other molecules on normal cells refers to the percentage of a normal cell type that has the antigen or molecule, and/or the density of the antigen on the cells. In some alternatives, not substantially found means that the antigen or molecule is found on less than 50% of normal cell type and/or at a 50% less density as compared to the amount of cells or antigen found on a tumor cell or other diseased cell.

"T cells" or "T lymphocytes" as used herein may be from any mammalian, preferably primate, species, including monkeys, dogs, and humans. In some alternatives the T cells are allogeneic (from the same species but different donor) as the recipient subject; in some alternatives the T cells are autologous (the donor and the recipient are the same); in some alternatives the T cells arc syngeneic (the donor and the recipients are different but are identical twins).

"Specific" or "Specificity" can refer to the characteristic of a ligand for the binding partner or alternatively, the binding partner for the ligand, and can include complementary shape, charge and hydrophobic specificity for binding. Specificity for binding can include stereospecificity, regioselectivity and chemoselectivity.

In some alternatives, a spacer is described such that the spacer is specific for a ligand. A spacer specific for a ligand can refer to a specific polypeptide length that can allow enhanced binding or targeting of the ligand binding domain for its specific or targeted ligand such that the spacer provides an increased T cell proliferation and/or cytokine production in response to the ligand as compared to a reference chimeric receptor.

"Targeting" as described herein, refers to the recognition of a unique part of the foreign target, such as for example, a protein epitope. Targeting can also refer to binding or recognition to a specific region of a protein, which can be referred to as an antigen. Similar antigenic sites can also be recognized by a targeting antibody, which can lead to the ability of the antibody to react with similar antigenic sites on different proteins, thus leading to a cross-reactive antibody.

"Cellular activities" can refer to humoral responses, cell-based immune responses, cellular responses, maturation pathways, growth pathways, and/or responsiveness of particular cell populations. In some alternatives, a chimeric antigen receptor is provided, wherein the chimeric antigen receptor comprises a spacer. In some alternatives, the spacer provides for enhanced or improved T cell proliferation, enhanced and/or decrease in in vivo cellular activities, and/or cytokine production.

Provided herein are chimeric receptor nucleic acids, and vectors and host cells including such nucleic acids. The chimeric receptor nucleic acid comprises a number of modular components that can be excised and replaced with other components in order to customize the chimeric receptor for targeting a specific target molecule. The disclosure provides that one of the modular components is the spacer component. It has been surprisingly found that the length of the spacer region affects the in vivo efficacy of the T cells modified to express the chimeric receptor and can be customized for individual target molecules for enhanced therapeutic activity.

In one aspect, methods and nucleic acid constructs are provided to design a chimeric receptor that has enhanced or improved tumor recognition, increased T cell proliferation and/or cytokine production in response to the ligand as compared to a reference chimeric receptor, especially in vivo, and/or that results in increased survival of cells bearing the chimeric receptor following specific binding or targeting of the receptor to the antigen, as compared with a reference chimeric receptor.

In some alternatives, the reference chimeric receptor is a chimeric receptor that is otherwise identical to the subject chimeric receptor, aside from having one or more modifications in a spacer, such as in the polypeptide spacer joining the ligand binding domain, e.g., antibody fragment, of the receptor and the transmembrane and/or intracellular portions of the receptor. For example, in some alternatives, the reference chimeric receptor is identical to the subject receptor aside from having a spacer that is different in length or sequence, for example, a spacer that is longer, such as at least 2, 3, 4, 5, 6, 7, 8, 9, or 10 times the number of amino acids in length, as compared to that of the subject chimeric receptor.

In some alternatives, a library of nucleic acids is provided, wherein each nucleic acid codes for a spacer region that differs from the others in sequence and/or length. Each of the nucleic acids can then be used to form a chimeric receptor nucleic acid construct that can be tested in vivo (in an animal model) and/or in vitro so that a spacer can be selected that provides for enhanced or improved tumor recognition, increased T cell proliferation and/or cytokine production in response to the ligand.

In some alternatives, a chimeric receptor nucleic acid comprises a polynucleotide coding for a ligand binding domain, wherein the ligand is a tumor antigen, a polynucleotide coding for a customized polypeptide spacer, wherein the spacer is optimized. In some alternatives, the spacer is optimized for increased T cell proliferation and/or cytokine production in response to the ligand as compared to a reference chimeric receptor.

The design of a chimeric receptor can be customized depending on the type of tumor, the target antigen or molecule present on the tumor, the affinity of the antibody for the target molecule, the flexibility needed for the antigen binding domain, and/or the intracellular signaling domain. In some alternatives, a number of chimeric receptor constructs are tested in vitro and in in vivo models to determine the ability of T cells modified with the receptor to kill tumor cells in immunodeficient mice and to proliferate and persist after adoptive transfer.

Depending on whether the target molecule is present on a subject's tumor cells, the chimeric receptor includes a ligand binding domain that specifically binds to and/or targets that target molecule. In some alternatives, a subject's tumor cells are characterized for cell surface tumor molecules. The target molecule may be selected based on a determination of its presence on a particular subject's tumor cells. In some alternatives, a target molecule or an epitope thereof is selected that is a cell surface molecule found predominantly on tumor cells and not found on normal tissues to any substantial degree. In some alternatives, an antibody is selected to bind to an epitope on the targeted cell surface molecule. In some alternatives, the target molecule is CD171. In some alternatives, the chimeric receptor specifically binds to and/or targets an epitope on CD171 recognized by the antibody known as CE7, and/or an epitope of CD171 or of another antigen, which epitope is of the same or similar distance from the surface plasma membrane of a CD171+ cell. In some alternatives, the antigen has an extracellular portion of a similar size or length as that of CD171, and thus a similar chimeric receptor configuration is appropriate.

In addition, the spacer region of the chimeric receptor may be varied to enhance or improve T cell recognition of the ligand on the target cell. In some alternatives, a spacer domain is selected from a short spacer domain of 15 amino acids or less (but not less than 1 or 2 amino acids), such as 15, 14, 13, 12, 11, 10, 9, 8, 7, 6, 5, 4, 3, or 2 amino acids or a number of amino acids within a range defined by any two of the aforementioned lengths. In some alternatives, a spacer domain is selected from an intermediate spacer domain of 119 amino acids or less (but not less than 1 or 2 amino acids), such as 119, 115, 110, 100, 95, 90, 85, 80, 75, 70, 65, 60, 55, 50, 45, 40, 35, 30, 25, 20, or 15 amino acids or a number of amino acids within a range defined by any two of the aforementioned lengths. In some alternatives, a spacer domain is selected from a long spacer of 229 amino acids or less (but not less than 1 or 2 amino acids), such as 229, 225, 220, 215, 210, 205, 200, 195, 190, 185, 180, 175, 170, 165, 160, 155, 150, 145, 140, 135, 130, 125, or 120 amino acids or a number of amino acids within a range defined by any two of the aforementioned lengths. In some alternatives, a spacer is a hinge region of a Fc receptor or a modified hinge region. In some alternatives, a spacer region is a hinge region in combinations with a CH2 or CH3 or both. In some alternatives, a spacer comprises an amino acid sequence $X_1PPX_2P$ (SEQ ID NO: 1). In alternative a spacer region does not include a full length Fc receptor, and/or does not include a CH2 and/or a CH3 domain. In some such alternatives, the spacer does include an antibody hinge region.

A variety of combinations of primary and costimulatory intracellular signaling domain may be employed to enhance the in vivo efficacy of the chimeric receptor. In some alternatives, different constructs of the chimeric receptor can be tested in an in vivo animal model to determine efficacy for tumor killing. In some alternatives, a costimulatory intracellular signaling domain is selected from the group consisting of CD28 and modified versions thereof, 4-1BB and modified versions thereof and/or combinations thereof. Other costimulatory domains, such as OX40 may be incorporated. In some alternatives, the costimulatory intracellular signaling portion of the receptor includes only intracellular domains derived from a single costimulatory molecule, such as only 4-1BB or only CD28, and does not further contain such a domain from another such molecule.

In some alternatives, chimeric receptor-modified, e.g., CD171 specific and/or targeting chimeric receptor-modified cells, e.g., cytotoxic T cells prepared from sort purified CD8+ central memory T cells, are administered in the presence or absence of CD4+ chimeric receptor-modified cells, e.g., CD171 specific and/or targeting chimeric receptor-modified, T cells. In some alternatives, tumor-specific or tumor targeting CD4+ expressing T cells exert anti-tumor reactivity and provide help to tumor-specific CD8+ expressing T cells in vitro and in vivo. In a specific alternative, tumor-specific or tumor-targeting CD4+ expressing T cells or CD4+ expressing T cells selected from the naïve or the central memory subsets are utilized alone or in combination with CD8+ $T_{CM}$.

Adoptive immunotherapy using chimeric antigen receptor (CAR) expressing T cells in some alternatives is useful for treating or inhibiting cancer. In some alternatives, a CAR directed to an epitope of the antigen CD171 (L1CAM) is prepared. Such CAR constructs are useful to treat or inhibit any cancer that expresses CD171 (L1CAM). In some alternatives, one cancer that expresses CD171 is neuroblastoma (NB). CD171 is expressed in 100% of high risk NB. Other cancers thought to over express CD171 include melanoma, cervical carcinoma, ovarian cancer, uterine carcinoma, pancreatic cancer, colon carcinoma, renal carcinoma, and glioblastoma.

The disclosure provides a chimeric receptor nucleic acid useful for transforming or transducing lymphocytes for use in adoptive immunotherapy. In some alternatives, the nucleic acid contains a number of modular components that provide for easy substitution of elements of the nucleic acid. While not meant to limit the scope of the disclosure, it is believed that the chimeric receptor for each tumor antigen is desirably customized in terms of components in order to provide for in vivo efficacy and efficient expression in mammalian cells. For example, in a specific alternative, for efficacy of a chimeric receptor comprising a scFV that binds to a CD171 L1CAM epitope, such as one that is the same or similar to that recognized the antibody deemed CE7, or an epitope on CD171 or other antigen of the same relative distance from the surface plasma membrane, a spacer that is 15 amino acids or less (but not less than 1 or 2 amino acids) is employed. In some alternatives, an expression vector comprises a chimeric nucleic acid as described herein. Polypeptides encoded by all of or a portion of the chimeric receptor nucleic acids are also included herein.

In some alternatives, the chimeric receptor nucleic acid comprises a polynucleotide coding for a ligand binding domain. In some alternatives, the ligand binding domain specifically binds to and/or targets CD171, or a tumor restricted epitope of CD171. In some alternatives, the ligand binding domain is an antibody or fragment thereof. A nucleic acid sequence coding for an antibody or binding fragment thereof can readily be determined. In a specific alternative, the polynucleotide codes for a single chain Fv that specifically binds and/or targets CD171 (L1CAM). An exemplary antibody is the CE7 antibody. An exemplary nucleic acid sequence for the antibody CE7 scFv is provided in FIG. 5. The sequences of other antibodies are known to or can readily be determined by those of skill in the art.

Tumor antigens are proteins that are produced by tumor cells that elicit an immune response. The selection of the ligand binding domain of the invention will depend on the type of cancer to be treated or inhibited, and may target tumor antigens or other tumor cell surface molecules. A tumor sample from a subject may be characterized for the presence of certain biomarkers or cell surface markers. For example, neuroblastoma cells from a subject are characterized for the presence of CD171 (L1CAM). Other cancer or tumor cells may also be characterized for the presence of CD171 (L1CAM) and can be treated or inhibited with the compositions described herein. In some alternatives a target molecule is a cell surface molecule that is found on tumor cells and is not substantially found on normal tissues, or restricted in its expression to non-vital normal tissues.

Once a tumor cell surface molecule that might be targeted with a chimeric receptor is identified, an epitope of the target molecule is selected and characterized. L1CAM is a cell membrane molecule involved in cell adhesion of neurons. L1CAM has several domains including amino acids 1-19 signal peptide, amino acids 35-125 Ig-like C2 type 1, amino acids 139-226 Ig-like C2 type 2, amino acids 240-328 Ig-like C2 type 3, amino acids 333-420 Ig-like C2 type 4, amino acids 425-507 Ig-like C2 type 5, amino acids 518-607 Ig-like C2 type 6, amino acids 615-712 fibronectin type III 1, amino acids 717-810 fibronectin type III 2, amino acids 814-916 fibronectin type III 3, amino acids 920-1015 fibronectin type III 4, and amino acids 1016-1115 fibronectin type III 5. Epitopes can be found in any of those domains. One epitope that has been characterized is known as the CE7 epitope. The CE7 epitope is an epitope found more often on tumor cells as compared to normal tissues. In some alternatives, an epitope of CD171 is selected that is found more often on tumor cells than healthy cells.

Antibodies that specifically bind and/or targets a tumor cell surface molecule can be prepared using methods of obtaining monoclonal antibodies, methods of phage display, methods to generate human or humanized antibodies, or methods using a transgenic animal or plant engineered to produce human antibodies. Phage display libraries of partially or fully synthetic antibodies are available and can be screened for an antibody or fragment thereof that can bind to the target molecule. Phage display libraries of human antibodies are also available. In some alternatives, antibodies specifically bind, and/or target a tumor cell surface molecule and do not cross react with nonspecific components such as bovine serum albumin or other unrelated antigens. Once identified, the amino acid sequence or polynucleotide sequence coding for the antibody can be isolated and/or determined.

Antibodies or antigen binding fragments include all or a portion of polyclonal antibodies, a monoclonal antibody, a human antibody, a humanized antibody, a synthetic antibody, a chimeric antibody, a bispecific antibody, a minibody, and a linear antibody. Antibody fragments comprise a portion of an intact antibody, preferably the antigen binding or variable region of the intact antibody and can readily be prepared. Examples of antibody fragments include Fab, Fab', F(ab')2, and Fv fragments; diabodies; linear antibodies; single-chain antibody molecules; and multispecific antibodies formed from antibody fragments. A number of anti CD171 antibodies are known and are commercially available.

In some alternatives, a number of different antibodies that bind to a particular tumor cell surface molecule can be isolated and characterized. In some alternatives, the antibodies are characterized based on epitope specificity and/or targeting of the targeted molecule. In addition, in some cases, antibodies that bind to the same epitope can be selected based on the affinity of the antibody for that epitope. In some alternatives, an antibody has an affinity of at least 1 mM, and preferably <50 nM. In some alternatives, an antibody is selected that has a higher affinity for the epitope as compared to other antibodies. For example, an antibody is selected that has at least a 2 fold, at least a 5 fold, at least a 10 fold, at least a 20 fold, at least a 30 fold, at least a 40 fold, or at least a 50 fold greater affinity than a reference antibody that binds to the same epitope.

In some alternatives, a polynucleotide coding for a ligand binding domain is operably linked to a polynucleotide coding for a spacer region. In some alternatives, the polynucleotide coding for a ligand binding domain may also have one or more restriction enzyme sites at the 5' and/or 3' ends of the coding sequence in order to provide for easy excision and replacement of the polynucleotide with another polynucleotide coding for a ligand binding domain coding for a different antigen or that has different binding characteristics. For example, a restriction site, Nhel, is encoded upstream of the leader sequence; and a 3' RsrII located within the hinge region allows subcloning of any desirable scFv into a chimeric receptor vector. In some alternatives, the polynucleotide is codon optimized for expression in mammalian cells.

In some alternatives, the polynucleotide coding for a ligand binding domain is operably linked to a signal peptide.

In some alternatives the signal peptide is a signal peptide for granulocyte colony stimulating factor. Polynucleotides coding for other signal peptides such as CD8 alpha can be utilized.

In some alternatives, the polynucleotide coding for a ligand binding domain is operably linked to a promoter. A promoter is selected that provides for expression of the chimeric antigen receptor in a mammalian cell. In a specific alternative the promoter is the elongation growth factor promoter (EF-1). Another example of a suitable promoter is the immediate early cytomegalovirus (CMV) promoter sequence. However, other constitutive promoter sequences may also be used, including, but not limited to the simian virus 40 (SV 40) early promoter, mouse mammary tumor virus (MMTV), human immunodeficiency virus (HIV) long terminal repeat (LTR) promoter, MuMoLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Inducible promoters are also contemplated. Examples of inducible promoters include, but are not limited to a metallothionine promoter, a glucocorticoid promoter, a progesterone promoter, and a tetracycline promoter. A specific alternative of a polynucleotide coding for a ligand binding domain is shown in FIG. 5 as the scFv from an antibody that specifically binds and/or targets epitope Ce7 on CD171.

In some alternatives, the chimeric receptor nucleic acid comprises a polynucleotide coding for a spacer region. It has been surprisingly found that the length of the spacer region affects the in vivo efficacy of the T cells modified to express the chimeric receptor and can be customized for individual target molecules for optimal tumor or target cell recognition. In some alternatives, the chimeric receptor nucleic acid comprises a polynucleotide coding for a customizable spacer region selected from a library of polynucleotides coding for spacer regions. In some alternatives, a spacer length is selected based upon the location of the epitope, affinity of the antibody for the epitope, and/or the ability of the T cells expressing the chimeric receptor to proliferate in vitro and/or in vivo in response to antigen recognition.

Typically a spacer region is found between the ligand binding domain and the transmembrane domain of the chimeric receptor. In some alternatives, a spacer region provides for flexibility of the ligand binding domain, allows for high expression levels in lymphocytes. A CD171 specific and/or targeting chimeric receptor having a spacer domain of 229 amino acids had less in vivo antitumor activity than a CD171-specific and/or targeting chimeric receptor with a short spacer region comprised of 15 amino acids or less (but not less than 1 or 2 amino acids).

In some alternatives, a spacer region has at least 10 to 229 amino acids, 10 to 200 amino acids, 10 to 175 amino acids, 10 to 150 amino acids, 10 to 125 amino acids, 10 to 115 amino acids, 10 to 100 amino acids, 10 to 75 amino acids, 10 to 50 amino acids, 10 to 40 amino acids, 10 to 30 amino acids, 10 to 20 amino acids, or 10 to 15 amino acids, or a length within a range defined by any two of the aforementioned amino acid lengths. In some alternatives, a spacer region has 15 amino acids or less (but not less than 1 or 2 amino acids), 119 amino acids or less (but not less than 1 or 2 amino acids), or 229 amino acids or less (but not less than 1 or 2 amino acids).

In some alternatives, the spacer region is derived from a hinge region of an immunoglobulin like molecule. In some alternatives, a spacer region comprises all or a portion of the hinge region from a human IgG1, human IgG2, a human IgG3, or a human IgG4, or modified variant thereof, and may contain one or more amino acid substitutions. Exemplary sequences of the hinge regions are provided in Table 6. In some alternatives, a portion of the hinge region includes the upper hinge amino acids found between the variable heavy chain and the core, and the core hinge amino acids including a polyproline region. Typically, the upper hinge region has 3, 4, 5, 6, 7, 8, 9, or 10 amino acids. In some cases, the spacer region comprises an amino acid sequence of $X_1PPX_2P$ (SEQ ID NO: 1). In some alternatives, $X_1$ is a cysteine, glycine, or arginine and $X_2$ is a cysteine or a threonine.

In some alternatives, hinge region sequences can be modified in one or more amino acids in order to avoid undesirable structural interactions such as dimerization. In a specific alternative, the spacer region comprises a portion of a modified human hinge region from IgG4, for example, as shown in Table 1 or Table 6. A representative of a polynucleotide coding for a portion of a modified IgG4 hinge region is provided in Table 1. In some alternatives, a hinge region can have at least 90%, 92%, 95%, or 100% sequence identity with a hinge region amino acid sequence identified in Table 1 or Table 6. In a specific alternative, a portion of a human hinge region from IgG4 has an amino acid substitution in the core amino acids from CPSP to CPPC.

In some alternatives, all or a portion of the hinge region is combined with one or more domains of a constant region of an immunoglobulin. For example, a portion of a hinge region can be combined with all or a portion of a CH2 or CH3 domain or variant thereof. In some alternatives, the spacer region does not include the 47-48 amino acid hinge region sequence from CD8 alpha, a full length Fc receptor, and/or the spacer region consisting of an extracellular portion of the CD28 molecule.

In some alternatives, a short spacer region has 15 amino acids or less (but not less than 1 or 2 amino acids) and comprises all or a portion of a IgG4 hinge region sequence or variant thereof, an intermediate spacer region has 119 amino acids or less (but not less than 1 or 2 amino acids) and comprises all or a portion of a IgG4 hinge region sequence and a CH3 region or variant thereof, and a long spacer has 229 amino acids or less (but not less than 1 or 2 amino acids) and comprises all or a portion of a IgG4 hinge region sequence, a CH2 region, and a CH3 region or variant thereof.

A polynucleotide coding for a spacer region can be readily prepared by synthetic or recombinant methods from the amino acid sequence. In some alternatives, a polynucleotide coding for a spacer region is operably linked to a polynucleotide coding for a transmembrane region. In some alternatives, the polynucleotide coding for the spacer region may also have one or more restriction enzyme sites at the 5' and/or 3' ends of the coding sequence in order to provide for easy excision and replacement of the polynucleotide with another polynucleotide coding for a different spacer region. In some alternatives, the polynucleotide coding for the spacer region is codon optimized for expression in mammalian cells, preferably humans.

In some alternatives, a library of polynucleotides, each coding for different spacer region is provided. In some alternatives, the spacer region is selected from the group consisting of a hinge region sequence from IgG1, IgG2, IgG3, or IgG4 or portion thereof, a hinge region sequence from IgG1, IgG2, IgG3, or IgG4 in combination with all or a portion of a CH2 region or variant thereof, a hinge region sequence from IgG1, IgG2, IgG3, or IgG4 in combination with all or a portion of a CH3 region or variant thereof, and a hinge region sequence from IgG1, IgG2, IgG3, or IgG4 in combination with all or a portion of a CH2 region or variant thereof, and a CH3 region or variant thereof. In some alternatives, a short spacer region is a modified IgG4 hinge sequence having 15 amino acids or less (but not less than 1 or 2 amino acids), an intermediate sequence is a IgG4 hinge sequence with a CH3 sequence having 119 amino acids or less (but not less than 1 or 2 amino acids) (SEQ ID NO:49); or a IgG4 hinge sequence with a CH2 and CH3 region having 229 amino acids or less (but not less than 1 or 2 amino acids).

In some alternatives, a method of selecting a spacer region for a chimeric receptor is provided herein. Surprisingly some chimeric receptor constructs, although effective to activate T cells and direct their killing of tumor cells in vitro, were not effective in vivo. In addition, the side effect profile of the chimeric receptor modified T cells can be such as to result in more cells undergoing activation induced cell death or causing an increase in in vivo cytokines. In some alternatives, a method comprises providing a plurality of chimeric receptor nucleic acids, wherein the chimeric receptor nucleic acids differ only in the spacer region; introducing each of the chimeric receptor nucleic acid into a separate T lymphocyte population; expanding each separate lymphocyte population in vitro, and introducing each lymphocyte population into an animal bearing a tumor to determine the anti-tumor efficacy of each of the chimeric receptors when expressed in T cells, and selecting a chimeric receptor that provides anti-tumor efficacy as compared to each of the other separate lymphocyte populations modified with each of the other chimeric receptors.

Animal models of different tumors are known. Anti-tumor efficacy can be measured by identifying a decrease in tumor volume, by determining animal death, persistence of the genetically modified T cells in vivo, activation of genetically modified T cells (for example, by detecting an increase in expression of CD25 and/CD69), and/or proliferation of genetically modified T cells in vivo. In some alternatives, a chimeric receptor is selected that provides for the best anti-tumor efficacy in vivo as determined by one or more of these parameters. Lack of anti-tumor efficacy can be determined by lack of persistence of the genetically modified lymphocytes in vivo, animal death, an increase in apoptosis as measured by an increase in induction of caspase −3, and/or a decrease in proliferation of genetically modified lymphocytes.

In some alternatives, a chimeric receptor is selected that provides for at least 30% of the cells proliferating through two generations in vitro and/or in vivo. In other alternatives a chimeric receptor is not selected if it results in at least 50% of the cells undergoing activation induced cell death in 72 hours.

In some alternatives, providing a plurality of chimeric receptor nucleic acids, wherein the chimeric receptor nucleic acids differ only in the spacer region comprises providing a chimeric receptor construct comprising a polynucleotide coding for a ligand binding domain, wherein the ligand is a tumor specific and/or tumor targeting antigen, or any other molecule expressed on a target cell population that is suitable to mediate recognition and elimination by a lymphocyte; a polynucleotide coding for a first polypeptide spacer having a defined restriction site at the 5' and 3' end of the coding sequence for the first polypeptide spacer; a polynucleotide coding for a transmembrane domain; and a polynucleotide coding for one or more intracellular signaling domains.

In some alternatives, a method further comprises providing one or more polynucleotides, each encoding a different spacer region. Exemplary constructs are provided in FIGS. 5, 7, and 9. In some alternatives, a method further comprises replacing the polynucleotide coding for the spacer region with a polynucleotide encoding a different spacer region to form a chimeric receptor nucleic acid with a different spacer region. The method can be repeated to form any number of chimeric receptor nucleic acids, each differing in the spacer region. In some alternatives, the chimeric receptor nucleic acids differ from one another only in the spacer region.

In some alternatives, the chimeric receptor nucleic acid comprises a polynucleotide coding for a transmembrane domain. The transmembrane domain provides for anchoring of the chimeric receptor in the membrane. In some alternatives, the transmembrane domain that naturally is associated with one of the domains in the chimeric receptor is used. In some cases, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or a synthetic source. When the source is natural, the domain may be derived from any membrane-bound or transmembrane protein. Transmembrane regions comprise at least the transmembrane region(s) of) the alpha, beta or zeta chain of the T-cell receptor, CD28, CD3, CD45, CD4, CD8, CD9, CD16, CD22; CD33, CD37, CD64, CD80, CD86, CD134, CD137 and/or CD154. In a specific alternative, the transmembrane domain comprises the amino acid sequence of the CD28 transmembrane domain as shown in Table 1. A representative polynucleotide sequence coding for the CD28 transmembrane domain is shown in Table 1 (SEQ ID NO:5).

A transmembrane domain may be synthetic or a variant of a naturally occurring transmembrane domain. In some alternatives, synthetic or variant transmembrane domains comprise predominantly hydrophobic residues such as leucine and valine. In some alternatives, a transmembrane domain can have at least 80%, 85%, 90%, 95%, or 100% amino acid sequence identity with a transmembrane domain as shown in Table 1 or Table 3. Variant transmembrane domains preferably have a hydrophobic score of at least 50 as calculated by Kyte-Doolittle.

A polynucleotide coding for a transmembrane domain can be readily prepared by synthetic or recombinant methods. In some alternatives, a polynucleotide coding for a transmembrane domain is operably linked to a polynucleotide coding for a intracellular signaling region. In some alternatives, the polynucleotide coding for a transmembrane domain may also have one or more restriction enzyme sites at the 5' and/or 3' ends of the coding sequence in order to provide for easy excision and replacement of the polynucleotide coding for a transmembrane domain with another polynucleotide coding for a different transmembrane domain. In some alternatives, the polynucleotide coding for a transmembrane domain is codon optimized for expression in mammalian cells.

In some alternatives, the chimeric receptor nucleic acid comprises a polynucleotide coding for an intracellular signaling domain. The intracellular signaling domain provides for activation of one function of the transduced cell expressing the chimeric receptor upon binding to the ligand expressed on tumor cells. In some alternatives, the intracellular signaling domain contains one or more costimulatory domains. In some alternatives, the intracellular signaling domain is a portion of and/or a variant of an intracellular signaling domain that provides for activation of at least one function of the transduced cell.

Examples of intracellular signaling domains for use in a chimeric receptor of the disclosure include the cytoplasmic sequences of the CD3 zeta chain, and/or co-receptors that act in concert to initiate signal transduction following chimeric receptor engagement, as well as any derivative or variant of these sequences and any synthetic sequence that has the same functional capability. T cell activation can be said to be mediated by two distinct classes of cytoplasmic signaling sequence: those that initiate antigen-dependent primary activation and provide a T cell receptor like signal (primary cytoplasmic signaling sequences) and those that act in an antigen-independent manner to provide a secondary or co-stimulatory signal (secondary cytoplasmic signaling sequences). Primary cytoplasmic signaling sequences that act in a stimulatory manner may contain signaling motifs which are known as receptor tyrosine-based activation motifs or ITAMs. Examples of ITAM containing primary cytoplasmic signaling sequences include those derived from CD3 zeta, FcR gamma, CD3 gamma, CD3 delta, CD3 epsilon, CD5, CD22, CD79a, CD79b, and/or CD66d. In some alternatives, the primary signaling intracellular domain can have at least 80%, 85%, 90%, or 95% sequence identity to CD3 zeta having a sequence provided in Table 1. In some alternatives, variants of CD3 zeta retain at least one, two, three or all ITAM regions as shown in Table 5.

In a preferred alternative, the intracellular signaling domain of the chimeric receptor can be designed to comprise the CD3-zeta signaling domain by itself or combined with any other desired cytoplasmic domain(s). For example, the intracellular signaling domain of the chimeric receptor can comprise a CD3-zeta chain and a costimulatory signaling region.

The costimulatory signaling region refers to a portion of the chimeric receptor comprising the intracellular domain of a costimulatory molecule. A costimulatory molecule is a cell surface molecule other than an antigen receptor or their ligands that is required for a response of lymphocytes to an antigen. Examples of such molecules include CD27, CD28, 4-1BB (CD 137), OX40, CD30, CD40, lymphocyte function-associated antigen-1 (LFA-1), CD2, CD7, LIGHT, NKG2C, B7-H3, and/or a ligand that specifically binds with CD83 and/or targets CD83. In some alternatives, the costimulatory signaling domain can have at least 80%, 85%, 90%, or 95% amino acid sequence identity to the intracellular domain of CD28 as shown in Table 3 or to 4-1BB having a sequence provided in Table 4. In some alternatives, a variant of the CD28 intracellular domain comprises an amino acid substitution at positions 186-187, wherein LL is substituted with GG.

The intracellular signaling sequences of the chimeric receptor may be linked to each other in a random or specified order. Optionally, a short oligo- or polypeptide linker, preferably between 2 and 10 amino acids in length may form the linkage. In one alternative, the intracellular signaling domains comprises all or a portion of the signaling domain of CD3-zeta or variant thereof and all or a portion of the signaling domain of CD28 or a variant thereof. In another alternative, the intracellular signaling domain comprises all or a portion of the signaling domain of CD3-zeta or variant thereof and all or a portion of the signaling domain of 4-1BB or variant thereof. In yet another alternative, the intracellular signaling domain comprises all or a portion of the signaling domain of CD3-zeta or variant thereof, all or a portion of the signaling domain of CD28 or variant thereof, and all or a portion of the signaling domain of 4-1BB or variant thereof. In a specific alternative, the amino acid sequence of the intracellular signaling domain comprising a variant of CD3 zeta and a portion of the 4-1BB intracellular signaling domain is provided in Table 1. A representative nucleic acid sequence is provided in Table 1.

In some alternatives, a polynucleotide coding for an intracellular signaling domain comprises a 4-1BB intracellular domain linked to a portion of a CD3-zeta domain. In other alternatives, the intracellular signaling domain includes only a single costimulatory domain and does not include dual costimulatory domains, such as CD28 cyto combined with 4-1BB costimulatory domains.

In some alternatives, a polynucleotide coding for an intracellular signaling domain that comprises a CD28 domain linked to a 4-1BB intracellular domain linked to a portion of a CD3-zeta domain is provided in FIG. 11. A polynucleotide coding for an intracellular signaling domain can be readily prepared by synthetic or recombinant methods from the amino acid sequence. In some alternatives, the polynucleotide coding for an intracellular signaling domain may also have one or more restriction enzyme sites at the 5' and/or 3' ends of the coding sequence in order to provide for easy excision and replacement of the polynucleotide coding for an intracellular signaling domain with another polynucleotide coding for a different intracellular signaling domain. In some alternatives, the polynucleotide coding for an intracellular signaling domain is codon optimized for expression in mammalian cells, preferably humans.

In some alternatives, the chimeric receptor nucleic acid optionally further comprises a polynucleotide sequence coding for a marker. A marker sequence preferably encodes a cell surface expressed marker that can allow for selection of transduced cells, and/or identification of transduced cells. In some alternatives, the marker sequence is operably linked to a polynucleotide sequence coding for a linker sequence. In some alternatives, the linker sequence is a cleavable linker sequence.

A number of different marker sequences can be employed. Typically a marker sequence has a functional characteristic that allows for selection of transduced cells and/or detection of transduced cells. In some alternatives, the marker sequence is compatible with transduction of human lymphocytes.

The positive selectable marker may be a gene, which upon being introduced into the host cell, expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and/or the multi-drug resistance (MDR) gene.

In some alternatives, a chimeric receptor nucleic acid further comprises a polynucleotide coding for a marker. In some alternatives, the marker sequence encodes a truncated epidermal growth factor receptor, which is expressed at the cell surface. An exemplary polynucleotide for the truncated epidermal growth factor receptor is shown in Table 1. In some alternatives, the polynucleotide coding for the marker is operably linked to a polynucleotide coding for a linker sequence. In a specific alternative, the linker sequence is a cleavable linker sequence T2A, as shown in Table 1. An exemplary polynucleotide sequence coding for the T2A linker is provided in Table 1.

A polynucleotide coding for marker can be readily prepared by synthetic or recombinant methods from the amino acid sequence. In some alternatives a polynucleotide coding for a marker is operably linked to a polynucleotide coding for an intracellular signaling domain. In some alternatives, the polynucleotide coding for a marker may also have one or more restriction enzyme sites at the 5' and/or 3' ends of the coding sequence in order to provide for easy excision and replacement of the polynucleotide coding for a marker with another polynucleotide coding for a different marker. In some alternatives, the polynucleotide coding for a marker is codon optimized for expression in mammalian cells.

The compositions described herein provide for CD4+ and/or CD8+ T lymphocytes. T lymphocytes can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques (including but not limited to those described in U.S. Pat. No. 6,040,177 to Riddell et al.), or variations thereof that will be apparent to those skilled in the art. In some alternatives, the T cells are autologous T cells obtained from the patient.

For example, the desired T cell population or subpopulation may be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T cells). The non-dividing feeder cells can comprise gamma-irradiated PBMC feeder cells. In some alternatives, the PBMC are irradiated with gamma rays in the range of 3000 to 3600 rads to prevent cell division. The order of addition of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least 25 degrees Celsius, preferably at least 30 degrees, more preferably 37 degrees.

The T lymphocytes expanded include CD8+ cytotoxic T lymphocytes (CTL) and CD4+ helper T lymphocytes that may be specific for an antigen present on a human tumor or a pathogen. Optionally, the expansion method may further comprise the step of adding non-dividing EBV-transformed lymphoblastoid cells (LCL) as feeder cells. LCL can be irradiated with gamma rays in the range of 6000 to 10,000 rads. The LCL feeder cells may be provided in any suitable amount, such as a ratio of LCL feeder cells to initial T lymphocytes of at least 10:1. Optionally, the expansion method may further comprise the step of adding anti-CD3 and/or anti CD28 antibody to the culture medium (e.g., at a concentration of at least 0.5 ng/ml). Optionally, the expansion method may further comprise the step of adding IL-2 and/or IL-15 to the culture medium (e.g., wherein the concentration of IL-2 is at least 10 units/ml). After isolation of T lymphocytes both cytotoxic and helper T lymphocytes can be sorted into naïve, memory, and effector T cell subpopulations either before or after expansion.

CD8+ T cells can be obtained by using standard methods. In some alternatives, CD8+ T cells are further sorted into naïve, central memory, and effector memory cells by identifying cell surface antigens that are associated with each of those types of CD8+ T cells. In some alternatives, memory T cells are present in both CD62L+ and CD62L− subsets of CD8+ peripheral blood lymphocytes. PBMC are sorted into CD62L-CD8+ and/or CD62L+CD8+ fractions after staining with anti-CD8 and anti-CD62L antibodies. In some alternatives, the expression of phenotypic markers of central memory $T_{CM}$ include CD45RO, CD62L, CCR7, CD28, CD3, and/or CD127 and are negative or low for granzyme B and/or CD45RA. In some alternatives, central memory T cells are CD45RO+, CD62L+, or CD8+ T cells. In some alternatives, effector $T_E$ are negative for CD62L, CCR7, CD28, and/or CD127, and positive for granzyme B and/or perforin. In some alternatives, naïve CD8+ T lymphocytes are characterized by the expression of phenotypic markers of naïve T cells including CD62L, CCR7, CD28, CD3, CD127, and/or CD45RA.

Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, positive refers to uniform staining of the cell population above the isotype control. In some alternatives, a decrease in expression of one or markers refers to loss of 1 log 10 in the mean fluorescence intensity and/or decrease of percentage of cells that exhibit the marker of at least 20% of the cells, 25% of the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 20 and 100% when compared to a reference cell population. In some alternatives, a cell population positive for one or markers refers to a percentage of cells that exhibit the marker of at least 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 50 and 100% when compared to a reference cell population.

CD4+ T helper cells are sorted into naïve, central memory, and effector cells by identifying cell populations that have cell surface antigens. CD4+ lymphocytes can be obtained by standard methods. In some alternatives, naïve CD4+ T lymphocytes are CD45RO−, CD45RA+, CD62L+, and/or CD4+ T cells. In some alternatives, central memory CD4+ cells are CD62L+ and/or CD45RO+. In some alternatives, effector CD4+ cells are CD62L− and/or CD45RO−.

In some alternatives, populations of CD4+ and CD8+ that are antigen specific can be obtained by stimulating naïve or antigen specific T lymphocytes with antigen. For example, antigen-specific T cell lines or clones can be generated to Cytomegalovirus antigens by isolating T cells from infected subjects and stimulating the cells in vitro with the same antigen. Naïve T cells may also be used. Any number of antigens from tumor cells may be utilized as targets to elicit T cell responses. In some alternatives, the adoptive cellular immunotherapy compositions are useful in the treatment of a disease or disorder including a solid tumor, hematologic malignancy, breast cancer or melanoma.

In some alternatives it may be desired to introduce functional genes into the T cells to be used in immunotherapy in accordance with the present disclosure. For example, the introduced gene or genes may enhance or improve the efficacy of therapy by promoting the viability and/or function of transferred T cells; or they may provide a genetic marker to permit selection and/or evaluation of in vivo survival or migration; or they may incorporate functions that enhance or improve the safety of immunotherapy, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. This can be carried out in accordance with known techniques (see, e.g., U.S. Pat. No. 6,040,177 to Riddell et al. at columns 14-17) or variations thereof that will be apparent to those skilled in the art based upon the present disclosure.

In some alternatives, T cells are modified with chimeric receptors, as described herein. In some alternatives, the T cells are obtained from the subject to be treated, in other alternatives, the lymphocytes are obtained from allogeneic human donors, preferably healthy human donors. Preferably, the T cells containing the chimeric antigen receptors, as described herein, are derived from thymocytes (naturally arising in humans), as well as, those that are derived from engineered precursors, such as iPS cells.

In some alternatives, chimeric receptors comprise a ligand binding domain that specifically binds and/or targets a tumor cell surface molecule, a polypeptide spacer region, a transmembrane domain and an intracellular signaling domain, as described herein. In some alternatives, the ligand binding domain is a single-chain antibody fragment (scFv) that is derived from the variable heavy (VH) and variable light (VL) chains of a monoclonal antibody (mAb). Costimulatory signals can also be provided through the chimeric receptor by fusing the costimulatory domain of CD28 and/or 4-1BB to the CD3 ζ chain. Chimeric receptors are specific and/or target cell surface molecules independent from HLA, thus overcoming the limitations of TCR-recognition including HLA-restriction and low levels of HLA-expression on tumor cells.

In some alternatives, the same or a different chimeric receptor can be introduced into each of population of CD4+ and CD8+ T lymphocytes. In some alternatives, the chimeric receptor in each of these populations has a ligand binding domain that specifically binds to and/or targets the same ligand on the tumor or infected cell. The cellular signaling modules can differ. In some alternatives, the intracellular signaling domain of the CD8+ cytotoxic T cells is the same as the intracellular signaling domain of the CD4+ helper T cells. In other alternatives, the intracellular signaling domain of the CD8+ cytotoxic T cells is different than the intracellular signaling domain of the CD4+ helper T cells.

In some alternatives each of the CD4 or CD8 T lymphocytes can be sorted in to naïve, central memory, effector memory or effector cells prior to transduction as described herein. In alternative alternatives, each of the CD4 or CD8 T lymphocytes can be sorted in to naïve, central memory, effector memory, or effector cells after transduction.

Various transduction techniques have been developed, which utilize recombinant infectious virus particles for gene delivery. This represents a currently preferred approach to the transduction of T lymphocytes of the present invention. The viral vectors which have been used in this way include virus vectors derived from simian virus 40, adenoviruses, adeno-associated virus (AAV), lentiviral vectors, and/or retroviruses. Thus, gene transfer and expression methods are numerous but essentially function to introduce and express genetic material in mammalian cells. Several of the above techniques have been used to transduce hematopoietic or lymphoid cells, including calcium phosphate transfection, protoplast fusion, electroporation, and/or infection with recombinant adenovirus, adeno-associated virus and/or retrovirus vectors. Primary T lymphocytes have been successfully transduced by electroporation and by retroviral or lentiviral infection.

Retroviral and lentiviral vectors provide a highly efficient method for gene transfer into eukaryotic cells. Moreover, retroviral or lentiviral integration takes place in a controlled fashion and results in the stable integration of one or a few copies of the new genetic information per cell.

In some alternatives it may be useful to include in the T cells a positive marker that enables the selection of cells of the negative selectable phenotype in vitro. The positive selectable marker may be a gene that upon being introduced into the host cell expresses a dominant phenotype permitting positive selection of cells carrying the gene. Genes of this type are known in the art, and include, inter alia, hygromycin-B phosphotransferase gene (hph), which confers resistance to hygromycin B, the amino glycoside phosphotransferase gene (neo or aph) from Tn5, which codes for resistance to the antibiotic G418, the dihydrofolate reductase (DHFR) gene, the adenosine deaminase gene (ADA), and/or the multi-drug resistance (MDR) gene.

A variety of methods can be employed for transducing T lymphocytes, as is well known in the art. In some alternatives, transduction is carried out using lentiviral vectors. In some alternatives, CD4+ and CD8+ T cells each can separately be modified with an expression vector encoding a chimeric receptor to form defined populations. In some alternatives, these cells are then further sorted into subpopulations of naïve, central memory and effector cells as described above by sorting for cell surface antigens unique to each of those cell populations. In addition, CD4+ or CD8+ T cell populations may be selected by their cytokine profile or proliferative activities. For example, CD4+ T lymphocytes that have enhanced production of cytokines such as IL-2, IL-4, IL-10, TNFα, and/or IFNγ as compared to sham transduced cells or transduced CD8+ cells when stimulated with antigen can be selected. In other alternatives, naïve or central memory CD4+ T cells that have enhanced production of IL-2 and/or TNFα are selected. Likewise, CD8+ cells that have enhanced IFNγ production are selected as compared to sham transduced CD8+ cells.

In some alternatives, CD4+ and CD8+ T cells that proliferate in response to antigen or tumor targets are selected. For example, CD4+ T cells that proliferate vigorously when stimulated with antigen or tumor targets as compared to sham transduced cells, or CD8+ transduced cells are selected. In some alternatives, CD4+ and CD8+ T cells are selected that are cytotoxic for antigen bearing cells. In some alternatives, CD4+ T cells are expected to be weakly cytotoxic, as compared to CD8+ T cells.

In a preferred alternative, transduced lymphocytes, such as CD8+ central memory cells, are selected that provide for tumor cell killing in vivo using an animal model established for the particular type of cancer. Such animal models are known to those of skill in the art and exclude human beings. As described herein, not all chimeric receptor constructs transduced into lymphocytes confer the ability to kill tumor cells in vivo despite the ability to become activated and kill tumor cells in vitro. In particular, for some target molecules T cells having chimeric receptor constructs with a long spacer region were less effective at killing tumor cells in vivo as compared to T cells having a chimeric receptor with short spacer region.

The disclosure contemplates that combinations of CD4+ and CD8+ T cells will be utilized in the compositions. In one alternative, combinations of chimeric receptor transduced CD4+ cells can be combined with chimeric receptor transduced CD8+ cells of the same ligand specificity or combined with CD8+ T cells that are specific and/or targets for a distinct tumor ligand. In other alternatives, chimeric receptor transduced CD8+ cells are combined with chimeric receptor transduced CD4+ cells specific for and/or can target a different ligand expressed on the tumor. In yet another alternative, chimeric receptor modified CD4+ and CD8+ cells are combined. In some alternatives CD8+ and CD4+ cells can be combined in different ratios for example, a 1:1 ratio of CD8+ and CD4+, a ratio of 10:1 of CD8+ to CD4+, or a ratio of 100:1 of CD8+ to CD4+. In some alternatives, the combined population is tested for cell proliferation in vitro and/or in vivo, and the ratio of cells that provides for proliferation of cells is selected.

As described herein, the disclosure contemplates that CD4+ and CD8+ T cells can be further separated into subpopulations, such as naïve, central memory, and effector memory cell populations. As described herein, in some alternatives, naïve CD4+ cells are CD45RO−, CD45RA+, CD62L+, CD4+ positive T cells. In some alternatives, central memory CD4+ cells are CD62L positive and CD45RO positive. In some alternatives, effector CD4+ cells are CD62L negative and CD45RO positive. Each of these populations may be independently modified with a chimeric receptor.

After transduction and/or selection for chimeric receptor bearing cells, the cell populations are preferably expanded in vitro until a sufficient number of cells are obtained to provide for at least one infusion into a human subject, typically around $10^4$ cells/kg to $10^9$ cells/kg. In some alternatives, the transduced cells are cultured in the presence of antigen bearing cells, anti CD3, anti CD28, and IL-2, IL-7, IL-15, or IL-21 or combinations thereof.

Each of the subpopulations of CD4+ and CD8+ cells can be combined with one another. In a specific alternative, modified naïve or central memory CD4+ cells are combined with modified central memory CD8+ T cells to provide a synergistic cytotoxic effect on antigen bearing cells, such as tumor cells.

The disclosure provides for an adoptive cellular immunotherapy composition comprising a genetically modified T lymphocyte cell preparation, as described herein.

In some alternatives, the T lymphocyte cell preparation comprises CD4+ T cells that have a chimeric receptor comprising an extracellular antibody variable domain specific for a ligand associated with the disease or disorder, a customizable spacer region, a transmembrane domain, and an intracellular signaling domain of a T cell receptor or other receptors, as described herein. In other alternatives, an adoptive cellular immunotherapy composition further comprises a chimeric receptor modified tumor-specific CD8+ cytotoxic T lymphocyte cell preparation that provides a cellular immune response, wherein the cytotoxic T lymphocyte cell preparation comprises CD8+ T cells that have a chimeric receptor comprising an extracellular single chain antibody specific for a ligand associated with the disease or disorder, a customizable spacer region, a transmembrane domain, and an intracellular signaling domain of a T cell receptor, as described herein.

In some alternatives, an adoptive cellular immunotherapy composition comprises a chimeric receptor modified tumor-specific CD8+ cytotoxic T lymphocyte cell preparation that provides a cellular immune response, wherein the cytotoxic T lymphocyte cell preparation comprises CD8+ T cells that have a chimeric receptor comprising an extracellular single chain antibody that can target and/or is specific for a ligand associated with the disease or disorder, a customizable spacer region, a transmembrane domain, and an intracellular signaling domain of a T cell receptor, in combination with an antigen-reactive chimeric receptor modified naïve CD4+ T helper cell derived from CD45RO−CD62L+CD4+ T cells, and a pharmaceutically acceptable carrier.

In other alternatives, an adoptive cellular immunotherapy composition comprises an antigen specific and/or targeting CD8+ cytotoxic T lymphocyte cell preparation that provides a cellular immune response derived from the patient combined with an antigen-reactive chimeric receptor modified naïve CD4+ T helper cell that augments the CD8+ immune response, wherein the helper T lymphocyte cell preparation comprises CD4$^+$ T cells that have a chimeric receptor comprising an extracellular antibody variable domain that can target and/or is specific for the antigen associated with the disease or disorder, a customizable spacer region, a transmembrane domain, and an intracellular signaling domain of a T cell receptor.

In a further alternative, an adoptive cellular immunotherapy composition comprises an antigen-reactive chimeric receptor modified naïve CD4+ T helper cell that augments the CD8+ immune response, wherein the helper T lymphocyte cell preparation comprises CD4+ T cells that have a chimeric receptor comprising an extracellular antibody variable domain that can target and/or is specific for a ligand associated with a disease or disorder, a customizable spacer region, a transmembrane domain, and an intracellular signaling domain of a T cell receptor.

In some alternatives, the CD4+ T helper lymphocyte cell is selected from the group consisting of naïve CD4+ T cells, central memory CD4+ T cells, effector memory CD4+ T cells, or bulk CD4+ T cells. In some alternatives, CD4+ helper lymphocyte cell is a naïve CD4+ T cell, wherein the naïve CD4+ T cell comprises a CD45RO−, CD45RA+, and/or CD62L+CD4+ T cell. In some alternatives, the CD8+ T cytotoxic lymphocyte cell is selected from the group consisting of naïve CD8+ T cells, central memory CD8+ T cells, effector memory CD8+ T cells or bulk CD8+ T cells. In some alternatives, the CD8+ cytotoxic T lymphocyte cell is a central memory T cell wherein the central memory T cell comprises a CD45RO+, CD62L+, and/or CD8+ T cell. In yet other alternatives, the CD8+ cytotoxic T lymphocyte cell is a central memory T cell and the CD4+ helper T lymphocyte cell is a naïve or central memory CD4+ T cell.

The disclosure provides methods of making adoptive immunotherapy compositions and uses or methods of using these compositions for performing cellular immunotherapy in a subject having a disease or disorder. Proliferation and persistence of the chimeric receptor modified T cells can be determined by using an animal model of the disease or disorder and administering the cells and determining persistence and/or proliferative capacity of the transferred cells. In other alternatives, proliferation and activation can be tested in vitro by going through multiple cycles of activation with antigen bearing cells.

In some alternatives, a method of manufacturing the compositions comprises obtaining a modified naïve CD4+ T helper cell, wherein the modified helper T lymphocyte cell preparation comprises CD4+ T cells that have a chimeric receptor comprising a ligand binding domain that can target and/or is specific for a tumor cell surface molecule, a customized spacer domain, a transmembrane domain, and an intracellular signaling domain as described herein.

In another alternative, a method further comprises obtaining a modified CD8+ cytotoxic T cell, wherein the modified cytotoxic T lymphocyte cell preparation comprises CD8+ cells that have a chimeric receptor comprising a ligand binding domain that can target and/or is specific for a tumor cell surface molecule, a customized spacer domain, a transmembrane domain, and an intracellular signaling domain as described herein.

In another alternative, a method comprises obtaining a modified CD8+ cytotoxic T cell, wherein the modified cytotoxic T lymphocyte cell preparation comprises CD8+ T cells that have a chimeric receptor comprising a ligand binding domain that can target and/or is specific for a tumor cell surface molecule, a customized spacer domain, a transmembrane domain, and an intracellular signaling domain, as described herein, and further comprising combining the modified CD8+ cytotoxic T cells with a CD4+ helper cell lymphocyte cell preparation.

The preparation of the CD4+ and CD8+ cells that are modified with a chimeric receptor has been described above as well as in the examples. Antigen specific or antigen targeting T lymphocytes can be obtained from a patient having the disease or disorder or can be prepared by in vitro stimulation of T lymphocytes in the presence of antigen. Subpopulations of CD4+ and CD8+ T lymphocytes that are not selected for antigen specificity or targeting can also be isolated as described herein and combined in the methods of manufacturing. In some alternatives, the combination of cell populations can be evaluated for uniformity of cell surface makers, the ability to proliferate through at least two generations, to have a uniform cell differentiation status. Quality control can be performed by coculturing an cell line expressing the target ligand with chimeric receptor modified T cells to determine if the chimeric receptor modified T cells recognize the cell line using cytotoxicity, proliferation, or cytokine production assays that are known in the field. Cell differentiation status and cell surface markers on the chimeric receptor modified T cells can be determined by flow cytometry. In some alternatives, the markers and cell differentiation status on the CD8+ cells include CD3, CD8, CD62L, CD28, CD27, CD69, CD25, PD-1, CTLA-4, CD45RO, and/or CD45RA. In some alternatives, the markers and the cell differentiation status on the CD4+ cells include CD3, CD4, CD62L, CD28, CD27, CD69, CD25, PD-1, CTLA-4 CD45RO, and/or CD45RA.

In some alternatives, a method of selecting a spacer region for a chimeric receptor is provided herein. Surprisingly some chimeric receptor constructs, although effective to activate T cells in vitro, were not effective in vivo. In some alternatives, a method comprises providing a plurality of chimeric receptor nucleic acids, wherein the chimeric receptor nucleic acids differ only in the spacer region; introducing each of the chimeric receptor nucleic acids into a separate T lymphocyte population; expanding each separate lymphocyte population in vitro, and introducing each lymphocyte population into an animal bearing a tumor to determine the anti-tumor efficacy of each of the chimeric receptor modified T cells, and selecting a chimeric receptor that provides anti-tumor efficacy as compared to each of the other separate lymphocyte populations modified with each of the other chimeric receptor modified T cells.

Animal models of different tumors are known. Anti-tumor efficacy can be measured by identifying a decrease in tumor volume, by determining animal death, persistence of the genetically modified T cells in vivo, activation of genetically modified T cells (for example, by detecting an increase in expression of CD25 and/or CD69), and/or proliferation of genetically modified T cells in vivo. In some alternatives, a chimeric receptor is selected that provides for the best anti-tumor efficacy in vivo as determined by one or more of these parameters. Lack of anti-tumor efficacy can be determined by lack of persistence of the genetically modified lymphocytes in vivo, animal death, an increase in apoptosis as measured by an increase in induction of caspase −3, and/or a decrease in proliferation of genetically modified lymphocytes.

In some alternatives, providing a plurality of chimeric receptor nucleic acids, wherein the chimeric receptor nucleic acids differ only in the spacer region comprises providing a chimeric receptor construct comprising a polynucleotide coding for a ligand binding domain, wherein the ligand is a tumor specific or tumor targeting antigen (e.g. CD171), or any other molecule expressed on a target cell population that is suitable to mediate recognition and elimination by a lymphocyte; a polynucleotide coding for a first polypeptide spacer having a defined restriction site at the 5' and 3' end of the coding sequence for the first polypeptide spacer; a polynucleotide coding for a transmembrane domain; and a polynucleotide coding for an intracellular signaling domain.

In some alternatives, the present disclosure provides a method of treating or inhibiting cancer, a method of inhibiting or delaying progression and/or metastasis of a cancer, a method of inhibiting or reducing the presence of a tumor or cancer cell, and/or a method of inhibiting or reducing a target population of CD171 expressing cells in a patient in need thereof. Such methods involve administering to a subject or a patient in need thereof a genetically modified cytotoxic T lymphocyte cell preparation that provides a cellular immune response, wherein the cytotoxic T lymphocyte cell preparation comprises CD8+ T cells that have a chimeric receptor comprising a polynucleotide coding for a ligand binding domain, wherein the ligand is a tumor specific or tumor targeting antigen, or any other molecule expressed on a target cell population (e.g. CD171) that is suitable to mediate recognition and elimination by a lymphocyte; a polynucleotide coding for a polypeptide spacer wherein the polypeptide spacer is of a customized length, wherein the spacer provides for enhanced T cell proliferation and/or cytokine production as compared to a reference chimeric receptor; a polynucleotide coding for a transmembrane domain; and a polynucleotide coding for one or more intracellular signaling domains. In some alternatives, the subject is identified or selected as a subject in need of a therapy to inhibit or treat cancer. Such selection or identification can be made by clinical or diagnostic evaluation.

The disclosure also provides methods of performing cellular immunotherapy in a subject having a disease or disorder comprising: administering a composition of lymphocytes expressing a chimeric receptor as described herein. In other alternatives, a method comprises administering to the subject a genetically modified cytotoxic T lymphocyte cell preparation that provides a cellular immune response, wherein the cytotoxic T lymphocyte cell preparation comprises CD8+ T cells that have a chimeric receptor comprising a ligand binding domain that can target and/or is specific for a tumor cell surface molecule, a customized spacer domain, a transmembrane domain, and an intracellular signaling domain as described herein, and a genetically modified helper T lymphocyte cell preparation that elicits direct tumor recognition and augments the genetically modified cytotoxic T lymphocyte cell preparations ability to mediate a cellular immune response, wherein the helper T lymphocyte cell preparation comprises CD4+ T cells that have a chimeric receptor comprising a ligand binding domain that can target and/or is specific for a tumor cell surface molecule, a customized spacer domain, a transmembrane domain, and an intracellular signaling domain as described herein. In some alternatives, the subject is identified or selected as a subject in need of a therapy to inhibit or treat cancer. Such selection or identification can be made by clinical or diagnostic evaluation.

While not limiting the scope of the disclosure, it is believed by selecting the chimeric receptor modified T cell population that can persist and proliferate in vivo prior to administration may result in the ability to use a lower dose of T cells and provide more uniform therapeutic activity. In some alternatives, the dose of T cells can be reduced at least 10%, 20%, or 30% or greater. Reduction in the dose of T cells may be beneficial to reduce the risk or tumor lysis syndrome and cytokine storm.

In another alternative, a method of performing cellular immunotherapy in a subject having a disease or disorder comprises: administering to the subject a genetically modified helper T lymphocyte cell preparation, wherein the modified helper T lymphocyte cell preparation comprises CD4+ T cells that have a chimeric receptor comprising a ligand binding domain that can target and/or is specific for a tumor cell surface molecule, a customized spacer domain, a transmembrane domain, and an intracellular signaling domain, as described herein. In some alternatives, the method further comprises administering to the subject a genetically modified cytotoxic T lymphocyte cell preparation, wherein the modified cytotoxic T lymphocyte cell preparation comprises CD8+ cells that have a chimeric receptor comprising a ligand binding domain that can target and/or is specific for a tumor cell surface molecule, a customized spacer domain, a transmembrane domain, and an intracellular signaling domain as described herein. In some alternatives, the subject is identified or selected as a subject in need of a therapy to inhibit or treat cancer. Such selection or identification can be made by clinical or diagnostic evaluation.

Another alternative describes a method of performing cellular immunotherapy in a subject having a disease or disorder comprising: analyzing a biological sample of the subject for the presence of a target molecule (e.g. CD171) associated with the disease or disorder and administering the adoptive immunotherapy compositions described herein, wherein the chimeric receptor specifically binds to and/or targets the target molecule. In some alternatives, the subject is identified or selected as a subject in need of a therapy to inhibit or treat cancer. Such selection or identification can be made by clinical or diagnostic evaluation.

In some alternatives, the CD4+ T helper lymphocyte cell is selected prior to introduction of the chimeric receptor from the group consisting of naïve CD4+ T cells, central memory CD4+ T cells, effector memory CD4+ T cells or bulk CD4+ T cells. In a specific alternative, CD4+ helper lymphocyte cell is a naïve CD4+ T cell, wherein the naïve CD4+ T cell comprises a CD45RO−, CD45RA+, and/or CD62L+CD4+ T cell. In yet other alternatives, the CD8+ T cytotoxic lymphocyte cell is selected prior to introduction of the chimeric receptor from the group consisting of naïve CD8+ T cells, central memory CD8+ T cells, effector memory CD8+ T cells or bulk CD8+ T cells. In a specific alternative, the CD8+ cytotoxic T lymphocyte cell is a central memory T cell wherein the central memory T cell comprises a CD45RO+, CD62L+, and/or CD8+ T cell. In a specific alternative, the CD8+ cytotoxic T lymphocyte cell is a central memory T cell and the CD4+ helper T lymphocyte cell is a naïve CD4+ T cell. In some alternatives, the subject is identified or selected as a subject in need of a therapy to inhibit or treat cancer. Such selection or identification can be made by clinical or diagnostic evaluation.

In some alternatives, the CD8+ T cell and the CD4+ T cell are both genetically modified with a chimeric receptor comprising an antibody heavy chain domain that specifically binds and/or targets a tumor-specific cell surface molecule. In other alternatives, the intracellular signaling domain of the CD8 cytotoxic T cells is the same as the intracellular signaling domain of the CD4 helper T cells. In yet other alternatives, the intracellular signaling domain of the CD8 cytotoxic T cells is different than the intracellular signaling domain of the CD4 helper T cells.

Subjects that can be provided the compositions described herein are, in general, human and other primate subjects, such as monkeys and apes for veterinary medicine purposes; however, the technology is also contemplated for use with domestic animals, such as horses, pigs, sheep, cattle, and goats, as well as, companion animals, such as dogs and cats. The subjects can be male or female and can be any suitable age, including infant, juvenile, adolescent, adult, and geriatric subjects.

The methods are useful in the treatment or inhibition of, for example, CD171 bearing cancer or tumor cells. In some alternatives, CD171 cancer or tumor cells include neuroblastoma, melanoma, cervical carcinoma, ovarian cancer, uterine carcinoma, pancreatic cancer, colon carcinoma, renal carcinoma, and glioblastoma.

Chimeric antigen T cells prepared as described above can be utilized in methods and compositions for adoptive immunotherapy in accordance with known techniques, or variations thereof that will be apparent to those skilled in the art based on the instant disclosure. In some alternatives, the T cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin, fetal bovine serum or other human serum components.

A treatment effective amount of cells in the composition is at least 2 cell subsets (for example, 1 CD8+ central memory T cell subset and 1 CD4+ helper T cell subset) or is more typically greater than $10^2$ cells, and up to $10^6$, up to and including $10^8$ or $10^9$ cells and can be more than $10^{10}$ cells. The number of cells will depend upon the ultimate use for which the composition is intended as will the type of cells included therein. For example, if cells that that can target and/or are specific for a particular antigen are desired, then the population will contain greater than 70%, generally greater than 80%, 85% and 90-95% of such cells. For uses provided herein, the cells are generally in a volume of a liter or less, can be 500 mls or less, even 250 mls or 100 mls or less. Hence the density of the desired cells is typically greater than $10^4$ cells/ml and generally is greater than $10^7$ cells/ml, generally $10^8$ cells/ml or greater. The clinically relevant number of immune cells can be apportioned into multiple infusions that cumulatively equal or exceed $10^6$, $10^7$, $10^8$, $10^8$, $10^9$, $10^{10}$ or $10^{11}$ cells.

In some alternatives, the lymphocytes of the invention may be used to confer immunity to individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, the cells are usually administered by infusion, with each infusion in a range of from 2 cells, up to at least $10^6$ to $3 \times 10^{10}$ cells, preferably in the range of at least $10^7$ to $10^9$ cells. The T cells may be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by routine examination. The generation of sufficient levels of T lymphocytes (including cytotoxic T lymphocytes and/or helper T lymphocytes) is readily achievable using the rapid expansion method of the present invention, as exemplified herein. See, e.g., U.S. Pat. No. 6,040,177 to Riddell et al. at column 17, which is expressly incorporated by reference in its entirety.

In some alternatives, the composition as described herein are administered intravenously, intraperitoneally, intratumorly, into the bone marrow, into the lymph node, and/or into cerebrospinal fluid. In some alternatives, the chimeric receptor engineered compositions are delivered to the site of the tumor. Alternatively, the compositions as described herein can be combined with a compound that targets the cells to the tumor or the immune system compartments and avoid sites such as the lung. In some alternatives, the compositions as described herein are administered with chemotherapeutic agents and/or immunosuppressants. In some alternatives, a patient is first treated with a chemotherapeutic agent that inhibits or destroys other immune cells followed by the compositions described herein. In some cases, chemotherapy may be avoided entirely.

The present invention is illustrated further in the additional alternatives set forth below.
Alternatives The following alternatives are intended to illustrate, but not to limit, the invention in any manner, shape, or form, either explicitly or implicitly. While they are typical of those that might be used, other procedures, methodologies, or techniques known to those skilled in the art may alternatively be used.
Customizing Spacer Domain Length for Optimal Recognition of CD171 with Chimeric Receptor Modified T Cells Chimeric receptors that can target and/or is specific for the CD171 molecule that is expressed on a large number of human malignancies including neuroblastoma were constructed. The CD171 chimeric receptors were designed from CD171 specific and/or targeting scFVs that specifically bind to and/or target epitope CE7 on CD171 and contain extracellular spacer domains of different lengths. The sequences for the Ce7scFv-IgG4hinge-CH2-CH3-CD28tm/4-1BB-zeta-T2A-EGFRt-epHIV7 (long construct) (SEQ ID NO: 54) are shown in FIG. 5 and FIG. 6. The sequences for the CE7scFv-IgG4hinge-CH3-CD28tm/4-1BB-zeta-T2A-EGFRt-epHIV7 (intermediate) (SEQ ID NO: 55) are shown in FIGS. 7 and 8. The sequences for CE7scFv-IgG4hinge-CD28tm/4-1BB-zeta-T2A-EGFRt-epHIV7 (short) (SEQ ID NO: 56) are shown in FIGS. 9 and 10. The sequence for construct CE7scFv-IgG4hinge-CD28tm/cyto-4-1BB-zeta-T2A-EGFRt-epHIV7 with two costimulatory domains (SEQ ID NO: 57) is shown in FIGS. 11-12. The ability of T-cells expressing each CD171 specific and/or targeting chimeric receptor to recognize CD171 neuroblastoma tumors in vitro, and to eliminate neuroblastoma tumor cells engrafted into immunodeficient mice was analyzed.

Human Subjects

Peripheral blood mononuclear cells (PBMC) were obtained from healthy donors and patients after written informed consent on research protocols.
Cell Lines The SK-N-BE 2 neuroblastoma cell line (Be2) was obtained from the American Type Culture Collection. EBV-transformed TMLCLs were made from PBMCs as previously described Pelloquin F, Lamelin J P, Lenoir G M. In vitro cell dev biol 1986; 22(12):689-694.
Immunophenotyping PBMC and cell lines were stained with the following conjugated mAbs: CD4, CD8, CD28, CD45RA, and CD62L, and matched isotype controls (BD Biosciences). Central memory T cells were isolated from PBMC by isolating CD8+ cells and depleting the CD8+ cell population of CD45RA cells using immunomagnetic beads. The CD8+ cells depleted of CD45RA were enriched for CD62L using immunomagnetic beads as shown in FIG. 1. Surface expression of CD171 chimeric receptor was analyzed using a polyclonal goat anti-mouse-IgG antibody (Fab-specific) (Jackson ImmunoResearch). Flow analyses were done on a FACSCanto®, sort-purifications on a FACSAriaII® (Becton Dickinson) and data analyzed using FlowJo® software (Treestar).
Vector Construction and Preparation of Chimeric Receptor Encoding Lentivirus CD171 specific and/or targeting chimeric receptors were constructed using VL and VH chain segments of the CE7 mAb (CD171). (Variable region sequences for CE7 are provided in FIGS. 5, 7, 9, and 11). Each scFV was linked to a spacer domain derived from IgG4-Fc (Uniprot Database: P01861; Table 2) comprising either 'Hinge-CH2-CH3' (long: 229 AA), 'Hinge-CH3' (intermediate:119 AA) or 'Hinge' only (Short:12 AA) sequences (Table 6). All spacers contained a S→P substitution within the 'Hinge' domain located at position 108 of the native IgG4-Fc protein, and were linked to the 27 AA transmembrane domain of human CD28 (Uniprot: P10747,Table 3) and to a signaling module comprising either (i) the 41 AA cytoplasmic domain of human CD28 with an LL→GG substitution located at positions 186-187 of the native CD28 protein (Table 3) linked to the 42 AA cytoplasmic domain of human 4-1BB (Uniprot: Q07011, Table 4) or (ii) the cytoplasmic domain of human 4-1BB alone, each module was linked to the 112 AA cytoplasmic domain of isoform 3 of human CD3ζ (Uniprot: P20963,Table 5). The construct encoded a T2A ribosomal skip element (Table 1) and a tEGFR sequence (Table 1) downstream of the chimeric receptor. Human codon-optimized nucleotide sequences encoding each transgene were synthesized (Life Technologies) and cloned into the epHIV7 lentiviral vector CD171-chimeric receptor or tEGFR-encoding lentiviruses were produced in 293T cells using the packaging vectors pCHGP-2, pCMV-Rev2 and pCMV-G, and Calphos® transfection reagent (Clontech).
Generation of T-Cell Lines Expressing CD171-Chimeric Receptors CD8+ CD45RA− CD62L+ central memory T-cells ($T_{CM}$) were sorted from PBMC of normal donors (see FIG. 1), activated with anti-CD3/CD28 beads (Life Technologies), and transduced on day 3 after activation by centrifugation at 800 g for 45 min at 32° C. with lentiviral supernatant (MOI=3) supplemented with 1 μg/mL polybrene (Millipore). T-cells were expanded in RPMI with 10% human serum, 2 mM L-glutamine (CTL medium), supplemented with recombinant human IL-2 to a final concentration of 50

U/mL. The tEGFR subset of each T-cell line was enriched by immunomagnetic selection with biotin-conjugated anti-EGFR mAb (ImClone Systems) and streptavidin-beads (Miltenyi).

Cytotoxicity, and Cytokine Secretion

Target cells, either Be2 cells or TML CL, were labeled with $^{51}$Cr (PerkinElmer), washed and incubated in triplicate at 1-2×10$^3$ cells/well with effector chimeric receptor modified T-cells at various effector to target (E:T) ratios. Supernatants were harvested for γ-counting after a 4-hour incubation and specific lysis calculated using the standard formula. For analysis of cytokine secretion, 5×10$^4$ T-cells were plated in triplicate with target cells at an E:T ratio of 30:1, 10:1, 3:1 or 1:1, and IFN-γ, TNF-α and IL-2 measured by ELISA or multiplex cytokine immunoassay (Luminex) in supernatant removed after 24-h incubation.

Experiments in NOD/SCID/γc$^{-/-}$ (NSG) Mice

Six- to 8-week old female NOD.Cg-Prkdc$^{scid}$ Il2rg$^{tm1Wjl}$/SzJ (NSG) mice were obtained from the Jackson Laboratory or bred in-house. Mice were injected with 0.2×10$^6$ neuroblastoma tumor cells intracranially and seven days later, received an intracranial injection of 2×10$^6$ chimeric receptor-modified or control T-cells. For bioluminescence imaging of tumor growth, mice received injections of luciferin substrate (Caliper Life Sciences) resuspended in PBS (15 μg/g body weight). Mice were anesthetized with isoflurane and imaged using an Xenogen IVIS Imaging System (Caliper) 15 minutes after the injection of luciferin in small or medium binning mode at an acquisition time of 1 s to 1 min to obtain unsaturated images. Luciferase activity was analyzed using Living Image Software (Caliper) and the photon flux analyzed within regions of interest that encompassed the entire body.

Statistical Analyses

Statistical analyses were performed using Prism Software (GraphPad®). Student's t-test was performed as a two-sided paired test with a confidence interval of 95% and results with a p-value of p<0.05 were considered significant. Statistical analysis of survival were done by log-rank testing and results with a p-value of p<0.05 considered significant.

The Longer Spacer Domain of the CD171 Chimeric Receptor Confers Superior Cytotoxic and Cytokine Secretion In Vivo The design of a CD171-specific and/or targeting chimeric receptor using the CE7 scFV was known. (Park J et al. Molecular Therapy 2007, April 15(4):825-33). This chimeric receptor conferred specific recognition and/or targeting of CD171 tumors in vitro, but it was hypothesized that adjusting the spacer domain would enhance tumor recognition and T-cell signaling. Therefore, chimeric receptors were constructed in which the spacer domain was selected from 'Hinge —CH2-CH3' (229 amino acids, long) 'Hinge-CH3' (119 AA, intermediate), and 'Hinge-only' (12 AA, short) variants. Each of the new receptors contained the identical CE7 scFV, and 4-1BB and CD3ζ signaling modules. The transgene cassette included a truncated EGFR (tEGFR) to serve as a transduction, selection and in vivo tracking marker for chimeric receptor-modified T-cells.

Figure 2A:
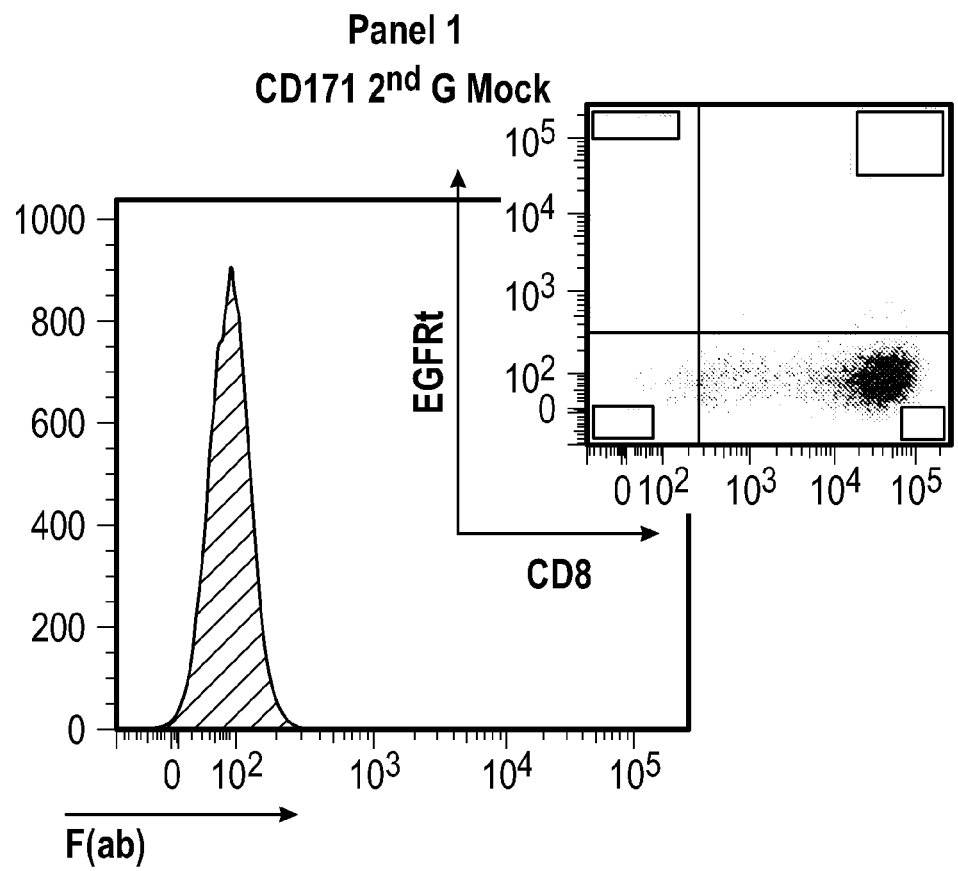
FIG. 2A shows flow cytometry profiles of CD8 central memory cells transduced with a CAR construct having a short, medium or long spacer. The expression of anti CD171 CAR is detected by an antibody that binds to a F(ab). The inset graphs for each panel shows the % of cells expressing CD8 and the truncated EGFR present in each construct in each cell population. Panel 1 is mock infected cells and exhibits no expression of F(ab) or EGFRt. Panel 2 shows expression of the short construct as determined by expression of CD8, EGFRt, and F(ab). Panel 3 shows expression of the intermediate construct as determined by expression of CD8, EGFRt, and F(ab). Panel 4 shows expression of the long construct as determined by expression of CD8, EGFRt, and F(ab). Expression of each of the constructs in CD8 cells is similar regardless of whether the short (Panel 2), medium (Panel 3), or long spacer (Panel 4) is present in the construct.
Figure 2A:
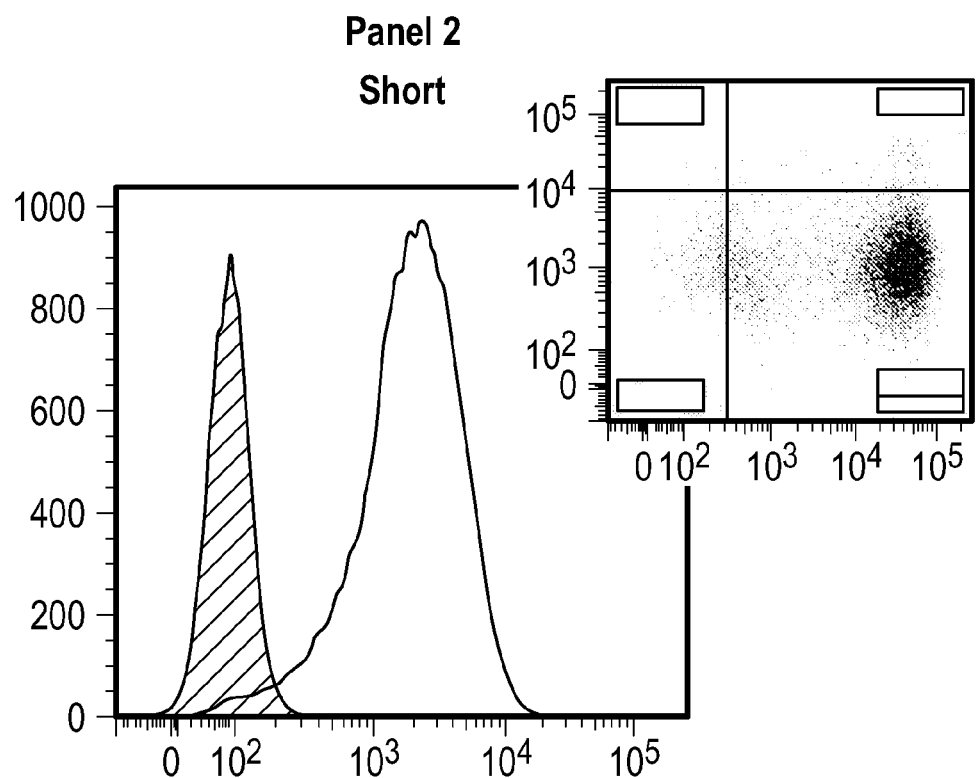
Figure 2A:
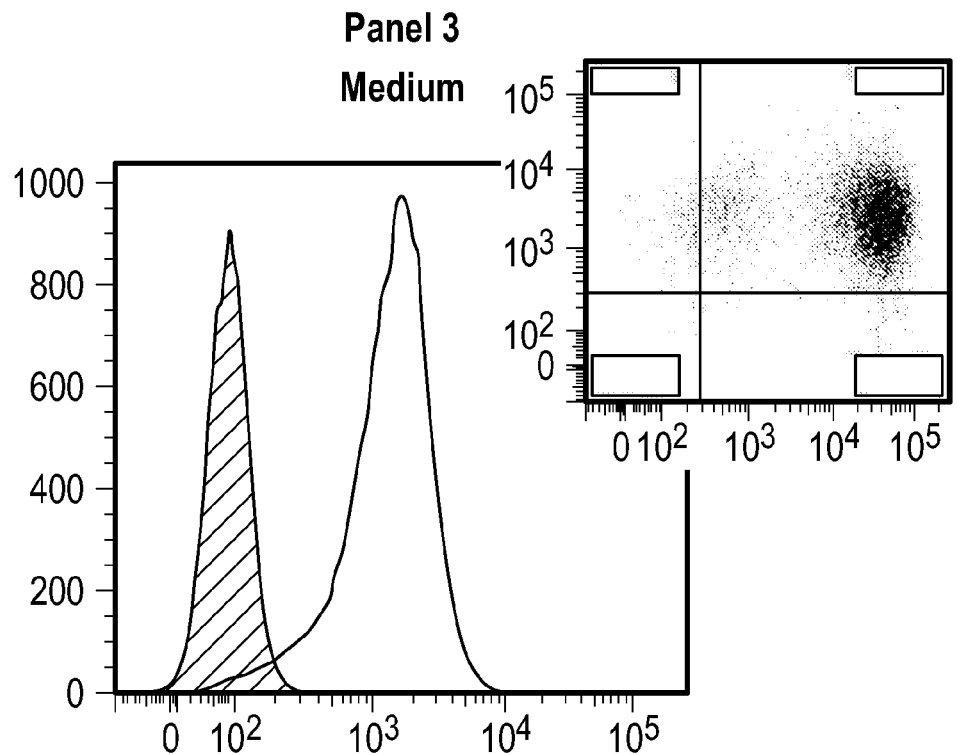
Figure 2A:
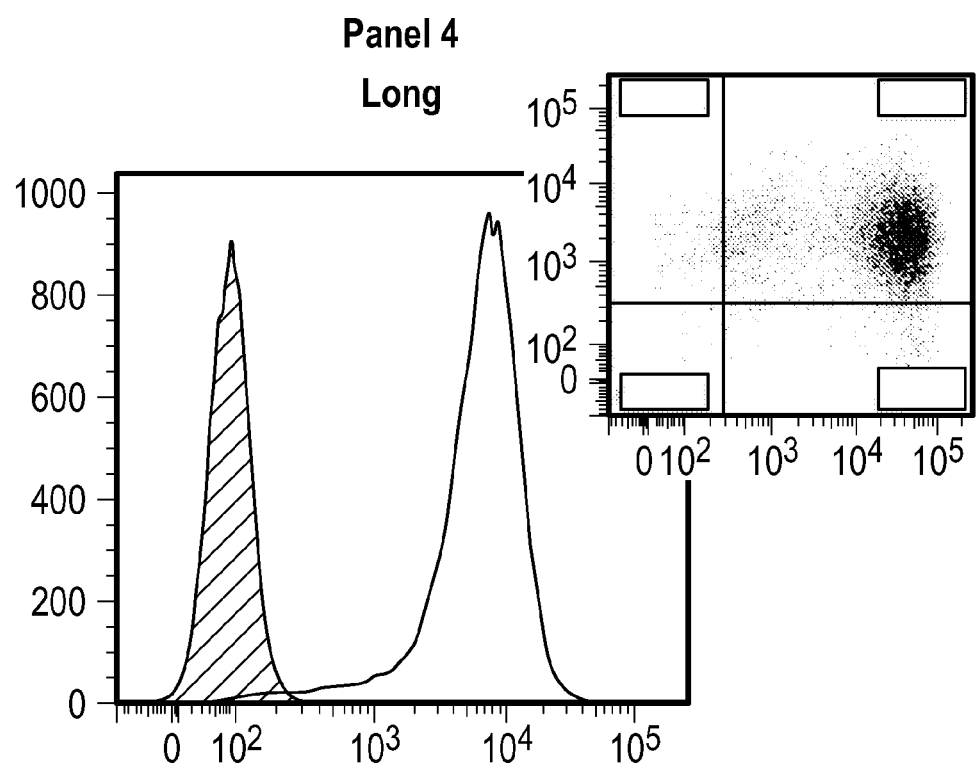
Figure 2B:
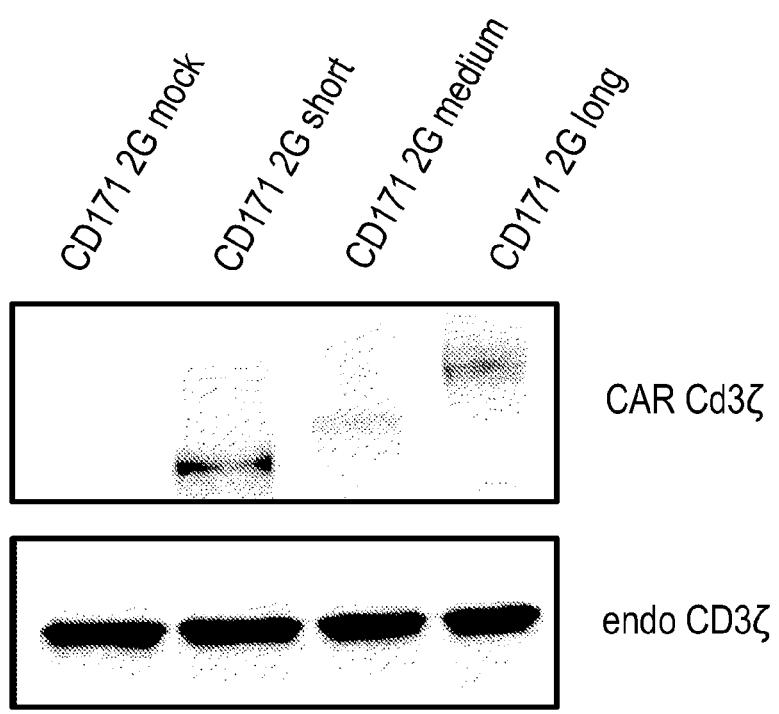
FIG. 2B shows a western blot using an antibody directed to CD3 zeta chain showing equivalent expression of each construct having a short, medium, or long spacer in transduced CD8 cells. Lane 2 shows expression of the short construct. Lane 3 shows expression of the intermediate construct. Lane 4 shows expression of the long construct.

Purified CD8$^+$ T$_{CM}$ were transduced with the CD171-chimeric receptors containing different length spacers, and with a tEGFR control vector. Surface expression of each of the chimeric receptors was confirmed by staining with F(ab)-specific antibodies (FIG. 2A). Western blot of the transduced cells with antibody specific for the CD3ζ shows expression of the short, medium, and long construct. (FIG. 2B). Similar expression of F(ab) and EGFRt were found with each of the short, medium, or long spacer domains.

Figure 2C:
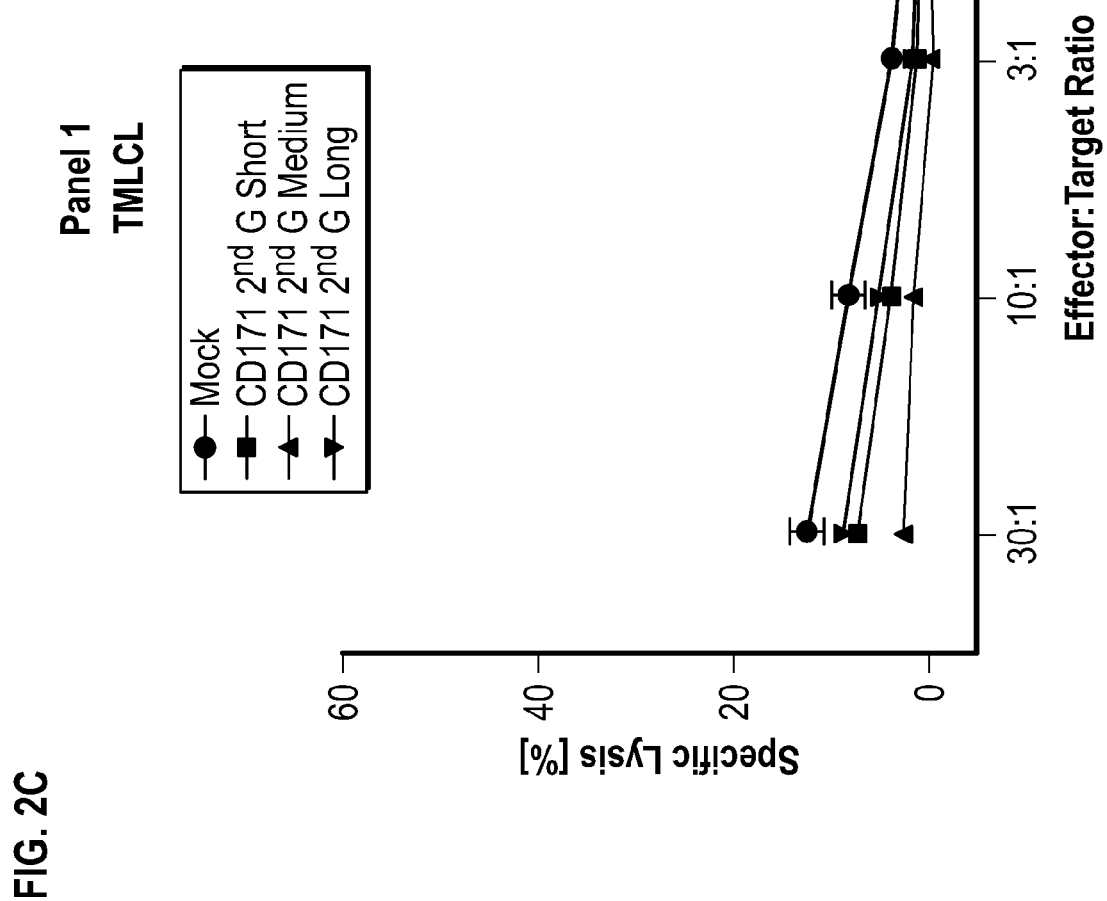
FIG. 2C shows cytolytic activity of mock infected CD8 cells (●) or CD8 cells transduced with a construct with a short spacer (■), an intermediate (▲) or a long spacer (▼) against SK-N-BE 2 neuroblastoma cell line (Be2) or control cell line TML(EBV-transformed TMLCLs were made from PBMCs as previously described (Pelloquin F, Lamelin J P, Lenoir G M. In vitro cell dev biol 1986; 22(12):689-694). Panel 1 shows lack of cytolytic activity of any of the CD8 cells against the control cell line TML. The inset graph shows that control TML cell line does not express CD171. Panel 2 shows that the cells transduced with the long construct (▼) are more effective at killing CD171 expressing neuroblastoma cells than the cells transduced with the intermediate (▲) or short (■) constructs. The inset graph shows that the neuroblastoma cell line Be2 expresses CD171. Panel 3 shows that TML control cells incubated with CD8 cells that can target and/or are specific for antigen CD3 (Okt3) as well as transduced with each of the constructs were killed by the effector cells that can target and/or are specific for CD3 despite the presence of the construct.
Figure 2C:
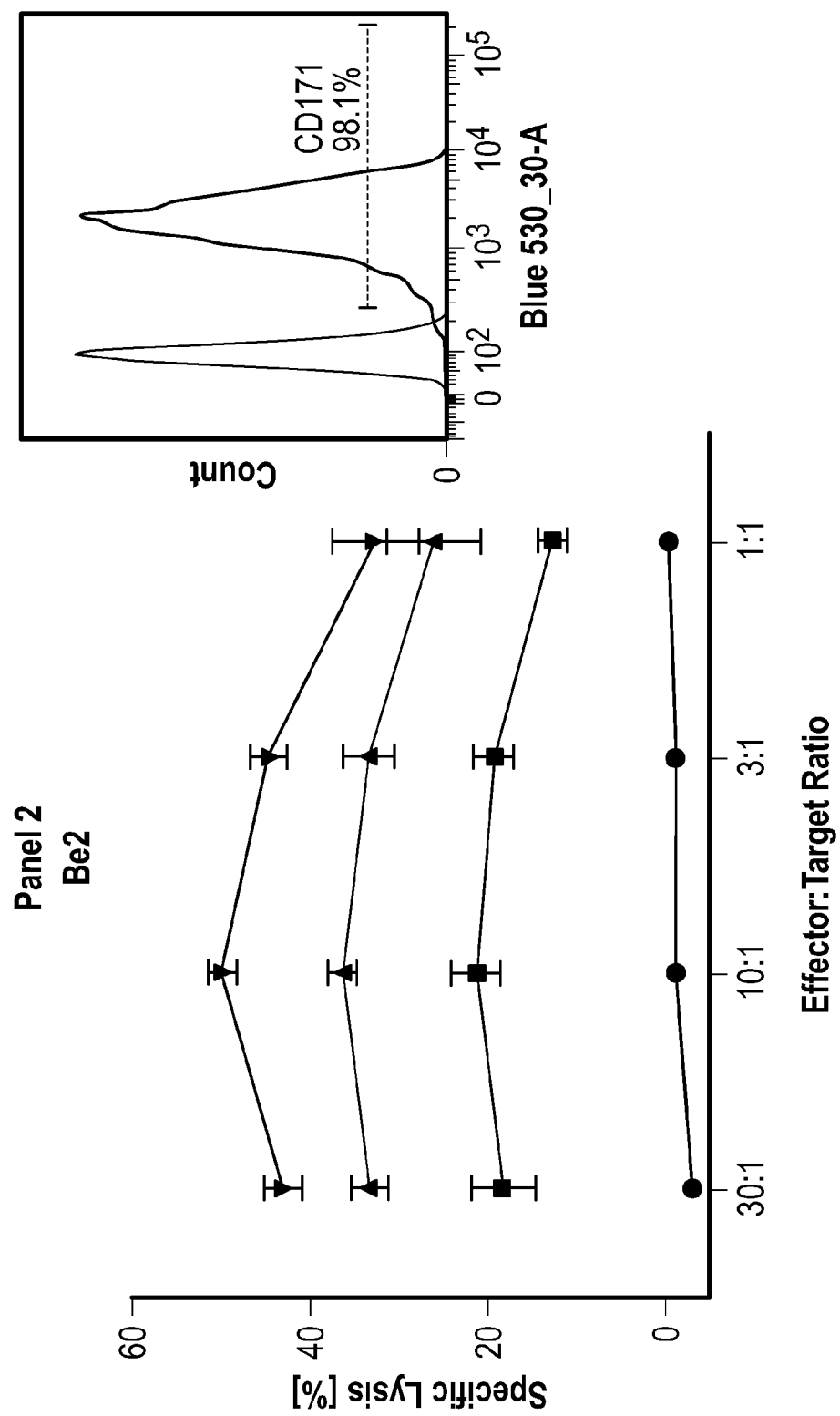
Figure 2C:
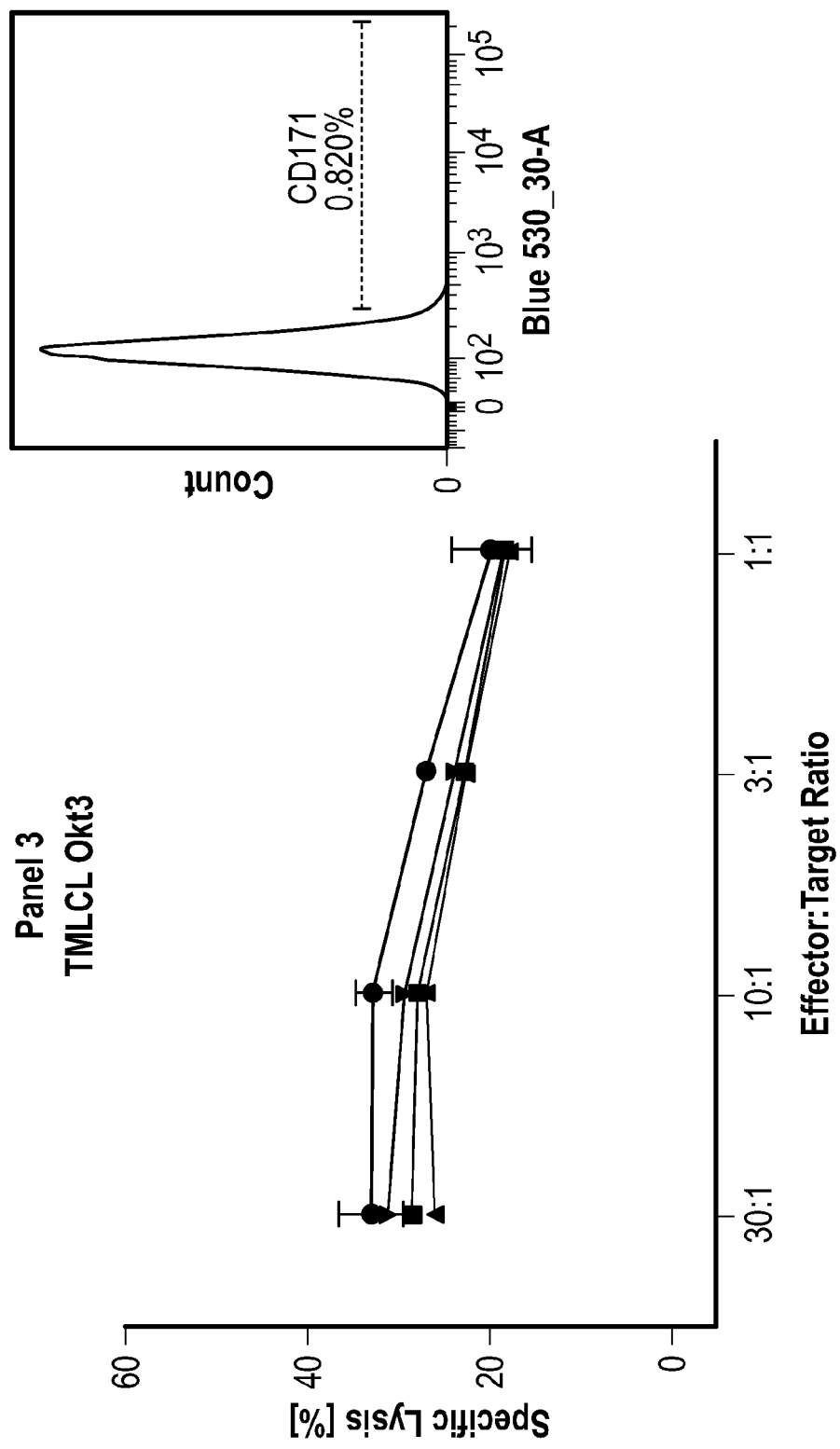

Analysis of the in vitro function of CD8$^+$ T-cells modified to express each of the CD171 chimeric receptors demonstrated that each receptor conferred specific lysis of Be2 cells that naturally express CD171, but did not confer recognition of control TML CL (FIG. 2C). T-cells expressing the long CD171-chimeric receptor had maximum cytolytic activity, and a hierarchy (long>>intermediate>>short) of tumor lysis was clearly evident against CD171 tumor targets (FIG. 2C).

Figure 2D:
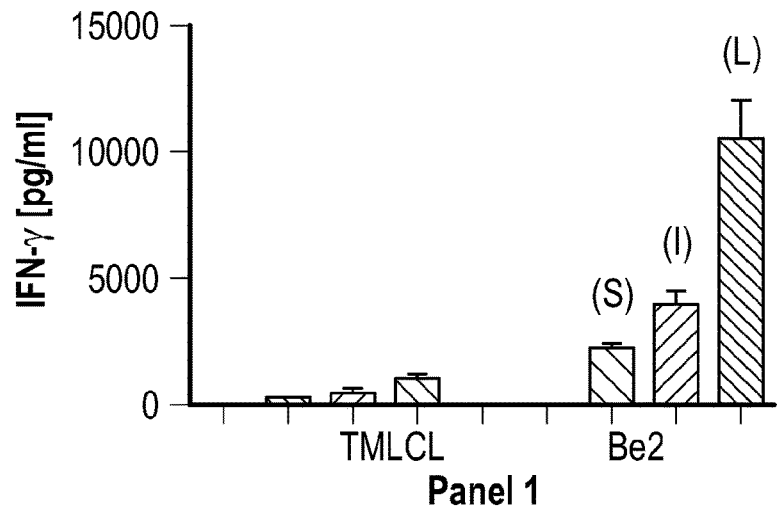
FIG. 2D shows cytokine production by CD8 cells transduced with a construct with a short spacer, an intermediate spacer or a long spacer when contacted with Be2 neuroblastoma cells or control TML. Panel 1 shows that CD8 transduced cells with the long spacer (L) produced more IFNγ than CD8 cells transduced with the intermediate (I) and short spacer (S) when contacted with Be2 neuroblastoma cells. Panel 2 shows that CD8 transduced cells with the long spacer (L) produced more IL-2 than CD8 cells transduced with the intermediate (I) and short spacer (S) when contacted with Be2 neuroblastoma cells. Panel 3 shows that CD8 transduced cells with the long spacer (L) produced more TNFα than CD8 cells transduced with the intermediate (I) and short spacer (S) when contacted with Be2 neuroblastoma cells.
Figure 2D:
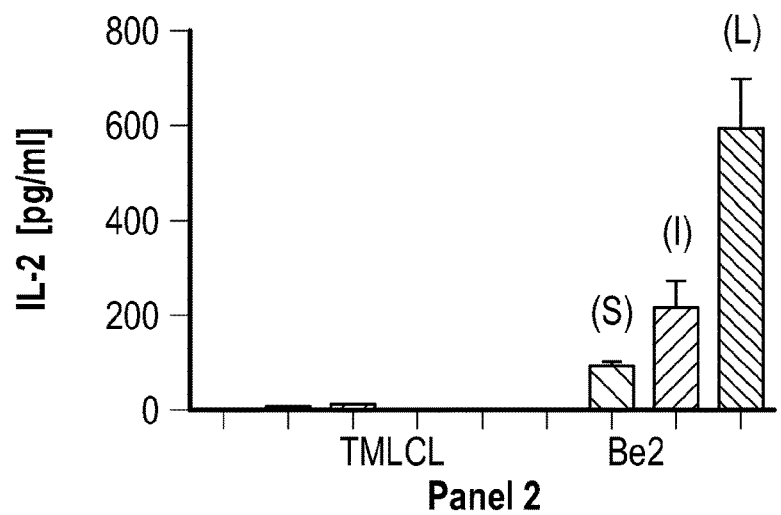
Figure 2D:
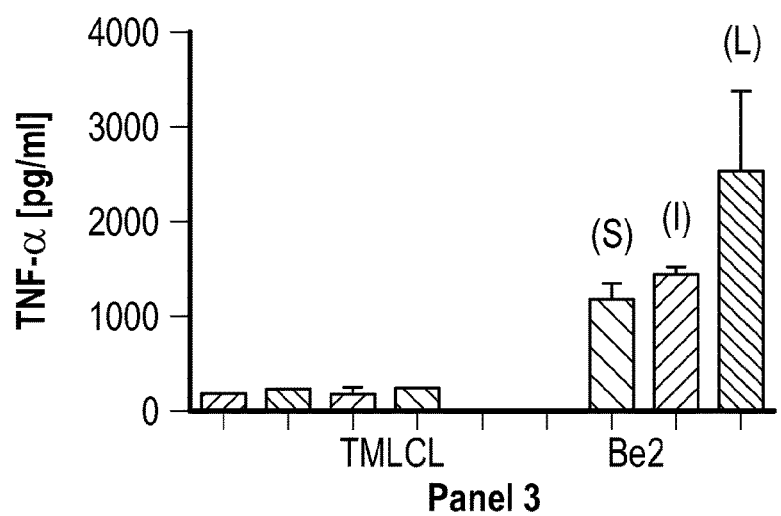

Quantitative analysis of cytokine production in response to stimulation with Be2 cells showed production of IFN-γ, TNF-α and IL-2 by T-cells expressing each of the CD171 chimeric receptors. As observed in cytotoxicity assays, the T cells having the long spacer construct was superior in mediating cytokine secretion after tumor recognition (FIG. 2D).

Figure 2E:
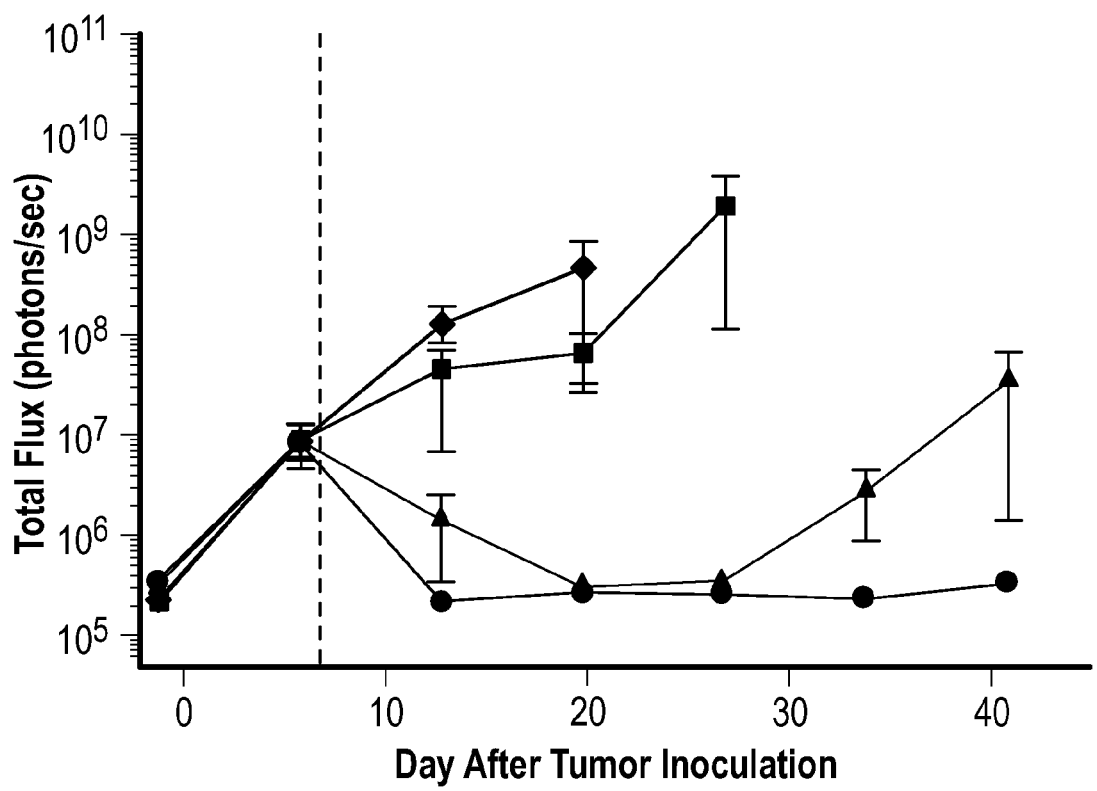
FIG. 2E shows tumor cell survival and proliferation of the intracranial neuroblastoma xenograft tumor model in NSG mice. The graph on the left shows that labelled neuroblastoma cells in mice treated with CD8 cells transduced with a short construct showed very little expression of the label (bottom line) as compared to CD8 cells transduced with the long construct (second line from the top) or control mice treated with sham transduced T cells (top line). The graph on the right shows survival of mice having a xenograft neuroblastoma tumor treated with CD8 cells transduced with a short, intermediate, or long spacer region. The mice treated with CD8 cells transduced with a construct with a short spacer (top line) survived much longer than intermediate (second line) or long spacer (third line from the top).
Figure 2E:
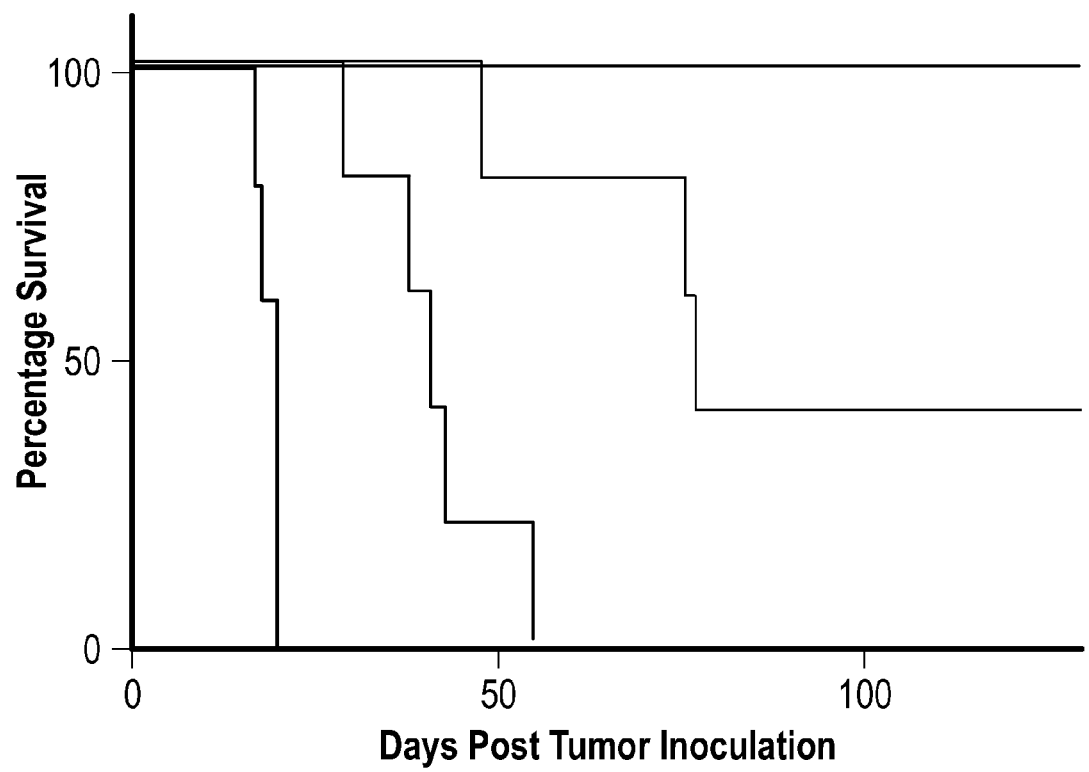

The CD171 Specific and/or Targeting CAR Requires a Short Extracellular Spacer Domain for In Vivo Activity It remained uncertain whether the superior in vitro activity of T-cells modified with the CD171 chimeric receptor with longer spacer would translate into enhanced or improved anti-tumor activity in vivo. To address these questions, cohorts of immunodeficient NSG mice were inoculated with the neuroblastoma cells by intracranial injection, and seven days later the mice were treated with a single intracranial dose of CD171 specific chimeric receptor CD8$^+$ T-cells with a short, intermediate, or long spacer. Control mice were treated with tEGFR T-cells or untreated. Untreated NSG/NB mice developed neuroblastoma necessitating euthanasia approximately 4 weeks after tumor inoculation (FIG. 2E, right panel).

Tumor regression and enhanced or improved survival was observed in all mice treated with CD171 chimeric receptor T-cells with the short spacer. Mice treated with CD171 chimeric receptor T-cells with short spacer had a superior anti-tumor response and survival compared to mice treated with CD171 chimeric receptor T-cells with a long spacer (FIG. 2E, right panel). Measuring total flux from tumor cells loaded with luciferin substrate shows that mice treated with CD8 cells transduced with a construct with a short or intermediate spacer exhibited much lower flux than the untreated mice or mice treated with CD8 cells transduced with a construct having a long spacer. (FIG. 2E, left panel).

Figure 2F:
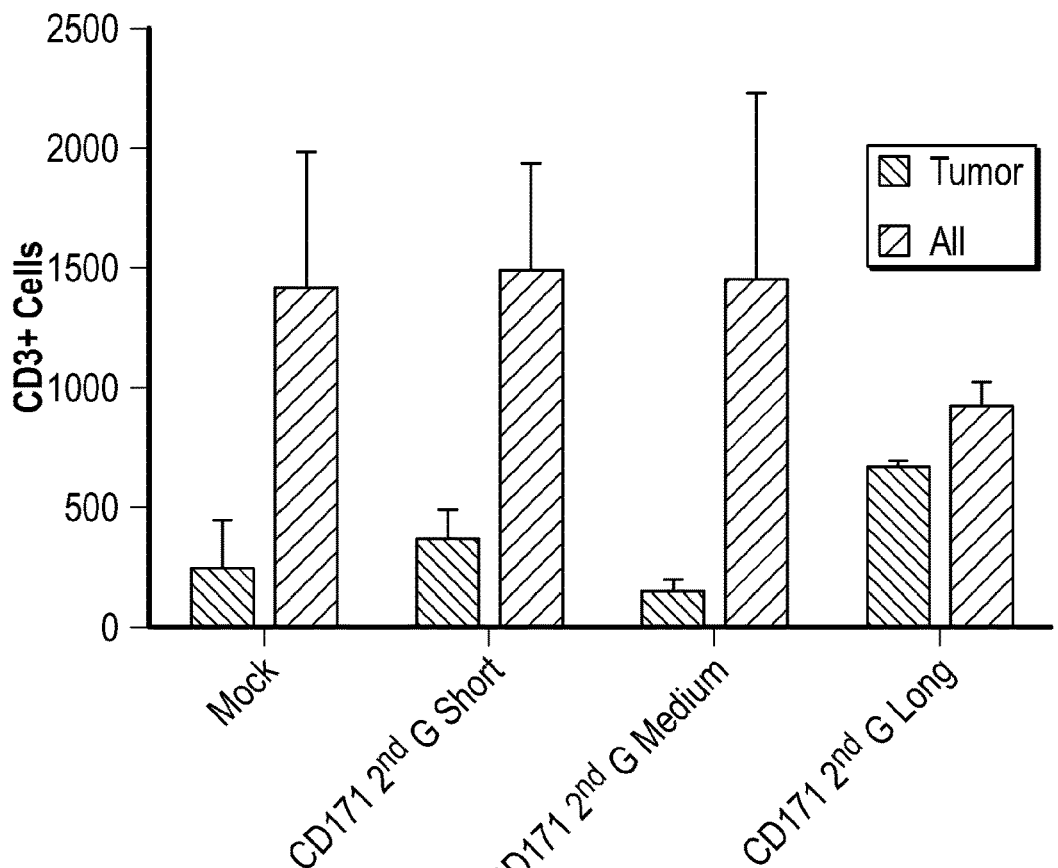
FIG. 2F shows that tumors from mice treated with CD8 cells transduced with a construct with a long spacer exhibited greater numbers of CD3+ cells in the tumor.
Figure 2G:
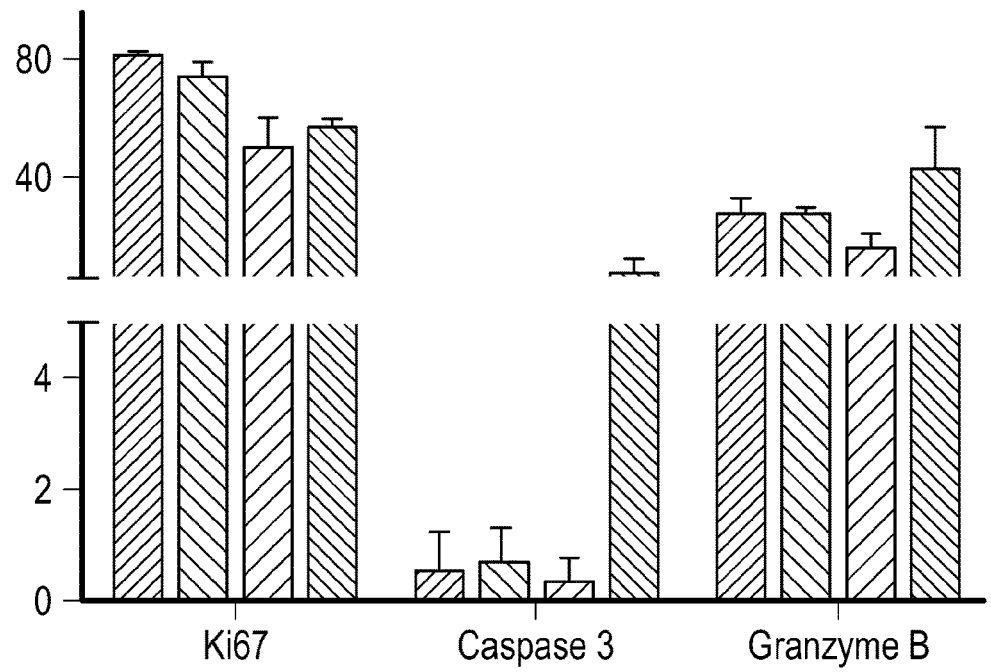
FIG. 2G shows that tumors from mice treated with CD8 cells transduced with a construct with a long spacer expressed more caspase 3 in the tumor.

Tumors from mice treated with long spacer CD171 CAR expressing CD8 Tcm showed higher percentage of CD3+ cells by immunohistochemistry than those from mice treated with mock, short or medium spacer CD171 CAR expressing CD8 Tcm (FIG. 2F). No difference of Ki67 was detectable by immunohistochemistry in the different CD8 Tcm but higher levels of caspase 3 and Granzyme B were found in CD8 Tcm expressing the long spacer CD171 CAR than in CD8 Tcm expressing short or medium spacer after 3 days of T cell injection (FIG. 2G).

The CD171 Specific and/or Targeting CAR Having a Long Extracellular Spacer Domain Showed More Activation Induced Cell Death In order to determine potential mechanisms underlying the inferior in vivo antitumor activity of T cells that express CD171 chimeric receptors with long spacer domains, the possibility that the T cells were not efficiently activated by tumor cells in vivo or conversely, that they underwent activation induced T cell death in vivo was considered.

CD8 central memory cells transduced with CD171CAR constructs with short, intermediate, or long spacer constructs were exposed to neuroblastoma cells in vitro for 24 hours (round 1). CD8 central memory cells were removed from the culture and characterized phenotypically, and then incubated with the tumor cells for another 24 hours (round 2). CD8 cells were removed from the culture, phenotypically characterized, and then placed in a culture with tumor cells for another 24 hours (round 3). The CD8 cells were then removed and characterized phenotypically.

The cells from each round were characterized for expression of activation markers CD25 and CD69 using flow cytometry. The percentage of dead cells in cells from each round was determined by Guava Viacount. NB cells were characterized for FasR expression after round I.

The results show that the short spacer CAR cells exhibited less activation and better viability relative to long spacer CAR-expressing cells following serial tumor cell co-culture challenge (round III: CD25+CD69+42% (short) vs 66% (long) (FIG. 3A), % dead cells 15% (short) vs 60% (long) (FIG. 3B). The long spacer CAR-expressing cells induced FasR expression in NB cells to a greater extent than short spacer CAR cells. (FIG. 3C).

Collectively, the data provides evidence that CD171 directed chimeric receptors with long extracellular spacer domain, despite mediating equivalent or superior effector function in vitro, induce a high level of activation induced cell death in vivo and fail to eradicate established neuroblastoma.

CD171 has attracted interest as a potential target for cancer immunotherapy due to its expression on the surface of many carcinomas. The design and function of CD171 chimeric receptors has been enhanced or improved through modification of the extracellular spacer domain. The results show that central memory T cells transduced with a CD171 directed CAR with a Hinge only short spacer domain performed much better in an in vivo model of neuroblastoma tumor eradication as compared to T cells transduced with a CD171 directed CAR with a hinge-CH3 (intermediate) or hinge-CH2-CH3(long) spacer domain.

Modification of Costimulatory Domains

Chimeric receptors that can target or are specific for the CD171 molecule that is expressed on a large number of human malignancies including neuroblastoma were constructed. The CD171 chimeric receptors were designed from CD171 specific and/or targeting scFVs that specifically bind to and/or target epitope CE7 on CD171 and contain a short extracellular spacer domain One construct contains the costimulatory domain 4-1BB linked to CD3 zeta domain (4-1BB) and the other construct includes a dual costimulatory domain including CD28cyto and 4-1BB linked to CD3 zeta (CD28cyto). The sequence for construct CE7scFv-IgG4hinge-CD28tm/cyto-4-1BB-zeta-T2A-EGFRt-epHIV7 with two costimulatory domains is shown in FIGS. 11-12. The sequence for CE7scFv-IgG4hinge-CD28tm/4-1BB-zeta-T2A-EGI-Rt-epHIV7 (short) is shown in FIGS. 9-10. The ability of T-cells expressing each CD171 specific chimeric receptor to recognize CD171 neuroblastoma tumors in vitro, and to eliminate neuroblastoma tumor cells engrafted into immunodeficient mice was analyzed.

Human Subjects

Peripheral blood mononuclear cells (PBMC) were obtained from healthy donors and patients after written informed consent on research protocols.

Cell Lines

The SK-N-BE 2 neuroblastoma cell line (Be2) was obtained from the American Type Culture Collection. EBV-transformed TMLCLs were made from PBMCs as previously described Pelloquin F, Lamelin J P, Lenoir G M. In vitro cell dev biol 1986; 22(12):689-694.

Immunophenotyping

PBMC and cell lines were stained with the following conjugated mAbs: CD4, CD8, CD28, CD45RA, and CD62L, and matched isotype controls (BD Biosciences). Central memory T cells were isolated from PBMC by isolating CD8$^+$ cells and depleting the CD8+ cell population of CD45RA cells using immuno magnetic beads. The CD8+ cells depleted of CD45RA were enriched for CD62L using immunomagnetic beads as shown in FIG. 1. Surface expression of CD171 chimeric receptor was analyzed using a polyclonal goat anti-mouse-IgG antibody (Fab-specific) (Jackson ImmunoResearch). Flow analyses were done on a FACSCanto®, sort-purifications on a FACSAriaII® (Becton Dickinson) and data analyzed using FlowJo® software (Treestar).

Vector Construction and Preparation of Chimeric Receptor Encoding Lentivirus

CD171 specific and/or targeting chimeric receptors were constructed using VL and VH chain segments of the CE7 mAb (CD171). (Variable region sequences for CE7 are provided in FIGS. 5, 7, 9, and 11) Each scFV was linked to a spacer domain derived from IgG4-Fc (Uniprot Database: P01861; Table 2) comprising either 'Hinge-CH2-CH3' (long: 229 AA), 'Hinge-CH3' (intermediate:119 AA) or 'Hinge' only (Short:12 AA) sequences (Table 6). All spacers contained a S→P substitution within the 'Hinge' domain located at position 108 of the native IgG4-Fc protein, and were linked to the 27 AA transmembrane domain of human CD28 (Uniprot: P10747,Table 3) and to a signaling module comprising either (i) the 41 AA cytoplasmic domain of human CD28 with an LL→GG substitution located at positions 186-187 of the native CD28 protein (Table 3) linked to the 42 AA cytoplasmic domain of human 4-1BB (Uniprot: Q07011, Table 4) or (ii) the cytoplasmic domain of human 4-1BB alone, each module was linked to the 112 AA cytoplasmic domain of isoform 3 of human CD3ζ (Uniprot: P20963,Table 5). One construct contained a costimulatory signaling module comprising the 42 AA cytoplasmic domain of human 4-1BB (Uniprot: Q07011, SEQ ID NO:15), which was linked to the 112 AA cytoplasmic domain of isoform 3 of human CD3ζ (Uniprot: P20963, SEQ ID NO:16). The constructs encoded a T2A ribosomal skip element (SEQ ID NO:8) and a tEGFR sequence (SEQ ID NO:9) downstream of the chimeric receptor. Human codon-optimized nucleotide sequences encoding each transgene were synthesized (Life Technologies) and cloned into the epHIV7 lentiviral vector.CD171-chimeric receptor or tEGFRt-encoding lentiviruses were produced in 293T cells using the packaging vectors pCHGP-2, pCMV-Rev2 and pCMV-G, and Calphos® transfection reagent (Clontech).

Generation of T-Cell Lines Expressing CD171-Chimeric Receptors

CD8$^+$ CD45RA− CD62L$^+$ central memory T-cells (T$_{CM}$) were sorted from PBMC of normal donors (See FIG. 1), activated with anti-CD3/CD28 beads (Life Technologies), and transduced on day 3 after activation by centrifugation at 800 g for 45 min at 32° C. with lentiviral supernatant (MOI=3) supplemented with 1 μg/mL polybrene (Millipore). T-cells were expanded in RPMI with 10% human serum, 2 mM L-glutamine (CTL medium), supplemented with recombinant human IL-2 to a final concentration of 50 U/mL and IL-15 to a final concentration of 10 ng/μl. The tEGFR$^+$ subset of each T-cell line was enriched by immunomagnetic selection with biotin-conjugated anti-EGFR mAb (ImClone Systems) and streptavidin-beads (Miltenyi).

Cytotoxicity, and Cytokine Secretion

Target cells, either Be2 cells or TML CL, were labeled with $^{51}$Cr (PerkinElmer), washed and incubated in triplicate at 1-2×10³ cells/well with effector chimeric receptor modified T-cells at various effector to target (E:T) ratios. Supernatants were harvested for γ-counting after a 4-hour incubation and specific lysis calculated using the standard formula. For analysis of cytokine secretion, 5×10⁴ T-cells were plated in triplicate with target cells at an E:T ratio of 30:1, 10:1, 3:1 or 1:1, and IFN-γ, TNF-α and IL-2 measured by ELISA or multiplex cytokine immunoassay (Luminex) in supernatant removed after 24-h incubation.

Experiments in NOD/SCID/γc$^{-/-}$ (NSG) Mice

Six- to 8-week old female NOD.Cg-Prkdc$^{scid}$ Il2rg$^{tm1Wj1}$/SzJ (NSG) mice were obtained from the Jackson Laboratory or bred in-house. Mice were injected with 0.2×10⁶ neuroblastoma tumor cells intracranially and received an intracranial injection of 2×10⁶ chimeric receptor-modified or control T-cells. For bioluminescence imaging of tumor growth, mice received injections of luciferin substrate (Caliper Life Sciences) resuspended in PBS (15 μg/g body weight). Mice were anesthetized with isoflurane and imaged using an Xenogen IVIS Imaging System (Caliper) 15 minutes after the injection of luciferin in small or medium binning mode at an acquisition time of 1 s to 1 min to obtain unsaturated images. Luciferase activity was analyzed using Living Image Software (Caliper) and the photon flux analyzed within regions of interest that encompassed the entire.

Statistical Analyses

Statistical analyses were performed using Prism Software (GraphPad®). Student's t-test was performed as a two-sided paired test with a confidence interval of 95% and results with a p-value of p<0.05 were considered significant. Statistical analysis of survival were done by log-rank testing and results with a p-value of p<0.05 considered significant.

The CD171 Chimeric Receptor with a Short Spacer Region and Two Costimulatory Domains Confers Superior Cytotoxic and Cytokine Secretion In Vivo We transduced purified CD8⁺ T$_{CM}$ with the CD171-chimeric receptors containing different costimulatory domains and with a tEGFR control vector. Surface expression of each of the chimeric receptors was confirmed by staining with F(ab)-specific antibodies (FIG. 4A). Similar expression of F(ab) and EGFRt were found with each of the construct with a single 4-1BB costimulatory domain (panel 2) and the construct with CD28cyto/4-1BB costimulatory domains (panel 3). Analysis of the in vitro function of CD8⁺ T-cells modified to express each of the CD171 chimeric receptors demonstrated that each receptor conferred specific lysis of Be2 cells that naturally express CD171, but did not confer recognition of control TML CL (FIG. 4B). T-cells expressing the CD171-chimeric receptor with CD28cyto/4-1BB costimulatory domains had higher cytolytic activity. Quantitative analysis of cytokine production in response to stimulation with Be2 cells showed production of IFN-γ by T-cells expressing each of the CD171 chimeric receptors. As observed in cytotoxicity assays, the construct with the CD28cyto/4-1BB costimulatory domains was superior in mediating cytokine secretion after tumor recognition (FIG. 4C).

The CD171 Specific and/or Targeting CAR with the CD28cyto/4-1BB Costimulatory Domains was Less Efficacious In Vivo It remained uncertain whether the superior in vitro activity of T-cells modified with the CD171 chimeric receptor with CD28cyto/4-1BB costimulatory domains would translate into enhanced or improved anti-tumor activity in vivo. To address these questions, we inoculated cohorts of immunodeficient NSG mice with the neuroblastoma cells by intracranial injection, and seven days later, treated the mice with a single intracranial dose of CD171 specific and/or targeting chimeric receptor CD8⁺ T-cells with a short, intermediate, or long spacer. Control mice were treated with tEGFR T-cells or untreated. Untreated NSG/NB mice developed neuroblastoma necessitating euthanasia approximately 4 weeks after tumor inoculation (FIG. 4D).

We observed tumor regression and improved survival in all mice treated with CD171 chimeric receptor T-cells with the construct with a single 4-1BB costimulatory domain. Mice treated with CD171 chimeric receptor T-cells with the construct with a single 4-1BB costimulatory domain had a superior anti-tumor response and survival compared to mice treated with CD171 chimeric receptor T-cells with the CD28cyto/4-1BB costimulatory domains (FIG. 4D).

The CD171 Specific and/or Targeting CAR Having a Long Extracellular Spacer Domain Showed More Activation Induced Cell Death We sought to determine potential mechanisms underlying the inferior in vivo antitumor activity of T cells that express CD171 chimeric receptors with the CD28cyto/4-1BB costimulatory domains. We considered the possibility that the T cells were not efficiently activated by tumor cells in vivo or conversely, that they underwent activation induced T cell death in vivo.

CD8 central memory cells transduced with CD171CAR constructs with the CD28cyto/4-1BB costimulatory domains or the 4-1BB costimulatory domain constructs were exposed to neuroblastoma cells in vitro for 24 hours (round 1). CD8 central memory cells were removed from the culture and characterized phenotypically, and then incubated with the tumor cells for another 24 hours (round 2). CD8 cells were removed from the culture, phenotypically characterized, and then placed in a culture with tumor cells for another 24 hours (round 3). The CD8 cells were then removed and characterized phenotypically. The cells from each round were characterized for expression of activation markers CD25 and CD69 using flow cytometry. The percentage of dead cells in cells from each round was determined by Guava Viacount.

The results show that the CAR cells with the 4-1BB costimulatory domain alone exhibited less activation and better viability relative to cells expressing CARs with the CD28/cyto/4-1BB co-stimulatory domain following serial tumor cell co-culture challenge (round III: CD25+CD69+ 40% (4-1BB) vs 60% (CD28cyto/4-1BB) (FIG. 4E), % dead cells 20% (4-1BB) vs 45% (CD28cyto/4-1BB) (FIG. 4F). Collectively, the data provides evidence that CD171 directed chimeric receptors with a dual CD28cyto/4-1BB costimulatory domain, despite mediating equivalent or superior effector function in vitro, induce a high level of activation induced cell death in vivo and had a decreased ability to eradicate established neuroblastoma.

The design and function of CD171 chimeric receptors has been enhanced or improved through modification of the costimulatory domain. The results show that Central memory T cells transduced with a CD171 directed CAR with a single 4-1BB costimulatory domain performed much better in an in vivo model of neuroblastoma tumor eradication than T cells transduced with a CD171 directed CAR with a dual CD28cyto/4-1BB costimulatory domain Contribution of Extracellular Spacer Length and Cytoplasmic Signaling Domain on the Performance of a CAR Targeting CD171 In Vitro and In Vivo.

The contribution of extracellular spacer length and cytoplasmic signaling domain on the performance of a CAR targeting CD171 was assessed in vitro and in vivo. In vitro, the focus was on analyzing cytotoxicity, cytokine secretion, activation status and cell death using standard assays and a new CAR T-cell stress test employing multiple sequential cycles of tumor cell exposure. Each study was performed multiple times using different donor T cells and the final analysis included either pooled data or representative experiments with sample replicates of two or more. In vivo experiments analyzed anti-tumor activity using live imaging, survival, and immunohistochemistry. All mouse experiments were designed to have at least 2 mice per group. All outliers were included in the data analysis.

CAR Construction and Lentiviral Production

CD171-specific and/or targeting CARs were constructed using $(G_4S)_3$ peptide linked VL and VH segments of the CE7 (anti-CD171) IgG2 monoclonal antibody. The scFv was codon optimized and subsequently linked to variable spacer length domains based on 12 AA (short spacer (SS)/"hinge-only"), 119 AA (medium spacer (MS)/"hinge-CH3") or 229 AA (long spacer (LS)/"hinge-CH2-CH3") derived from human IgG4-Fc. All spacers contained a S→P substitution within the "Hinge" domain located at position 108 of the IgG4-Fc protein and were linked to the transmembrane domain of human CD28 and to signaling modules comprising either (i) the cytoplasmic domain of 4-1BB alone (2G CAR) or (ii) of CD28 (mutant) and 4-1BB (3G CAR), with each signaling module being fused on their carboxyl terminus to human CD3-ζ endodomain. The portion of the cytoplasmic domain of CD28 used in the constructs contained an LL→GG substitution located at positions 186 to 187 of the native CD28 protein. The cDNA clones encoding CAR variants were linked to a downstream T2A ribosomal skip element and truncated EGF receptor (EGFRt), cloned into the epHIV7 lentiviral vector and CD171-CAR lentiviruses were produced in 293T cells.

Real-Time PCR

Total RNA was extracted from T cells using the RNeasy Minikit according to the manufacturer's instructions (Qiagen). cDNA was synthesized by reverse transcription using the First Strand Kit (Life Technologies). RNA quantitation for specific genes was performed using real-time primers for FasL (IDT) and the CFX96 real-time detection system (Biorad). Actin was used as a house keeping gene. Data was analyzed using the CFX Manager Software version 3.0.

Protein Expression

Western Blot (WB) T-cells were harvested, washed twice in PBS and lysed in protease inhibitor (Millipore). Proteins were analyzed using SDS/PAGE followed by Western blotting using anti-CD247 (CD3-ζ, BD Biosciences), according to manufacturer's instructions. Signals were detected using an Odyssey Infrared Imager and band intensities were quantified using Odyssey v2.0 software (LI-COR).

Flow Cytometry

Immunophenotyping was conducted with fluorophore-conjugated mAbs: CD4, CD8, CD27, CD28, CD45RA, CD45RO, CD62L, CCR7 (Biolegend). Cell surface expression of L1CAM was analyzed using a fluorophore-conjugated mAb (Clone 014, Sino Biological). EGFRt expression was analyzed using biotinylated cetuximab (Bristol-Myers-Squibb) and a fluorophore conjugated streptavidin secondary reagent. To assess activation and AICD fluorophore conjugated mABs for CD25, CD69, CD137, C178 (Fas Ligand) and CD95 (Fas, all Biolegend) were used. Caspase 3 activity was measured using CaspGlow (eBioscience) following the manufacturer's protocol. Flow analyses were performed on an LSRFortessa (BD Biosciences) and data were analyzed using FlowJo software (Treestar).

Generation of T Cell Lines Expressing CD171 CARs

Samples of heparinized whole blood were obtained from healthy donors after written informed consent following a research protocol approved by the Institutional Review Board of Seattle Children's Research Institute (SCRI IRB #13795). Peripheral blood mononuclear cells (PBMC) were isolated by standard protocol using ficoll (GE Healthcare Life Sciences) and $CD8^+CD45RO^+CD62L^+$ central memory T cells ($T_{CM}$) were isolated by using immunomagnetic microbeads according to the manufacturer's instruction (Miltenyi Biotec). First, $CD8^+$ $CD45RO^+$ cells were obtained by negative selection using a CD8 T cell isolation kit and CD45RA beads, then cells were enriched for CD62L, activated with anti-CD3/CD28 beads at a bead to cell ratio of 3:1 (Life Technologies, Thermo Fisher Scientific) and transduced on day 3 by centrifugation at 800 g for 30 minutes at 32° C. with lentiviral supernatant (multiplicity of infection MOH=5) supplemented with 1 mg/mL protamine sulfate (APP Pharmaceuticals). T cells were expanded in RPMI (Cellgro) containing 10% heat-inactivated fetal calf serum (Atlas, Fort Collins, Colo.), 2 mmol/L L-glutamine (Cellgro), supplemented with a final concentration of 50 U/ml recombinant human interleukin (IL)-2 (Chiron Corporation), and 10 ng/µl IL-15 (Miltenyi Biotec). The EGFRt+ subset of each T-cell line was enriched by immunomagnetic selection with biotin-conjugated Erbitux (Bristol-Myers-Squibb) and streptavidin-microbeads (Miltenyi Biotec). CD171-CAR and mock control T cells were expanded using a rapid expansion protocol (T cells used for in vivo assays were frozen at $S_1R_2D_{14}$ and thawed on day of injection.

Cell Lines

The NB cell lines Be2 and SK-N-DZ were obtained from the American Type Culture Collection (ATCC). Be2 GFP-ffLuc_epH1V7 and SK-N-DZ GFP-ffLuc_epHIV7 were derived by lentiviral transduction with the firefly luciferase (ffLuc) gene and purified by sorting on GFP. Both cell lines were further transduced with CD19t-2A-IL2_pHIV7 in order to generate IL-2 secreting neuroblastoma cell lines purified by sorting on CD19t. All NB cell lines were cultured in DMEM (Cellgro) supplemented with 10% heat-inactivated fetal calf serum and 2 mmol/L L-glutamine EBV-transformed lymphoblastoid cell lines (TMLCL) and TMLCL that expressed membrane tethered CD3 epsilon specific scFvFc derived from OKT3 mAb (TMLCL-OKT3) were cultured in RPMI 1640 supplemented with 10% heat-inactivated fetal calf serum and 2 mmol/L L-glutamine.

CAR T Cell Receptor Signaling

After co-culturing $1\times10^6$ effector and target cells for 4-8 min, cells were processed to measure Erk/MAP Kinase ½ activity according to the 7-Plex T cell receptor signaling kit (Millipore). Protein concentration was measured using the Pierce BCA Protein Assay Kit (Thermo Scientific).

In Vitro T Cell Assays

Cytotoxicity measured by Chromium Release Assay. Target cells were labeled with $^{51}Cr$ (Perkin Elmer), washed and incubated in triplicate at $5\times10^3$ cells per well with T cells ($S_1R_2D_{12-14}$) at various effector to target (E:T) ratios. Supernatants were harvested after a 4-hour incubation for γ-counting using Top Count NTX (Perkin Elmer) and specific lysis was calculated as previously described.

Cytotoxicity Measured by Biophotonic Luciferase Assay

NB cell lines containing GFP-ffLuc_epHIV7 were co-cultured with effector cells at a 5:1 E:T ratio. The effector cells were on their first, second or third round of tumor cell encounter as described above. To assess the amount of viable tumor cells left after T cell encounter, D-Luciferin was added and after 5 minutes the biophotonic signal from the NB cells was measured using an IVIS Spectrum Imaging System (Perkin Elmer).

Cytokine Release

A total of $5 \times 10^5$ T cells ($S_1R_2D_{12-14}$) were plated with stimulator cells at an E:T ratio of 2:1 for 24 hours. IFN-γ, TNF-α, and IL-2 in the supernatant were measured using Bio-plex cytokine assay and Bioplex-200 system (Bio-rad Laboratories).

Stress Test

To mimic recursive antigen encounters, a co-culture of adherent target cells and freshly thawed non-adherent effector cells at a 1:1 E:T ratio was started. After 24 (round I) and 48 (round II) hours, T cell viability was assessed using the Guava ViaCount Assay (Millipore) and non-adherent effector cells were moved to a new set of adherent target cells at a 1:1 E:T ratio. After round I, II and III (72 hours) T cells were harvested and treated with a dead cell removal kit (Miltenyi) before further analysis.

Immunohistochemistry

Mouse brains were harvested post-mortem, fixed for 24 hours in 10% neutral buffered formalin (Thermo), processed, paraffin embedded and cut into 5 μm sections. Antigen retrieval was performed using Diva decloaker RTU (Biocare Medical). Primary antibodies were incubated with sections overnight at 4° C. and diluted in blocking buffer as follows: rat monoclonal anti human CD3 (Clone CD3-12, AbD Serotec/Bio-rad) 1:100, mouse monoclonal anti human Ki67 (Clone MIB-1, Dako) 1:200, rabbit polyclonal anti human cleaved caspase-3 (Biocare Medical) 1:100, rabbit polyclonal anti human granzyme B (Covance) 1:200. Secondary antibodies (Life technologies) were incubated with sections for 2 hours at room temperature and diluted 1:500 in PBS with 0.2% BSA.

Slides were imaged at 40× magnification on an Eclipse Ci upright epifluorescence microscope (Nikon) equipped with a Nuance multispectral imaging system (Perkin Elmer). The imaging data were analyzed by using InForm analysis software (Perkin Elmer).

Experiments in NOD/SCID/γc$^{-/-}$ mice

NSG mouse tumor models were conducted under SCRI IACUC approved protocols.

Intracranial NSG Mouse Human Neuroblastoma Xenograft Model

Adult male NOD.Cg-Prkdc$^{scid}$Il2rg$^{tm1Wjl}$/SzJ [NOD scid gamma(NSG)] mice were obtained from the Jackson Laboratory or bred in-house. Mice were injected intracranially (i.c.) on day 0 with $2 \times 10^5$ IL-2 secreting, ffLuc expressing Be2 or SK-N-DZ tumor cells 2 mm lateral, 0.5 mm anterior to the bregma and 2.5 mm deep from the dura. Mice received a subsequent intra tumoral injection of $2 \times 10^6$ CAR-modified $CD8^+T_{E(CM)}$ either seven (therapy response model) or fourteen (stress test model) days later. In the stress test model the mice were euthanized 3 days after T cell injection and brains were harvested for IHC analysis. For bioluminescent imaging of tumor growth, mice received intra peritoneal (i.p.) injections of D-luciferin (Perkin Elmer; 4.29 mg/mouse). Mice were anesthetized with isoflurane and imaged using an IVIS Spectrum Imaging System (Perkin Elmer) 15 minutes after D-luciferin injection. Luciferase activity was analyzed using Living Image Software Version 4.3 (Perkin Elmer) and the photon flux analyzed within regions of interest.

Statistical Analyses

Statistical analyses were conducted using Prism Software (GraphPad). Data are presented as means±SD or SEM as stated in the figure legends. Student t test was conducted as a two-sided unpaired test with a confidence interval of 95% and results with a P value less than 0.05 were considered significant. Statistical analyses of survival were conducted by log-rank testing and results with a P value less than 0.05 were considered significant.

Magnitude of CAR Triggered Cytolytic and Cytokine Functional Outputs can be Incrementally Modulated Based on CAR Extracellular Spacer Size The biophysical synapse between CAR expressing T cell and tumor cell is influenced by the epitope location on the tumor cell surface target molecule relative to the distance from the tumor cell's plasma membrane. It was hypothesized that CAR extracellular spacer size tuning to accommodate a functional signaling synapse is a key attribute to engineering bioactive CARs. In order to assess the impact of CD171-specific and/or targeting CAR extracellular spacer size, a set of spacers were assembled using modular domains of human IgG4 as follows: "long spacer" (LS) IgG4 hinge-CH2-CH3, "medium spacer" (MS) IgG4 hinge-CH3 fusion, and "short spacer" (SS) IgG4 hinge. Each spacer variant was fused to a CD28 transmembrane domain followed by a second generation (2G) 4-1BB:zeta endodomain, that in turn was linked to the cell surface EGFRt tag using a T2A ribosome skip peptide (FIG. 13A). Sets of spacer variant 2G-CAR$^+$/EGFRt$^+$ human CD8$^+$ central memory derived effector T cell lines ($T_{E(CM)}$) from purified CD8$^+$CD45RO$^+$ CD62L$^+$ central memory precursors by immunomagnetic selection were generated (FIGS. 19A and B). Following expansion of lentivirally transduced $T_{E(CM)}$, lines were further enriched for homogeneous levels of EGFRt expression by cetuximab immunomagnetic positive selection (18). Similar surface expression levels of each of the CAR spacer variants by anti-murine F(ab)- and EGFR-specific flow cytometric staining and protein expression quantified by western blot for CD3ζ of each T cell line was confirmed (FIGS. 13B and C).

Following the results it was to be determined if the magnitude of 2G-CAR triggered in vitro activation of CD8$^+$ $T_{E(CM)}$ is influenced by spacer domain size. Following activation by CD171+ human neuroblastoma (NB) tumor cells, CD171-specific and/or targeting 2G-CAR(LS) CD8+ T E(CM) exhibited 3.1-fold higher levels of phospho-ERK (p=0.003), and 5.7-fold higher percentage of cells expressing the activation marker CD137 (p=0.015) as compared to their CD171-CAR(SS) counterparts (FIGS. 13D and E). 2G-CAR(MS) exhibited intermediate levels of phospho-ERK and CD137 induction as compared to LS and SS 2G-CARs. Next, it was determined if spacer size also modulated the magnitude of anti-tumor cytolytic activity in a LS>MS>SS pattern. Using 4-hour chromium release assays, lysis of CD171+NB target cells was observed following the same potency gradient of LS>MS>SS against both CD171 high Be2 and CD171 low SK-N-DZ NB cell lines (FIG. 13F and FIG. 20A). Further, activation for cytokine secretion followed the same incremental output hierarchy such that 2G-CAR(LS) produced 8.4-fold higher amount of IFN-γ (p=0.003), 6.3-fold more IL-2 (p<0.0001) and 6.1-fold higher levels of TNF-α (p=0.005; FIG. 13G) as compared to 2G-CAR(SS), with 2G-CAR(MS) falling between the two extremes. These data demonstrate that the biophysical synapse created by CARs can be tuned by spacer size such that incremental levels of activation and functional outputs are achieved. Based on standard CAR development criteria typically utilized in the field, the 2G-CAR(LS) spacer variant would be a lead candidate for further development for clinical applications.

Inverse Correlation of Spacer Modulated CAR Redirected CTL Functional Potency In Vitro with In Vivo Anti-Tumor Activity In order to delineate the relationship of the observed potency of CAR signaling based on in vitro assays to therapeutic activity in vivo, adoptive transfer experiments in NSG mice with established human NB xenografts stereotactically implanted in the cerebral hemisphere were performed (FIG. 14A). Surprisingly, Be2 tumor engrafted mice treated with intratumoral injection of 2G-CAR(LS) exhibited no therapeutic activity necessitating animal euthanasia approximately 3 weeks after tumor inoculation (FIGS. 14B and C). In comparison, biophotonic tumor signal was reduced and survival enhanced in mice treated with 2G-CAR(SS) CAR CD8+ $T_{E(CM)}$ and to an intermediate extent in mice treated with the 2G-CAR(MS) variant (p=0.001; median survival of the different groups: LS=20d, mock=21d, MS=59.5d, SS=76d). SK-N-DZ tumor engrafted mice exhibited a SS>MS>>LS hierarchy of tumor responses with uniform tumor clearance and 100% survival of animals treated with 2G-CAR(SS) CD8+ $T_{E(CM)}$ (FIGS. 20C and D). Failure of 2G-CAR(LS) redirected CTLs, which are injected directly into engrafted tumors, could not be attributed to their failure to survive adoptive transfer and be activated in situ, as equivalent intratumor densities of transferred T cells which expressed granzyme B and Ki67 were observed by IHC early after adoptive transfer (day 3) (FIGS. 14D-G). While not statistically significant (p=0.34), 2G-CAR(LS) CD8+ $T_{E(CM)}$ in which activated caspase 3 was detected were 12.1-fold more frequent than their 2G-CAR(SS) counterparts. These data reveal an unexpected discordance between the in vitro anti-tumor potency of CAR redirected T cells dictated by extracellular spacer size, and their in vivo anti-tumor therapeutic activity.

Augmented Activation Induced Cell Death Accompanies Hyperactive Signaling Outputs of Long Spacer Formatted Second Generation CAR Upon Recursive Antigen Exposure It was hypothesized that whereas in vitro activation for cytolysis in a 4-hour CRA is the consequence of a limited duration of CAR mediated signaling, the in vivo tumor model requires recursive rounds of activation to achieve tumor eradication. Thus, the signaling performance of a particular CAR format that dictates superior metrics in vitro may fail to reveal the consequences of the signaling amplitude in vivo. In order to reproduce recursive serial stimulation in vitro, a CAR T cell-tumor cell co-culture "stress test" assay was devised whereby every 24 hours, CAR T cells are harvested and recursively transferred to culture dishes seeded with tumor cells adjusting for a constant viable T cell:tumor cell ratio of 1:1 (FIG. 15A). Be2 modified to express firefly luciferase was utilized to concurrently track tumor cell killing upon each of three rounds of serial transfer. The recursive activation of the 2G-CAR spacer variant lines resulted in equivalent loss of anti-tumor activity by round III (FIG. 15B). Additionally, analysis of each spacer variant expressing effector cells after each round by flow cytometric measurement revealed that 2G-CAR(LS) CD8+ $T_{E(CM)}$ displayed higher frequencies of cells expressing activation markers CD25 and CD69, as compared to their 2G-CAR(SS) counterparts (round I 79.4 vs 46.8%, p=0.007; round II 74.0 vs 47.6%; round III 65.7 vs 42.1%, p=0.037) (FIG. 15C).

In contrast to the LS>MS>SS pattern of upregulation of activation markers in round I that mimicked earlier in vitro analysis, it was observed that a LS/MS>SS loss of T cell viability that was most substantial in round III (round III percent dead cells LS 58.7%, MS 62.6% vs SS 21.1%, LS vs SS p=0.024 and MS vs SS p=0.007) (FIG. 15D). To substantiate that the asymmetric loss of T cell viability by 2G-CAR(LS) CTLs occurring with recursive activation was the result of exaggerated AICD, the mechanism of cell death was assessed, focusing on FasL-Fas mediated T cell fratricide. It was observed that tumor-induced CAR activation dependent upregulation of FasL followed a LS>MS>SS hierarchy as 2G-CAR(LS) CD8+$T_{E(CM)}$ displayed 4.8- and 2.5-fold higher FasL surface expression, and, 5.5- and 3.3-fold higher FasL mRNA abundance than the short or medium spacer CAR T cells, respectively (long vs short: p<0.0001 and p=0.002; long vs medium: p<0.0001 and p=0.016) (FIGS. 15E and F). To link FasL expression with increased Fas mediated apoptosis, caspase 3 activity was analyzed and 13.2-fold higher levels of cleaved caspase 3 in 2G-CAR(LS) CD8+ $T_{E(CM)}$ as compared to their SS counterpart (p<0.0001) was observed (FIG. 15G). Lastly, 2G-CAR(LS) CD8+$T_{E(CM)}$ were subjected to siRNA knockdown of Fas or FasL, then exposed to tumor and a 1.4-fold (Fas) (p=0.005) and 1.6-fold (FasL) (p=0.0001) increase in T cell viability after round III, was observed, respectively (FIG. 15H). To verify that the siRNA knock-down led to a reduction of Fas/FasL, their surface expression on the 2G-CAR(LS) CD8+ $T_{E(CM)}$ was assessed and a 91.3% reduction in Fas+(p<0.0001) and 80.1% reduction in FasL+ CTLs (p<0.0001) was observed than 2G-CAR(LS) CD8+ $T_{E(CM)}$ treated with scrambled siRNA (FIGS. 21A and B). In aggregate, these data demonstrate that tuning of CAR spacer size can modulate downstream signaling events that result not only in differential magnitudes of anti-tumor functional outputs but coordinated increases in susceptibility to AICD. The balance between these two processes for optimal in vivo anti-tumor activity may not always be achieved by spacer tuning to achieve the highest levels of CAR signaling outputs as exemplified by these comparisons of 2G-CAR (LS) and 2G-CAR(SS) structural variants.

Augmentation of CAR Cytoplasmic Endodomain Composition Reverts Short Spacer CD171-CAR to AICD Prone Variant Upon Recursive Tumor Encounter Third generation CARs contain two co-stimulatory endodomain modules in series with the CD3-ζ activation module and have been reported to augment the magnitude of cytolysis and cytokine production levels over their second generation counterparts. CD171-specific and/or targeting 3G-CAR were assembled through the addition of a CD28 endodomain to the 2G 4-1BB:zeta endodomain (FIG. 16A). CD8+ $T_{E(CM)}$ expressing comparable levels of 2G-CAR(SS) and 3G-CAR(SS) were derived from purified TCM precursors by immunomagnetic selection (FIGS. 16B and C). 3G-CAR(SS) CD8+ $T_{E(CM)}$ demonstrated an 8.4-fold higher induction of CD137 expression upon tumor contact than their second generation counterparts (p<0.0001) (FIG. 16D), a 1.3-fold increase in cytolytic activity against Be2 targets (effector to target ratio 1:10, p=0.0001) (FIG. 16E) and 5.1-fold more IL-2 and 2.5-fold more TNF-α secretion (p<0.0001 and p=0.003) (FIG. 16F).

Next it was assessed whether heightened T cell activation through an augmented CAR mediated by the 3G endodomain, in the context of an extracellular short spacer, could selectively enhance anti-tumor activity in vivo without exacerbation of AICD. Surprising, Be2 (FIG. 17A) and SK-N-DZ (FIG. 17B) was inferior, though not to a statistically significant degree to their 2G-CAR(SS) counterparts. These findings could not be attributable to differences in short term persistence of CAR T cells within tumors based on similar densities of human CD3+ T cells detected 3 days after adoptive transfer (FIG. 17C). Despite the finding of higher frequencies of granzyme B+3G-CAR(SS) T cells compared to 2G-CAR(SS) intratumoral T cells, augmented numbers of third generation T cells with activated caspase 3 was again observed, suggesting that the augmented costimulation through a combined effect of CD28 and 4-1BB in the third generation CAR was capable of hyperstimulation resulting in heightened AICD, despite the context of a short spacer extracellular domain (FIG. 17D). This was confirmed by comparing their performance using the in vitro stress test assay. Following each round of tumor stimulation, higher frequencies of CD25+CD69+ T cells in the 3G-CAR(SS) T cell population was observed (FIG. 18A) accompanied by increased frequencies of dead T cells through successive rounds of activation (FIG. 18B). Augmented AICD was again associated with heightened levels of FasL expression by surface staining and mRNA content, that in turn coincided with increased levels of activated caspase 3 (FIGS. 18C-E). These data demonstrate that over tuning of CAR signaling outputs based on intracellular signaling domain composition negatively impacted on a tuned short spacer dimension in a combinatorial manner by enhancing FasL-mediated T cell AICD.

CARs are capable of mediating multiplexed signaling outputs that trigger redirected anti-tumor T cell effector function. Despite the irrefutable therapeutic potency of CAR T cells redirected to CD19 in patients with acute lymphoblastic leukemia, the biophysical structure-function attributes of this class of synthetic receptor remain incompletely understood. While it stands to reason that the tuning of CARs for effective T cell anti-tumor activity will be more stringent in solid tumor applications, empiric designs of CARs based on limited understanding of the impact of their composition on in vivo anti-tumor function will only hamper progress in human clinical applications. Here, CAR structure-function in human central memory derived CD8+ effector CTL's focusing on the combinatorial effect(s) of extracellular spacer dimension in the context of cytoplasmic signaling module composition was systematically interrogated. By surveying CAR signaling strength using in vitro assays, a potency hierarchy of CAR structural variants was identified. These analyses have revealed a range of CAR signaling outputs that is permissive for in vivo anti-tumor activity above which in vivo potency is attenuated by heightened AICD.

The evolution of CAR design has proceeded to date via a largely empiric process, and has focused predominantly on the augmentation of signaling outputs through combinatorial modules of costimulatory receptor cytoplasmic domains fused in series to ITAM containing activation domains, such as the zeta chain of the CD3 complex. Comparisons of the function of CTL's expressing first, second, or third generation CARs have typically been made in the context of a "stock" extracellular spacer domain preferred by a particular laboratory, ranging from full length IgGs to relatively short CD8a hinges or membrane proximal portions of CD28 Many have studied the impact of spacer dimension on CAR signaling and functional activity. Unlike a TcR contact with peptide loaded HLA Class I or II, which defines a scripted biophysical gap between T cell plasma membrane and target cell plasma membrane that is permissive for assembly of a supramolecular activation complex (SMAC), CARs do not conform to this dimensional relationship as a consequence of the target molecule's structural dimensions, the scFv's epitope location on the target molecule, and the CAR's spacer size. The molecular assembly of a SMAC via CARs is relatively unknown, but analysis to date suggests that it does not replicate the orderly architecture of a TcR SMAC. While the first two dimensions are unique to each selected antigen and antibody binding domain choice, the CAR spacer is size tunable and can compensate to some extent in normalizing the orthogonal synapse distance between CAR T cell and target cell. This topography of the immunologic synapse between T cell and target cell also defines distances that cannot be functionally bridged by a CAR due to a membrane distal epitope on a cell surface target molecule that, even with a short spacer CAR, cannot bring the synapse distance in to an approximation for signaling. Likewise, membrane proximal CAR target antigen epitopes have been described for which signaling outputs are only observed in the context of a long spacer CAR.

Using a CD171-specific and/or targeting scFv binding domain derived from the CE7 mAb, the impact of extracellular spacer size on signaling outputs from a 4-1BB:zeta second generation CAR was first assessed. It was observed that incremental gains of function in signaling outputs based on in vitro assays as spacer size increased from the short IgG4 hinge spacer, to an intermediate hinge:CH3, to the full length IgG4 hinge:Fc spacer. Unexpectedly, upon in vivo testing against established stereotactically implanted intraparenchymal brain neuroblastoma xenografts in NSG mice, the anti-tumor potency of intratumorally injected CAR CD8+ CTL was inversely correlated to spacer size (i.e. SS>MS>>LS) and in vitro functional potency. The direct intratumoral route of T cell administration was used to eliminate potential spacer effects on T cell migration or interactions with mouse Fc+ cells that could affect survival. Given these findings, it was hypothesized that commonly employed in vitro assays that assess CAR T cell function (i.e. tumor cell cytolysis, stimulation of cytokine secretion, and proliferation), upon a single limited duration tumor cell encounter fail to detect the subsequent fate of CAR T cells upon recursive tumor exposure, as would be predicted to occur within solid tumors in vivo. To better assess this possibility an in vitro assay was devised in which CAR T cells are recursively exposed to equal numbers of biophotonic reporter gene expressing tumor cells. Tumor cell killing can thereby be quantitated biophotonically and retrieved CAR T cells can be interrogated for activation status, viability, and caspase activity after each round of tumor co-culture. It was observed that upon three recursive tumor encounters in vitro, disproportionate increases in the frequency of T cells undergoing apoptosis among 2G-CAR (LS) T cells as compared to 2G-CAR(SS) T cells. The exaggerated AICD correlated with heightened LS CAR induced expression of FasL and activated caspase 3 relative to SS CAR. AICD in LS CAR T cells was reduced by siRNA knockdown of FAS or FasL prior to exposure to tumor cells. These in vitro findings correlated with limited intratumor persistence of LS CAR T cells within tumor xenografts as compared with SS CAR T cells. In aggregate these data demonstrate that the non-signaling extracellular spacer is a major tunable CAR design element that impacts not only on signaling activity but persistence of CAR T cells in solid tumors.

Given the relation between spacer dimension and in vivo survival in the context of a 4-1BBzeta second generation (2G) CAR, endeavors to determine if the short spacer dimension would be generically optimal in the context of the augmenting signaling outputs of a third generation (3G) CD28:4-1BB:zeta CAR endodomain format were performed. Consistent with observations made by multiple other groups, the CD171-specific and/or targeting 3G-CAR (SS) stimulated heightened levels of cytolytic activity and cytokine synthesis compared to the 2G-CAR(SS) upon in vitro tumor stimulation. However, the augmented signaling outputs of the 3G-CAR in the context of its short spacer also increased FasL expression, exacerbated apoptosis as indicated by increased levels of activated caspase 3 and resulted in higher frequencies of cell death. Correspondingly, impaired in vivo anti-tumor efficacy of the 3G-CAR(SS) T cells, as compared to the 2G-CAR(SS) due to attenuated in vivo intratumoral survival was observed. While CD28 costimulates T cells upon initial antigen activation and enhances T cell viability by deflecting AICD through NFAT regulated increases in cFLIPshort, published studies have also revealed that recursive CD28 costimulation of previously activated T cells can reduce their subsequent survival via augmented FasL expression and consequently, increased AICD. It is interesting therefore, to speculate if recursive CD28 signaling mediated by anti-CD19 CD28:zeta CAR T cells is responsible for the relatively short persistence duration in treated ALL patients, as compared to the often prolonged persistence of anti-CD19 4-1BB:zeta treated patients in reported clinical trials (2, 35). In aggregate, these data demonstrate that in vivo potency of CAR redirected T cells is dependent, in part, on identifying permissive combinations of size optimized extracellular spacer domains in the context of a particular cytoplasmic signaling domain composition. Further, in vitro assay for assessing the proclivity of a CAR construct to induce AICD in primary human $CD8^+$ CTL upon recursive activation events was described. These studies reveal a caveat of "overtuning" of CARs based on the combinatorial net effect of spacer dimension and cytoplasmic signaling module selection.

There is as yet no predictive structural model that can reliably direct a priori how CARs should be built based on target molecule epitope location relative to the plasma membrane of the tumor cell. Moreover, commonly used surrogate in vitro bioassays may instruct away from a definitive choice of CAR composition that results in the greatest differential between high-level functional anti-tumor CAR T cell outputs and low-level AICD. The work here demonstrates that a CAR structural library screen technique using the in vitro stress test assay may be a valuable additional parameter to integrate into CAR engineering. It is conceivable that genetic strategies might limit susceptibility of hyperactive CAR constructs to undergo AICD, such as forced over expression of cFLIP or Toso, or, vector directed synthesis of siRNAs that knock down FasL or Fas. Manipulation of T cell susceptibility to undergo apoptosis will require commensurately stringent safety features, such as inclusion of inducible suicide constructs, or, transgene expression control rheostats under clinician control, such as small molecule regulated transcriptional or translational control systems. Additional secondary consequences of CAR overtuning also require interrogation, such as predilection of hyperactive CARs to trigger augmented expression of inhibitory receptors, such as PD-1, capable of enforcing an exhausted T cell functional status within PD-L1. The data demonstrate that: 1.) CAR structure-function in vitro testing using commonly employed functional assays can misdirect selection of candidate constructs as common practice is to focus on those constructs that display the highest functional activity, and; 2.) potency tuning of CAR redirected effector CTLs has an upper limit above which gains in the magnitude of effector outputs are negated by augmentation in AICD upon recursive triggering through the CAR. These results have guided the selection of a CD171-specific and/or targeting short spacer CAR for a Phase I study in children with relapsed/refractory neuroblastoma.

Additional Alternatives

In some alternatives, a chimeric receptor nucleic acid is provided. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is can target and/or is specific for the ligand, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less. In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the spacer is optimized for increased T cell proliferation and/or cytokine production in response to the ligand as compared to a reference chimeric receptor.

In some alternatives, a chimeric receptor polypeptide is provided. In some alternatives, the chimeric receptor polypeptide is coded for by a chimeric receptor nucleic acid. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is specific for the ligand, wherein the spacer is optimized, c) a polynucleotide coding for a transmembrane domain and d) a polynucleotide coding for an intracellular signaling domain. In some alternatives, the ligand binding domain is an antibody fragment. In some alternatives, the spacer is optimized for increased T cell proliferation and/or cytokine production in response to the ligand as compared to a reference chimeric receptor. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence.

In some alternatives, an expression vector comprising an isolated chimeric receptor nucleic acid is provided. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is specific for the ligand, wherein the spacer is optimized, c) a polynucleotide coding for a transmembrane domain and d) a polynucleotide coding for an intracellular signaling domain. In some alternatives, the spacer is optimized for increased T cell proliferation and/or cytokine production in response to the ligand as compared to a reference chimeric receptor. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence.

In some alternatives a host cell is provided. In some alternatives, the host cell comprises an expression vector. In some alternatives, the expression vector comprises an isolated chimeric receptor nucleic acid is provided. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is specific for the ligand, wherein the spacer is optimized, c) a polynucleotide coding for a transmembrane domain and d) a polynucleotide coding for an intracellular signaling domain. In some alternatives, the spacer is optimized for increased T cell proliferation and/or cytokine production in response to the ligand as compared to a reference chimeric receptor. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and/or CD8+. In some alternatives, wherein the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and/or CD4+ and/or negative for CD45RO.

In some alternatives, a composition is provided. In some alternatives, the composition comprises a host cell in a pharmaceutically acceptable excipient. In some alternatives, the host cell comprises an expression vector. In some alternatives, the expression vector comprises an isolated chimeric receptor nucleic acid is provided. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is specific for the ligand, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell, wherein the central memory T cell is positive for CD45RO+, CD62L+, and/or CD8+. In some alternatives, wherein the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and/or CD4+ and/or negative for CD45RO. In some alternatives, the composition comprises a host cell, wherein the host cell is a CD8+ T cytotoxic lymphocyte cell selected from the group consisting of naïve CD8+ T cells, central memory CD8+ T cells, effector memory CD8+ T cells and bulk CD8+ T cells or wherein the CD8+ cytotoxic T lymphocyte cell is a central memory T cell wherein the central memory T cell is positive for CD45RO+, CD62L+, and/or CD8+ and another host cell, wherein the host cell is a CD4+ T helper lymphocyte cell is selected from the group consisting of naïve CD4+ T cells, central memory CD4+ T cells, effector memory CD4+ T cells, and bulk CD4+ T cells or wherein the CD4+ helper lymphocyte cell is a naïve CD4+ T cell, wherein the naïve CD4+ T cell is positive for CD45RA+, CD62L+ and/or CD4+ and/or negative for CD45RO. In some alternatives, the spacer is optimized for increased T cell proliferation and/or cytokine production in response to the ligand as compared to a reference chimeric receptor.

In some alternatives, an in vitro method for preparing a host cell is provided. In some alternatives, the in vitro method for preparing a host cell comprises: a) providing a library of nucleic acids coding for a chimeric receptor wherein each of the plurality of nucleic acids code for a chimeric receptor that differs in length, b) introducing each of the plurality of the nucleic acids into a separate isolated T lymphocyte population and expanding each T lymphocyte population in vitro, c) administering each genetically modified T lymphocyte population into an animal model bearing a tumor and determining whether a genetically modified T lymphocyte population has anti-tumor efficacy and d) selecting a nucleic acid coding for the chimeric receptor that provides for anti-tumor efficacy in vitro and/or in an animal model. In some alternatives, the host cell comprises an expression vector. In some alternatives, the expression vector comprises an isolated chimeric receptor nucleic acid is provided. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is specific for the ligand, wherein the is optimized, c) a polynucleotide coding for a transmembrane domain and d) a polynucleotide coding for an intracellular signaling domain. In some alternatives, the spacer is optimized for increased T cell proliferation and/or cytokine production in response to the ligand as compared to a reference chimeric receptor. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and/or CD8+. In some alternatives, wherein the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and/or CD4+ and negative for CD45RO. In some alternatives, the nucleic acids coding for a chimeric receptor comprises an expression vector. In some alternatives, the expression vector comprises an isolated chimeric receptor nucleic acid. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is specific for the ligand, wherein the spacer is optimized, c) a polynucleotide coding for a transmembrane domain and d) a polynucleotide coding for an intracellular signaling domain. In some alternatives, the spacer is optimized for increased T cell proliferation and/or cytokine production in response to the ligand as compared to a reference chimeric receptor. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the method further comprises introducing the selected nucleic acid coding for the chimeric receptor into a host cell.

In some alternatives, an in vitro method for preparing a host cell is provided. In some alternatives, the method comprises a) introducing a chimeric receptor nucleic acid or an expression vector into a lymphocyte population that has a CD45RA−, CD45RO+, and/or CD62L+ phenotype and b) culturing the cells in the presence of anti-CD3 and/or anti CD28, and at least one homeostatic cytokine until the cells expand sufficiently for use as a cell infusion. In some alternatives, the host cell comprises an expression vector. In some alternatives, the expression vector comprises an isolated chimeric receptor nucleic acid is provided. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is specific for the ligand, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is optimized for increased T cell proliferation and/or cytokine production in response to the ligand as compared to a reference chimeric receptor. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and/or CD8+. In some alternatives, wherein the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and/or CD4+ and/or negative for CD45RO. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is specific for the ligand, wherein the spacer is optimized, c) a polynucleotide coding for a transmembrane domain and d) a polynucleotide coding for an intracellular signaling domain. In some alternatives, the ligand binding domain is an antibody fragment. In some alternatives, the spacer is optimized for increased T cell proliferation and/or cytokine production in response to the ligand as compared to a reference chimeric receptor. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the expression vector comprises an isolated chimeric receptor nucleic acid. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is specific for the ligand, wherein the spacer is optimized, c) a polynucleotide coding for a transmembrane domain and d) a polynucleotide coding for an intracellular signaling domain. In some alternatives, the spacer is optimized for increased T cell proliferation and/or cytokine production in response to the ligand as compared to a reference chimeric receptor. In some alternatives, the ligand binding domain is an antibody fragment. In some alternatives, the ligand binding domain is single chain variable fragment. In some alternatives, the spacer is 15 amino acids or less. In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the lymphocyte is CD8+ or CD4+.

In some alternatives, a use of a host cell or composition in the treatment of cancer or a solid tumor expressing CD171 is provided. In some alternatives, the composition comprises a host cell in a pharmaceutically acceptable excipient. In some alternatives, the host cell comprises an expression vector. In some alternatives, the expression vector comprises an isolated chimeric receptor nucleic acid is provided. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is specific for the ligand, wherein the spacer is optimized, c) a polynucleotide coding for a transmembrane domain and d) a polynucleotide coding for an intracellular signaling domain. In some alternatives, the spacer is optimized for increased T cell proliferation and/or cytokine production in response to the ligand as compared to a reference chimeric receptor. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and/or CD8+. In some alternatives, wherein the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and/or CD4+ and/or negative for CD45RO. In some alternatives, the composition comprises a host cell, wherein the host cell is a CD8+ T cytotoxic lymphocyte cell selected from the group consisting of naïve CD8+ T cells, central memory CD8+ T cells, effector memory CD8+ T cells and bulk CD8+ T cells or wherein the CD8+ cytotoxic T lymphocyte cell is a central memory T cell, wherein the central memory T cell is positive for CD45RO+, CD62L+, and/or CD8+ and another host cell, wherein the host cell is a CD4+ T helper lymphocyte cell is selected from the group consisting of naïve CD4+ T cells, central memory CD4+ T cells, effector memory CD4+ T cells, and bulk CD4+ T cells or wherein the CD4+ helper lymphocyte cell is a naïve CD4+ T cell, wherein the naïve CD4+ T cell is positive for CD45RA+, CD62L+ and/or CD4+ and/or negative for CD45RO. In some alternatives, the host cell comprises an expression vector. In some alternatives, the expression vector comprises an isolated chimeric receptor nucleic acid is provided. In some alternatives, the chimeric receptor nucleic acid comprises: a) a polynucleotide coding for a ligand binding domain, wherein the ligand binding domain binds to and/or targets CD171, b)

a polynucleotide coding for a polypeptide spacer of a length that is specific for the ligand, wherein the spacer is optimized, c) a polynucleotide coding for a transmembrane domain and d) a polynucleotide coding for an intracellular signaling domain. In some alternatives, the spacer is optimized for increased T cell proliferation and/or cytokine production in response to the ligand as compared to a reference chimeric receptor. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and/or CD8+. In some alternatives, wherein the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and/or CD4+ and/or negative for CD45RO. In some alternatives, the cancer is a neuroblastoma. In some alternatives, the solid tumor is selected from the group consisting of a colon cancer, renal cancer, pancreatic cancer, and ovarian cancer.

In some alternatives, a method of performing cellular immunotherapy in a subject having cancer or tumor is provided. In some alternatives, the method comprises administering a composition or a host cell to the subject. In some alternatives, the host cell comprises an expression vector. In some alternatives, the expression vector comprises an isolated chimeric receptor nucleic acid is provided. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is specific for the ligand, wherein the spacer is optimized, c) a polynucleotide coding for a transmembrane domain and d) a polynucleotide coding for an intracellular signaling domain. In some alternatives, the ligand binding domain is an antibody fragment. In some alternatives, the spacer is optimized for increased T cell proliferation and/or cytokine production in response to the ligand as compared to a reference chimeric receptor. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and/or CD8+. In some alternatives, wherein the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and/or CD4+ and/or negative for CD45RO. In some alternatives, the composition comprises a host cell in a pharmaceutically acceptable excipient. In some alternatives, the host cell comprises an expression vector. In some alternatives, the expression vector comprises an isolated chimeric receptor nucleic acid is provided. In some alternatives, the chimeric receptor nucleic acid comprises: a) a polynucleotide coding for a ligand binding domain, wherein the ligand binding domain binds to and/or targets CD171, b) a polynucleotide coding for a polypeptide spacer of a length that is specific for the ligand, wherein the spacer is optimized, c) a polynucleotide coding for a transmembrane domain and d) a polynucleotide coding for an intracellular signaling domain. In some alternatives, the ligand binding domain is an antibody fragment. In some alternatives, the ligand binding domain is single chain variable fragment. In some alternatives, the spacer is 15 amino acids or less (but not less than 1 or 2 amino acids). In some alternatives, the spacer comprises an amino acid sequence of $X_1PPX_2P$ (SEQ ID NO: 1). In some alternatives, the spacer region comprises a portion of a hinge region of a human antibody. In some alternatives, the intracellular signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the intracellular signaling domain comprises a portion of CD3 zeta and a portion of 4-1BB. In some alternatives, the chimeric receptor nucleic acid further comprises a nucleic acid that codes for a marker sequence. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell wherein the central memory T cell is positive for CD45RO+, CD62L+, and/or CD8+. In some alternatives, wherein the host cell is a CD4+ T helper lymphocyte cell is selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell, wherein the naïve CD4+ T cell is positive for CD45RA+, CD62L+ and/or CD4+ and/or negative for CD45RO. In some alternatives, the composition comprises a host cell, wherein the host cell is a CD8+ T cytotoxic lymphocyte cell selected from the group consisting of naïve CD8+ T cells, central memory CD8+ T cells, effector memory CD8+ T cells and bulk CD8+ T cells or wherein the CD8+ cytotoxic T lymphocyte cell is a central memory T cell wherein the central memory T cell is positive for CD45RO+, CD62L+, and/or CD8+ and another host cell, wherein the host cell is a CD4+ T helper lymphocyte cell is selected from the group consisting of naïve CD4+ T cells, central memory CD4+ T cells, effector memory CD4+ T cells, and bulk CD4+ T cells or wherein the CD4+ helper lymphocyte cell is a naïve CD4+ T cell, wherein the naïve CD4+ T cell is positive for CD45RA+, CD62L+ and/or CD4+ and/or negative for CD45RO. In some alternatives, the cancer is neuroblastoma. In some alternatives, the tumor is selected from the group consisting of a colon cancer, renal cancer, pancreatic cancer, and ovarian cancer.

TABLE 1

Exemplary sequences

IgG4hinge
DNA: GAGAGCAAGTACGGA
AA:   E  S  K  Y  G

CD28tm
DNA: CCGCCCTGCCCCCCTTGCCCT:ATGTTCTGGGTGCTGGTGGTGGTCGGAGGC
AA:   P  P  C  P  P  C  P  M  F  W  V  L  V  V  V  G  G

DNA: GTGCTGGCCTGCTACAGCCTGCTGGTCACCGTGGCCTTCATCATCTTTTGG
AA:   V  L  A  C  Y  S  L  L  V  T  V  A  F  I  I  F  W

41BB
DNA: GTG:AAACGGGGCAGAAAGAAACTCCTGTATATATTCAAACAACCATTTATG
AA:   V  K  R  G  R  K  K  L  L  Y  I  F  K  Q  P  F  M

DNA: AGACCAGTACAAACTACTCAAGAGGAAGATGGCTGTAGCTGCCGATTTCCA
AA:   R  P  V  Q  T  T  Q  E  E  D  G  C  S  C  R  F  P

CD3Zeta
DNA: GAAGAAGAAGAAGGAGGATGTGAACTGCGGGTGAAG:TTCAGCAGAAGCGCC
AA:   E  E  E  E  G  G  C  E  L  R  V  K  F  S  R  S  A DNA: GACGCCCCTGCCTACCAGCAGGGCCAGAATCAGCTGTACAACGAGCTGAAC
AA:   D  A  P  A  Y  Q  Q  G  Q  N  Q  L  Y  N  E  L  N DNA: CTGGGCAGAAGGGAAGAGTACGACGTCCTGGATAAGCGGAGAGGCCGGGAC
AA:   L  G  R  R  E  E  Y  D  V  L  D  K  R  R  G  R  D DNA: CCTGAGATGGGCGGCAAGCCTCGGCGGAAGAACCCCCAGGAAGGCCTGTAT
AA:   P  E  M  G  G  K  P  R  R  K  N  P  Q  E  G  L  Y DNA: AACGAACTGCAGAAAGACAAGATGGCCGAGGCCTACAGCGAGATCGGCATG
AA:   N  E  L  Q  K  D  K  M  A  E  A  Y  S  E  I  G  M DNA: AAGGGCGAGCGGAGGCGGGGCAAGGGCCACGACGGCCTGTATCAGGGCCTG
AA:   K  G  E  R  R  R  G  K  G  H  D  G  L  Y  Q  G  L DNA: TCCACCGCCACCAAGGATACCTACGACGCCCTGCACATGCAGGCCCTGCCC
AA:   S  T  A  T  K  D  T  Y  D  A  L  H  M  Q  A  L  P T2A
DNA: CCAAGG:CTCGAGGGCGGCGGAGAGGGCAGAGGAAGTCTTCTAACATGCGGT
AA:   P  R  L  E  G  G  G  E  G  R  G  S  L  L  T  C  G

EGFRt
DNA: GACGTGGAGGAGAATCCCGGCCCTAGG:ATGCTTCTCCTGGTGACAAGCCTT
AA:   D  V  E  E  N  P  G  P  M  L  L  L  V  T  S  L

DNA: CTGCTCTGTGAGTTACCACACCCAGCATTCCTCCTGATCCCACGCAAAGTG
AA:   L  L  C  E  L  P  H  P  A  F  L  L  I  P  R  K  V

DNA: TGTAACGGAATAGGTATTGGTGAATTTAAAGACTCACTCTCCATAAATGCT
AA:   C  N  G  I  G  I  G  E  F  K  D  S  L  S  I  N  A

DNA: ACGAATATTAAACACTTCAAAAACTGCACCTCCATCAGTGGCGATCTCCAC
AA:   T  N  I  K  H  F  K  N  C  T  S  I  S  G  D  L  H

DNA: ATCCTGCCGGTGGCATTTAGGGGTGACTCCTTCACACATACTCCTCCTCTG
AA:   I  L  P  V  A  F  R  G  D  S  F  T  H  T  P  P  L

DNA: GATCCACAGGAACTGGATATTCTGAAAACCGTAAAGGAAATCACAGGGTTT
AA:   D  P  Q  E  L  D  I  L  K  T  V  K  E  I  T  G  F

DNA: TTGCTGATTCAGGCTTGGCCTGAAAACAGGACGGACCTCCATGCCTTTGAG
AA:   L  L  I  Q  A  W  P  E  N  R  T  D  L  H  A  F  E

TABLE 1-continued

Exemplary sequences

```
DNA: AACCTAGAAATCATACGCGGCAGGACCAAGCAACATGGTCAGTTTTCTCTT
AA:   N  L  E  I  I  R  G  R  T  K  Q  H  G  Q  F  S  L

DNA: GCAGTCGTCAGCCTGAACATAACATCCTTGGGATTACGCTCCCTCAAGGAG
AA:   A  V  V  S  L  N  I  T  S  L  G  L  R  S  L  K  E

DNA: ATAAGTGATGGAGATGTGATAATTTCAGGAAACAAAAATTTGTGCTATGCA
AA:   I  S  D  G  D  V  I  T  S  G  N  K  N  L  C  Y  A

DNA: AATACAATAAACTGGAAAAAACTGTTTGGGACCTCCGGTCAGAAAACCAAA
AA:   N  T  I  N  W  K  K  L  F  G  T  S  G  Q  K  T  K

DNA: ATTATAAGCAACAGAGGTGAAAACAGCTGCAAGGCCACAGGCCAGGTCTGC
AA:   I  I  S  N  R  G  E  N  S  C  K  A  T  G  Q  V  C

DNA: CATGCCTTGTGCTCCCCCGAGGGCTGCTGGGGCCCGGAGCCCAGGGACTGC
AA:   H  A  L  C  S  P  E  G  C  W  G  P  E  P  R  D  C

DNA: GTCTCTTGCCGGAATGTCAGCCGAGGCAGGGAATGCGTGGACAAGTGCAAC
AA:   V  S  C  R  N  V  S  R  G  R  E  C  V  D  K  C  N

DNA: CTTCTGGAGGGTGAGCCAAGGGAGTTTGTGGAGAACTCTGAGTGCATACAG
AA:   L  L  E  G  E  P  R  E  F  V  E  N  S  E  C  I  Q

DNA: TGCCACCCAGAGTGCCTGCCTCAGGCCATGAACATCACCTGCACAGGACGG
AA:   C  H  P  E  C  L  P  Q  A  M  N  I  T  C  T  G  R

DNA: GGACCAGACAACTGTATCCAGTGTGCCCACTACATTGACGGCCCCCACTGC
AA:   G  P  D  N  C  I  Q  C  A  H  Y  I  D  G  P  H  C

DNA: GTCAAGACCTGCCCGGCAGGAGTCATGGGAGAAAACAACACCCTGGTCTGG
AA:   V  K  T  C  P  A  G  V  M  G  E  N  N  T  L  V  W

DNA: AAGTACGCAGACGCCGGCCATGTGTGCCACCTGTGCCATCCAAACTGCACC
AA:   K  Y  A  D  A  G  H  V  C  H  L  C  H  P  N  C  T

DNA: TACGGATGCACTGGGCCAGGTCTTGAAGGCTGTCCAACGAATGGGCCTAAG
AA:   Y  G  C  T  G  P  G  L  E  G  C  P  T  N  G  P  K

DNA: ATCCCGTCCATCGCCACTGGGATGGTGGGGGCCCTCCTCTTGCTGCTGGTG
AA:   I  P  S  I  A  T  G  M  V  G  A  L  L  L  L  L  V

DNA: GTGGCCCTGGGGATCGGCCTCTTCATGTGA (SEQ ID NO: 10)
AA:   V  A  L  G  I  G  L  F  M  * (SEQ ID NO: 11)
```

TABLE 2

Exemplary Sequence Uniprot P0861 IgG4-Fc (SEQ ID NO: 13)

```
         10         20         30         40         50         60
ASTKGPSVFP LAPCSRSTSE STAALGCLVK DYFPEPVTVS WNSGALTSGV HTFPAVLQSS 70         80         90        100        110        120
GLYSLSSVVT VPSSSLGTKT YTCNVDHKPS NTKVDKRVES KYGPPCPSCP APEFLGGPSV 130        140        150        160        170        180
FLFPPKPKDT LMISRTPEVT CVVVDVSQED PEVQFNWYVD GVEVHNAKTK PREEQFNSTY 190        200        210        220        230        240
KVVSVLTVLH QDWLNGKEYK CKVSNKGLPS SIEKTISKAK GQPREPQVYT LPPSQEEMTK 250        260        270        280        290        300
NQVSLTCLVK GFYPSDIAVE WESNGQPENN YKTTPPVLDS DGEFFLYSRL TVDKSRWQEG 310        320
NVFSCSVMHE ALHNHYTQKS LSLSLGK
```

1-98 CH1
99-110 Hinge
111-220 CH2
221-327 CH3
Position 108 S→P

TABLE 3

Exemplary sequence/Uniprot P10747 CD28 (SEQ ID NO: 14)

```
              70          80          90         100
SAVEVCVVYG  NYSQQLQVYS  KTGFNCDGKL  GNESVTFYLQ
             110         120         130         140
NLYVNQTDIY  FCKIEVMYPP  PYLDNEKSNG  TIIHVKGKHL
             150         160         170         180
CPSPLFPGPS  KPFWVLVVVG  GVLACYSLLV  TVAFTIFWVR
             190         200         210         220
SKRSRLLHSD  YMNMTPRRPG  PTRKHYQPYA  PPRDFAAYRS
```

1-18 signal peptide
19-152 extracellular domain
153-179 transmembrane domain
180-220 intracellular domain
Position 186-187 LL→GG

TABLE 4

Exemplary Sequence/Uniprot Q07011 4-1BB (SEQ ID NO: 15)

```
              10          20          30          40
MGNSCYNIVA  TLLLVLNFER  TRSLQDPCSN  CPAGTFCDNN
              50          60          70          80
RNQICSPCPP  NSFSSAGGQR  TCDICRQCKG  VFRTRKECSS
              90         100         110         120
TSNAECDCTP  GFHCLGAGCS  MCEQDCKQGQ  ELTKKGCKDC
             130         140         150         160
CFGTFNDQKR  GICRPWTNCS  LDGKSVLVNG  TKERDVVCGP
             170         180         190         200
SPADLSPGAS  SVTPPAPARE  PGHSPQIISF  FLALTSTALL
             210         220         230         240
FLLFFLTLRF  SVVKRGRKKL  LYIFKQPFMR  PVQTTQEEDG
             250
CSCRFPEEEE  GGCEL
```

1-23 signal peptide
24-186 extracellular domain
187-213 transmembrane domain
214-255 intracellular domain

TABLE 5

Exemplary sequence/Uniprot P20963 human CD3 isoform 3 (SEQ ID NO: 16)

```
              10          20          30          40
MKWKALFTAA  ILQAQLPITE  AQSFGLLDPK  LCYLLDGILF
              50          60          70          80
IYGVILTALF  LRVKFSRSAD  APAYQQGQNQ  LYNELNLGRR
              90         100         110         120
EEYDVLDKRR  GRDPEMGGKP  QRRKNPQEGL  YNELQKDKMA
```

TABLE 5-continued

Exemplary sequence/Uniprot P20963 human CD3 isoform 3 (SEQ ID NO: 16)

```
             130         140         150         160
EAYSEIGMKG  ERRRGKGHDG  LYQGLSTATK  DTYDALHMQA
LPPR
```

1-21 signal peptide
22-30 extracellular
31-51 transmembrane
52-164 intracellular domain
61-89 ITAM1
100-128 ITAM2
131-159 ITAM3

TABLE 6

Exemplary Hinge region Sequences

| | |
|---|---|
| Human IgG1 | EPKSCDKTHTCPPCP (SEQ ID NO:17) |
| Human IgG2 | ERKCCVECPPCP (SEQ ID NO:18) |
| Human IgG3 | ELKTPLGDTHTCPRCP (SEQ ID NO:19) (EPKSCDTPPPCPRCP)3 |
| Human IgG4 | ESKYGPPCPSCP (SEQ ID NO:20) |
| Modified Human IgG4 | ESKYGPPCPPCP (SEQ ID NO:21) |
| Modified Human IgG4 | YGPPCPPCP (SEQ ID NO:51) |
| Modified Human IgG4 | KYGPPCPPCP (SEQ ID NO:52) |
| Modified Human IgG4 | EVVKYGPPCPPCP (SEQ ID NO:53) |

TABLE 7

Medium spacer IgG4hinge-CH3 (SEQ ID NO: 37)
IgG4 spacer
TA CGGACCG CCCTGCCCCCCTTGCCCT

CH3
GGCCAGCCTCGCGAGCCCCAGGTGTACACCCTGCCTCCCTCCCAGGAAGA

GATGACCAAGAACCAGGTGTCCCTGACCTGCCTGGTGAAGGGCTTCTACC

CCAGCGACATCGCCGTGGAGTGGGAGAGCAACGGCCAGCCTGAGAACAAC

TACAAGACCACCCCTCCCGTGCTGGACAGCGACGGCAGCTTCTTCCTGTA

CAGCCGGCTGACCGTGGACAAGAGCCGGTGGCAGGAAGGCAACGTCTTTA

GCTGCAGCGTGATGCACGAGGCCCTGCACAACCACTACACCCAGAAGAGC

CTGAGCCTGTCCCTGGGCAAG

Long spacer IgG4hinge-CH2-CH3 (SEQ ID NO: 58)
IgG4 spacer
TA CGGACCG CCCTGCCCCCCTTGCCCT

CH2
GCCCCCGAGTTCCTGGGCGGACCCAGCGTGTTCCTGTTCCCCCCAAGCC

CAAGGACACCCTGATGATCAGCCGGACCCCCGAGGTGACCTGCGTGGTGG

TGGACGTGAGCCAGGAAGATCCCGAGGTCCAGTTCAATTGGTACGTGGAC

GGCGTGGAAGTGCACAACGCCAAGACCAAGCCCAGAGAGGAACAGTTCAA

CAGCACCTACCGGGTGGTGTCTGTGCTGACCGTGCTGCACCAGGACTGGC

TGAACGGCAAAGAATACAAGTGCAAGGTGTCCAACAAGGGCCTGCCCAGC

AGCATCGAAAAGACCATCAGCAAGGCCAAG

TABLE 7-continued

```
CH3
GGCCAGCCTCGCGAGCCCCAGGTGTACACCCTGCCTCCCTCCCAGGAAGA

GATGACCAAGAACCAGGTGTCCCTGACCTGCCTGGTGAAGGGCTTCTACC

CCAGCGACATCGCCGTGGAGTGGGAGAGCAACGGCCAGCCTGAGAACAAC

TACAAGACCACCCCTCCCGTGCTGGACAGCGACGGCAGCTTCTTCCTGTA

CAGCCGGCTGACCGTGGACAAGAGCCGGTGGCAGGAAGGCAACGTCTTTA

GCTGCAGCGTGATGCACGAGGCCCTGCACAACCACTACACCCAGAAGAGC

CTGAGCCTGTCCCTGGGCAAG
```

TABLE 8

```
Short spacer (SEQ ID NO: 21)
Hinge Spacer
ESKYGPPCPPCP

Medium spacer (SEQ ID NO: 59)
Hinge Spacer
ESKYGPPCPPCP
```

TABLE 8-continued

```
CH3
GQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKS

LSLSLGK

Long spacer (SEQ ID NO: 60)
Hinge Spacer
ESKYGPPCPPCP

CH2
APEFLGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

SIEKTISKAK

CH3
GQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKS

LSLSLGK
```

---

What is claimed is:

1. A nucleic acid encoding a chimeric receptor comprising:
   a) a polynucleotide encoding a ligand binding domain comprising the nucleotide sequence of residues 2150 to 2875 set forth in SEQ ID NO:54, wherein the ligand binding domain specifically binds to or interacts with CD171;
   b) a polynucleotide encoding a polypeptide spacer comprising the amino acid sequence set forth in SEQ ID NO:01, and wherein the spacer has a length greater than or equal to 12 and less than or equal to 119 consecutive amino acids;
   c) a polynucleotide encoding a transmembrane domain; and
   d) a polynucleotide encoding an intracellular signaling domain;
   wherein the chimeric receptor comprises an increased in vivo activity for a survival rate of a subject having a neuroblastoma and for neuroblastoma regression in the subject compared to an anti-CD171 chimeric receptor comprising a spacer having a length greater than 119 consecutive amino acids.

2. The nucleic acid of claim 1, wherein the spacer comprises a portion of a hinge region of a human antibody.

3. The nucleic acid of claim 2, wherein the intracellular signaling domain comprises all of or a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, B7-H3, and a combination thereof.

4. The nucleic acid of claim 3, wherein the intracellular signaling domain comprises a portion of CD3 zeta and a portion of 4-1BB.

5. The nucleic acid of claim 4, further comprising a polynucleotide encoding a marker sequence.

6. An engineered cell comprising the nucleic acid of claim 1.

7. The engineered cell of claim 6, wherein the engineered cell is a CD8+ cytotoxic T lymphocyte cell selected from the group consisting of a naïve CD8+ T cell, a central memory CD8+ T cell, an effector memory CD8+ T cell, and a bulk CD8+ T cell.

8. The engineered cell of claim 7, wherein the CD8+ cytotoxic T lymphocyte cell is a central memory T cell positive for CD45RO, CD62L, and CD8.

9. The engineered cell of claim 6, wherein the engineered cell is a CD4+ helper T lymphocyte cell selected from the group consisting of a naïve CD4+ T cell, a central memory CD4+ T cell, an effector memory CD4+ T cell, and a bulk CD4+ T cell.

10. The engineered cell of claim 9, wherein the CD4+ helper T lymphocyte cell is a naïve CD4+ T cell positive for CD45RA, CD62L, CD4, and negative for CD45RO.

11. The engineered cell of claim 6, wherein the engineered cell is a precursor T cell.

12. The engineered cell of claim 6, wherein the engineered cell is a hematopoietic stem cell.

13. A nucleic acid encoding a chimeric receptor comprising:
    a) a polynucleotide encoding a ligand binding domain, wherein the ligand binding domain specifically binds to or interacts with CD171;
    b) a polynucleotide encoding a polypeptide spacer comprising the amino acid sequence set forth in SEQ ID NO:01;
    c) a polynucleotide encoding a transmembrane domain; and
    d) a polynucleotide encoding an intracellular signaling domain;
    wherein the chimeric receptor comprises the sequence set forth in SEQ ID NO:55 or SEQ ID NO:56; and
    wherein the chimeric receptor comprises an increased in vivo activity for a survival rate of a subject having a neuroblastoma and for neuroblastoma regression in the subject compared to an anti-CD171 chimeric receptor comprising a spacer having a length greater than 119 consecutive amino acids.

14. The nucleic acid of claim 1, wherein the nucleic acid comprises at least 95% sequence identity to the sequence as set forth in SEQ ID NO:55 or SEQ ID NO:56.

15. The nucleic acid of claim 1, wherein the spacer has a length greater than or equal to 12 and less than or equal to 15 consecutive amino acids.

16. The nucleic acid of claim 1, wherein the spacer comprises the amino acid sequence set forth in SEQ ID NO:21.

17. The nucleic acid of claim 1, wherein the spacer comprises the amino acid sequence set forth in SEQ ID NO:59.

* * * * *

SEQUENCE LISTING

```
<160> NUMBER OF SEQ ID NOS: 60

<210> SEQ ID NO 1
<211> LENGTH: 5
<212> TYPE: PRT
<213> ORGANISM: Artificial Sequence
<220> FEATURE:
<223> OTHER INFORMATION: Spacer Region
<220> FEATURE:
<221> NAME/KEY: VARIANT
<222> LOCATION: 1
<223> OTHER INFORMATION: Xaa = cysteine, glycine, or arginine
<220> FEATURE:
<221> NAME/KEY: VARIANT
<222> LOCATION: 4
<223> OTHER INFORMATION: Xaa = cysteine or threonine

<400> SEQUENCE: 1

Xaa Pro Pro Xaa Pro
1               5

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5
```

```
<211> LENGTH: 34
<212> TYPE: PRT
<213> ORGANISM: Artificial Sequence
<220> FEATURE:
<223> OTHER INFORMATION: CD28 transmembrane domain polynucleotide

<400> SEQUENCE: 5

Pro Pro Cys Pro Pro Cys Pro Met Phe Trp Val Leu Val Val Val Gly
1               5                   10                  15

Gly Val Leu Ala Cys Tyr Ser Leu Leu Val Thr Val Ala Phe Ile Ile
            20                  25                  30

Phe Trp

<210> SEQ ID NO 6

<400> SEQUENCE: 6

000

<210> SEQ ID NO 7

<400> SEQUENCE: 7

000

<210> SEQ ID NO 8
<211> LENGTH: 9
<212> TYPE: PRT
<213> ORGANISM: Artificial Sequence
<220> FEATURE:
<223> OTHER INFORMATION: T2A ribosomal skip element

<400> SEQUENCE: 8

Tyr Gly Pro Pro Cys Pro Pro Cys Pro
1               5

<210> SEQ ID NO 9
<211> LENGTH: 9
<212> TYPE: PRT
<213> ORGANISM: Artificial Sequence
<220> FEATURE:
<223> OTHER INFORMATION: tEGFR

<400> SEQUENCE: 9

Tyr Gly Pro Pro Cys Pro Pro Cys Pro
1               5

<210> SEQ ID NO 10
<211> LENGTH: 1152
<212> TYPE: DNA
<213> ORGANISM: Artificial Sequence
<220> FEATURE:
<223> OTHER INFORMATION: T2A domain

<400> SEQUENCE: 10
ccaaggctcg agggcggcgg agagggcaga ggaagtcttc taacatgcgg tgacgtggag      60
gagaatcccg gccctaggat gcttctcctg gtgacaagcc ttctgctctg tgagttacca     120
cacccagcat tcctcctgat cccacgcaaa gtgtgtaacg gaataggtat tggtgaattt     180
aaagactcac tctccataaa tgctacgaat attaaacact tcaaaaactg cacctccatc     240
agtggcgatc tccacatcct gccggtggca tttaggggtg actccttcac acatactcct     300
cctctggatc cacaggaact ggatattctg aaaaccgtaa aggaaatcac agggttttg      360 ctgattcagg cttggcctga aaacaggacg gacctccatg cctttgagaa cctagaaatc     420
```

-continued

```
atacgcggca ggaccaagca acatggtcag ttttctcttg cagtcgtcag cctgaacata    480
acatccttgg gattacgctc cctcaaggag ataagtgatg gagatgtgat aatttcagga    540
aacaaaaatt tgtgctatgc aaatacaata aactggaaaa aactgtttgg gacctccggt    600
cagaaaacca aaattataag caacagaggt gaaaacagct gcaaggccac aggccaggtc    660
tgccatgcct tgtgctcccc cgagggctgc tggggcccgg agcccaggga ctgcgtctct    720
tgccggaatg tcagccgagg cagggaatgc gtggacaagt gcaaccttct ggagggtgag    780
ccaagggagt ttgtggagaa ctctgagtgc atacagtgcc acccagagtg cctgcctcag    840
gccatgaaca tcacctgcac aggacgggga ccagacaact gtatccagtg tgcccactac    900
attgacggcc cccactgcgt caagacctgc ccggcaggag tcatgggaga aaacaacacc    960
ctggtctgga agtacgcaga cgccggccat gtgtgccacc tgtgccatcc aaactgcacc   1020
tacggatgca ctgggccagg tcttgaaggc tgtccaacga atgggcctaa gatcccgtcc   1080
atcgccactg ggatggtggg ggccctcctc ttgctgctgg tggtggccct ggggatcggc   1140
ctcttcatgt ga                                                      1152
```

<210> SEQ ID NO 11
<211> LENGTH: 383
<212> TYPE: PRT
<213> ORGANISM: Artificial Sequence
<220> FEATURE:
<223> OTHER INFORMATION: T2A domain

<400> SEQUENCE: 11

```
Pro Arg Leu Glu Gly Gly Glu Gly Arg Gly Ser Leu Leu Thr Cys
 1               5                  10                  15
Gly Asp Val Glu Glu Asn Pro Gly Pro Arg Met Leu Leu Leu Val Thr
                20                  25                  30
Ser Leu Leu Leu Cys Glu Leu Pro His Pro Ala Phe Leu Leu Ile Pro
            35                  40                  45
Arg Lys Val Cys Asn Gly Ile Gly Ile Gly Glu Phe Lys Asp Ser Leu
        50                  55                  60
Ser Ile Asn Ala Thr Asn Ile Lys His Phe Lys Asn Cys Thr Ser Ile
65                  70                  75                  80
Ser Gly Asp Leu His Ile Leu Pro Val Ala Phe Arg Gly Asp Ser Phe
                85                  90                  95
Thr His Thr Pro Pro Leu Asp Pro Gln Glu Leu Asp Ile Leu Lys Thr
            100                 105                 110
Val Lys Glu Ile Thr Gly Phe Leu Leu Ile Gln Ala Trp Pro Glu Asn
        115                 120                 125
Arg Thr Asp Leu His Ala Phe Glu Asn Leu Glu Ile Ile Arg Gly Arg
    130                 135                 140
Thr Lys Gln His Gly Gln Phe Ser Leu Ala Val Val Ser Leu Asn Ile
145                 150                 155                 160
Thr Ser Leu Gly Leu Arg Ser Leu Lys Glu Ile Ser Asp Gly Asp Val
                165                 170                 175
Ile Ile Ser Gly Asn Lys Asn Leu Cys Tyr Ala Asn Thr Ile Asn Trp
            180                 185                 190
Lys Lys Leu Phe Gly Thr Ser Gly Gln Lys Thr Lys Ile Ile Ser Asn
        195                 200                 205
Arg Gly Glu Asn Ser Cys Lys Ala Thr Gly Gln Val Cys His Ala Leu
    210                 215                 220
```

```
Cys Ser Pro Glu Gly Cys Trp Gly Pro Glu Pro Arg Asp Cys Val Ser
225                 230                 235                 240

Cys Arg Asn Val Ser Arg Gly Arg Glu Cys Val Asp Lys Cys Asn Leu
            245                 250                 255

Leu Glu Gly Glu Pro Arg Glu Phe Val Glu Asn Ser Glu Cys Ile Gln
        260                 265                 270

Cys His Pro Glu Cys Leu Pro Gln Ala Met Asn Ile Thr Cys Thr Gly
    275                 280                 285

Arg Gly Pro Asp Asn Cys Ile Gln Cys Ala His Tyr Ile Asp Gly Pro
290                 295                 300

His Cys Val Lys Thr Cys Pro Ala Gly Val Met Gly Glu Asn Asn Thr
305                 310                 315                 320

Leu Val Trp Lys Tyr Ala Asp Ala Gly His Val Cys His Leu Cys His
            325                 330                 335

Pro Asn Cys Thr Tyr Gly Cys Thr Gly Pro Gly Leu Glu Gly Cys Pro
        340                 345                 350

Thr Asn Gly Pro Lys Ile Pro Ser Ile Ala Thr Gly Met Val Gly Ala
    355                 360                 365

Leu Leu Leu Leu Leu Val Val Ala Leu Gly Ile Gly Leu Phe Met
370                 375                 380

<210> SEQ ID NO 12

<400> SEQUENCE: 12

000

<210> SEQ ID NO 13
<211> LENGTH: 326
<212> TYPE: PRT
<213> ORGANISM: Artificial Sequence
<220> FEATURE:
<223> OTHER INFORMATION: Exemplary IgG4-Fc

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Lys Tyr Gly Pro Pro Cys Pro Ser Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

```
Ser Thr Tyr Arg Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 14
<211> LENGTH: 219
<212> TYPE: PRT
<213> ORGANISM: Artificial Sequence
<220> FEATURE:
<223> OTHER INFORMATION: Modified IgG4 hinge region

<400> SEQUENCE: 14

Leu Arg Leu Leu Leu Ala Leu Asn Leu Phe Pro Ser Ile Gln Val Thr
1               5                   10                  15

Gly Asn Lys Ile Leu Val Lys Gln Ser Pro Met Leu Val Ala Tyr Asp
            20                  25                  30

Asn Ala Val Asn Leu Ser Cys Lys Tyr Ser Tyr Asn Leu Phe Ser Arg
        35                  40                  45

Glu Phe Arg Ala Ser Leu His Lys Gly Leu Asp Ser Ala Val Glu Val
    50                  55                  60

Cys Val Val Tyr Gly Asn Tyr Ser Gln Gln Leu Gln Val Tyr Ser Lys
65                  70                  75                  80

Thr Gly Phe Asn Cys Asp Gly Lys Leu Gly Asn Glu Ser Val Thr Phe
                85                  90                  95

Tyr Leu Gln Asn Leu Tyr Val Asn Gln Thr Asp Ile Tyr Phe Cys Lys
            100                 105                 110

Ile Glu Val Met Tyr Pro Pro Pro Tyr Leu Asp Asn Glu Lys Ser Asn
        115                 120                 125

Gly Thr Ile Ile His Val Lys Gly Lys His Leu Cys Pro Ser Pro Leu
    130                 135                 140

Phe Pro Gly Pro Ser Lys Pro Phe Trp Val Leu Val Val Val Gly Gly
145                 150                 155                 160

Val Leu Ala Cys Tyr Ser Leu Leu Val Thr Val Ala Phe Ile Ile Phe
                165                 170                 175

Trp Val Arg Ser Lys Arg Ser Arg Leu Leu His Ser Asp Tyr Met Asn
            180                 185                 190

Met Thr Pro Arg Arg Pro Gly Pro Thr Arg Lys His Tyr Gln Pro Tyr
        195                 200                 205
```

Ala Pro Pro Arg Asp Phe Ala Ala Tyr Arg Ser
    210                 215

<210> SEQ ID NO 15
<211> LENGTH: 255
<212> TYPE: PRT
<213> ORGANISM: Artificial Sequence
<220> FEATURE:
<223> OTHER INFORMATION: Cytoplasmic domain of human 4-1BB

<400> SEQUENCE: 15

Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 16
<211> LENGTH: 164
<212> TYPE: PRT
<213> ORGANISM: Artificial Sequence
<220> FEATURE:
<223> OTHER INFORMATION: Cytoplasmic domain of isoform 3 of human CD3
      zeta

<400> SEQUENCE: 16

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
 50                  55                  60

Gln Gln Gly Gln Asn Gln Leu Tyr Asn Glu Leu Asn Leu Gly Arg Arg
 65                  70                  75                  80

Glu Glu Tyr Asp Val Leu Asp Lys Arg Arg Gly Arg Asp Pro Glu Met
                 85                  90                  95

Gly Gly Lys Pro Gln Arg Arg Lys Asn Pro Gln Glu Gly Leu Tyr Asn
                100                 105                 110

Glu Leu Gln Lys Asp Lys Met Ala Glu Ala Tyr Ser Glu Ile Gly Met
            115                 120                 125

Lys Gly Glu Arg Arg Arg Gly Lys Gly His Asp Gly Leu Tyr Gln Gly
130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 17
<211> LENGTH: 15
<212> TYPE: PRT
<213> ORGANISM: Artificial Sequence
<220> FEATURE:
<223> OTHER INFORMATION: Human IgG1 hinge region

<400> SEQUENCE: 17

Glu Pro Lys Ser Cys Asp Lys Thr His Thr Cys Pro Pro Cys Pro
1               5                   10                  15

<210> SEQ ID NO 18
<211> LENGTH: 12
<212> TYPE: PRT
<213> ORGANISM: Artificial Sequence
<220> FEATURE:
<223> OTHER INFORMATION: Human IgG2 hinge region

<400> SEQUENCE: 18

Glu Arg Lys Cys Cys Val Glu Cys Pro Pro Cys Pro
1               5                   10

<210> SEQ ID NO 19
<211> LENGTH: 61
<212> TYPE: PRT
<213> ORGANISM: Artificial Sequence
<220> FEATURE:
<223> OTHER INFORMATION: Human IgG3 hinge region

<400> SEQUENCE: 19

Glu Leu Lys Thr Pro Leu Gly Asp Thr His Thr Cys Pro Arg Cys Pro
1               5                   10                  15

Glu Pro Lys Ser Cys Asp Thr Pro Pro Pro Cys Pro Arg Cys Pro Glu
                20                  25                  30

Pro Lys Ser Cys Asp Thr Pro Pro Pro Cys Pro Arg Cys Pro Glu Pro
            35                  40                  45

Lys Ser Cys Asp Thr Pro Pro Pro Cys Pro Arg Cys Pro
50                  55                  60

<210> SEQ ID NO 20
<211> LENGTH: 12
<212> TYPE: PRT
<213> ORGANISM: Artificial Sequence

```
<220> FEATURE:
<223> OTHER INFORMATION: Human IgG4 hinge region

<400> SEQUENCE: 20

Glu Ser Lys Tyr Gly Pro Pro Cys Pro Ser Cys Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Modified Human IgG4 hinge region

<400> SEQUENCE: 21

Glu Ser Lys Tyr Gly Pro Pro Cys Pro Pro Cys Pro
1               5                   10

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30
```

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36
<211> LENGTH: 348
<212> TYPE: DNA
<213> ORGANISM: Artificial Sequence
<220> FEATURE:
<223> OTHER INFORMATION: Medium spacer IgG4 hinge-CH3

<400> SEQUENCE: 36

```
tacggaccgc cctgccccc ttgccctggc cagcctcgcg agccccaggt gtacaccctg      60
cctccctccc aggaagagat gaccaagaac caggtgtccc tgacctgcct ggtgaagggc     120
ttctacccca gcgacatcgc cgtggagtgg gagagcaacg ccagcctga aacaactac       180
aagaccaccc ctcccgtgct ggacagcgac ggcagcttct cctgtacag ccggctgacc      240
gtggacaaga gccggtggca ggaaggcaac gtctttagct gcagcgtgat gcacgaggcc     300
ctgcacaacc actacaccca gaagagcctg agcctgtccc tgggcaag                  348
```

<210> SEQ ID NO 37

<400> SEQUENCE: 37

000

<210> SEQ ID NO 38

<400> SEQUENCE: 38

000

<210> SEQ ID NO 39

```
<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49
<211> LENGTH: 5
<212> TYPE: PRT
<213> ORGANISM: Artificial Sequence
<220> FEATURE:
<223> OTHER INFORMATION: IgG4 hinge

<400> SEQUENCE: 49

Glu Ser Lys Tyr Gly
1               5
```

<210> SEQ ID NO 50

<400> SEQUENCE: 50

000

<210> SEQ ID NO 51
<211> LENGTH: 9
<212> TYPE: PRT
<213> ORGANISM: Artificial Sequence
<220> FEATURE:
<223> OTHER INFORMATION: Modified Human IgG4 hinge region

<400> SEQUENCE: 51

Tyr Gly Pro Pro Cys Pro Pro Cys Pro
1               5

<210> SEQ ID NO 52
<211> LENGTH: 10
<212> TYPE: PRT
<213> ORGANISM: Artificial Sequence
<220> FEATURE:
<223> OTHER INFORMATION: Modified Human IgG4 hinge region

<400> SEQUENCE: 52

Lys Tyr Gly Pro Pro Cys Pro Pro Cys Pro
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Modified Human IgG4 hinge region

<400> SEQUENCE: 53

Glu Val Val Lys Tyr Gly Pro Pro Cys Pro Pro Cys Pro
1               5                   10

<210> SEQ ID NO 54
<211> LENGTH: 10024
<212> TYPE: DNA
<213> ORGANISM: Artificial Sequence
<220> FEATURE:
<223> OTHER INFORMATION: Ce7scFv-IgG4hinge-CH2-CH3-CD28tm/4-1BB-zeta-
      T2A-EGFRt-epHIV7

<400> SEQUENCE: 54
gttagaccag atctgagcct gggagctctc tggctaacta gggaacccac tgcttaagcc     60
tcaataaagc ttgccttgag tgcttcaagt agtgtgtgcc cgtctgttgt gtgactctgg    120
taactagaga tccctcagac ccttttagtc agtgtggaaa atctctagca gtggcgcccg    180
aacagggact tgaaagcgaa agggaaacca gaggagctct ctcgacgcag gactcggctt    240
gctgaagcgc gcacggcaag aggcgagggg cggcgactgg tgagtacgcc aaaaattttg    300
actagcggag gctagaagga gagagatggg tgcgagagcg tcagtattaa gcggggggaga    360 attagatcga tgggaaaaaa ttcggttaag gccagggggga agaaaaaat ataaattaaa    420 acatatagta tgggcaagca gggagctaga acgattcgca gttaatcctg gcctgttaga    480
aacatcagaa ggctgtagac aaatactggg acagctacaa ccatcccttc agacaggatc    540
agaagaactt agatcattat ataatacagt agcaaccctc tattgtgtgc atcaaaggat    600
agagataaaa gacaccaagg aagctttaga caagatagag gaagagcaaa acaaaagtaa    660

```
gaaaaaagca cagcaagcag cagctgacac aggacacagc aatcaggtca gccaaaatta    720
ccctatagtg cagaacatcc aggggcaaat ggtacatcag gccatatcac ctagaacttt    780
aaatgcatgg gtaaaagtag tagaagagaa ggctttcagc ccagaagtga tacccatgtt    840
ttcagcatta tcagaaggag ccaccccaca agatttaaac accatgctaa acacagtggg    900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaatttcaa   1320
aagaaagggg gggattgggg ggtacagtgc aggggaaaga atagtagaca taatagcaac   1380
agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt ggggggaggg gtcggcaatt gaaccggtgc   1620
ctagagaagg tggcgcgggg taaactggga aagtgatgtc gtgtactggc tccgcctttt   1680
tcccgagggt gggggagaac cgtatataag tgcagtagtc gccgtgaacg ttcttttttcg   1740 caacgggttt gccgccagaa cacagctgaa gcttcgaggg gctcgcatct ctccttcacg   1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt ctttgtttcg ttttctgttc tgcgccgtta   2040
cagatccaag ctgtgaccgg cgcctacggc tagcgccgcc accatgctgc tgctggtgac   2100
cagcctgctg ctgtgcgagc tgccccaccc cgcctttctg ctgatccccc aggtgcagct   2160
gcagcagcct ggcgccgagc tggtgaagcc aggcgccagc gtgaagctgt cctgcaaggc   2220
cagcggctac accttcaccg gctactggat gcactgggtg aagcagagac ccggccacgg   2280
cctggaatgg atcggcgaga tcaaccccag caacggccgg accaactaca acgagcggtt   2340
caagagcaag gccaccctga ccgtggacaa gagcagcacc accgccttca tgcagctgtc   2400
cggcctgacc agcgaggaca cgcgccgtgta cttctgcgcc agggactact acggcaccag   2460
ctacaacttc gactactggg gccagggcac cacactgacc gtgagcagcg gcggagggg   2520 ctctggcggc ggaggatctg ggggaggggg cagcgacatc cagatgaccc agagcagcag   2580
cagcttcagc gtgagcctgg gcgaccgggt gaccatcacc tgtaaggcca acgaggacat   2640
caacaaccgg ctggcctggt atcagcagac ccccggcaac agccccaggc tgctgatcag   2700
cggcgccacc aacctggtga ccggcgtgcc cagccggttt agcggcagcg gctccggcaa   2760
ggactacacc ctgaccatca aagcctgca ggccgaggac ttcgccacct actactgcca   2820
gcagtactgg tccacccct tcaccttcgg cagcggcacc gagctggaaa tcaaagagag   2880
caagtacgga ccgccctgcc ccccttgccc tgccccgag ttcctgggcg acccagcgt   2940 gttcctgttc ccccccaagc ccaaggacac cctgatgatc agccggaccc ccgaggtgac   3000
```

```
ctgcgtggtg gtggacgtga gccaggaaga tcccgaggtc cagttcaatt ggtacgtgga    3060
cggcgtggaa gtgcacaacg ccaagaccaa gcccagagag gaacagttca acagcaccta    3120
ccgggtggtg tctgtgctga ccgtgctgca ccaggactgg ctgaacggca agaatacaa     3180 gtgcaaggtg tccaacaagg gcctgcccag cagcatcgaa aagaccatca gcaaggccaa    3240
gggccagcct cgcgagcccc aggtgtacac cctgcctccc tcccaggaag agatgaccaa    3300
gaaccaggtg tccctgacct gcctggtgaa gggcttctac cccagcgaca tcgccgtgga    3360
gtgggagagc aacggccagc tgagaacaa ctacaagacc accctcccg tgctggacag      3420 cgacggcagc ttcttcctgt acagccggct gaccgtggac aagagccggt ggcaggaagg    3480
caacgtcttt agctgcagcg tgatgcacga ggccctgcac aaccactaca cccagaagag    3540
cctgagcctg tccctgggca gatgttctg ggtgctggtg gtggtgggcg gggtgctggc     3600
ctgctacagc ctgctggtga cagtggcctt catcatcttt tgggtgaaac ggggcagaaa    3660
gaaactcctg tatatattca aacaaccatt tatgagacca gtacaaacta ctcaaggaga    3720
agatggctgt agctgccgat ttccagaaga agaagaagga ggatgtgaac tgcgggtgaa    3780
gttcagcaga agcgccgacg cccctgccta ccagcagggc cagaatcagc tgtacaacga    3840
gctgaacctg gcagaaggg aagagtacga cgtcctggat aagcggagag ccgggaccc     3900 tgagatgggc ggcaagcctc ggcggaagaa ccccccaggaa ggcctgtata cgaactgca    3960 gaaagacaag atggccgagg cctacagcga gatcggcatg aagggcgagc ggaggcgggg   4020
caagggccac gacggcctgt atcagggcct gtccaccgcc accaaggata cctacgacgc    4080
cctgcacatg caggccctgc ccccaaggct cgagggcggc ggagagggca gaggaagtct    4140
tctaacatgc ggtgacgtgg aggagaatcc cggccctagg atgcttctcc tggtgacaag    4200
ccttctgctc tgtgagttac cacacccagc attcctcctg atcccacgca aagtgtgtaa    4260
cggaataggt attggtgaat ttaaagactc actctccata aatgctacga atattaaaca    4320
cttcaaaaac tgcacctcca tcagtggcga tctccacatc ctgccggtgg catttagggg    4380
tgactccttc acacatactc ctcctctgga tccacaggaa ctggatattc tgaaaaccgt    4440
aaaggaaatc acagggtttt tgctgattca ggcttggcct gaaaacagga cggacctcca    4500
tgcctttgag aacctagaaa tcatacgcgg caggaccaag caacatggtc agttttctct    4560
tgcagtcgtc agcctgaaca taacatcctt gggattacgc tccctcaagg agataagtga    4620
tggagatgtg ataatttcag gaaacaaaaa tttgtgctat gcaaatacaa taaactggaa    4680
aaaactgttt gggacctccg gtcagaaaac caaaattata agcaacagag gtgaaaacag    4740
ctgcaaggcc acaggccagg tctgccatgc cttgtgctcc cccgagggct gctgggcccc   4800
ggagcccagg gactgcgtct cttgccgaa tgtcagccga ggcagggaat gcgtggacaa     4860
gtgcaacctt ctggagggtg agccaaggga gtttgtggag aactctgagt gcatacagtg    4920 ccaccccag tgcctgcctc aggccatgaa catcacctgc acaggacggg gaccagacaa     4980
ctgtatccag tgtgcccact acattgacgg cccccactgc gtcaagacct gcccggcagg    5040
agtcatggga gaaaacaaca ccctggtctg gaagtacgca gacgccggcc atgtgtgcca    5100
cctgtgccat ccaaactgca cctacggatg cactgggcca ggtcttgaag ctgtccaac    5160 gaatgggcct aagatcccgt ccatcgccac tgggatggtg ggggccctcc tcttgctgct    5220
ggtggtggcc ctggggatcg gcctcttcat gtgagcggcc gctctagacc cgggctgcag    5280
gaattcgata tcaagcttat cgataatcaa cctctggatt acaaaatttg tgaaagattg    5340
actggtattc ttaactatgt tgctcctttt acgctatgtg gatacgctgc tttaatgcct    5400
```

```
ttgtatcatg ctattgcttc ccgtatggct ttcattttct cctccttgta taaatcctgg   5460
ttgctgtctc tttatgagga gttgtggccc gttgtcaggc aacgtggcgt ggtgtgcact   5520
gtgtttgctg acgcaacccc cactggttgg ggcattgcca ccacctgtca gctccttttcc  5580 gggactttcg ctttccccct ccctattgcc acggcggaac tcatcgccgc ctgccttgcc   5640
cgctgctgga caggggctcg gctgttgggc actgacaatt ccgtggtgtt gtcggggaaa   5700
tcatcgtcct ttccttggct gctcgcctgt gttgccacct ggattctgcg cgggacgtcc   5760
ttctgctacg tcccttcggc cctcaatcca gcggaccttc cttcccgcgg cctgctgccg   5820
gctctgcggc ctcttccgcg tcttcgcctt cgccctcaga cgagtcggat ctccctttgg   5880
gccgcctccc cgcatcgata ccgtcgacta gccgtacctt aagaccaat gacttacaag    5940 gcagctgtag atcttagcca cttttttaaaa gaaaaggggg gactgaagg gctaattcac    6000 tcccaaagaa gacaagatct gcttttttgcc tgtactgggt ctctctggtt agaccagatc   6060
tgagcctggg agctctctgg ctaactaggg aacccactgc ttaagcctca ataaagcttg    6120
ccttgagtgc ttcaagtagt gtgtgcccgt ctgttgtgtg actctggtaa ctagagatcc    6180
ctcagaccct tttagtcagt gtggaaaatc tctagcagaa ttcgatatca agcttatcga   6240
taccgtcgac ctcgaggggg ggcccggtac ccaattcgcc ctatagtgag tcgtattaca   6300
attcactggc cgtcgtttta caacgtcgtg actgggaaaa ccctggcgtt acccaactta   6360
atcgccttgc agcacatccc cctttcgcca gctggcgtaa tagcgaagag gcccgcaccg   6420 atcgccttc ccaacagttg cgcagcctga atggcgaatg gaaattgtaa gcgttaatat    6480
tttgttaaaa ttcgcgttaa attttttgtta aatcagctca ttttttaacc aataggccga   6540
aatcggcaaa atcccttata aatcaaaaga atagaccgag atagggttga gtgttgttcc   6600
agtttggaac aagagtccac tattaaagaa cgtggactcc aacgtcaaag ggcgaaaaac   6660
cgtctatcag ggcgatggcc cactacgtga accatcaccc taatcaagtt ttttggggtc   6720
gaggtgccgt aaagcactaa atcggaaccc taaagggagc ccccgattta gagcttgacg   6780
gggaaagccg cgaacgtgg cgagaaagga agggaagaaa gcgaaaggag cgggcgctag    6840
ggcgctggca agtgtagcgg tcacgctgcg cgtaaccacc acacccgccg cgcttaatgc   6900
gccgctacag ggcgcgtcag gtggcacttt tcggggaaat gtgcgcggaa cccctatttg   6960
tttatttttc taaatacatt caaatatgta tccgctcatg agacaataac cctgataaat    7020
gcttcaataa tattgaaaaa ggaagagtat gagtattcaa catttccgtg tcgcccttat   7080 tcccttttt gcggcatttt gccttcctgt ttttgctcac ccagaaacgc tggtgaaagt    7140
aaaagatgct gaagatcagt tgggtgcacg agtgggttac atcgaactgg atctcaacag   7200
cggtaagatc cttgagagtt ttcgccccga agaacgtttt ccaatgatga gcacttttaa   7260
agttctgcta tgtggcgcgg tattatcccg tattgacgcc gggcaagagc aactcggtcg   7320
ccgcatacac tattctcaga atgacttggt tgagtactca ccagtcacag aaaagcatct   7380
tacggatggc atgacagtaa gagaattatg cagtgctgcc ataaccatga gtgataacac   7440
tgcggccaac ttacttctga caacgatcgg aggaccgaag gagctaaccg cttttttgca   7500
caacatggga gatcatgtaa ctcgccttga tcgttgggaa ccggagctga atgaagccat   7560
accaaacgac gagcgtgaca ccacgatgcc tgtagcaatg gcaacaacgt tgcgcaaact   7620
attaactggc gaactactta ctctagcttc ccggcaacaa ttaatagact ggatggaggc   7680
ggataaagtt gcaggaccac ttctgcgctc ggcccttccg gctggctggt ttattgctga   7740
```

```
taaatctgga gccggtgagc gtgggtctcg cggtatcatt gcagcactgg ggccagatgg      7800
taagccctcc cgtatcgtag ttatctacac gacggggagt caggcaacta tggatgaacg      7860
aaatagacag atcgctgaga taggtgcctc actgattaag cattggtaac tgtcagacca      7920
agtttactca tatatacttt agattgattt aaaacttcat ttttaattta aaaggatcta      7980
ggtgaagatc cttttgata atctcatgac caaaatccct taacgtgagt tttcgttcca      8040
ctgagcgtca gacccgtag aaaagatcaa aggatcttct tgagatcctt tttttctgcg       8100
cgtaatctgc tgcttgcaaa caaaaaaacc accgctacca gcggtggttt gtttgccgga      8160
tcaagagcta ccaactcttt ttccgaaggt aactggcttc agcagagcgc agataccaaa      8220
tactgttctt ctagtgtagc cgtagttagg ccaccacttc aagaactctg tagcaccgcc      8280
tacatacctc gctctgctaa tcctgttacc agtggctgct gccagtggcg ataagtcgtg      8340
tcttaccggg ttggactcaa gacgatagtt accggataag gcgcagcggt cgggctgaac      8400
ggggggttcg tgcacacagc ccagcttgga gcgaacgacc tacaccgaac tgagatacct      8460
acagcgtgag ctatgagaaa gcgccacgct tcccgaaggg agaaaggcgg acaggtatcc      8520
ggtaagcggc agggtcggaa caggagagcg cacgagggag cttccagggg gaaacgcctg      8580
gtatctttat agtcctgtcg gtttcgcca cctctgactt gagcgtcgat ttttgtgatg       8640
ctcgtcaggg gggcggagcc tatggaaaaa cgccagcaac gcggcctttt tacggttcct      8700
ggccttttgc tggccttttg ctcacatgtt ctttcctgcg ttatccctg attctgtgga       8760 taaccgtatt accgcctttg agtgagctga taccgctcgc cgcagccgaa cgaccgagcg      8820
cagcgagtca gtgagcgagg aagcggaaga gcgcccaata cgcaaaccgc ctctccccgc      8880
gcgttggccg attcattaat gcagctggca cgacaggttt cccgactgga aagcgggcag      8940
tgagcgcaac gcaattaatg tgagttagct cactcattag gcaccccagg ctttacactt      9000
tatgcttccg gctcgtatgt tgtgtggaat tgtgagcgga taacaatttc acacaggaaa      9060
cagctatgac catgattacg ccaagctcga aattaaccct cactaaaggg aacaaaagct      9120
ggagctccac cgcggtggcg gcctcgaggt cgagatccgg tcgaccagca accatagtcc      9180 cgccctaac tccgcccatc ccgccctaa ctccgcccag ttccgcccat tctccgcccc        9240
atggctgact aatttttttt atttatgcag aggccgaggc cgcctcggcc tctgagctat      9300
tccagaagta gtgaggaggc ttttttggag gcctaggctt ttgcaaaaag cttgacggt       9360 atcgattggc tcatgtccaa cattaccgcc atgttgacat tgattattga ctagttatta     9420
atagtaatca attacggggt cattagttca tagcccatat atggagttcc gcgttacata     9480
acttacggta aatggcccgc ctggctgacc gcccaacgac ccccgcccat tgacgtcaat     9540
aatgacgtat gttcccatag taacgccaat agggactttc cattgacgtc aatgggtgga     9600
gtatttacgg taaactgccc acttggcagt acatcaagtg tatcatatgc caagtacgcc     9660
ccctattgac gtcaatgacg gtaaatggcc cgcctggcat tatgcccagt acatgacctt     9720
atgggacttt cctacttggc agtacatcta cgtattagtc atcgctatta ccatggtgat     9780
gcggttttgg cagtacatca atgggcgtgg atagcggttt gactcacggg gatttccaag     9840
tctccacccc attgacgtca atgggagttt gttttggcac caaaatcaac gggactttcc     9900
aaaatgtcgt aacaactccg ccccattgac gcaaatgggc ggtaggcgtg tacggaattc     9960
ggagtggcga gccctcagat cctgcatata agcagctgct ttttgcctgt actgggtctc     10020
tctg                                                                  10024
```

<210> SEQ ID NO 55
<211> LENGTH: 9694
<212> TYPE: DNA
<213> ORGANISM: Artificial Sequence
<220> FEATURE:
<223> OTHER INFORMATION: Ce7scFv-IgG4hinge-CH3-CD28tm/4-1BB-zeta-T2A-
      EGFRt-epHIV7 (intermediate)

<400> SEQUENCE: 55

| | | | | | |
|---|---|---|---|---|---|
| gttagaccag | atctgagcct | gggagctctc | tggctaacta | gggaacccac | tgcttaagcc | 60 |
| tcaataaagc | ttgccttgag | tgcttcaagt | agtgtgtgcc | cgtctgttgt | gtgactctgg | 120 |
| taactagaga | tccctcagac | ccttttagtc | agtgtggaaa | atctctagca | gtggcgcccg | 180 |
| aacagggact | tgaaagcgaa | agggaaacca | gaggagctct | ctcgacgcag | gactcggctt | 240 |
| gctgaagcgc | gcacggcaag | aggcgagggg | cggcgactgg | tgagtacgcc | aaaaattttg | 300 |
| actagcggag | gctagaagga | gagagatggg | tgcgagagcg | tcagtattaa | gcggggggaga | 360 |
| attagatcga | tgggaaaaaa | ttcggttaag | gccagggggga | aagaaaaaat | ataaattaaa | 420 |
| acatatagta | tgggcaagca | gggagctaga | acgattcgca | gttaatcctg | gcctgttaga | 480 |
| aacatcagaa | ggctgtagac | aaatactggg | acagctacaa | ccatcccttc | agacaggatc | 540 |
| agaagaactt | agatcattat | ataatacagt | agcaaccctc | tattgtgtgc | atcaaaggat | 600 |
| agagataaaa | gacaccaagg | aagctttaga | caagatagag | gaagagcaaa | acaaaagtaa | 660 |
| gaaaaaagca | cagcaagcag | cagctgacac | aggacacagc | aatcaggtca | gccaaaatta | 720 |
| ccctatagtg | cagaacatcc | aggggcaaat | ggtacatcag | gccatatcac | ctagaacttt | 780 |
| aaatgcatgg | gtaaaagtag | tagaagagaa | ggctttcagc | ccagaagtga | tacccatgtt | 840 |
| ttcagcatta | tcagaaggag | ccaccccaca | agatttaaac | accatgctaa | acacagtggg | 900 |
| gggacatcaa | gcagccatgc | aaatgttaaa | agagaccatc | aatgaggaag | ctgcaggcaa | 960 |
| agagaagagt | ggtgcagaga | gaaaaaagag | cagtgggaat | aggagctttg | ttccttgggt | 1020 |
| tcttgggagc | agcaggaagc | actatgggcg | cagcgtcaat | gacgctgacg | gtacaggcca | 1080 |
| gacaattatt | gtctggtata | gtgcagcagc | agaacaattt | gctgagggct | attgaggcgc | 1140 |
| aacagcatct | gttgcaactc | acagtctggg | gcatcaagca | gctccaggca | agaatcctgg | 1200 |
| ctgtggaaag | atacctaaag | gatcaacagc | tcctggggat | ttggggttgc | tctggaaaac | 1260 |
| tcatttgcac | cactgctgtg | ccttggatct | acaaatggca | gtattcatcc | acaattttaa | 1320 |
| aagaaaaggg | gggattgggg | ggtacagtgc | aggggaaaga | atagtagaca | taatagcaac | 1380 |
| agacatacaa | actaaagaat | tacaaaaaca | aattacaaaa | attcaaaatt | ttcgggttta | 1440 |
| ttacagggac | agcagagatc | cagtttgggg | atcaattgca | tgaagaatct | gcttagggtt | 1500 |
| aggcgttttg | cgctgcttcg | cgaggatctg | cgatcgctcc | ggtgcccgtc | agtgggcaga | 1560 |
| gcgcacatcg | cccacagtcc | ccgagaagtt | gggggggaggg | gtcggcaatt | gaaccggtgc | 1620 |
| ctagagaagg | tggcgcgggg | taaactggga | aagtgatgtc | gtgtactggc | tccgcctttt | 1680 |
| tcccgagggt | gggggagaac | cgtatataag | tgcagtagtc | gccgtgaacg | ttctttttcg | 1740 |
| caacgggttt | gccgccagaa | cacagctgaa | gcttcgaggg | gctcgcatct | ctccttcacg | 1800 |
| cgcccgccgc | cctacctgag | gccgccatcc | acgccggttg | agtcgcgttc | tgccgcctcc | 1860 |
| cgcctgtggt | gcctcctgaa | ctgcgtccgc | cgtctaggta | agtttaaagc | tcaggtcgag | 1920 |
| accgggcctt | tgtccggcgc | tcccttggag | cctacctaga | ctcagccggc | tctccacgct | 1980 |
| ttgcctgacc | ctgcttgctc | aactctacgt | ctttgtttcg | ttttctgttc | tgcgccgtta | 2040 |
| cagatccaag | ctgtgaccgg | cgcctacggc | tagcgccgcc | accatgctgc | tgctggtgac | 2100 |

```
cagcctgctg ctgtgcgagc tgccccaccc cgcctttctg ctgatccccc aggtgcagct   2160
gcagcagcct ggcgccgagc tggtgaagcc aggcgccagc gtgaagctgt cctgcaaggc   2220
cagcggctac accttcaccg gctactggat gcactgggtg aagcagagac ccggccacgg   2280
cctggaatgg atcggcgaga tcaaccccag caacggccgg accaactaca acgagcggtt   2340
caagagcaag gccaccctga ccgtggacaa gagcagcacc accgccttca tgcagctgtc   2400
cggcctgacc agcgaggaca cgccgtgta cttctgcgcc agggactact acggcaccag   2460
ctacaacttc gactactggg gccagggcac cacactgacc gtgagcagcg cggaggggg   2520 ctctggcggc ggaggatctg ggggaggggg cagcgacatc cagatgaccc agagcagcag   2580
cagcttcagc gtgagcctgg gcgaccgggt gaccatcacc tgtaaggcca acgaggacat   2640
caacaaccgg ctggcctggt atcagcagac ccccggcaac agcccaggc tgctgatcag   2700 cggcgccacc aacctggtga ccggcgtgcc cagccggttt agcggcagcg gctccggcaa   2760
ggactacacc ctgaccatca aagcctgca ggccgaggac ttcgccacct actactgcca   2820
gcagtactgg tccaccccct tcaccttcgg cagcggcacc gagctggaaa tcaaagaatc   2880
taagtacgga ccgccctgcc cccttgccc tggccagcct agagaaccc aggtgtacac   2940 cctgcctccc agccaggaag agatgaccaa gaaccaggtg tccctgacct gcctggtcaa   3000
aggcttctac cccagcgata tcgccgtgga atgggagagc aacggccagc ccgagaacaa   3060
ctacaagacc ccccccctg tgctggacag cgacggcagc ttcttcctgt actcccggct   3120
gaccgtggac aagagccggt ggcaggaagg caacgtcttc agctgcagcg tgatgcacga   3180
ggccctgcac aaccactaca cccagaagtc cctgagcctg agcctgggca gatgttctg   3240 ggtgctggtg gtggtcggag gcgtgctggc ctgctacagc ctgctggtca ccgtggcctt   3300
catcatcttt tgggtgaaac ggggcagaaa gaaactcctg tatatattca acaaccatt   3360 tatgagacca gtacaaacta ctcaaggaga agatggctgt agctgccgat tccagaaga   3420 agaagaagga ggatgtgaac tgcgggtgaa gttcagcaga agcgccgacg cccctgccta   3480
ccagcagggc cagaatcagc tgtacaacga gctgaacctg gcagaaggg aagagtacga   3540 cgtcctggat aagcggagag ccgggaccc tgagatgggg gcaagcctc ggcggaagaa   3600 ccccaggaa ggcctgtata cgaactgca gaaagacaag atggccgagg cctacagcga   3660
gatcggcatg aagggcgagc ggaggcgggg caagggccac gacggcctgt atcagggcct   3720
gtccaccgcc accaaggata cctacgacgc cctgcacatg caggccctgc cccaaggct   3780 cgagggcggg ggagaggca gaggaagtct tctaacatgc ggtgacgtgg aggagaatcc   3840
cggccctagg atgcttctcc tggtgacaag ccttctgctc tgtgagttac cacacccagc   3900
attcctcctg atcccacgca aagtgtgtaa cggaataggt attggtgaat ttaaagactc   3960
actctccata aatgctacga atattaaaca cttcaaaaac tgcacctcca tcagtggcga   4020
tctccacatc ctgccggtgg catttagggg tgactccttc acacatactc ctcctctgga   4080
tccacaggaa ctggatattc tgaaaaccgt aaaggaaatc acagggtttt tgctgattca   4140
ggcttggcct gaaaacagga cggacctcca tgcctttgag aacctagaaa tcatacgcgg   4200
caggaccaag caacatggtc agttttctct tgcagtcgtc agcctgaaca taacatcctt   4260
gggattacgc tccctcaagg agataagtga tggagatgtg ataatttcag gaaacaaaaa   4320
tttgtgctat gcaaatacaa taactgaa aaaactgttt gggacctccg gtcagaaac   4380 caaaattata agcaacagag gtgaaaacag ctgcaaggcc acaggccagg tctgccatgc   4440
```

```
cttgtgctcc cccgagggct gctggggccc ggagcccagg gactgcgtct cttgccggaa   4500
tgtcagccga ggcagggaat gcgtggacaa gtgcaaccct ctggagggtg agccaaggga   4560
gtttgtggag aactctgagt gcatacagtg ccacccagag tgcctgcctc aggccatgaa   4620
catcaccctg caaggacggg gaccagacaa ctgtatccag tgtgcccact acattgacgg   4680
cccccactgc gtcaagacct gcccggcagg agtcatggga gaaaacaaca ccctggtctg   4740
gaagtacgca gacgccggcc atgtgtgcca cctgtgccat ccaaactgca cctacggatg   4800
cactgggcca ggtcttgaag gctgtccaac gaatgggcct aagatcccgt ccatcgccac   4860
tgggatggtg ggggccctcc tcttgctgct ggtggtggcc ctggggatcg gcctcttcat   4920
gtgagcggcc gctctagacc cgggctgcag gaattcgata tcaagcttat cgataatcaa   4980
cctctggatt acaaaatttg tgaaagattg actggtattc ttaactatgt tgctcctttt   5040
acgctatgtg gatacgctgc tttaatgcct ttgtatcatg ctattgcttc ccgtatggct   5100
ttcattttct cctccttgta taaatcctgg ttgctgtctc tttatgagga gttgtggccc   5160
gttgtcaggc aacgtggcgt ggtgtgcact gtgtttgctg acgcaacccc cactggttgg   5220
ggcattgcca ccacctgtca gctcctttcc gggactttcg ctttcccccct ccctattgcc   5280
acggcggaac tcatcgccgc ctgccttgcc cgctgctgga caggggctcg gctgttgggc   5340
actgacaatt ccgtggtgtt gtcggggaaa tcatcgtcct ttccttggct gctcgcctgt   5400
gttgccacct ggattctgcg cgggacgtcc ttctgctacg tcccttcggc cctcaatcca   5460
gcggaccttc cttcccgcgg cctgctgccg gctctgcggc ctcttccgcg tcttcgcctt   5520
cgccctcaga cgagtcggat ctccctttgg gccgcctccc cgcatcgata ccgtcgacta   5580
gccgtacctt taagaccaat gacttacaag gcagctgtag atcttagcca cttttttaaaa   5640
gaaaaggggg gactggaagg gctaattcac tcccaaagaa gacaagatct gcttttttgcc   5700
tgtactgggt ctctctggtt agaccagatc tgagcctggg agctctctgg ctaactaggg   5760
aacccactgc ttaagcctca ataaagcttg ccttgagtgc ttcaagtagt gtgtgcccgt   5820
ctgttgtgtg actctggtaa ctagagatcc ctcagaccct tttagtcagt gtggaaaatc   5880
tctagcagaa ttcgatatca agcttatcga taccgtcgac ctcagggggg gcccggtac   5940
ccaattcgcc ctatagtgag tcgtattaca attcactggc cgtcgtttta caacgtcgtg   6000
actgggaaaa ccctggcgtt acccaactta atcgccttgc agcacatccc cctttcgcca   6060
gctggcgtaa tagcgaagag gcccgcaccg atcgcccttc ccaacagttg cgcagcctga   6120
atggcgaatg gaaattgtaa gcgttaatat tttgttaaaa ttcgcgttaa attttttgtta   6180
aatcagctca ttttttaacc aataggccga atcggcaaa atcccttata aatcaaaaga   6240
atagaccgag atagggttga gtgttgttcc agtttggaac aagagtccac tattaaagaa   6300
cgtggactcc aacgtcaaag ggcgaaaaac cgtctatcag ggcgatggcc cactacgtga   6360
accatcaccc taatcaagtt ttttggggtc gaggtgccgt aaagcactaa atcggaaccc   6420
taaagggagc ccccgattta gagcttgacg gggaaagccg gcgaacgtgg cgagaaagga   6480
agggaagaaa gcgaaaggag cgggcgctag ggcgctggca agtgtagcgg tcacgctgcg   6540
cgtaaccacc acacccgccg cgcttaatgc gccgctacag ggcgcgtcag gtggcacttt   6600
tcggggaaat gtgcgcggaa cccctatttg tttatttttc taaatacatt caaatatgta   6660
tccgctcatg agacaataac cctgataaat gcttcaataa tattgaaaaa ggaagagtat   6720
gagtattcaa catttccgtg tcgcccttat tccttttttt gcggcatttt gccttcctgt   6780
ttttgctcac ccagaaacgc tggtgaaagt aaaagatgct gaagatcagt tgggtgcacg   6840
```

```
agtgggttac atcgaactgg atctcaacag cggtaagatc cttgagagtt ttcgcccga   6900 agaacgtttt ccaatgatga gcacttttaa agttctgcta tgtggcgcgg tattatcccg   6960
tattgacgcc gggcaagagc aactcggtcg ccgcatacac tattctcaga atgacttggt   7020
tgagtactca ccagtcacag aaaagcatct tacggatggc atgacagtaa gagaattatg   7080
cagtgctgcc ataaccatga gtgataacac tgcggccaac ttacttctga caacgatcgg   7140
aggaccgaag gagctaaccg cttttttgca caacatgggg gatcatgtaa ctcgccttga   7200
tcgttgggaa ccggagctga atgaagccat accaaacgac gagcgtgaca ccacgatgcc   7260
tgtagcaatg gcaacaacgt tgcgcaaact attaactggc gaactactta ctctagcttc   7320
ccggcaacaa ttaatagact ggatggaggc ggataaagtt gcaggaccac ttctgcgctc   7380
ggcccttccg gctggctggt ttattgctga taaatctgga gccggtgagc gtgggtctcg   7440
cggtatcatt gcagcactgg ggccagatgg taagccctcc cgtatcgtag ttatctacac   7500
gacggggagt caggcaacta tggatgaacg aaatagacag atcgctgaga taggtgcctc   7560
actgattaag cattggtaac tgtcagacca agtttactca tatatacttt agattgattt   7620
aaaacttcat ttttaattta aaaggatcta ggtgaagatc ctttttgata atctcatgac   7680
caaaatccct taacgtgagt tttcgttcca ctgagcgtca gaccccgtag aaaagatcaa   7740
aggatcttct tgagatcctt ttttttctgcg cgtaatctgc tgcttgcaaa caaaaaaacc   7800
accgctacca gcggtggttt gtttgccgga tcaagagcta ccaactcttt ttccgaaggt   7860
aactggcttc agcagagcgc agataccaaa tactgttctt ctagtgtagc cgtagttagg   7920
ccaccacttc aagaactctg tagcaccgcc tacatacctc gctctgctaa tcctgttacc   7980
agtggctgct gccagtggcg ataagtcgtg tcttaccggg ttggactcaa gacgatagtt   8040
accggataag gcgcagcggt cgggctgaac ggggggttcg tgcacacagc ccagcttgga   8100
gcgaacgacc tacaccgaac tgagatacct acagcgtgag ctatgagaaa gcgccacgct   8160
tcccgaaggg agaaaggcgg acaggtatcc ggtaagcggc agggtcggaa caggagagcg   8220
cacgagggag cttccagggg gaaacgcctg gtatctttat agtcctgtcg ggtttcgcca   8280
cctctgactt gagcgtcgat ttttgtgatg ctcgtcaggg gggcggagcc tatggaaaaa   8340
cgccagcaac gcggcctttt tacggttcct ggccttttgc tggccttttg ctcacatgtt   8400
ctttcctgcg ttatccctg attctgtgga taaccgtatt accgcctttg agtgagctga   8460
taccgctcgc cgcagccgaa cgaccgagcg cagcgagtca gtgagcgagg aagcggaaga   8520
gcgcccaata cgcaaaccgc ctctccccgc gcgttggccg attcattaat gcagctggca   8580
cgacaggttt cccgactgga aagcgggcag tgagcgcaac gcaattaatg tgagttagct   8640
cactcattag gcaccccagg ctttacactt tatgcttccg gctcgtatgt tgtgtggaat   8700
tgtgagcgga taacaatttc acacaggaaa cagctatgac catgattacg ccaagctcga   8760
aattaaccct cactaaaggg aacaaaagct ggagctccac cgcggtggcg gcctcgaggt   8820
cgagatccgg tcgaccagca accatagtcc cgcccctaac tccgcccatc ccgcccctaa   8880
ctccgcccag ttccgcccat tctccgcccc atggctgact aattttttttt atttatgcag   8940 aggccgaggc cgcctcggcc tctgagctat tccagaagta gtgaggaggc ttttttggag   9000
gcctaggctt ttgcaaaaag cttcgacggt atcgattggc tcatgtccaa cattaccgcc   9060
atgttgacat tgattattga ctagttatta atagtaatca attacggggt cattagttca   9120
tagcccatat atggagttcc gcgttacata acttacggta aatggcccgc ctggctgacc   9180
```

```
gcccaacgac ccccgcccat tgacgtcaat aatgacgtat gttcccatag taacgccaat    9240
agggactttc cattgacgtc aatgggtgga gtatttacgg taaactgccc acttggcagt    9300
acatcaagtg tatcatatgc caagtacgcc ccctattgac gtcaatgacg gtaaatggcc    9360
cgcctggcat tatgcccagt acatgacctt atgggacttt cctacttggc agtacatcta    9420
cgtattagtc atcgctatta ccatggtgat gcggttttgg cagtacatca atgggcgtgg    9480
atagcggttt gactcacggg gatttccaag tctccacccc attgacgtca atgggagttt    9540
gttttggcac caaaatcaac gggactttcc aaaatgtcgt aacaactccg ccccattgac    9600
gcaaatgggc ggtaggcgtg tacggaattc ggagtggcga gccctcagat cctgcatata    9660
agcagctgct ttttgcctgt actgggtctc tctg                                9694
```

<210> SEQ ID NO 56
<211> LENGTH: 9373
<212> TYPE: DNA
<213> ORGANISM: Artificial Sequence
<220> FEATURE:
<223> OTHER INFORMATION: Ce7scFv-IgG4hinge-CD28tm/4-1BB-zeta-T2A-EGFRt-
      epHIV7

<400> SEQUENCE: 56

```
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac ccttttagtc agtgtggaaa atctctagca gtggcgcccg     180
aacagggact tgaaagcgaa agggaaacca gaggagctct ctcgacgcag gactcggctt     240
gctgaagcgc gcacggcaag aggcgagggg cggcgactgg tgagtacgcc aaaaattttg     300
actagcggag gctagaagga gagagatggg tgcgagagcg tcagtattaa gcgggggaga     360
attagatcga tgggaaaaaa ttcggttaag gccaggggga agaaaaaat ataaattaaa     420 acatatagta tgggcaagca gggagctaga acgattcgca gttaatcctg gcctgttaga     480
aacatcagaa ggctgtagac aaatactggg acagctacaa ccatcccttc agacaggatc     540
agaagaactt agatcattat ataatacagt agcaaccctc tattgtgtgc atcaaaggat     600
agagataaaa gacaccaagg aagctttaga caagatagag gaagagcaaa acaaaagtaa     660
gaaaaaagca cagcaagcag cagctgacac aggacacagc aatcaggtca gccaaaatta     720
ccctatagtg cagaacatcc aggggcaaat ggtacatcag gccatatcac ctagaacttt     780
aaatgcatgg gtaaaagtag tagaagagaa ggctttcagc ccagaagtga tacccatgtt     840
ttcagcatta tcagaaggag ccaccccaca agatttaaac accatgctaa acacagtggg     900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt    1020
tcttgggagc agcaggaagc actatgggcg cagcgtcaat gacgctgacg gtacaggcca    1080
gacaattatt gtctggtata gtgcagcagc agaacaattt gctgagggct attgaggcgc    1140
aacagcatct gttgcaactc acagtctggg gcatcaagca gctccaggca agaatcctgg    1200
ctgtggaaag atacctaaag gatcaacagc tcctggggat ttggggttgc tctggaaaac    1260
tcatttgcac cactgctgtg ccttggatct acaaatggca gtattcatcc acaatttaa    1320 aagaaaaggg gggattgggg ggtacagtgc aggggaaaga atagtagaca taatagcaac    1380
agacatacaa actaaagaat tacaaaaaca aattacaaaa attcaaaatt ttcgggttta    1440
ttacagggac agcagagatc cagtttgggg atcaattgca tgaagaatct gcttagggtt    1500
```

```
aggcgttttg cgctgcttcg cgaggatctg cgatcgctcc ggtgcccgtc agtgggcaga    1560
gcgcacatcg cccacagtcc ccgagaagtt gggggagg gtcggcaatt gaaccggtgc     1620
ctagagaagg tggcgcgggg taaactggga aagtgatgtc gtgtactggc tccgcctttt   1680
tcccgagggt gggggagaac cgtatataag tgcagtagtc gccgtgaacg ttcttttttcg  1740 caacggg ttt gccgccagaa cacagctgaa gcttcgaggg gctcgcatct ctccttcacg  1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt ctttgtttcg ttttctgttc tgcgccgtta   2040
cagatccaag ctgtgaccgg cgcctacggg tagcgccgcc accatgctgc tgctggtgac   2100
cagcctgctg ctgtgcgagc tgcccacc cgcctttctg ctgatccccc aggtgcagct    2160
gcagcagcct ggcgccgagc tggtgaagcc aggcgccagc gtgaagctgt cctgcaaggc   2220
cagcggctac accttcaccg gctactggat gcactgggtg aagcagagac ccggccacgg   2280
cctggaatgg atcggcgaga tcaaccccag caacggccgg accaactaca acgagcggtt   2340
caagagcaag gccaccctga ccgtggacaa gagcagcacc accgccttca tgcagctgtc   2400
cggcctgacc agcgaggaca gccgcgtgta cttctgcgcc agggactact acggcaccag   2460
ctacaacttc gactactggg gccagggcac cacactgacc gtgagcagcg gcggagggg    2520 ctctggcggc ggaggatctg ggggagggg gcagcgacatc cagatgaccc agagcagcag   2580
cagcttcagc gtgagcctgg gcgaccgggt gaccatcacc tgtaaggcca acgaggacat   2640
caacaaccgg ctggcctggt atcagcagac ccccggcaac agccccaggc tgctgatcag   2700
cggcgccacc aacctggtga ccggcgtgcc cagccggttt agcggcagcg gctccggcaa   2760
ggactacacc ctgaccatca aagcctgca ggccgaggac ttcgccacct actactgcca   2820
gcagtactgg tccacccccct tcaccttcgg cagcggcacc gagctggaaa tcaaagaatc   2880
taagtacgga ccgccctgcc cccttgccc tatgttctgg gtgctggtgg tggtcggagg   2940
cgtgctggcc tgctacagcc tgctggtcac cgtggccttc atcatctttt gggtgaaacg   3000
gggcagaaag aaactcctgt atatattcaa acaaccattt atgagaccag tacaaactac   3060
tcaagaggaa gatggctgta gctgccgatt tccagaagaa gaagaaggag atgtgaact    3120 gcgggtgaag ttcagcagaa gcgccgacgc ccctgcctac cagcagggcc agaatcagct   3180
gtacaacgag ctgaacctgg gcagaaggga agagtacgac gtcctggata gcgagagg    3240 ccgggaccct gagatgggcg gcaagcctcg gcggaagaac ccccaggaag gcctgtataa   3300
cgaactgcag aaagacaaga tggccgaggc ctacagcgag atcggcatga agggcgagcg   3360
gaggcggggc aagggccacg acggcctgta tcagggcctg tccaccgcca ccaaggatac   3420
ctacgacgcc ctgcacatgc aggccctgcc cccaaggctc gagggcggcg agaggggcag   3480
aggaagtctt ctaacatgcg gtgacgtgga ggagaatccc ggccctagga tgcttctcct   3540
ggtgacaagc cttctgctct gtgagttacc acacccagca ttcctcctga tcccacgcaa   3600
agtgtgtaac ggaataggta ttggtgaatt taaagactca ctctccataa atgctacgaa   3660
tattaaacac ttcaaaaact gcacctccat cagtggcgat ctccacatcc tgccggtggc   3720 atttagggt gactccttca cacatactcc tcctctggat ccacaggaac tggatattct   3780
gaaaaccgta aaggaaatca cagggttttt gctgattcag gcttggcctg aaaacaggac   3840
ggacctccat gcctttgaga acctagaaat catacgcggc aggaccaagc aacatggtca   3900
```

```
gttttctctt gcagtcgtca gcctgaacat aacatccttg ggattacgct ccctcaagga   3960
gataagtgat ggagatgtga taatttcagg aaacaaaaat ttgtgctatg caaatacaat   4020
aaactggaaa aaactgtttg ggacctccgg tcagaaaacc aaaattataa gcaacagagg   4080
tgaaaacagc tgcaaggcca caggccaggt ctgccatgcc ttgtgctccc ccgagggctg   4140
ctggggcccg gagcccaggg actgcgtctc ttgccggaat gtcagccgag cagggaatg   4200
cgtggacaag tgcaaccttc tggagggtga gccaagggag tttgtggaga actctgagtg   4260
catacagtgc cacccagagt gcctgcctca ggccatgaac atcacctgca caggacgggg   4320
accagacaac tgtatccagt gtgcccacta cattgacggc ccccactgcg tcaagacctg   4380
cccggcagga gtcatgggag aaaacaacac cctggtctgg aagtacgcag acgccggcca   4440
tgtgtgccac ctgtgccatc aaactgcac ctacggatgc actgggccag gtcttgaagg   4500
ctgtccaacg aatgggccta agatcccgtc catcgccact gggatggtgg gggccctcct   4560
cttgctgctg gtggtggccc tggggatcgg cctcttcatg tgagcggccg ctctagaccc   4620
gggctgcagg aattcgatat caagcttatc gataatcaac ctctggatta caaaatttgt   4680
gaaagattga ctggtattct taactatgtt gctccttta cgctatgtgg atacgctgct   4740
ttaatgcctt tgtatcatgc tattgcttcc cgtatggctt tcattttctc ctccttgtat   4800
aaatcctggt tgctgtctct ttatgaggag ttgtggcccg ttgtcaggca acgtggcgtg   4860
gtgtgcactg tgtttgctga cgcaacccc actggttggg gcattgccac cacctgtcag   4920
ctcctttccg ggactttcgc tttccccctc cctattgcca cggcggaact catcgccgcc   4980
tgccttgccc gctgctggac aggggctcgg ctgttgggca ctgacaattc cgtggtgttg   5040
tcggggaaat catcgtcctt ccttggctg ctcgcctgtg ttgccacctg gattctgcgc   5100
gggacgtcct tctgctacgt cccttcggcc ctcaatccag cggaccttcc ttcccgcggc   5160
ctgctgccgg ctctgcggcc tcttccgcgt cttcgccttc gccctcagac gagtcggatc   5220
tccctttggg ccgcctcccc gcatcgatac cgtcgactag ccgtaccttt aagaccaatg   5280
acttacaagg cagctgtaga tcttagccac ttttaaaag aaaagggggg actgaaggg   5340
ctaattcact cccaaagaag acaagatctg cttttgcct gtactgggtc tctctggtta   5400
gaccagatct gagcctggga gctctctggc taactaggga acccactgct taagcctcaa   5460
taaagcttgc cttgagtgct tcaagtagtg tgtgcccgtc tgttgtgtga ctctggtaac   5520
tagagatccc tcagaccctt ttagtcagtg tggaaaatct ctagcagaat tcgatatcaa   5580
gcttatcgat accgtcgacc tcgaggggg gcccggtacc caattcgccc tatagtgagt   5640
cgtattacaa ttcactggcc gtcgttttac aacgtcgtga ctgggaaaac cctggcgtta   5700
cccaacttaa tcgccttgca gcacatcccc ctttcgccag ctggcgtaat agcgaagagg   5760
cccgcaccga tcgcccttcc caacagttgc gcagcctgaa tggcgaatgg aaattgtaag   5820
cgttaatatt ttgttaaaat tcgcgttaaa ttttgttaa atcagctcat ttttaacca   5880
ataggccgaa atcggcaaaa tcccttataa atcaaagaa tagaccgaga tagggttgag   5940
tgttgttcca gtttggaaca agagtccact attaaagaac gtggactcca acgtcaaagg   6000
gcgaaaaacc gtctatcagg gcgatggccc actacgtgaa ccatcaccct aatcaagttt   6060
tttggggtcg aggtgccgta aagcactaaa tcggaaccct aaagggagcc cccgatttag   6120
agcttgacgg ggaaagccgg cgaacgtggc gagaaaggaa gggaagaaag cgaaaggagc   6180
gggcgctagg gcgctggcaa gtgtagcggt cacgctgcgc gtaaccacca cacccgccgc   6240
```

```
gcttaatgcg ccgctacagg gcgcgtcagg tggcactttt cggggaaatg tgcgcggaac      6300
ccctatttgt ttattttctc aaatacattc aaatatgtat ccgctcatga acaataacc       6360
ctgataaatg cttcaataat attgaaaaag gaagagtatg agtattcaac atttccgtgt      6420
cgcccttatt cccttttttg cggcattttg ccttcctgtt tttgctcacc cagaaacgct      6480
ggtgaaagta aaagatgctg aagatcagtt gggtgcacga gtgggttaca tcgaactgga      6540
tctcaacagc ggtaagatcc ttgagagttt tcgccccgaa gaacgttttc caatgatgag      6600
cacttttaaa gttctgctat gtggcgcggt attatcccgt attgacgccg ggcaagagca      6660
actcggtcgc cgcatacact attctcagaa tgacttggtt gagtactcac cagtcacaga      6720
aaagcatctt acggatggca tgacagtaag agaattatgc agtgctgcca taaccatgag      6780
tgataacact gcggccaact tacttctgac aacgatcgga ggaccgaagg agctaaccgc      6840
tttttttgcac aacatggggg atcatgtaac tcgccttgat cgttgggaac cggagctgaa      6900
tgaagccata ccaaacgacg agcgtgacac cacgatgcct gtagcaatgg caacaacgtt      6960
gcgcaaacta ttaactggcg aactacttac tctagcttcc cggcaacaat taatagactg      7020
gatggaggcg gataaagttg caggaccact tctgcgctcg gcccttccgg ctggctggtt      7080
tattgctgat aaatctggag ccggtgagcg tgggtctcgc ggtatcattg cagcactggg      7140
gccagatggt aagccctccc gtatcgtagt tatctacacg acggggagtc aggcaactat      7200
ggatgaacga aatagacaga tcgctgagat aggtgcctca ctgattaagc attggtaact      7260
gtcagaccaa gtttactcat atatacttta gattgattta aaacttcatt tttaatttaa      7320
aaggatctag gtgaagatcc tttttgataa tctcatgacc aaaatccctt aacgtgagtt      7380
ttcgttccac tgagcgtcag accccgtaga aaagatcaaa ggatcttctt gagatccttt      7440
ttttctgcgc gtaatctgct gcttgcaaac aaaaaaacca ccgctaccag cggtggtttg      7500
tttgccggat caagagctac caactctttt tccgaaggta actggcttca gcagagcgca      7560
gataccaaat actgttcttc tagtgtagcc gtagttaggc caccacttca agaactctgt      7620
agcaccgcct acatacctcg ctctgctaat cctgttacca gtggctgctg ccagtggcga      7680
taagtcgtgt cttaccgggt tggactcaag acgatagtta ccggataagg cgcagcggtc      7740
gggctgaacg gggggttcgt gcacacagcc cagcttggag cgaacgacct acaccgaact      7800
gagataccta cagcgtgagc tatgagaaag cgccacgctt cccgaaggga gaaaggcgga      7860
caggtatccg gtaagcggca gggtcggaac aggagagcgc acgagggagc ttccagggggg     7920
aaacgcctgg tatctttata gtcctgtcgg gtttcgccac ctctgacttg agcgtcgatt      7980
tttgtgatgc tcgtcagggg ggcggagcct atggaaaaac gccagcaacg cggccttttt      8040
acggttcctg gccttttgct ggccttttgc tcacatgttc tttcctgcgt tatcccctga      8100
ttctgtggat aaccgtatta ccgcctttga gtgagctgat accgctcgcc gcagccgaac      8160
gaccgagcgc agcgagtcag tgagcgagga agcggaagag cgcccaatac gcaaaccgcc      8220
tctccccgcg cgttggccga ttcattaatg cagctggcac acaggtttc ccgactggaa       8280
agcgggcagt gagcgcaacg caattaatgt gagttagctc actcattagg cacccccaggc     8340
tttacacttt atgcttccgg ctcgtatgtt gtgtggaatt gtgagcggat aacaatttca      8400
cacaggaaac agctatgacc atgattacgc caagctcgaa attaaccctc actaaaggga      8460
acaaaagctg gagctccacc gcggtggcgg cctcgaggtc gagatccggt cgaccagcaa      8520
ccatagtccc gcccctaact ccgcccatcc cgcccctaac tccgcccagt tccgcccatt      8580
ctccgcccca tggctgacta atttttttta tttatgcaga ggccgaggcc gcctcggcct      8640
```

-continued

```
ctgagctatt ccagaagtag tgaggaggct tttttggagg cctaggcttt tgcaaaaagc    8700
ttcgacggta tcgattggct catgtccaac attaccgcca tgttgacatt gattattgac    8760
tagttattaa tagtaatcaa ttacggggtc attagttcat agcccatata tggagttccg    8820
cgttacataa cttacggtaa atggcccgcc tggctgaccg cccaacgacc cccgcccatt    8880
gacgtcaata atgacgtatg ttcccatagt aacgccaata gggactttcc attgacgtca    8940
atgggtggag tatttacggt aaactgccca cttggcagta catcaagtgt atcatatgcc    9000
aagtacgccc cctattgacg tcaatgacgg taaatggccc gcctggcatt atgcccagta    9060
catgacctta tgggactttc ctacttggca gtacatctac gtattagtca tcgctattac    9120
catggtgatg cggttttggc agtacatcaa tgggcgtgga tagcggtttg actcacgggg    9180
atttccaagt ctccacccca ttgacgtcaa tgggagtttg ttttggcacc aaaatcaacg    9240
ggactttcca aaatgtcgta acaactccgc cccattgacg caaatgggcg gtaggcgtgt    9300
acggaattcg gagtggcgag ccctcagatc ctgcatataa gcagctgctt tttgcctgta    9360
ctgggtctct ctg                                                       9373
```

<210> SEQ ID NO 57
<211> LENGTH: 9496
<212> TYPE: DNA
<213> ORGANISM: Artificial Sequence
<220> FEATURE:
<223> OTHER INFORMATION: Ce7scFv-IgG4hinge-CD28tm/cyto-4-1BB-zeta-T2A-
      EGFRt-epHIV7 (short two costimulatory domains)

<400> SEQUENCE: 57

```
gttagaccag atctgagcct gggagctctc tggctaacta gggaacccac tgcttaagcc      60
tcaataaagc ttgccttgag tgcttcaagt agtgtgtgcc cgtctgttgt gtgactctgg     120
taactagaga tccctcagac ccttttagtc agtgtggaaa atctctagca gtggcgcccg     180
aacagggact tgaaagcgaa agggaaacca gaggagctct ctcgacgcag gactcggctt     240
gctgaagcgc gcacggcaag aggcgagggg cggcgactgg tgagtacgcc aaaaattttg     300
actagcggag gctagaagga gagagatggg tgcgagagcg tcagtattaa gcggggggaga    360 attagatcga tgggaaaaaa ttcggttaag gccaggggga agaaaaaat ataaattaaa    420 acatatagta tgggcaagca gggagctaga acgattcgca gttaatcctg gcctgttaga    480
aacatcagaa ggctgtagac aaatactggg acagctacaa ccatcccttc agacaggatc    540
agaagaactt agatcattat ataatacagt agcaaccctc tattgtgtgc atcaaaggat    600
agagataaaa gacaccaagg aagctttaga caagatagag gaagagcaaa acaaaagtaa    660
gaaaaaagca cagcaagcag cagctgacac aggacacagc aatcaggtca gccaaaatta    720
ccctatagtg cagaacatcc aggggcaaat ggtacatcag gccatatcac ctagaacttt    780
aaatgcatgg gtaaaagtag tagaagagaa ggctttcagc ccagaagtga tacccatgtt    840
ttcagcatta tcagaaggag ccaccccaca agatttaaac accatgctaa acacagtggg    900
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
```

```
tcatttgcac cactgctgtg ccttggatct acaaatggca gtattcatcc acaattttaa   1320
aagaaaaggg gggattgggg ggtacagtgc aggggaaaga atagtagaca taatagcaac   1380
agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt ggggggaggg gtcggcaatt gaaccggtgc   1620
ctagagaagg tggcgcgggg taaactggga aagtgatgtc gtgtactggc tccgccttt    1680 tcccgagggt gggggagaac cgtatataag tgcagtagtc gccgtgaacg ttcttttcg   1740 caacgggttt gccgccagaa cacagctgaa gcttcgaggg gctcgcatct ctccttcacg   1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt cttttgtttcg ttttctgttc tgcgccgtta   2040
cagatccaag ctgtgaccgg cgcctacggc tagcgccgcc accatgctgc tgctggtgac   2100
cagcctgctg ctgtgcgagc tgccccaccc cgcctttctg ctgatccccc aggtgcagct   2160
gcagcagcct ggcgccgagc tggtgaagcc aggcgccagc gtgaagctgt cctgcaaggc   2220
cagcggctac accttcaccg gctactggat gcactgggtg aagcagagac ccggccacgg   2280
cctggaatgg atcggcgaga tcaacccag caacggccgg accaactaca acgagcggtt   2340
caagagcaag gccacactga ccgtggacaa gagcagcacc accgccttca tgcagctgtc   2400
cggcctgacc agcgaggaca cgccgtgta cttctgcgcc agggactact acggcaccag   2460
ctacaacttc gactactggg gccagggcac cacactgacc gtgagcagcg gcggagggggg   2520 ctctggcggc ggaggatctg ggggagggggg cagcgacatc cagatgaccc agagcagcag   2580
cagcttcagc gtgagcctgg gcgaccgggt gaccatcacc tgtaaggcca acgaggacat   2640
caacaaccgg ctggcctggt atcagcagac ccccggcaac agccccaggc tgctgatcag   2700
cggcgccacc aacctggtga ccggcgtgcc cagccggttt agcggcagcg gctccggcaa   2760
ggactacacc ctgaccatca aagcctgcag ggccgaggac ttcgccacct actactgcca   2820
gcagtactgg tccaccccct tcaccttcgg cagcggcacc gagctggaaa tcaaagaatc   2880
taagtacgga ccgccctgcc ccccttgccc tatgttctgg gtgctggtgg tggtcggagg   2940
cgtgctggcc tgctacagcc tgctggtcac cgtggccttc atcatctttt gggtccgcag   3000
caagcggagc agaggcggcc acagcgacta catgaacatg ccccctagac ggcctggccc   3060
caccagaaag cactaccagc cctacgcccc tcccgggac tttgccgcct acagaagcaa   3120
acggggcaga aagaaactcc tgtatatatt caaacaacca tttatgagac cagtacaaac   3180
tactcaagag gaagatggct gtagctgccg atttccagaa gaagaagaag gaggatgtga   3240
actgcgggtg aagttcagca gaagcgccga cgcccctgcc taccagcagg gccagaatca   3300
gctgtacaac gagctgaacc tgggcagaag ggaagagtac gacgtcctgg ataagcggag   3360
aggccgggac cctgagatgg gcggcaagcc tcggcggaag aacccccagg aaggcctgta   3420
taacgaactg cagaaagaca agatggccga ggcctacagc gagatcggca tgaagggcga   3480
gcggaggcgg ggcaagggcc acgacggcct gtatcagggc ctgtccaccg ccaccaagga   3540
tacctacgac gccctgcaca tgcaggccct gccccaagg ctcgagggcg gcggagaggg   3600
```

```
cagaggaagt cttctaacat gcggtgacgt ggaggagaat cccggccta ggatgcttct   3660
cctggtgaca agccttctgc tctgtgagtt accacaccca gcattcctcc tgatcccacg   3720
caaagtgtgt aacggaatag gtattggtga atttaaagac tcactctcca taaatgctac   3780
gaatattaaa cacttcaaaa actgcacctc catcagtggc gatctccaca tcctgccggt   3840
ggcatttagg ggtgactcct tcacacatac tcctcctctg gatccacagg aactggatat   3900
tctgaaaacc gtaaaggaaa tcacagggtt tttgctgatt caggcttggc ctgaaaacag   3960
gacggacctc catgcctttg agaacctaga aatcatacgc ggcaggacca agcaacatgg   4020
tcagttttct cttgcagtcg tcagcctgaa cataacatcc ttgggattac gctccctcaa   4080
ggagataagt gatggagatg tgataatttc aggaaacaaa atttgtgct atgcaaatac    4140
aataaactgg aaaaaactgt ttgggacctc cggtcagaaa accaaaatta taagcaacag   4200
aggtgaaaac agctgcaagg ccacaggcca ggtctgccat gccttgtgct cccccgaggg   4260
ctgctggggc ccggagccca gggactgcgt ctcttgccgg aatgtcagcc gaggcaggga   4320
atgcgtggac aagtgcaacc ttctggaggg tgagccaagg gagtttgtgg agaactctga   4380
gtgcatacag tgccacccag agtgcctgcc tcaggccatg aacatcacct gcacaggacg   4440
gggaccagac aactgtatcc agtgtgccca ctacattgac ggcccccact gcgtcaagac   4500
ctgcccggca ggagtcatgg gagaaaacaa caccctggtc tggaagtacg cagacgccgg   4560
ccatgtgtgc cacctgtgcc atccaaactg cacctacgga tgcactgggc caggtcttga   4620
aggctgtcca acgaatgggc ctaagatccc gtccatcgcc actgggatgg tgggggccct   4680
cctcttgctg ctggtggtgg ccctggggat cggcctcttc atgtgagcgg ccgctctaga   4740
cccgggctgc aggaattcga tatcaagctt atcgataatc aacctctgga ttacaaaatt   4800
tgtgaaagat tgactggtat tcttaactat gttgctcctt ttacgctatg tggatacgct   4860
gctttaatgc ctttgtatca tgctattgct tcccgtatgg ctttcatttt ctcctccttg   4920
tataaatcct ggttgctgtc tctttatgag gagttgtggc ccgttgtcag gcaacgtggc   4980
gtggtgtgca ctgtgtttgc tgacgcaacc cccactggtt ggggcattgc caccacctgt   5040
cagctccttt ccgggacttt cgctttcccc ctccctattg ccacggcgga actcatcgcc   5100
gcctgccttg cccgctgctg gacaggggct cggctgttgg gcactgacaa ttccgtggtg   5160
ttgtcgggga atcatcgtc cttccttgg ctgctcgcct gtgttgccac ctggattctg    5220
cgcgggacgt ccttctgcta cgtcccttcg gccctcaatc cagcggacct tccttcccgc   5280
ggcctgctgc cggctctgcg gcctcttccg cgtcttcgcc ttcgccctca gacgagtcgg   5340
atctcccttt gggccgcctc cccgcatcga taccgtcgac tagccgtacc tttaagacca   5400
atgacttaca aggcagctgt agatcttagc cactttttaa aagaaagggg gggactggaa   5460
gggctaattc actcccaaag aagacaagat ctgcttttg cctgtactgg gtctctctgg    5520
ttagaccaga tctgagcctg ggagctctct ggctaactag ggaacccact gcttaagcct   5580
caataaagct tgccttgagt gcttcaagta gtgtgtgccc gtctgttgtg tgactctggt   5640
aactagagat ccctcagacc cttttagtca gtgtggaaaa tctctagcag aattcgatat   5700
caagcttatc gataccgtcg acctcgaggg ggggcccggt acccaattcg ccctatagtg   5760
agtcgtatta caattcactg gccgtcgttt tacaacgtcg tgactgggaa aaccctggcg   5820
ttacccaact taatcgcctt gcagcacatc cccctttcgc cagctggcgt aatagcgaag   5880
aggcccgcac cgatcgccct tcccaacagt tgcgcagcct gaatggcgaa tggaaattgt   5940
aagcgttaat attttgttaa aattcgcgtt aaattttgt taaatcagct cattttttaa    6000
```

```
ccaataggcc gaaatcggca aaatccctta taaatcaaaa gaatagaccg agatagggtt   6060
gagtgttgtt ccagtttgga acaagagtcc actattaaag aacgtggact ccaacgtcaa   6120
agggcgaaaa accgtctatc agggcgatgg cccactacgt gaaccatcac cctaatcaag   6180
ttttttgggg tcgaggtgcc gtaaagcact aaatcggaac cctaaaggga gcccccgatt   6240
tagagcttga cggggaaagc cggcgaacgt ggcgagaaag gaagggaaga aagcgaaagg   6300
agcgggcgct agggcgctgg caagtgtagc ggtcacgctg cgcgtaacca ccacacccgc   6360
cgcgcttaat gcgccgctac agggcgcgtc aggtggcact tttcggggaa atgtgcgcgg   6420 aaccccctatt tgtttatttt tctaaataca ttcaaatatg tatccgctca tgagacaata   6480
accctgataa atgcttcaat aatattgaaa aggaagagt atgagtattc aacatttccg    6540
tgtcgccctt attccttttt tgcggcatt ttgccttcct gttttttgctc acccagaaac    6600 gctggtgaaa gtaaaagatg ctgaagatca gttgggtgca cgagtgggtt acatcgaact   6660
ggatctcaac agcggtaaga tccttgagag ttttcgcccc gaagaacgtt ttccaatgat   6720
gagcactttt aaagttctgc tatgtggcgc ggtattatcc cgtattgacg ccgggcaaga   6780
gcaactcggt cgccgcatac actattctca gaatgacttg gttgagtact caccagtcac   6840
agaaaagcat cttacggatg gcatgacagt aagagaatta tgcagtgctg ccataaccat   6900
gagtgataac actgcggcca acttacttct gacaacgatc ggaggaccga aggagctaac   6960
cgcttttttg cacaacatgg ggatcatgt aactcgcctt gatcgttggg aaccggagct    7020
gaatgaagcc ataccaaacg acgagcgtga ccacgatg cctgtagcaa tggcaacaac     7080
gttgcgcaaa ctattaactg gcgaactact tactctagct tcccggcaac aattaataga   7140
ctggatggag gcggataaag ttgcaggacc acttctgcgc tcggcccttc cggctggctg   7200
gtttattgct gataaatctg gagccggtga gcgtgggtct cgcggtatca ttgcagcact   7260
ggggccagat ggtaagccct cccgtatcgt agttatctac acgacgggga gtcaggcaac   7320 tatgatgaa cgaaatagac agatcgctga gataggtgcc tcactgatta gcattggta     7380 actgtcagac caagtttact catatatact ttagattgat ttaaaacttc attttaatt    7440 taaaaggatc taggtgaaga tcctttttga atctcatg accaaaatcc cttaacgtga     7500
gttttcgttc cactgagcgt cagaccccgt agaaaagatc aaaggatctt cttgagatcc   7560
tttttttctg cgcgtaatct gctgcttgca acaaaaaaa ccaccgctac cagcggtggt    7620
ttgtttgccg gatcaagagc taccaactct ttttccgaag gtaactggct tcagcagagc   7680
gcagatacca aatactgttc ttctagtgta gccgtagtta ggccaccact tcaagaactc   7740
tgtagcaccg cctacatacc tcgctctgct aatcctgtta ccagtggctg ctgccagtgg   7800
cgataagtcg tgtcttaccg ggttggactc aagacgatag ttaccggata aggcgcagcg   7860
gtcgggctga acggggggtt cgtgcacaca gcccagcttg gagcgaacga cctacaccga   7920
actgagatac ctacagcgtg agctatgaga aagcgccacg cttcccgaag ggagaaaggc   7980
ggacaggtat ccggtaagcg gcagggtcgg aacaggagag cgcacgaggg agcttccagg   8040
gggaaacgcc tggtatcttt atagtcctgt cgggtttcgc cacctctgac ttgagcgtcg   8100
atttttgtga tgctcgtcag gggggcggag cctatgaaa aacgccagca acgcggcctt    8160
tttacggttc ctggcctttt gctggccttt tgctcacatg ttctttcctg cgttatcccc   8220
tgattctgtg gataaccgta ttaccgcctt tgagtgagct gataccgctc gccgcagccg   8280
aacgaccgag cgcagcgagt cagtgagcga ggaagcggaa gagcgcccaa tacgcaaacc   8340
```

```
gcctctcccc gcgcgttggc cgattcatta atgcagctgg cacgacaggt ttcccgactg    8400
gaaagcgggc agtgagcgca acgcaattaa tgtgagttag ctcactcatt aggcacccca    8460
ggctttacac tttatgcttc cggctcgtat gttgtgtgga attgtgagcg ataacaatt     8520 tcacacagga acagctatg accatgatta cgccaagctc gaaattaacc ctcactaaag     8580
ggaacaaaag ctggagctcc accgcggtgg cggcctcgag gtcgagatcc ggtcgaccag    8640
caaccatagt cccgccccta actccgccca tcccgcccct aactccgccc agttccgccc    8700
attctccgcc ccatggctga ctaattttt  ttatttatgc agaggccgag gccgcctcgg    8760
cctctgagct attccagaag tagtgaggag gcttttttgg aggcctaggc ttttgcaaaa    8820
agcttcgacg gtatcgattg gctcatgtcc aacattaccg ccatgttgac attgattatt    8880
gactagttat taatagtaat caattacggg gtcattagtt catagcccat atatggagtt    8940
ccgcgttaca taacttacgg taaatggccc gcctggctga ccgcccaacg acccccgccc    9000
attgacgtca ataatgacgt atgttcccat agtaacgcca atagggactt tccattgacg    9060
tcaatgggtg gagtatttac ggtaaactgc ccacttggca gtacatcaag tgtatcatat    9120
gccaagtacg ccccctattg acgtcaatga cggtaaatgg cccgcctggc attatgccca    9180
gtacatgacc ttatgggact ttcctacttg gcagtacatc tacgtattag tcatcgctat    9240
taccatggtg atgcggtttt ggcagtacat caatgggcgt ggatagcggt ttgactcacg    9300
gggatttcca agtctccacc ccattgacgt caatgggagt ttgttttggc accaaaatca    9360
acgggacttt ccaaaatgtc gtaacaactc cgccccattg acgcaaatgg cggtaggcg     9420 tgtacggaat tcggagtggc gagccctcag atcctgcata taagcagctg cttttttgcct  9480 gtactgggtc tctctg                                                    9496

<210> SEQ ID NO 58
<211> LENGTH: 679
<212> TYPE: DNA
<213> ORGANISM: Artificial Sequence
<220> FEATURE:
<223> OTHER INFORMATION: Long Spacer IgG4 hinge-CH2-CH3

<400> SEQUENCE: 58
tacggaccgt ccctgccccc cttgccctgc ccccgagttc ctgggcggac ccagcgtgtt     60
cctgttcccc cccaagccca aggacaccct gatgatcagc cggaccccc  aggtgacctg    120 cgtggtggtg gacgtgagcc aggaagatcc cgaggtccag ttcaattggt acgtggacgg    180
cgtggaagtg cacaacgcca agaccaagcc cagagaggaa cagttcaaca gcacctaccg    240
ggtggtgtct gtgctgaccg tgctgcacca ggactggctg aacggcaaag aatacaagtg    300
caaggtgtcc aacaagggcc tgcccagcag catcgaaaag accatcagca aggccaaggg    360
ccagcctcgc gagcccagg  tgtacaccct gcctccctcc aggaagaga  tgaccaagaa    420 ccaggtgtcc ctgacctgcc tggtgaaggg cttctacccc agcgacatcg ccgtggagtg    480
ggagagcaac ggccagcctg agaacaacta caagaccacc cctcccgtgc tggacagcga    540
cggcagcttc ttcctgtaca gccggctgac cgtggacaag agccggtggc aggaaggcaa    600
cgtctttagc tgcagcgtga tgcacgaggc cctgcacaac cactacaccc agaagagcct    660
gagcctgtcc ctgggcaag                                                 679

<210> SEQ ID NO 59
<211> LENGTH: 119
<212> TYPE: PRT
<213> ORGANISM: Artificial Sequence
```

```
<220> FEATURE:
<223> OTHER INFORMATION: Medium spacer

<400> SEQUENCE: 59

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 60
<211> LENGTH: 229
<212> TYPE: PRT
<213> ORGANISM: Artificial Sequence
<220> FEATURE:
<223> OTHER INFORMATION: Long spacer

<400> SEQUENCE: 60

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Gly Asn Val Phe Ser Cys Ser
        195                 200                 205

Val Met His Glu Ala Leu His Asn His Tyr Thr Gln Lys Ser Leu Ser
```

```
            210             215             220
Leu Ser Leu Gly Lys
225
```